US012552796B2

(12) United States Patent
Qi et al.

(10) Patent No.: US 12,552,796 B2
(45) Date of Patent: Feb. 17, 2026

(54) EED INHIBITOR, AND PREPARATION METHOD THEREFOR AND USE THEREOF

(71) Applicants: SHANGHAITECH UNIVERSITY, Shanghai (CN); JING MEDICINE TECHNOLOGY (SHANGHAI) LTD., Shanghai (CN)

(72) Inventors: Wei Qi, Shanghai (CN); Haizhen Zhang, Shanghai (CN); Xin Ma, Shanghai (CN); Hui Lei, Shanghai (CN); Yuhua George Zhang, Shanghai (CN); Yuxiu Qu, Shanghai (CN)

(73) Assignees: JING MEDICINE TECHNOLOGY (SHANGHAI) LTD., Shanghai (CN); SHANGHAITECH UNIVERSITY, Shanghai (CN)

( * ) Notice: Subject to any disclaimer, the term of this patent is extended or adjusted under 35 U.S.C. 154(b) by 834 days.

(21) Appl. No.: 17/773,554

(22) PCT Filed: Nov. 2, 2020

(86) PCT No.: PCT/CN2020/125873

§ 371 (c)(1),
(2) Date: Apr. 29, 2022

(87) PCT Pub. No.: WO2021/083380

PCT Pub. Date: May 6, 2021

(65) Prior Publication Data

US 2023/0028221 A1 Jan. 26, 2023

(30) Foreign Application Priority Data

Nov. 1, 2019 (CN) ........................ 201911059072.2

(51) Int. Cl.
*C07D 487/04* (2006.01)
*A61K 31/519* (2006.01)
(Continued)

(52) U.S. Cl.
CPC .......... *C07D 487/04* (2013.01); *A61K 31/519* (2013.01); *A61K 31/5377* (2013.01); *A61P 35/00* (2018.01)

(58) Field of Classification Search
CPC ................ C07D 487/04; A61K 31/519; A61K 31/5377; A61K 45/06; A61P 35/00; A61P 35/02
See application file for complete search history.

(56) References Cited

FOREIGN PATENT DOCUMENTS

| | | |
|---|---|---|
| CN | 111518100 A | 8/2020 |
| JP | 2004-238296 A | 8/2004 |

(Continued)

OTHER PUBLICATIONS

WO-2019158025-A1—machine translation. (Year: 2019).*
(Continued)

*Primary Examiner* — Clinton A Brooks
*Assistant Examiner* — Izabela Schmidt
(74) *Attorney, Agent, or Firm* — McCarter & English, LLP; Xin Zhang

(57) ABSTRACT

The present invention relates to a compound of formula (X) or a tautomer, stereoisomer, prodrug, crystal form, pharmaceutically acceptable salt, hydrate or solvate thereof, and a pharmaceutical composition containing the compound and a use.

(X)

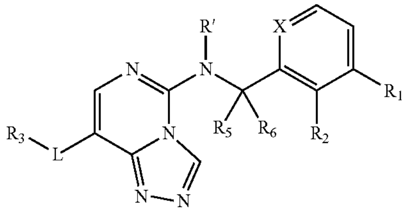

21 Claims, 1 Drawing Sheet

Tumor growth curve in Karpas422 CDX efficacy model

(51) Int. Cl.
*A61K 31/5377* (2006.01)
*A61P 35/00* (2006.01)

(56) References Cited

FOREIGN PATENT DOCUMENTS

| | | | | |
|---|---|---|---|---|
| WO | 2016/103155 | A1 | 6/2016 | |
| WO | 2017/219948 | A1 | 12/2017 | |
| WO | 2019/062435 | A1 | 4/2019 | |
| WO | WO-2019158025 | A1 * | 8/2019 | .............. A61P 35/00 |

OTHER PUBLICATIONS

Reynolds et. al., Cancer Discov (2023) 13 (5): 1058-1083 (Year: 2023).*
Prodrugs: Challenges and Rewards, Part 1, 2007. (Year: 2007).*
Oxford English Dictionary, https://www.oed.com/dictionary/prevent_v (Year: 2024).*
International Search Report and Written Opinion for Application No. PCT/CN2020/125873, dated Feb. 5, 2021, 21 pages.
International Preliminary Report on Patentability for Application No. PCT/CN2020/125873, dated May 3, 2022, 13 pages.

* cited by examiner

EED INHIBITOR, AND PREPARATION METHOD THEREFOR AND USE THEREOF

CROSS REFERENCE TO RELATED APPLICATIONS

The present application is a national application of PCT/CN2020/125873 filed on Nov. 2, 2020, which claims the priority of the Chinese Patent Application No. 201911059072.2 filed on Nov. 1, 2019. The Chinese Patent Application No. 201911059072.2 is incorporated herein by reference as part of the disclosure of the present application.

FIELD OF THE INVENTION

The present disclosure belongs to the field of medicinal chemistry, and in particular, relates to a new class of EED inhibitors, preparation methods thereof, and pharmaceutical compositions comprising the class of compounds. The class of compounds can be used for the treatment of tumor-related diseases, such as breast cancer, prostate cancer, liver cancer, sarcoma, gastric cancer, diffuse large B-cell lymphoma, follicular lymphoma, and melanoma.

BACKGROUND OF THE INVENTION

Polycombgroup protein (PcG) is an important family of epigenetic regulators, wherein dysregulation of the members has been found in a variety of tumors. One of important members, Polycomb repressive complex 2 (PRC2), is a protein methyltransferase complex that can methylate the lysine at 27th position of histone H3 (H3K27) near the promoter region of downstream target genes, thereby inhibiting the transcriptional activity of target genes, and playing an important role in development and tissue differentiation and regeneration. The PRC2 complex contains three core subunits: EZH2, EED and SUZ12, all of which are required for PRC2 activity. EZH2 can directly binds to the methyl group donor S-adenosylmethionine (SAM) and is an enzymatic subunit; EED can bind to trimethylated H3K27 (H3K27me3) to allosterically activate EZH2, and is an allosteric subunit; and SUZ12 assists in the formation and activity of the complex. EZH1 is a homologous protein of EZH2, and can also participate in the formation of PRC2 but with weak enzymatic activity. In recent years, studies have found that the expressions of EZH2, EED and SUZ12 are up-regulated in a variety of tumors, including but not limited to breast cancer, prostate cancer, liver cancer, sarcoma, and gastric cancer. Activating mutations in EZH2 have also been found in tumors such as diffuse large B lymphoma, follicular lymphoma, and melanoma. Reducing the level and activity of PRC2 by siRNA or PRC2 inhibitor can inhibit the proliferation of tumors such as lymphoma, which reveals that abnormal PRC2 activity is the cause of cancer occurrence and metastasis, and PRC2 can be used as a drug target for treatment. In addition, many studies have reported that PRC2 is also closely related to immune responses mediated by T cells and NK cells. Therefore, PRC2 is a promising drug target for the treatment of lymphoma and other tumors.

At present, there are mainly two drug development mechanisms targeting PRC2: the first is to compete with SAM to bind to EZH2 to exert an inhibitory effect, wherein EPZ-6438 (Epizyme, FDA approved), CPI-1205 (Constellation, Phase II clinical trial) and DS-3201 (Daiichi, Phase II clinical trial) have entered into clinical trials; and another is to allosterically inhibit the activity of PRC2 by targeting EED, wherein only one case, MAK683 (Novartis, Phase I/II clinical trial), has entered into clinical trials. The published tool compounds are A-395 (Abbott) and EED226 (Novartis), which can overcome the resistance problem of the first class of inhibitors due to different binding pockets. To sum up, the PRC2 complex is a proven and promising drug target, and the PRC2 inhibitor targeting EED is still in a relatively early stage of development at present. In-depth research on inhibitors of this target is beneficial to the development of new drugs related to the target, which has broad application value.

SUMMARY OF THE INVENTION

Therefore, the object of the present disclosure is to provide a new class of small molecule EED inhibitors, which can be used for the treatment and/or prevention of EED- and/or PRC2-mediated diseases.

In this regard, the present disclosure adopts the following technical solutions:

In one aspect, the present disclosure relates to a compound of formula (X), or a tautomer, stereoisomer, prodrug, crystal form, pharmaceutically acceptable salt, hydrate or solvate thereof:

(X)

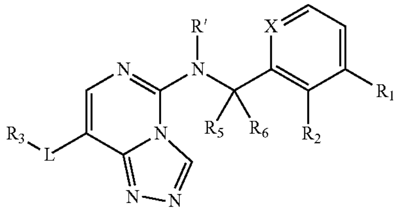

wherein

X is N or $C(R_x)$;

wherein $R_x$ is selected from H, halogen, $C_{1-6}$ alkyl, $C_{1-6}$ haloalkyl or $C_{1-6}$ alkoxy;

$R_1$ is selected from H, halogen, $C_{1-6}$ alkyl, $C_{1-6}$ haloalkyl or $C_{1-6}$ alkoxy;

$R_2$ is selected from H, halogen, $C_{1-6}$ alkyl, $C_{1-6}$ haloalkyl or $C_{1-6}$ alkoxy;

or $R_1$ and $R_2$ together form $—(CH_2)_pY—$, $—Y(CH_2)_p—$ or $—Y(CH_2)_pZ—$ group;

wherein p is 1, 2, 3, 4 or 5;

Y is selected from O, S, NH or chemical bond;

Z is selected from O, S, NH or chemical bond;

R' is selected from H, $C_{1-6}$ alkyl or $C_{1-6}$ haloalkyl;

L is selected from —C(O)—N(R)—, —C(O)—O—, —N($R_3$')—C(O)—, —O—C(O)—, $—S(O)_q—N(R)—$, $—S(O)_q—O—$, —O—, —S—, —N(R")—, $—C_{1-4}$ alkylene- or $—C_{2-4}$ alkenylene-;

wherein R is selected from H, $C_{1-6}$ alkyl or $C_{1-6}$ haloalkyl;

$R_3$' is selected from H, $(CH_2)_m—C_{1-6}$ alkyl, $(CH_2)_m—C_{1-6}$ haloalkyl or $(CH_2)_n—C_{3-7}$ cycloalkyl;

R" is selected from H, $C_{1-6}$ alkyl or $C_{1-6}$ haloalkyl;

q is 0, 1 or 2;

$R_3$ is selected from $(CH_2)_m—C_{1-6}$ alkyl, $(CH_2)_m—C_{1-6}$ haloalkyl, $(CH_2)_n—C_{1-6}$ alkoxy, $(CH_2)_n—C_{1-6}$ haloalkoxy, $(CH_2)_n—NR_aR_b$, $(CH_2)_n—OR_a$, $(CH_2)_n—C_{3-7}$ cycloalkyl, $(CH_2)_n$-3- to 10-membered heterocyclyl, $(CH_2)_n—C_{6-10}$ aryl or $(CH_2)_n$-5- to 10-membered heteroaryl; or $R_3$ is connected to R to form $—C_{1-6}$ alkylene-;

or, $R_3$, $R_3$' and the N atom to which they are attached together form a 4- to 7-membered heterocyclyl group; wherein m is 0, 1, 2, 3, 4 or 5;

n is 0, 1, 2, 3, 4 or 5;

$R_a$ is selected from H, $C_{1-6}$ alkyl or $C_{1-6}$ haloalkyl;

$R_b$ is selected from H, $C_{1-6}$ alkyl or $C_{1-6}$ haloalkyl;

$R_5$ and $R_6$ are independently selected from H, D, $C_{1-6}$ alkyl or $C_{1-6}$ haloalkyl;

wherein $R_3$ is optionally substituted by one or more substituent groups selected from H, D, halogen, CN, OH, =O, $NR_cR_d$, $C_{1-6}$ alkyl, $C_{1-6}$ haloalkyl, $C_{1-6}$ alkoxy, $C_{3-7}$ cycloalkyl, 4- to 7-membered heterocyclyl, $C_{6-10}$ aryl, 5- to 10-membered heteroaryl, $(CH_2)_m$—$C_{1-6}$ alkyl, $(CH_2)_m$—$C_{1-6}$ haloalkyl, $(CH_2)_n$—$C_{1-6}$ alkoxy, $(CH_2)_n$—$C_{1-6}$ haloalkoxy, —O—$C_{3-7}$ cycloalkyl, —O-4- to 7-membered heterocyclyl, —O—$C_{6-10}$ aryl, —O-5- to 10-membered heteroaryl, —C(O)—$C_{1-6}$ alkyl, —C(O)—$C_{1-6}$ haloalkyl, —C(O)—$C_{3-7}$ cycloalkyl, —C(O)-4- to 7-membered heterocyclyl, —C(O)—$C_{6-10}$ aryl, —C(O)-5- to 10-membered heteroaryl, —$S(O)_q$—$C_{1-6}$ alkyl, —$S(O)_q$—$C_{1-6}$ haloalkyl, —$S(O)_q$—$C_{1-6}$ alkoxy, —$S(O)_q$—$C_{3-7}$ cycloalkyl, —$S(O)_q$-4- to 7-membered heterocyclyl, —$S(O)_q$—$C_{6-10}$ aryl or —$S(O)_q$-5- to 10-membered heteroaryl;

wherein $R_c$ is selected from H, $C_{1-6}$ alkyl, $C_{1-6}$ haloalkyl, —C(O)—$C_{3-7}$ cycloalkyl, —C(O)-4- to 7-membered heterocyclyl, —C(O)—$C_{6-10}$ aryl or —C(O)-5- to 10-membered heteroaryl;

$R_d$ is selected from H, $C_{1-6}$ alkyl, $C_{1-6}$ haloalkyl, —C(O)—$C_{3-7}$ cycloalkyl, —C(O)-4- to 7-membered heterocyclyl, —C(O)—$C_{6-10}$ aryl or —C(O)-5- to 10-membered heteroaryl;

wherein the alkyl, haloalkyl, alkoxy, haloalkoxy, cycloalkyl, heterocyclyl, aryl, heteroaryl, alkylene and alkenylene are optionally substituted with substituent groups selected from H, D, CN, OH, =O, halogen, $C_{1-6}$ alkyl, $C_{1-6}$ haloalkyl, $C_{1-6}$ alkoxy, $C_{3-7}$ cycloalkyl, 4- to 7-membered heterocyclyl, $C_{6-10}$ aryl, 5- to 10-membered heteroaryl, —O—$C_{3-7}$ cycloalkyl, —O-4- to 7-membered heterocyclyl, —O—$C_{6-10}$ aryl, —O-5- to 10-membered heteroaryl, —C(O)—$C_{1-6}$ alkyl, —C(O)—$C_{1-6}$ haloalkyl, —C(O)—$C_{3-7}$ cycloalkyl, —C(O)-4- to 7-membered heterocyclyl, —C(O)—$C_{6-10}$ aryl or —C(O)-5- to 10-membered heteroaryl, or substituted with one or more D, up to complete deuteration.

In another aspect, the present disclosure relates to a compound of formula (I), or a tautomer, stereoisomer, prodrug, crystal form, pharmaceutically acceptable salt, hydrate or solvate thereof:

(I)

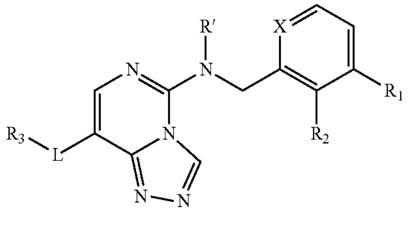

wherein

X is N or $C(R_x)$;

wherein $R_x$ is selected from H, halogen, $C_{1-6}$ alkyl, $C_{1-6}$ haloalkyl or $C_{1-6}$ alkoxy;

$R_1$ is selected from H, halogen, $C_{1-6}$ alkyl, $C_{1-6}$ haloalkyl or $C_{1-6}$ alkoxy;

$R_2$ is selected from H, halogen, $C_{1-6}$ alkyl, $C_{1-6}$ haloalkyl or $C_{1-6}$ alkoxy;

or $R_1$ and $R_2$ together form —$(CH_2)_pY$—, —$Y(CH_2)_p$— or —$Y(CH_2)_pZ$— group;

wherein p is 1, 2, 3, 4 or 5;

Y is selected from O, S, NH or chemical bond;

Z is selected from O, S, NH or chemical bond;

R' is selected from H, $C_{1-6}$ alkyl or $C_{1-6}$ haloalkyl;

L is selected from —C(O)—N(R)—, —N($R_3$')—C(O)—, —O—, —S—, —N(R")—, —$C_{1-4}$ alkylene- or —$C_{2-4}$ alkenylene-;

wherein R is selected from H, $C_{1-6}$ alkyl or $C_{1-6}$ haloalkyl;

$R_3$' is selected from H, $(CH_2)_m$—$C_{1-6}$ alkyl, $(CH_2)_m$—$C_{1-6}$ haloalkyl or $(CH_2)_n$—$C_{3-7}$ cycloalkyl;

R" is selected from H, $C_{1-6}$ alkyl or $C_{1-6}$ haloalkyl;

$R_3$ is selected from $(CH_2)_m$—$C_{1-6}$ alkyl, $(CH_2)_m$—$C_{1-6}$ haloalkyl, $(CH_2)_n$—$C_{1-6}$ alkoxy, $(CH_2)_n$—$C_{1-6}$ haloalkoxy, $(CH_2)_n$—$C_{3-7}$ cycloalkyl, $(CH_2)_n$-3- to 10-membered heterocyclyl, $(CH_2)_n$—$C_{6-10}$ aryl or $(CH_2)_n$-5- to 10-membered heteroaryl;

or, $R_3$, $R_3$' and the N atom to which they are attached together form a 4- to 7-membered heterocyclyl group;

wherein m is 0, 1, 2, 3, 4 or 5;

n is 0, 1, 2, 3, 4 or 5.

In another aspect, the present disclosure provides methods for the preparation of compounds of the present disclosure.

In another aspect, the present disclosure provides a pharmaceutical composition, which comprises a compound disclosed herein and pharmaceutically acceptable excipient (s). In a specific embodiment, the compound disclosed herein is provided in a therapeutically effective amount. In a specific embodiment, the compound disclosed herein is provided in a prophylactically effective amount. In another aspect, the pharmaceutical composition of the present disclosure is used in combination with immune checkpoint inhibitor such as PD-1, PD-L1, CTLA-4 antibodies, etc.

In another aspect, the present disclosure provides the use of a compound of the present disclosure or a pharmaceutical composition of the present disclosure in the manufacture of a medicament for the treatment and/or prevention of EED- and/or PRC2-mediated diseases. In another aspect, the present disclosure provides the use of the compound of the present disclosure or the pharmaceutical composition of the present disclosure in the manufacture of a medicament for the treatment and/or prevention of immunodeficiency diseases and autoimmune diseases, etc.

In another aspect, the present disclosure provides a method of treating and/or preventing EED- and/or PRC2-mediated diseases in a subject, comprising administering to the subject a compound of the present disclosure or a pharmaceutical composition thereof.

In another aspect, the present disclosure provides a compound of the present disclosure or a pharmaceutical composition thereof for use in the treatment and/or prevention of EED- and/or PRC2-mediated diseases.

In another aspect, the EED- and/or PRC2-mediated disease is a tumor-related disease, an immunodeficiency disease or an autoimmune disease; alternatively, the tumor-related disease is selected from diffuse large B-cell lymphoma, follicular lymphoma, other lymphomas, leukemia, multiple myeloma, mesothelioma, gastric cancer, malignant rhabdomyoma, liver cancer, prostate cancer, breast cancer, bile duct and gallbladder cancer, bladder cancer, brain tumors (including neuroblastoma, schwannoma, glioma, glioblastoma and astrocytoma), cervical cancer, colon cancer, melanoma, endometrial cancer, esophageal cancer, head and neck cancer, lung cancer, nasopharyngeal cancer, ovarian cancer, pancreatic cancer, renal cell cancer, rectal cancer, thyroid cancer, parathyroid tumor, uterine tumor and soft tissue sarcoma; the immunodeficiency disease or autoimmune disease includes, but is not limited to, systemic lupus erythematosus, Crohn's disease, ulcerative colitis, multiple sclerosis, aplastic anemia due to autoimmunity and rejection reaction due to organ transplantation, etc.

In another aspect, the present disclosure provides the use of the compound of the present disclosure or the pharmaceutical composition thereof in the manufacture of a medicament for tumor immunization.

In another aspect, the present disclosure provides a method for tumor immunization in a subject, comprising administering to the subject a compound of the present disclosure or a pharmaceutical composition thereof.

In another aspect, the present disclosure provides a compound of the present disclosure or a pharmaceutical composition thereof for use in tumor immunization.

In another aspect, the present disclosure provides a drug combination comprising a compound of the present disclosure or a pharmaceutical composition thereof, and an immune checkpoint inhibitor.

Other objects and advantages of the present disclosure will be apparent to those skilled in the art from the detailed description, examples and claims that follow.

Definitions

Chemical Definitions

The definitions of specific functional groups and chemical terms are described in more detail below.

When a range of values is listed, it is intended to encompass each value and sub-range within the range. For example, "$C_{1-6}$ alkyl" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"$C_{1-6}$ alkyl" refers to a linear or branched, saturated hydrocarbon group having 1 to 6 carbon atoms, and is also referred to herein as "lower alkyl". In some embodiments, $C_{1-4}$ alkyl is alternative. Examples of alkyl include, but are not limited to, methyl ($C_1$), ethyl ($C_2$), n-propyl ($C_3$), iso-propyl ($C_3$), n-butyl ($C_4$), t-butyl ($C_4$), sec-butyl ($C_4$), iso-butyl ($C_4$), n-pentyl ($C_5$), 3-pentyl ($C_5$), pentyl ($C_5$), neo-pentyl ($C_5$), 3-methyl-2-butyl ($C_5$), t-pentyl ($C_5$) and n-hexyl ($C_6$). Regardless of whether or not the alkyl group is modified with "substituted", each alkyl group is independently optionally substituted, for example, with 1 to 5 substituents, 1 to 3 substituents or 1 substituent. Appropriate substituents are defined as follows.

"$C_{2-6}$ alkenyl" refers to a linear or branched, hydrocarbon group having 2-6 carbon atoms and one or more carbon-carbon double bonds (e.g., 1, 2, or 3 carbon-carbon double bonds). One or more carbon-carbon double bonds can be internal (e.g., in 2-butenyl) or terminal (e.g., in 1-butenyl). In some embodiments, $C_{2-4}$ alkenyl is alternative. Examples of alkenyl include, but are not limited to, vinyl ($C_2$), 1-propenyl ($C_3$), 2-propenyl ($C_3$), 1-butenyl ($C_4$), 2-butenyl ($C_4$), butadienyl ($C_4$), pentenyl ($C_5$), pentadienyl ($C_5$), hexenyl ($C_6$), etc. Regardless of whether or not the alkenyl group is modified with "substituted", each alkenyl group is independently optionally substituted, for example, with 1 to 5 substituents, 1 to 3 substituents or 1 substituent. Appropriate substituents are defined as follows.

"$C_{2-6}$ alkynyl" refers to a linear or branched, hydrocarbon group having 2-6 carbon atoms, one or more carbon-carbon triple bonds (e.g., 1, 2 or 3 carbon-carbon triple bonds) and optionally one or more carbon-carbon double bonds (e.g., 1, 2 or 3 carbon-carbon double bonds). In some embodiments, $C_{2-4}$ alkynyl is alternative. In some embodiments, alkynyl does not contain any double bond. One or more carbon-carbon triple bonds can be internal (e.g., in 2-butynyl) or terminal (e.g., in 1-butynyl). Examples of alkynyl include, but are not limited to, ethynyl ($C_2$), 1-propynyl ($C_3$), 2-propynyl ($C_3$), 1-butynyl ($C_4$), 2-butynyl ($C_4$), pentynyl ($C_5$), hexynyl ($C_6$), etc. Regardless of whether or not the alkynyl group is modified with "substituted", each alkynyl group is independently optionally substituted, for example, with 1 to 5 substituents, 1 to 3 substituents or 1 substituent. Appropriate substituents are defined as follows.

"$—C_{1-6}$ alkylene-, $—C_{2-6}$ alkenylene- or $—C_{2-6}$ alkynylene-" refers to a divalent group of "$C_{1-6}$ alkyl, $C_{2-6}$ alkenyl or $C_{2-6}$ alkynyl" as defined above.

"$C_{1-6}$ alkylene" refers to a divalent group formed by removing another hydrogen from a $C_{1-6}$ alkyl group, and can be a substituted or unsubstituted alkylene group. In some embodiments, $C_{1-4}$ alkylene groups are particularly alternative. The unsubstituted alkylene groups include, but are not limited to, methylene ($—CH_2—$), ethylene ($—CH_2CH_2—$), propylene ($—CH_2CH_2CH_2—$), butylene ($—CH_2CH_2CH_2CH_2—$), pentylene ($—CH_2CH_2CH_2CH_2CH_2—$), hexylene ($—CH_2CH_2CH_2CH_2CH_2CH_2—$), etc. Exemplary substituted alkylene groups, e.g., alkylene groups substituted with one or more alkyl (methyl) groups, include, but are not limited to, substituted methylene ($—CH(CH_3)—$, $—C(CH_3)_2—$), substituted ethylene ($—CH(CH_3)CH_2—$, $—CH_2CH(CH_3)—$, $—C(CH_3)_2CH_2—$, $—CH_2C(CH_3)_2$), substituted propylene ($—CH(CH_3)CH_2CH_2—$, $—CH_2CH(CH_3)CH_2—$, $—CH_2CH_2CH(CH_3)—$, $—C(CH_3)_2CH_2CH_2—$, $—CH_2C(CH_3)_2CH_2—$, $—CH_2CH_2C(CH_3)_2—$), etc.

"$C_{2-6}$ alkenylene" refers to a divalent group formed by removing another hydrogen from a $C_{2-6}$ alkenyl group, and may be a substituted or unsubstituted alkenylene group. In some embodiments, $C_{2-4}$ alkenylene groups are particularly alternative. Exemplary unsubstituted alkenylene groups include, but are not limited to, vinylene ($—CH{=}CH—$) and propylene (e.g., $—CH{=}CHCH_2—$, $—CH_2—CH{=}CH—$). Exemplary substituted alkenylene groups, e.g., alkenylene groups substituted with one or more alkyl (methyl) groups, include, but are not limited to, substituted ethylene ($—C(CH_3){=}CH—$, $—CH{=}C(CH_3)—$), substituted propenylene ($—C(CH_3){=}CHCH_2—$, $—CH{=}C(CH_3)CH_2—$, $—CH{=}CHCH(CH_3)—$, $—CH{=}CHC(CH_3)_2—$, $—CH(CH_3)—CH{=}CH—$, $—C(CH_3)_2—CH{=}CH—$, $—CH_2—C(CH_3){=}CH—$, $—CH_2—CH{=}C(CH_3)—$), etc.

"$C_{1-6}$ alkoxyl" refers to a —OR group, wherein R is substituted or unsubstituted $C_{1-6}$ alkyl. In some embodiments, $C_{1-4}$ alkoxyl is alternative. Specifically, alkoxyl includes, but is not limited to, methoxy, ethoxy, n-propoxy, iso-propoxy, n-butoxy, t-butoxy, sec-butoxy, n-pentyloxy, n-hexyloxy and 1,2-dimethylbutoxy.

"Halo" or "halogen" refers to fluoro (F), chloro (Cl), bromo (Br) and iodo (I). In some embodiments, the halo group is F, Cl or Br. In some embodiments, the halo group is F or Cl. In some embodiments, the halo group is F.

Therefore, "$C_{1-6}$ haloalkyl" and "$C_{1-6}$ haloalkoxyl" refer to the above "$C_{1-6}$ alkyl" and "$C_{1-6}$ alkoxyl" substituted with one or more halo groups. In some embodiments, $C_{1-4}$ haloalkyl is alternative, and $C_{1-2}$ haloalkyl is yet alternative. In some embodiments, $C_{1-4}$ haloalkoxyl is alternative, and $C_{1-2}$ haloalkoxyl is yet alternative. Examples of haloalkyl include, but are not limited to, $—CF_3$, $—CH_2F$, $—CHF_2$, $—CHFCH_2F$, $—CH_2CHF_2$, $—CF_2CF_3$, $—CCl_3$, $—CH_2Cl$, —$CHCl_2$, 2,2,2-trifluoro-1,1-dimethyl-ethyl, etc. Examples of haloalkoxyl include, but are not limited to, —$OCH_2F$, —$OCHF_2$, —$OCF_3$, etc.

"$C_{3-10}$ cycloalkyl" refers to a non-aromatic cyclic hydrocarbon group having 3-10 ring carbon atoms and zero heteroatoms. In some embodiments, $C_{3-7}$ cycloalkyl is alternative, $C_{3-6}$ cycloalkyl is alternative, and $C_{5-6}$ cycloalkyl and $C_{3-4}$ cycloalkyl are yet alternative. Cycloalkyl also includes a ring system in which the above cycloalkyl ring is fused with one or more aryl or heteroaryl groups, wherein the point of attachment is on the cycloalkyl ring, and in such instances, the number of carbons continue to designate the number of carbons in the cycloalkyl system. Examples of cycloalkyl include, but are not limited to, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl (C), cyclohexadienyl (C), cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptyl ($C_7$), bicyclo[2.2.2]octyl ($C_8$), cyclononyl ($C_9$), cyclononenyl ($C_9$), cyclodecyl ($C_{10}$), cyclodecenyl ($C_{10}$), octahydro-1H-indenyl ($C_9$), decahydronaphthyl ($C_{10}$), spiro[4.5]decyl ($C_{10}$), etc. Regardless of whether or not the cycloalkyl group is modified with "substituted", each cycloalkyl group is independently optionally substituted, for example, with 1 to 5 substituents, 1 to 3 substituents or 1 substituent. Appropriate substituents are defined as follows.

"3- to 10-membered heterocyclyl" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon. In heterocyclyl groups that contain one or more nitrogen atoms, the point of attachment can be a carbon or nitrogen atom, as valency permits. In some embodiments, 4- to 7-membered heterocyclyl is alternative, and it is a 4- to 7-membered non-aromatic ring system having ring carbon atoms and 1-3 ring heteroatoms. In some embodiments, 3- to 6-membered heterocyclyl is alternative, and it is a 3- to 6-membered non-aromatic ring system having ring carbon atoms and 1-3 ring heteroatoms. 5- to 6-membered heterocyclyl is yet alternative, and it is a 5- to 6-membered non-aromatic ring system having ring carbon atoms and 1-3 ring heteroatoms. "Heterocyclyl" also includes ring systems wherein the heterocyclyl, as defined above, is fused with one or more cycloalkyl, aryl or heteroaryl groups wherein the point of attachment is on the heterocyclyl ring, and in such instances, the number of ring members continues to designate the number of ring members in the heterocyclyl ring system. Regardless of whether or not the heterocyclyl group is modified with "substituted", each heterocyclyl group is independently optionally substituted, for example, with 1 to 5 substituents, 1 to 3 substituents or 1 substituent. Appropriate substituents are defined as follows.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing three heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclyl) include, without limitation, indolinyl, isoindolinyl, dihydrobenzofuranyl, dihydrobenzothienyl, benzoxazolinonyl, and the like. Exemplary 6-membered heterocyclyl groups fused to a $C_6$ aryl ring (also referred to herein as a 6,6-bicyclic heterocyclyl) include, without limitation, tetrahydroquinolinyl, tetrahydroisoquinolinyl, and the like.

"$C_{6-14}$ aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms. In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{1-4}$ aryl"; e.g., anthracyl). In some embodiments, $C_{6-10}$ aryl is alternative, and $C_6$ aryl is yet alternative. "Aryl" also includes ring systems wherein the aryl ring, as defined above, is fused with one or more cycloalkyl or heterocyclyl groups wherein the point of attachment is on the aryl ring, and in such instances, the number of carbon atoms continues to designate the number of carbon atoms in the aryl ring system. Regardless of whether or not the aryl group is modified with "substituted", each aryl group is independently optionally substituted, for example, with 1 to 5 substituents, 1 to 3 substituents or 1 substituent. Appropriate substituents are defined as follows.

"5- to 10-membered heteroaryl" refers to a radical of a 5- to 10-membered monocyclic or bicyclic 4n+2 aromatic ring system (e.g., having 6 or 10 pi electrons shared in a cyclic array) having ring carbon atoms and 1-4 ring heteroatoms, wherein each heteroatom is independently selected from nitrogen, oxygen and sulfur. In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" also includes ring systems wherein the heteroaryl ring, as defined above, is fused with one or more cycloalkyl or heterocyclyl groups wherein the point of attachment is on the heteroaryl ring, and in such instances, the number of carbon atoms continues to designate the number of carbon atoms in the heteroaryl ring system. In some embodiments, 5- to 6-membered heteroaryl is alternative, and it is a 5- to 6-membered monocyclic or bicyclic 4n+2 aromatic ring system having ring carbon atoms and 1-4 ring heteroatoms. Regardless of whether or not the heteroaryl group is modified with "substituted", each heteroaryl group is independently optionally substituted, for example, with 1 to 5 substituents, 1 to 3 substituents or 1 substituent. Appropriate substituents are defined as follows.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Exemplary substituents on carbon atoms include, but are not limited to, halo, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3{}^+X^-$, —$N(OR^{cc})R^{bb}$, —SH, —$SR^{aa}$, —$SSR^{cc}$, —$C(=O)R^{aa}$, —$CO_2H$, —CHO, —$C(OR^{cc})_2$, —$CO_2R^{aa}$, —$OC(=O)R^{aa}$, —$OCO_2R^{aa}$, —$C(=O)N(R^{bb})_2$, —$OC(=O)N(R^{bb})_2$, —$NR^{bb}C(=O)R^{aa}$, —$NR^{bb}CO_2R^{aa}$, —$NR^{bb}C(=O)N(R^{bb})_2$, —$C(=NR^{bb})R^{aa}$, —$C(=NR^{bb})OR^{aa}$, —$OC(=NR^{bb})R^{aa}$, —$OC(=NR^{bb})OR^{aa}$, —$C(=NR^{bb})N(R^{bb})_2$, —$OC(=NR^{bb})N(R^{bb})_2$, —$NR^{bb}C(=NR^{bb})N(R^{bb})_2$, —$C(=O)NR^{bb}SO_2R^{aa}$, —$NR^{bb}SO_2R^{aa}$, —$SO_2N(R^{bb})_2$, —$SO_2R^{aa}$, —$SO_2OR^{aa}$—$OSO_2R^{aa}$, —$S(=O)R^{aa}$, —$OS(=O)R^{aa}$, —$Si(R^{aa})_3$, —$OSi(R^{aa})_3$, —$C(=S)N(R^{bb})_2$, —$C(=O)SR^{aa}$, —$C(=S)SR^{aa}$, —$SC(=S)SR^{aa}$, —$SC(=O)SR^{aa}$, —$OC(=O)SR^{aa}$, —$SC(=O)OR^{aa}$, —$SC(=O)R^{aa}$, —$P(=O)_2R^{aa}$, —$OP(=O)_2R^{aa}$, —$P(=O)(R^{aa})_2$, —$OP(=O)(R^{aa})_2$, —$OP(=O)(OR^{cc})_2$, —$P(=O)_2N(R^{bb})_2$, —$OP(=O)_2N(R^{bb})_2$, —$P(=O)(NR^{bb})_2$, —$OP(=O)(NR^{bb})_2$, —$NR^{bb}P(=O)(OR^{cc})_2$, —$NR^{bb}P(=O)(NR^{bb})_2$, —$P(R^{cc})_2$, —$P(R^{cc})_3$, —$OP(R^{cc})_2$, —$OP(R^{cc})_3$, —$B(R^{aa})_2$, —$B(OR^{cc})_2$, —$BR^{aa}(OR^{cc})$, alkyl, haloalkyl, alkenyl, alkynyl, carbocyclyl, heterocyclyl, aryl and heteroaryl, wherein each of alkyl, alkenyl, alkynyl, carbocyclyl, heterocyclyl, aryl and heteroaryl is independently substituted with 0, 1, 2, 3, 4 or 5 $R^{dd}$ groups;

or two geminal hydrogens on a carbon atom are replaced with the group =O, =S, =$NN(R^{bb})_2$, =$NNR^{bb}C(=O)R^{aa}$, =$NNR^{bb}C(=O)OR^{aa}$, =$NNR^{bb}S(=O)_2R^{aa}$, =$NR^{bb}$ or =$NOR^{cc}$;

each $R^{aa}$ is independently selected from alkyl, haloalkyl, alkenyl, alkynyl, carbocyclyl, heterocyclyl, aryl and heteroaryl, or two $R^{aa}$ groups are bound to form heterocyclyl or heteroaryl ring, wherein each of alkyl, alkenyl, alkynyl, carbocyclyl, heterocyclyl, aryl and heteroaryl is independently substituted with 0, 1, 2, 3, 4 or 5 $R^{dd}$ groups;

each $R^{bb}$ is independently selected from: hydrogen, —OH, —$OR^{aa}$, —$N(R^{cc})_2$, —CN, —$C(=O)R^{aa}$, —$C(=O)N(R^{cc})_2$, —$CO_2R^{aa}$, —$SO_2R^{aa}$, —$C(=NR^{cc})OR^{aa}$, —$C(=NR^{cc})N(R^{cc})_2$, —$SO_2N(R^{cc})_2$, —$SO_2R^{cc}$, —$SO_2OR^{cc}$, —$SOR^{aa}$, —$C(=S)N(R^{cc})_2$, —$C(=O)SR^{cc}$, —$C(=S)SR^{cc}$, —$P(=O)_2R^{aa}$, —$P(=O)(R^{aa})_2$, —$P(=O)_2N(R^{cc})_2$, —$P(=O)(NR^{cc})_2$, alkyl, haloalkyl, alkenyl, alkynyl, carbocyclyl, heterocyclyl, aryl and heteroaryl, or two $R^{bb}$ groups are bound to form heterocyclyl or heteroaryl ring, wherein each of alkyl, alkenyl, alkynyl, carbocyclyl, heterocyclyl, aryl and heteroaryl is independently substituted with 0, 1, 2, 3, 4 or 5 $R^{dd}$ groups;

each $R^{cc}$ is independently selected from hydrogen, alkyl, haloalkyl, alkenyl, alkynyl, carbocyclyl, heterocyclyl, aryl and heteroaryl, or two $R^{cc}$ groups are bound to form heterocyclyl or heteroaryl ring, wherein each of alkyl, alkenyl, alkynyl, carbocyclyl, heterocyclyl, aryl and heteroaryl is independently substituted with 0, 1, 2, 3, 4 or 5 $R^{dd}$ groups;

each $R^{dd}$ is independently selected from: halo, —CN, —$NO_2$, —$N_3$, —$SO_2H$, —$SO_3H$, —OH, —$OR^{ee}$, —$ON(R^{ff})_2$, —$N(R^{ff})_2$, —$N(R^{ff})_3{}^+X^-$, —$N(OR^{ee})R^{ff}$, —SH, —$SR^{ee}$, —$SSR^{ee}$, —$C(=O)R^{ee}$, —$CO_2H$, —$CO_2R^{ee}$, —$OC(=O)R^{ee}$, —$OCO_2R^{ee}$, —$C(=O)N(R^{ff})_2$, —$OC(=O)N(R^{ff})_2$, —$NR^{ff}C(=O)R^{ee}$, —$NR^{ff}CO_2R^{ee}$, —$NR^{ff}C(=O)N(R^{ff})_2$, —$C(=NR^{ff})OR^{ee}$, —$OC(=NR^{ff})R^{ee}$, —$OC(=NR^{ff})OR^{ee}$, —$C(=NR^{ff})N(R^{ff})_2$, —$OC(=NR^{ff})N(R^{ff})_2$, —$NR^{ff}C(=NR^{ff})N(R^{ff})_2$, —$NR^{ff}SO_2R^{ee}$, —$SO_2N(R^{ff})_2$, —$SO_2R^{ee}$, —$SO_2OR^{ee}$, —$OSO_2R^{ee}$, —$S(=O)R^{ee}$, —$Si(R^{ee})_3$, —$OSi(R^{ee})_3$, —$C(=S)N(R^{ff})_2$, —$C(=O)SR^{ee}$, —$C(=S)SR^{ee}$, —$SC(=S)SR^{ee}$, —$P(=O)_2R^{ee}$, —$P(=O)(R^{ee})_2$, —$OP(=O)(R^{ee})_2$, —$OP(=O)(OR^{ee})_2$, alkyl, haloalkyl, alkenyl, alkynyl, carbocyclyl, heterocyclyl, aryl, and heteroaryl, wherein each of alkyl, alkenyl, alkynyl, carbocyclyl, heterocyclyl, aryl and heteroaryl is independently substituted with 0, 1, 2, 3, 4 or 5 $R^{gg}$ groups, or two geminal $R^{dd}$ substituents can be bound to form =O or =S;

each $R^{ee}$ is independently selected from alkyl, haloalkyl, alkenyl, alkynyl, carbocyclyl, aryl, heterocyclyl and heteroaryl, wherein each of alkyl, alkenyl, alkynyl, carbocyclyl, heterocyclyl, aryl and heteroaryl is independently substituted with 0, 1, 2, 3, 4 or 5 $R^{gg}$ groups;

each $R^{ff}$ is independently selected from hydrogen, alkyl, haloalkyl, alkenyl, alkynyl, carbocyclyl, heterocyclyl, aryl and heteroaryl, or two $R^{ff}$ groups are bound to form heterocyclyl or heteroaryl ring, wherein each of alkyl, alkenyl, alkynyl, carbocyclyl, heterocyclyl, aryl and heteroaryl is independently substituted with 0, 1, 2, 3, 4 or 5 $R^{gg}$ groups;

each $R^{gg}$ is independently: halo, —CN, —$NO_2$, —$N_3$, —$SO_2H$, —$SO_3H$, —OH, —$OC_{1-6}$ alkyl, —$ON(C_{1-6}$ alkyl$)_2$, —$N(C_{1-6}$ alkyl$)_2$, —$N(C_{1-6}$ alkyl$)_3{}^+X^-$, —$NH(C_{1-6}$ alkyl$)_2{}^+X^-$, —$NH_2(C_{1-6}$ alkyl$)^+X^-$, —$NH_3{}^+X^-$, —$N(OC_{1-6}$ alkyl)($C_{1-6}$ alkyl), —N(OH)($C_{1-6}$ alkyl), —NH(OH), —SH, —$SC_{1-6}$ alkyl, —SS($C_{1-6}$ alkyl), —C(=O)($C_{1-6}$ alkyl), —$CO_2H$, —$CO_2(C_{1-6}$ alkyl), —OC(=O)($C_{1-6}$ alkyl), —$OCO_2(C_{1-6}$ alkyl), —C(=O)$NH_2$, —C(=O)N($C_{1-6}$ alkyl$)_2$, —OC(=O)NH($C_{1-6}$ alkyl), —NHC(=O)($C_{1-6}$ alkyl), —N($C_{1-6}$ alkyl)C(=O)($C_{1-6}$ alkyl), —$NHCO_2(C_{1-6}$ alkyl), —NHC(=O)N($C_{1-6}$ alkyl$)_2$, —NHC(=O)NH($C_{1-6}$ alkyl), —NHC(=O)$NH_2$, —C(=NH)O($C_{1-6}$ alkyl), —OC(=NH)($C_{1-6}$ alkyl), —OC(=NH)$OC_{1-6}$ alkyl, —C(=NH)N($C_{1-6}$ alkyl$)_2$, —C(=NH)NH($C_{1-6}$ alkyl), —C(=NH)$NH_2$, —OC(=NH)N($C_{1-6}$ alkyl$)_2$, —OC(NH)NH($C_{1-6}$ alkyl), —OC(NH)$NH_2$, —NHC(NH)N($C_{1-6}$ alkyl$)_2$, —NHC(=NH)$NH_2$, —$NHSO_2(C_{1-6}$ alkyl), —$SO_2N(C_{1-6}$ alkyl$)_2$, —$SO_2NH(C_{1-6}$ alkyl), —$SO_2NH_2$, —$SO_2C_{1-6}$ alkyl, —$SO_2OC_{1-6}$ alkyl, —$OSO_2C_{1-6}$ alkyl, —$SOC_{1-6}$ alkyl, —Si($C_{1-6}$ alkyl$)_3$, —OSi($C_{1-6}$ alkyl$)_3$, —C(=S)N($C_{1-6}$ alkyl$)_2$, C(=S)NH($C_{1-6}$ alkyl), C(=S)$NH_2$, —C(=O)S($C_{1-6}$ alkyl), —C(=S)$SC_{1-6}$ alkyl, —SC(=S)$SC_{1-6}$ alkyl, —$P(=O)_2(C_{1-6}$ alkyl), —P(=O)($C_{1-6}$ alkyl$)_2$, —OP(=O)($C_{1-6}$ alkyl$)_2$, —OP(=O)($OC_{1-6}$ alkyl$)_2$, $C_{1-6}$ alkyl, $C_{1-6}$ haloalkyl, $C_2$-$C_6$ alkenyl, $C_2$-$C_6$ alkynyl, $C_3$-$C_7$ carbocyclyl, $C_6$-$C_{10}$ aryl, 3- to 7-membered heterocyclyl, or 5- to 10-membered heteroaryl; or two geminal $R^{gg}$ substituents can be bound to form =O or =S, wherein X is a counter ion.

Exemplary substituents on the nitrogen atom include but are not limited to, hydrogen, —OH, —$OR^{aa}$, —$N(R^{cc})_2$, —CN, —C(=O)$R^{aa}$, —C(=O)$N(R^{cc})_2$, —$CO_2R^{aa}$, —$SO_2R^{aa}$, —C(=$NR^{bb}$)$R^{aa}$, —C(=$NR^{cc}$)$OR^{aa}$, —C(=$NR^{cc}$)$N(R^{cc})_2$, —$SO_2N(R^{cc})_2$, —$SO_2R^{cc}$, —$SO_2OR^{cc}$, —$SOR^{aa}$, —C(=S)$N(R^{cc})_2$, —C(=O)$SR^{cc}$, —C(=S)$SR^{cc}$, —P(=O)$_2R^{aa}$, —P(=O)$(R^{aa})_2$, —P(=O)$_2N(R^{cc})_2$, —P(=O)$(NR^{cc})_2$, alkyl, haloalkyl, alkenyl, alkynyl, carbocyclyl, heterocyclyl, aryl and heteroaryl, or two $R^{cc}$ groups connected to the nitrogen atom are bound to form heterocyclyl or heteroaryl ring, wherein each of alkyl, alkenyl, alkynyl, carbocyclyl, heterocyclyl, aryl and heteroaryl is independently substituted with 0, 1, 2, 3, 4 or 5 $R^{dd}$ groups, and wherein $R^{aa}$, $R^{bb}$, $R^{cc}$ and $R^{dd}$ are as defined above.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in J. Pharmaceutical Sciences (1977) 66:1-19. Pharmaceutically acceptable salts of the compounds disclosed herein include those derived from suitable inorganic and organic acids and bases. Examples of pharmaceutically acceptable, nontoxic acid addition salts are salts formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid. Salts formed using conventional methods in the art such as ion exchange are also included. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In some embodiments, the subject is a human. In some embodiments, the subject is a non-human animal. The terms "human," "patient," and "subject" are used interchangeably herein.

"Disease", "disorder" and "condition" are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

"Combination", "combined", and related terms refer to the simultaneous or sequential administration of the therapeutic agents of the present disclosure. For example, the compound disclosed herein may be administered with another therapeutic agent simultaneously or sequentially in separate unit dosage forms, or together in a single unit dosage form.

DETAILED DESCRIPTION OF THE INVENTION

Compounds

Figure 1:
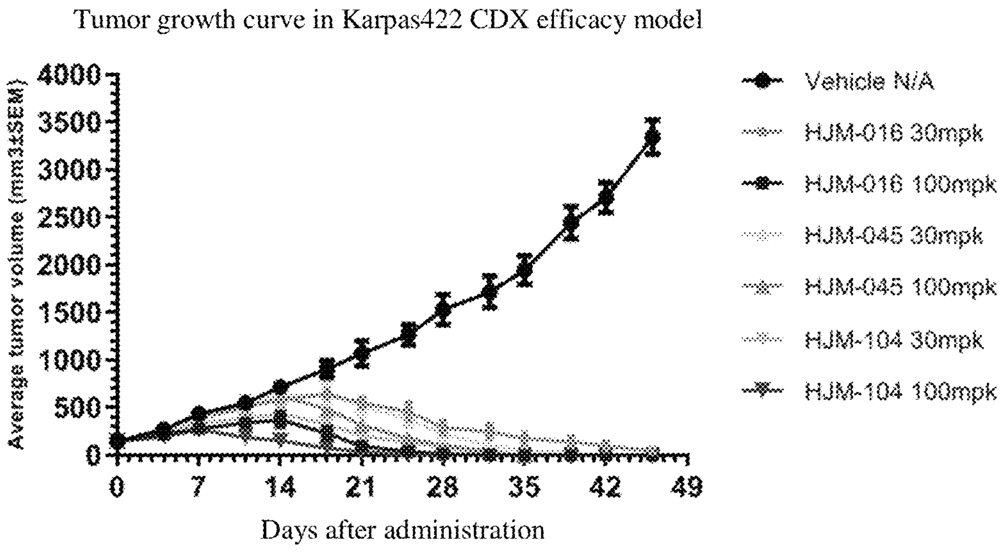
FIG. 1 shows the changes in tumor volume in the Karpas422 CDX efficacy study.

As used herein, "compounds of the present disclosure" refers to compounds of formula (X) or formulas (I) to (VII) below (including subsets of each formula), or a pharmaceutically acceptable salt, hydrate, or solvate thereof.

In one embodiment, the present disclosure relates to a compound of formula (X), or a tautomer, stereoisomer, prodrug, crystal form, pharmaceutically acceptable salt, hydrate or solvate thereof:

(X)

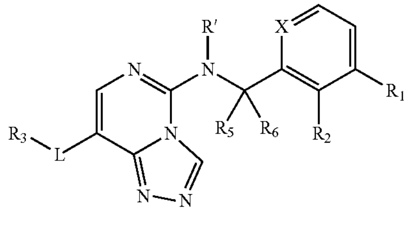

wherein

X is N or $C(R_x)$;

wherein $R_x$ is selected from H, halogen, $C_{1-6}$ alkyl, $C_{1-6}$ haloalkyl or $C_{1-6}$ alkoxy;

$R_1$ is selected from H, halogen, $C_{1-6}$ alkyl, $C_{1-6}$ haloalkyl or $C_{1-6}$ alkoxy;

$R_2$ is selected from H, halogen, $C_{1-6}$ alkyl, $C_{1-6}$ haloalkyl or $C_{1-6}$ alkoxy;

or $R_1$ and $R_2$ together form —$(CH_2)_pY$—, —$Y(CH_2)_p$— or —$Y(CH_2)_pZ$— group;

wherein p is 1, 2, 3, 4 or 5;

Y is selected from O, S, NH or chemical bond;

Z is selected from O, S, NH or chemical bond;

R' is selected from H, $C_{1-6}$ alkyl or $C_{1-6}$ haloalkyl;

L is selected from —C(O)—N(R)—, —C(O)—O—, —N($R_3$')—C(O)—, —O—C(O)—, —$S(O)_q$—N(R)—, —$S(O)_q$—O—, —O—, —S—, —N(R")—, —$C_{1-4}$ alkylene- or —$C_{2-4}$ alkenylene-;

wherein R is selected from H, $C_{1-6}$ alkyl or $C_{1-6}$ haloalkyl;

$R_3$' is selected from H, $(CH_2)_m$—$C_{1-6}$ alkyl, $(CH_2)_m$—$C_{1-6}$ haloalkyl or $(CH_2)_n$—$C_{3-7}$ cycloalkyl;

R" is selected from H, $C_{1-6}$ alkyl or $C_{1-6}$ haloalkyl;

q is 0, 1 or 2;

$R_3$ is selected from $(CH_2)_m$—$C_{1-6}$ alkyl, $(CH_2)_m$—$C_{1-6}$ haloalkyl, $(CH_2)_n$—$C_{1-6}$ alkoxy, $(CH_2)_n$—$C_{1-6}$ haloalkoxy, $(CH_2)_n$—$NR_aR_b$, $(CH_2)_n$—$OR_a$, $(CH_2)_n$—$C_{3-7}$ cycloalkyl, $(CH_2)_n$-3- to 10-membered heterocyclyl, $(CH_2)_n$—$C_{6-10}$ aryl or $(CH_2)_n$-5- to 10-membered heteroaryl; or $R_3$ is connected to R to form —$C_{1-6}$ alkylene-;

or, $R_3$, $R_3$' and the N atom to which they are attached together form a 4- to 7-membered heterocyclyl group;

wherein m is 0, 1, 2, 3, 4 or 5;

n is 0, 1, 2, 3, 4 or 5;

$R_a$ is selected from H, $C_{1-6}$ alkyl or $C_{1-6}$ haloalkyl;

$R_b$ is selected from H, $C_{1-6}$ alkyl or $C_{1-6}$ haloalkyl;

$R_5$ and $R_6$ are independently selected from H, D, $C_{1-6}$ alkyl or $C_{1-6}$ haloalkyl;

wherein $R_3$ is optionally substituted by one or more substituent groups selected from H, D, halogen, CN, OH, =O, $NR_cR_d$, $C_{1-6}$ alkyl, $C_{1-6}$ haloalkyl, $C_{1-6}$ alkoxy, $C_{3-7}$ cycloalkyl, 4- to 7-membered heterocyclyl, $C_{6-10}$ aryl, 5- to 10-membered heteroaryl, $(CH_2)_m$—$C_{1-6}$ alkyl, $(CH_2)_m$—$C_{1-6}$ haloalkyl, $(CH_2)_n$—$C_{1-6}$ alkoxy, $(CH_2)_n$—$C_{1-6}$ haloalkoxy, —O—$C_{3-7}$ cycloalkyl, —O-4- to 7-membered heterocyclyl, —O—$C_{6-10}$ aryl, —O-5- to 10-membered heteroaryl, —C(O)—$C_{1-6}$ alkyl, —C(O)—$C_{1-6}$ haloalkyl, —C(O)—$C_{3-7}$ cycloalkyl, —C(O)-4- to 7-membered heterocyclyl, —C(O)—$C_{6-10}$ aryl, —C(O)-5- to 10-membered heteroaryl, —$S(O)_q$—$C_{1-6}$ alkyl, —$S(O)_q$—$C_{1-6}$ haloalkyl, —$S(O)_q$—$C_{1-6}$ alkoxy, —$S(O)_q$—$C_{3-7}$ cycloalkyl, —$S(O)_q$-4- to 7-membered heterocyclyl, —$S(O)_q$—$C_{6-10}$ aryl or —$S(O)_q$-5- to 10-membered heteroaryl;

wherein $R_c$ is selected from H, $C_{1-6}$ alkyl, $C_{1-6}$ haloalkyl, —C(O)—$C_{3-7}$ cycloalkyl, —C(O)-4- to 7-membered heterocyclyl, —C(O)—$C_{6-10}$ aryl or —C(O)-5- to 10-membered heteroaryl;

$R_d$ is selected from H, $C_{1-6}$ alkyl, $C_{1-6}$ haloalkyl, —C(O)—$C_{3-7}$ cycloalkyl, —C(O)-4- to 7-membered heterocyclyl, —C(O)—$C_{6-10}$ aryl or —C(O)-5- to 10-membered heteroaryl;

wherein the alkyl, haloalkyl, alkoxy, haloalkoxy, cycloalkyl, heterocyclyl, aryl, heteroaryl, alkylene and alkenylene are optionally substituted with substituent groups selected from H, D, CN, OH, =O, halogen, $C_{1-6}$ alkyl, $C_{1-6}$ haloalkyl, $C_{1-6}$ alkoxy, $C_{3-7}$ cycloalkyl, 4- to 7-membered heterocyclyl, $C_{6-10}$ aryl, 5- to 10-membered heteroaryl, —O—$C_{3-7}$ cycloalkyl, —O-4- to 7-membered heterocyclyl, —O—$C_{6-10}$ aryl, —O-5- to 10-membered heteroaryl, —C(O)—$C_{1-6}$ alkyl, —C(O)—$C_{1-6}$ haloalkyl, —C(O)—$C_{3-7}$ cycloalkyl, —C(O)-4- to 7-membered heterocyclyl, —C(O)—$C_{6-10}$ aryl or —C(O)-5- to 10-membered heteroaryl, or substituted with one or more D, up to complete deuteration.

X

In one embodiment, X is N; in another embodiment, X is C($R_x$).

In more specific embodiments, $R_x$ is selected from H, halogen, $C_{1-6}$ alkyl, $C_{1-6}$ haloalkyl or $C_{1-6}$ alkoxy; in another specific embodiment, $R_x$ is H; in another specific embodiment, $R_x$ is halogen, alternatively F; in another specific embodiment, $R_x$ is $C_{1-6}$ alkyl; in another specific embodiment, $R_x$ is $C_{1-6}$ haloalkyl; in another specific embodiment, $R_x$ is $C_{1-6}$ alkoxy.

$R_1$ and $R_2$

In one embodiment, $R_1$ is selected from H, halogen, $C_{1-6}$ alkyl, $C_{1-6}$ haloalkyl or $C_{1-6}$ alkoxy; in another embodiment, $R_1$ is H; in another embodiment, $R_1$ is halogen; in another embodiment, $R_1$ is $C_{1-6}$ alkyl; in another embodiment, $R_1$ is $C_{1-6}$ haloalkyl; in another embodiment, $R_1$ is $C_{1-6}$ alkoxy.

In one embodiment, $R_2$ is selected from H, halogen, $C_{1-6}$ alkyl, $C_{1-6}$ haloalkyl or $C_{1-6}$ alkoxy; in another embodiment, $R_2$ is H; in another embodiment, $R_2$ is halogen; in another embodiment, $R_2$ is $C_{1-6}$ alkyl; in another embodiment, $R_2$ is $C_{1-6}$ haloalkyl; in another embodiment, $R_2$ is $C_{1-6}$ alkoxy.

In one embodiment, $R_1$ and $R_2$ together form —$(CH_2)_p$Y—, —Y$(CH_2)_p$— or —Y$(CH_2)_p$Z— group; in another embodiment, $R_1$ and $R_2$ together form —$(CH_2)_p$Y—; in another embodiment, $R_1$ and $R_2$ together form —Y$(CH_2)_p$—; in another embodiment, $R_1$ and $R_2$ together form —Y$(CH_2)_p$Z—.

In more specific embodiments, p is 1, 2, 3, 4 or 5; in another specific embodiment, p is 1; in another specific embodiment, p is 2; in another specific embodiment, p is 3; in another specific embodiment, p is 4; in another specific embodiment, p is 5.

In more specific embodiments, Y is selected from O, S, NH or chemical bond; in another specific embodiment, Y is O; in another specific embodiment, Y is S; in another specific embodiment, Y is NH; in another specific embodiment, Y is a chemical bond.

In more specific embodiments, Z is selected from O, S, NH or chemical bond; in another specific embodiment, Z is O; in another specific embodiment, Z is S; in another specific embodiment, Z is NH; in another specific embodiment, Z is a chemical bond.

R'

In one embodiment, R' is selected from H, $C_{1-6}$ alkyl or $C_{1-6}$ haloalkyl; in another embodiment, R' is H; in another embodiment, R' is $C_{1-6}$ alkyl; in another embodiment, R' is $C_{1-6}$ haloalkyl; in another specific embodiment, R' is $C_{1-6}$ alkyl or $C_{1-6}$ haloalkyl, which is optionally substituted with 1, 2, 3, 4, 5, 6, 7, 8 or 9 D, up to complete deuteration.

L

In one embodiment, L is selected from —C(O)—N(R)—, —C(O)—O—, —N($R_3$')—C(O)—, —O—C(O)—, —$S(O)_q$—N(R)—, —$S(O)_q$—O—, —O—, —S—, —N(R")—, —$C_{1-4}$ alkylene- or —$C_{2-4}$ alkenylene-; in another embodiment, L is —C(O)—N(R)—; in another embodiment, L is —C(O)—O—; in another embodiment, L is —N($R_3$')—C(O)—; in another embodiment, L is —O—C(O)—; in another embodiment, L is —$S(O)_q$—N(R)—; in another embodiment, L is —$S(O)_q$—O—; in another embodiment, L is —O—; in another embodiment, L is —S—; in another embodiment, L is —N(R")—; in another embodiment, L is —$C_{1-4}$ alkylene-; in another embodiment, L is —$C_{2-4}$ alkenylene-.

In a more specific embodiment, L is —C(O)—N(R)—, —C(O)—O—, —$S(O)_q$—N(R)— or —$S(O)_q$—O—.

In a more specific embodiment, L is —C(O)—N(R)— or —C(O)—O—.

In more specific embodiments, R is selected from H, $C_{1-6}$ alkyl or $C_{1-6}$ haloalkyl; in another specific embodiment, R is H; in another specific embodiment, R is $C_{1-6}$ alkyl; in another specific embodiment, R is $C_{1-6}$ haloalkyl; in another specific embodiment, R is $C_{1-6}$ alkyl or $C_{1-6}$ haloalkyl, which is optionally substituted with 1, 2, 3, 4, 5, 6, 7, 8 or 9 D, up to complete deuteration.

In more specific embodiments, $R_3$' is selected from H, $(CH_2)_m$—$C_{1-6}$ alkyl, $(CH_2)_m$—$C_{1-6}$ haloalkyl or $(CH_2)_n$—$C_{3-7}$ cycloalkyl; in another specific embodiment, $R_3$' is H; in another specific embodiment, $R_3$' is $(CH_2)_m$—$C_{1-6}$ alkyl; in another specific embodiment, $R_3$' is $(CH_2)_m$—$C_{1-6}$ haloalkyl; in another specific embodiment, $R_3$' is $(CH_2)_n$—$C_{3-7}$ cycloalkyl.

In more specific embodiments, R" is selected from H, $C_{1-6}$ alkyl or $C_{1-6}$ haloalkyl; in another specific embodiment, R" is H; in another specific embodiment, R" is $C_{1-6}$ alkyl; in another specific embodiment, R" is $C_{1-6}$ haloalkyl.

In more specific embodiments, q is 0; in another specific embodiment, q is 1; in another specific embodiment, q is 2.

$R_3$

In one embodiment, $R_3$ is selected from $(CH_2)_m$—$C_{1-6}$ alkyl, $(CH_2)_m$—$C_{1-6}$ haloalkyl, $(CH_2)_n$—$C_{1-6}$ alkoxy, $(CH_2)_n$—$C_{1-6}$ haloalkoxy, $(CH_2)_n$—$NR_aR_b$, $(CH_2)_nOR_a$, $(CH_2)_n$—$C_{3-7}$ cycloalkyl, $(CH_2)_n$-3- to 10-membered heterocyclyl, $(CH_2)_n$—$C_{6-10}$ aryl or $(CH_2)_n$-5- to 10-membered heteroaryl; or $R_3$ is connected to R to form —$C_{1-6}$ alkylene-; in another embodiment, $R_3$ is $(CH_2)_m$—$C_{1-6}$ alkyl; in another embodiment, $R_3$ is $(CH_2)_m$—$C_{1-6}$ haloalkyl; in another embodiment, $R_3$ is $(CH_2)_n$—$C_{1-6}$ alkoxy; in another embodiment, $R_3$ is $(CH_2)_n$—$C_{1-6}$ haloalkoxy; in another embodiment, $R_3$ is $(CH_2)_n$—$NR_aR_b$; in another embodiment, $R_3$ is $(CH_2)_n$—$OR_a$; in another embodiment, $R_3$ is $(CH_2)_n$—$C_{3-7}$ cycloalkyl; in another embodiment, $R_3$ is $(CH_2)_n$-3- to 10-membered heterocyclyl; in another embodiment, $R_3$ is $(CH_2)_n$—$C_{6-10}$ aryl; in another embodiment, $R_3$ is $(CH_2)_n$-5- to 10-membered heteroaryl; in another embodiment, $R_3$ is connected to R to form —$C_{1-6}$ alkylene-.

In a more specific embodiment, $R_3$ is selected from $(CR_7R_8)_m$—$C_{1-6}$ alkyl, $(CR_7R_8)_m$—$C_{1-6}$ haloalkyl, $(CR_7R_8)_n$—$C_{1-6}$ alkoxy, $(CR_7R_8)_n$—$C_{1-6}$ haloalkoxy, $(CR_7R_8)_n$—$NR_aR_b$, $(CR_7R_8)_n$—$OR_a$, $(CR_7R_8)_n$—$C_{3-7}$ cycloalkyl, $(CR_7R_8)_n$-3- to 10-membered heterocyclyl, $(CR_7R_8)_n$—$C_{6-10}$ aryl or $(CR_7R_8)_n$-5- to 10-membered heteroaryl; or $R_3$ is connected to R to form —$C_{1-6}$ alkylene-; in another more specific embodiment, $R_3$ is $(CR_7R_8)_m$—$C_{1-6}$ alkyl; in another more specific embodiment, $R_3$ is $(CR_7R_8)_m$—$C_{1-6}$ haloalkyl; in another more specific embodiment, $R_3$ is $(CR_7R_8)_n$—$C_{1-6}$ alkoxy; in another more specific embodiment, $R_3$ is $(CR_7R_8)_n$—$C_{1-6}$ haloalkoxy; in another more specific embodiment, $R_3$ is $(CR_7R_8)_n$—$NR_aR_b$; in another more specific embodiment, $R_3$ is $(CR_7R_8)_n$—$OR_a$; in another more specific embodiment, $R_3$ is $(CR_7R_8)_n$—$C_{3-7}$ cycloalkyl; in another more specific embodiment, $R_3$ is $(CR_7R_8)_n$-3- to 10-membered heterocyclyl; in another more specific embodiment, $R_3$ is $(CR_7R_8)_n$—$C_{6-10}$ aryl; in another more specific embodiment, $R_3$ is $(CR_7R_8)_n$-5- to 10-membered heteroaryl.

In a more specific embodiment, $R_3$ is selected from $(CR_7R_8)_m$—$C_{1-6}$ alkyl, $(CR_7R_8)_m$—$C_{1-6}$ haloalkyl, $(CR_7R_8)_n$—$C_{1-6}$ alkoxy, $(CR_7R_8)_n$—$C_{1-6}$ haloalkoxy, $(CR_7R_8)_n$—$NR_aR_b$, $(CR_7R_8)_n$—$C_{3-7}$ cycloalkyl, $(CR_7R_8)_n$-4- to 7-membered heterocyclyl, $(CR_7R_8)_n$—$C_{6-10}$ aryl or $(CR_7R_8)_n$-5- to 10-membered heteroaryl; or $R_3$ is connected to R to form —$C_{1-6}$ alkylene-.

In a more specific embodiment, $R_3$ is selected from $(CR_7R_8)_m$—$C_{1-6}$ alkyl, $(CR_7R_8)_m$—$C_{1-6}$ haloalkyl, $(CR_7R_8)_n$—$C_{1-6}$ alkoxy, $(CR_7R_8)_n$—$NR_aR_b$, $(CR_7R_8)_n$—$C_{3-7}$ cycloalkyl, $(CR_7R_8)_n$—$C_{6-10}$ aryl or $(CR_7R_8)_n$-5- to 10-membered heteroaryl; or $R_3$ is connected to R to form —$C_{1-6}$ alkylene-.

In a more specific embodiment, $R_3$ is selected from $(CR_7R_8)_m$—$C_{1-6}$ alkyl, $(CR_7R_8)_m$—$C_{1-6}$ haloalkyl, $(CR_7R_8)_n$—$C_{1-6}$ alkoxy, $(CR_7R_8)_n$—$NR_aR_b$ or $(CR_7R_8)_n$—$C_{3-4}$ cycloalkyl; or $R_3$ is connected to R to form a $C_{1-6}$ alkylene.

In a more specific embodiment, $R_3$ is selected from $(CR_7R_8)_m$—$C_{1-6}$ haloalkyl or $(CR_7R_8)_n$—$C_{3-4}$ cycloalkyl.

In a more specific embodiment, $R_3$ is selected from $(CR_7R_8)_m$—$C_{1-6}$ alkyl, $(CR_7R_8)_m$—$C_{1-6}$ haloalkyl, $(CR_7R_8)_n$—$C_{3-7}$ cycloalkyl, $(CR_7R_8)_n$-4- to 7-membered heterocyclyl, $(CR_7R_8)_n$—$C_{6-10}$ aryl or $(CR_7R_8)_n$-5- to 10-membered heteroaryl.

In a more specific embodiment, $R_3$ is selected from $(CR_7R_8)_m$—$C_{1-6}$ alkyl, $(CR_7R_8)_m$—$C_{1-6}$ haloalkyl, $(CR_7R_8)_n$—$C_{3-7}$ cycloalkyl or $(CR_7R_8)_n$-4- to 7-membered heterocyclyl, only containing O as heteroatom.

In a more specific embodiment, $R_3$ is selected from $(CR_7R_8)_m$—$C_{1-6}$ alkyl, $(CR_7R_8)_m$—$C_{1-6}$ haloalkyl or $(CR_7R_8)_n$-4- to 7-membered heterocyclyl, only containing O as heteroatom.

In another embodiment, $R_3$, $R_3$' and the N atom to which they are attached together form a 4- to 7-membered heterocyclyl group.

m and n

In one embodiment, m is 0, 1, 2, 3, 4 or 5; in another embodiment, m is 0; in another embodiment, m is 1; in another embodiment, m is 2; in another embodiment, m is 3; in another embodiment, m is 4; in another embodiment, m is 5.

In one embodiment, n is 0, 1, 2, 3, 4 or 5; in another embodiment, n is 0; in another embodiment, n is 1; in another embodiment, n is 2; in another embodiment, n is 3; in another embodiment, n is 4; in another embodiment, n is 5.

$R_a$, $R_b$, $R_5$, $R_6$, $R_7$ and $R_8$

In one embodiment, $R_a$ is H; in another embodiment, $R_a$ is $C_{1-6}$ alkyl; in another embodiment, $R_a$ is $C_{1-6}$ haloalkyl.

In one embodiment, $R_b$ is H; in another embodiment, $R_b$ is $C_{1-6}$ alkyl; in another embodiment, $R_b$ is $C_{1-6}$ haloalkyl.

In one embodiment, $R_5$ is H; in another embodiment, $R_5$ is D; in another embodiment, $R_5$ is $C_{1-6}$ alkyl; in another embodiment, $R_5$ is $C_{1-6}$ haloalkyl; in another specific embodiment, $R_5$ is $C_{1-6}$ alkyl or $C_{1-6}$ haloalkyl, which is optionally substituted with 1, 2, 3, 4, 5, 6, 7, 8 or 9 D, up to complete deuteration.

In one embodiment, $R_6$ is H; in another embodiment, $R_6$ is D; in another embodiment, $R_6$ is $C_{1-6}$ alkyl; in another embodiment, $R_6$ is $C_{1-6}$ haloalkyl; in another specific embodiment, $R_6$ is $C_{1-6}$ alkyl or $C_{1-6}$ haloalkyl, which is optionally substituted with 1, 2, 3, 4, 5, 6, 7, 8 or 9 D, up to complete deuteration.

In one embodiment, $R_7$ is H; in another embodiment, $R_7$ is D; in another embodiment, $R_7$ is $C_{1-6}$ alkyl; in another embodiment, $R_7$ is $C_{1-6}$ haloalkyl; in another specific embodiment, $R_7$ is $C_{1-6}$ alkyl or $C_{1-6}$ haloalkyl, which is optionally substituted with 1, 2, 3, 4, 5, 6, 7, 8 or 9 D, up to complete deuteration.

In one embodiment, $R_8$ is H; in another embodiment, $R_8$ is D; in another embodiment, $R_8$ is $C_{1-6}$ alkyl; in another embodiment, $R_8$ is $C_{1-6}$ haloalkyl; in another specific embodiment, $R_8$ is $C_{1-6}$ alkyl or $C_{1-6}$ haloalkyl, which is optionally substituted with 1, 2, 3, 4, 5, 6, 7, 8 or 9 D, up to complete deuteration.

In another specific embodiment, $R_7$ and $R_8$ on the same carbon atom are combined to form =O.

Substituent Groups of $R_3$

In one embodiment, $R_3$ is optionally substituted with one, two, three or more substituent groups selected from H, D, halogen, CN, OH, =O, $NR_cR_d$, $C_{1-6}$ alkyl, $C_{1-6}$ haloalkyl, $C_{1-6}$ alkoxy, $C_{3-7}$ cycloalkyl, 4- to 7-membered heterocyclyl, $C_{6-10}$ aryl, 5- to 10-membered heteroaryl, $(CH_2)_m$—$C_{1-6}$ alkyl, $(CH_2)_m C_{1-6}$ haloalkyl, $(CH_2)_n$—$C_{1-6}$ alkoxy, $(CH_2)_n$—$C_{1-6}$ haloalkoxy, —O—$C_{3-7}$ cycloalkyl, —O-4- to 7-membered heterocyclyl, —O—$C_{6-10}$ aryl, —O-5- to 10-membered heteroaryl, —C(O)—$C_{1-6}$ alkyl, —C(O)—$C_{1-6}$ haloalkyl, —C(O)—$C_{3-7}$ cycloalkyl, —C(O)-4- to 7-membered heterocyclyl, —C(O)—$C_{6-10}$ aryl, —C(O)-5- to 10-membered heteroaryl, —$S(O)_q$—$C_{1-6}$ alkyl, —$S(O)_q$—$C_{1-6}$ haloalkyl, —$S(O)_q$—$C_{1-6}$ alkoxy, —$S(O)_q$—$C_{3-7}$ cycloalkyl, —$S(O)_q$-4- to 7-membered heterocyclyl, —$S(O)_q$—$C_6$-10 aryl or —$S(O)_q$-5- to 10-membered heteroaryl.

In one embodiment, $R_3$ is optionally substituted with one, two, three or more substituent groups selected from H, D, halogen, CN, OH, $C_{1-6}$ alkyl, $C_{1-6}$ haloalkyl, $C_{3-7}$ cycloalkyl, 4- to 7-membered heterocyclyl, $C_{6-10}$ aryl, 5- to 10-membered heteroaryl, $(CR_7R_8)_n$—$C_{1-6}$ alkoxy or —$S(O)_q$—$C_{1-6}$ alkyl.

In one embodiment, $R_3$ is optionally substituted with a group selected from H, D, halogen, $C_{1-6}$ alkyl, $C_{1-6}$ haloalkyl, $C_{1-6}$ alkoxy or $C_{3-7}$ cycloalkyl.

In one embodiment, $R_3$ is optionally substituted by one or more substituent groups selected from H, D, halogen, CN, OH, =O, $NR_cR_d$, $C_{1-6}$ alkyl, $C_{1-6}$ haloalkyl, $C_{1-6}$ alkoxy, $C_{3-7}$ cycloalkyl, 4- to 7-membered heterocyclyl, $C_{6-10}$ aryl, 5- to 10-membered heteroaryl, —O—$C_{3-7}$ cycloalkyl, —O-4- to 7-membered heterocyclyl, —O—$C_{6-10}$ aryl, —O-5- to 10-membered heteroaryl, —C(O)—$C_{1-6}$ alkyl, —C(O)—$C_{1-6}$ haloalkyl, —C(O)—$C_{3-7}$ cycloalkyl, —C(O)-4- to 7-membered heterocyclyl, —C(O)—$C_{6-10}$ aryl, —C(O)-5- to 10-membered heteroaryl.

In one embodiment, $R_3$ is optionally substituted by one or more substituent groups selected from H, D, halogen, CN, OH, =O, $NR_cR_d$, $C_{1-6}$ alkyl, $C_{1-6}$ haloalkyl, $C_{1-6}$ alkoxy, $C_{3-7}$ cycloalkyl, —C(O)—$C_{1-6}$ alkyl, —C(O)—$C_{3-7}$ cycloalkyl or —O—$C_{6-10}$ aryl.

In one embodiment, $R_3$ is optionally substituted with a group selected from H, D, $C_{1-6}$ alkyl, $C_{1-6}$ haloalkyl or $C_{1-6}$ alkoxy.

Any technical solution in any of the above specific embodiments or any combination thereof can be combined with any technical solution in other specific embodiments or any combination thereof. For example, any technical solution of X or any combination thereof can be combined with any technical solution of $R_1$, $R_2$, R', L and $R_3$, etc. or any combination thereof. The present disclosure is intended to include the combination of all these technical solutions, which is not listed one by one due to space limitation.

In more specific embodiments, the present disclosure relates to a compound of formula (II), or a tautomer, stereoisomer, prodrug, crystal form, pharmaceutically acceptable salt, hydrate or solvate thereof:

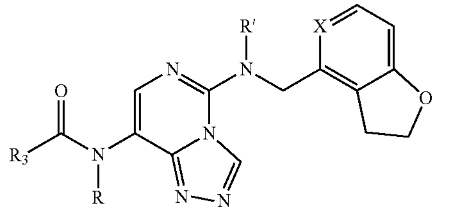

(II)

wherein

X is N or $C(R_x)$; alternatively, X is $C(R_x)$;

wherein $R_x$ is selected from H, halogen, $C_{1-6}$ alkyl, $C_{1-6}$ haloalkyl or $C_{1-6}$ alkoxy; alternatively, $R_x$ is selected from H or halogen;

R' is selected from H, $C_{1-6}$ alkyl or $C_{1-6}$ haloalkyl;

R is selected from H, $C_{1-6}$ alkyl or $C_{1-6}$ haloalkyl;

$R_3$ is selected from $(CH_2)_m$—$C_{1-6}$ alkyl, $(CH_2)_m$—$C_{1-6}$ haloalkyl, $(CH_2)_n$—$C_{1-6}$ alkoxy, $(CH_2)_n$—$C_{1-6}$ haloalkoxy, $(CH_2)_n$—$C_{3-7}$ cycloalkyl, $(CH_2)_n$-4- to 7-membered heterocyclyl, $(CH_2)_n$—$C_{6-10}$ aryl or $(CH_2)_n$-5- to 10-membered heteroaryl;

wherein m is 0, 1, 2, 3, 4 or 5;

n is 0, 1, 2, 3, 4 or 5.

In another more specific embodiment, the present disclosure relates to a compound of formula (II), or a tautomer, stereoisomer, prodrug, crystal form, pharmaceutically acceptable salt, hydrate or solvate thereof: wherein X is N or $C(R_x)$; alternatively, X is $C(R_x)$;

wherein $R_x$ is selected from H, halogen, $C_{1-6}$ alkyl or $C_{1-6}$ haloalkyl; alternatively, $R_x$ is selected from H or halogen;

R' is selected from H, $C_{1-6}$ alkyl or $C_{1-6}$ haloalkyl;

R is selected from H, $C_{1-6}$ alkyl or $C_{1-6}$ haloalkyl;

$R_3$ is selected from $(CH_2)_m$—$C_{1-6}$ alkyl, $(CH_2)_m$—$C_{1-6}$ haloalkyl, $(CH_2)_n$—$C_{1-6}$ alkoxy, $(CH_2)_n$—$C_{1-6}$ haloalkoxy, $(CH_2)_n$—$C_{3-4}$ cycloalkyl or $(CH_2)_n$—$C_{6-10}$ aryl;

wherein m is 0, 1, 2, 3, 4 or 5;

n is 0, 1, 2, 3, 4 or 5.

In another more specific embodiment, the present disclosure relates to a compound of formula (II), or a tautomer, stereoisomer, prodrug, crystal form, pharmaceutically acceptable salt, hydrate or solvate thereof: wherein X is N or $C(R_x)$; alternatively, X is $C(R_x)$;

wherein $R_x$ is selected from H, halogen, $C_{1-6}$ alkyl or $C_{1-6}$ haloalkyl; alternatively, $R_x$ is selected from H or halogen;

R' is selected from H, $C_{1-6}$ alkyl or $C_{1-6}$ haloalkyl;

R is selected from H, $C_{1-6}$ alkyl or $C_{1-6}$ haloalkyl;

$R_3$ is selected from $(CH_2)_m$—$C_{1-6}$ alkyl, $(CH_2)_m$—$C_{1-6}$ haloalkyl or $(CH_2)_n$—$C_{3-4}$ cycloalkyl; alternatively, $R_3$ is selected from $(CH_2)_m$—$C_{1-6}$ haloalkyl or $(CH_2)_n$—$C_{3-4}$ cycloalkyl;

wherein m is 0, 1, 2, 3, 4 or 5;

n is 0, 1, 2, 3, 4 or 5.

In another more specific embodiment, the present disclosure relates to a compound of formula (II), or a tautomer, stereoisomer, prodrug, crystal form, pharmaceutically acceptable salt, hydrate or solvate thereof:

wherein

X is $C(R_x)$;

wherein $R_x$ is selected from H or halogen;

R' is selected from H, $C_{1-6}$ alkyl or $C_{1-6}$ haloalkyl;

R is selected from H, $C_{1-6}$ alkyl or $C_{1-6}$ haloalkyl;

$R_3$ is selected from $(CH_2)_m$—$C_{1-6}$ haloalkyl or $(CH_2)_n$—$C_{3-4}$ cycloalkyl;

wherein m is 0, 1, 2 or 3;

n is 0, 1, 2 or 3.

In another more specific embodiment, the present disclosure relates to a compound of formula (III), or a tautomer, stereoisomer, prodrug, crystal form, pharmaceutically acceptable salt, hydrate or solvate thereof:

(III)

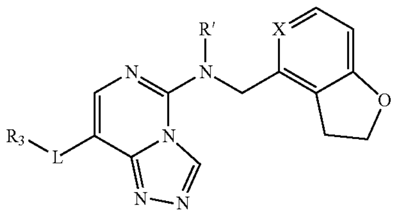

wherein

X is N or $C(R_x)$; alternatively, X is $C(R_x)$;

wherein $R_x$ is selected from H, halogen, $C_{1-6}$ alkyl, $C_{1-6}$ haloalkyl or $C_{1-6}$ alkoxy; alternatively, $R_x$ is selected from H or halogen;

R' is selected from H, $C_{1-6}$ alkyl or $C_{1-6}$ haloalkyl;

L is selected from —O—, —S—, —N(R")—, —$C_{1-4}$ alkylene- or —$C_{2-4}$ alkenylene-; alternatively, L is —O—;

wherein R" is selected from H, $C_{1-6}$ alkyl or $C_{1-6}$ haloalkyl;

$R_3$ is selected from $(CH_2)_m$—$C_{1-6}$ alkyl, $(CH_2)_m$—$C_{1-6}$ haloalkyl, $(CH_2)_n$—$C_{1-6}$ alkoxy, $(CH_2)_n$—$C_{1-6}$ haloalkoxy, $(CH_2)_n$—$C_{3-7}$ cycloalkyl, $(CH_2)_n$-4- to 7-membered heterocyclyl, $(CH_2)_n$—$C_{6-10}$ aryl or $(CH_2)_n$-5- to 10-membered heteroaryl; alternatively, $R_3$ is selected from $(CH_2)_m$—$C_{1-6}$ alkyl, $(CH_2)_m$—$C_{1-6}$ haloalkyl, $(CH_2)_n$—$C_{3-7}$ cycloalkyl, $(CH_2)_n$-4- to 7-membered heterocyclyl, $(CH_2)_n$—$C_{6-10}$ aryl or $(CH_2)_n$-5- to 10-membered heteroaryl;

wherein m is 0, 1, 2, 3, 4 or 5;

n is 0, 1, 2, 3, 4 or 5.

In another more specific embodiment, the present disclosure relates to a compound of formula (III), or a tautomer, stereoisomer, prodrug, crystal form, pharmaceutically acceptable salt, hydrate or solvate thereof: wherein X is $C(R_x)$;

wherein $R_x$ is selected from H or halogen;

R' is selected from H, $C_{1-6}$ alkyl or $C_{1-6}$ haloalkyl;

L is —O—;

$R_3$ is selected from $(CH_2)_n$—$C_{3-7}$ cycloalkyl or $(CH_2)_n$-4- to 7-membered heterocyclyl only containing O as heteroatom;

wherein m is 0, 1, 2, 3, 4 or 5;

n is 0, 1, 2, 3, 4 or 5.

In another more specific embodiment, the present disclosure relates to a compound of formula (III), or a tautomer, stereoisomer, prodrug, crystal form, pharmaceutically acceptable salt, hydrate or solvate thereof: wherein X is N or $C(R_x)$; alternatively, X is $C(R_x)$;

wherein $R_x$ is selected from H, halogen, $C_{1-6}$ alkyl or $C_{1-6}$ haloalkyl; alternatively, wherein $R_x$ is selected from H or halogen;

R' is selected from H, $C_{1-6}$ alkyl or $C_{1-6}$ haloalkyl;

L is O;

$R_3$ is selected from $(CH_2)_m$—$C_{1-6}$ alkyl, $(CH_2)_m$—$C_{1-6}$ haloalkyl, $(CH_2)_n$—$C_{3-7}$ cycloalkyl or $(CH_2)_n$-5- to 6-membered heteroaryl containing O as heteroatom;

wherein m is 0, 1, 2, 3, 4 or 5;

n is 0, 1, 2, 3, 4 or 5.

In another more specific embodiment, the present disclosure relates to a compound of formula (III), or a tautomer, stereoisomer, prodrug, crystal form, pharmaceutically acceptable salt, hydrate or solvate thereof: wherein X is N or $C(R_x)$; alternatively, X is $C(R_x)$;

wherein $R_x$ is selected from H, halogen, $C_{1-6}$ alkyl or $C_{1-6}$ haloalkyl; alternatively, wherein $R_x$ is selected from H or halogen;

R' is selected from H, $C_{1-6}$ alkyl or $C_{1-6}$ haloalkyl;

L is —O—;

$R_3$ is selected from $(CH_2)_m$—$C_{1-6}$ alkyl, $(CH_2)_m$—$C_{1-6}$ haloalkyl or $(CH_2)_n$—$C_{3-7}$ cycloalkyl;

wherein m is 0, 1, 2, 3, 4 or 5;

n is 0, 1, 2, 3, 4 or 5.

In another more specific embodiment, the present disclosure relates to a compound of formula (IV), or a tautomer, stereoisomer, prodrug, crystal form, pharmaceutically acceptable salt, hydrate or solvate thereof:

(IV)

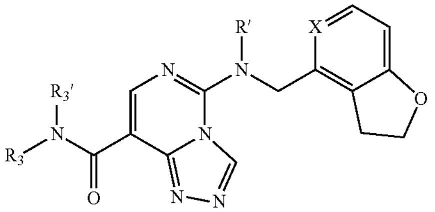

wherein

X is N or $C(R_x)$; alternatively, X is $C(R_x)$;

wherein $R_x$ is selected from H, halogen, $C_{1-6}$ alkyl, $C_{1-6}$ haloalkyl or $C_{1-6}$ alkoxy; alternatively, $R_x$ is selected from H or halogen;

R' is selected from H, $C_{1-6}$ alkyl or $C_{1-6}$ haloalkyl;

$R_3$ is selected from $(CH_2)_m$—$C_{1-6}$ alkyl, $(CH_2)_m$—$C_{1-6}$ haloalkyl, $(CH_2)_n$—$C_{3-7}$ cycloalkyl, $(CH_2)_n$-4- to 7-membered heterocyclyl, $(CH_2)_n$—$C_{6-10}$ aryl or $(CH_2)_n$-5- to 10-membered heteroaryl;

$R_3$' is selected from H, $(CH_2)_m$—$C_{1-6}$ alkyl, $(CH_2)_m$—$C_{1-6}$ haloalkyl or $(CH_2)_n$—$C_{3-7}$ cycloalkyl; or, $R_3$, $R_3$' and the N atom to which they are attached together form a 4- to 7-membered heterocyclyl group;

wherein m is 0, 1, 2, 3, 4 or 5;

n is 0, 1, 2, 3, 4 or 5.

In another more specific embodiment, the present disclosure relates to a compound of formula (IV), or a tautomer, stereoisomer, prodrug, crystal form, pharmaceutically acceptable salt, hydrate or solvate thereof:

wherein

X is N or $C(R_x)$; alternatively, X is $C(R_x)$;

wherein $R_x$ is selected from H, halogen, $C_{1-6}$ alkyl, $C_{1-6}$ haloalkyl or $C_{1-6}$ alkoxy; alternatively, $R_x$ is selected from H or halogen;

R' is selected from H, $C_{1-6}$ alkyl or $C_{1-6}$ haloalkyl;

$R_3$ is selected from $(CH_2)_m$—$C_{1-6}$ alkyl, $(CH_2)_m$—$C_{1-6}$ haloalkyl or $(CH_2)_n$—$C_{3-7}$ cycloalkyl;

$R_3$' is selected from H, $(CH_2)_m$—$C_{1-6}$ alkyl, $(CH_2)_m$—$C_{1-6}$ haloalkyl or $(CH_2)_n$—$C_{3-7}$ cycloalkyl;

or, $R_3$, $R_3$' and the N atom to which they are attached together form a 4- to 7-membered heterocyclyl group;

wherein m is 0, 1, 2, 3, 4 or 5;

n is 0, 1, 2, 3, 4 or 5.

In another more specific embodiment, the present disclosure relates to a compound of formula (V), or a tautomer, stereoisomer, prodrug, crystal form, pharmaceutically acceptable salt, hydrate or solvate thereof:

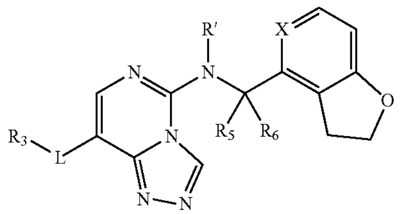

(V)

wherein

X is N or $C(R_x)$; alternatively, X is $C(R_x)$, wherein $R_x$ is selected from H, halogen, $C_{1-6}$ alkyl, $C_{1-6}$ haloalkyl or $C_{1-6}$ alkoxy; alternatively, $R_x$ is selected from H or halogen;

R' is selected from H, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration;

L is —C(O)—N(R)—, —C(O)—O—, —$S(O)_q$—N(R)— or —$S(O)_q$—O—;

wherein R is selected from H, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration;

q is 0, 1 or 2;

$R_3$ is selected from $(CR_7R_8)_m$—$C_{1-6}$ alkyl, $(CR_7R_8)_m$—$C_{1-6}$ haloalkyl, $(CR_7R_8)_n$—$C_{1-6}$ alkoxy, $(CR_7R_8)_n$—$C_{1-6}$ haloalkoxy, $(CR_7R_8)_n$—$NR_aR_b$, $(CR_7R_8)_n$—$C_{3-7}$ cycloalkyl, $(CR_7R_8)_n$-4- to 7-membered heterocyclyl, $(CR_7R_8)_n$—$C_{6-10}$ aryl or $(CR_7R_8)_n$-5- to 10-membered heteroaryl; or $R_3$ is connected to R to form —$C_{1-6}$ alkylene-;

wherein m is 0, 1, 2, 3, 4 or 5;

n is 0, 1, 2, 3, 4 or 5;

$R_a$ is selected from H, $C_{1-6}$ alkyl or $C_{1-6}$ haloalkyl;

$R_b$ is selected from H, $C_{1-6}$ alkyl or $C_{1-6}$ haloalkyl;

$R_7$ and $R_8$ are independently selected from H, D, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration;

$R_5$ and $R_6$ are independently selected from H, D, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration;

wherein $R_3$ is optionally substituted with a group selected from H, D, halogen, CN, OH, $C_{1-6}$ alkyl, $C_{1-6}$ haloalkyl, $C_{3-7}$ cycloalkyl, 4- to 7-membered heterocyclyl, $C_{6-10}$ aryl, 5- to 10-membered heteroaryl, $(CR_7R_8)_n$—$C_{1-6}$ alkoxy or —$S(O)_q$—$C_{1-6}$ alkyl;

wherein the alkyl, haloalkyl, alkoxy, haloalkoxy, cycloalkyl, heterocyclyl, aryl and heteroaryl are optionally substituted with one or more D, up to complete deuteration.

In another more specific embodiment, the present disclosure relates to a compound of formula (V), or a tautomer, stereoisomer, prodrug, crystal form, pharmaceutically acceptable salt, hydrate or solvate thereof:

wherein

X is $C(R_x)$, wherein $R_x$ is selected from H or halogen;

R' is selected from H, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration;

L is —C(O)—N(R)—, —C(O)—O—, —$S(O)_q$—N(R)— or —$S(O)_q$—O—;

wherein R is selected from H, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration;

q is 0, 1 or 2;

$R_3$ is selected from $(CR_7R_8)_m$—$C_{1-6}$ alkyl, $(CR_7R_8)_m$—$C_{1-6}$ haloalkyl, $(CR_7R_8)_n$—$C_{1-6}$ alkoxy, $(CR_7R_8)_n$—$NR_aR_b$, $(CR_7R_8)_n$—$C_{3-7}$ cycloalkyl, $(CR_7R_8)_n$—$C_{6-10}$ aryl or $(CR_7R_8)_n$-5- to 10-membered heteroaryl; or $R_3$ is connected to R to form —$C_{1-6}$ alkylene-;

wherein m is 0, 1, 2, 3, 4 or 5;

n is 0, 1, 2, 3, 4 or 5;

$R_a$ is selected from H, $C_{1-6}$ alkyl or $C_{1-6}$ haloalkyl;

$R_b$ is selected from H, $C_{1-6}$ alkyl or $C_{1-6}$ haloalkyl;

$R_7$ and $R_8$ are independently selected from H, D, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration;

$R_5$ and $R_6$ are independently selected from H, D, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration;

wherein $R_3$ is optionally substituted with a group selected from H, D, halogen, $C_{1-6}$ alkyl, $C_{1-6}$ haloalkyl, $C_{1-6}$ alkoxy or $C_{3-7}$ cycloalkyl.

In another more specific embodiment, the present disclosure relates to a compound of formula (V), or a tautomer, stereoisomer, prodrug, crystal form, pharmaceutically acceptable salt, hydrate or solvate thereof: wherein X is $C(R_x)$, wherein $R_x$ is selected from H or halogen;

R' is selected from H, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration;

L is —C(O)—N(R)— or —C(O)—O—;

wherein R is selected from H, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration;

$R_3$ is selected from $(CR_7R_8)_m$—$C_{1-6}$ alkyl, $(CR_7R_8)_m$—$C_{1-6}$ haloalkyl, $(CR_7R_8)_n$—$C_{1-6}$ alkoxy, $(CR_7R_8)_n$—$NR_aR_b$ or $(CR_7R_8)_n$—$C_{3-4}$ cycloalkyl; or $R_3$ is connected to R to form a $C_{1-6}$ alkylene;

wherein m is 0, 1, 2, 3, 4 or 5;

n is 0, 1, 2, 3, 4 or 5;

$R_a$ is selected from H, $C_{1-6}$ alkyl or $C_{1-6}$ haloalkyl;

$R_b$ is selected from H, $C_{1-6}$ alkyl or $C_{1-6}$ haloalkyl;

$R_7$ and $R_8$ are independently selected from H or D;

$R_5$ and $R_6$ are independently selected from H or D;

wherein $R_3$ is optionally substituted with a group selected from H, D, $C_{1-6}$ alkyl, $C_{1-6}$ haloalkyl or $C_{1-6}$ alkoxy.

In another more specific embodiment, the present disclosure relates to a compound of formula (V), or a tautomer, stereoisomer, prodrug, crystal form, pharmaceutically acceptable salt, hydrate or solvate thereof:

wherein

X is $C(R_x)$, wherein $R_x$ is selected from H or halogen;

R' is selected from H, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration;

L is —C(O)—N(R)—;

wherein R is selected from H, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration;

$R_3$ is selected from $(CR_7R_8)_m$—$C_{1-6}$ haloalkyl or $(CR_7R_8)_n$—$C_{3-4}$ cycloalkyl;

wherein m is 0, 1, 2, 3, 4 or 5;

n is 0, 1, 2, 3, 4 or 5;

$R_7$ and $R_8$ are independently selected from H or D;

$R_5$ and $R_6$ are independently selected from H or D.

In another more specific embodiment, the present disclosure relates to a compound of formula (VI), or a tautomer, stereoisomer, prodrug, crystal form, pharmaceutically acceptable salt, hydrate or solvate thereof:

(VI)

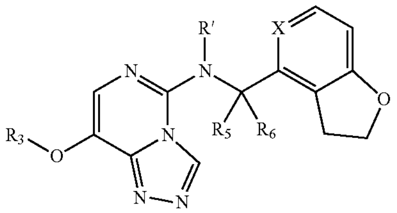

wherein

X is N or $C(R_x)$; alternatively, X is $C(R_x)$;

wherein $R_x$ is selected from H, halogen, $C_{1-6}$ alkyl, $C_{1-6}$ haloalkyl or $C_{1-6}$ alkoxy; alternatively, $R_x$ is selected from H or halogen;

R' is selected from H, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration;

$R_3$ is selected from $(CR_7R_8)_m$—$C_{1-6}$ alkyl, $(CR_7R_8)_m$—$C_{1-6}$ haloalkyl, $(CR_7R_8)_n$—$C_{3-7}$ cycloalkyl, $(CR_7R_8)_n$-4- to 7-membered heterocyclyl, $(CR_7R_8)_n$—$C_{6-10}$ aryl or $(CR_7R_8)_n$-5- to 10-membered heteroaryl; wherein m is 0, 1, 2, 3, 4 or 5;

n is 0, 1, 2, 3, 4 or 5;

$R_7$ and $R_8$ are independently selected from H, D, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration; or $R_7$ and $R_8$ on the same carbon atom are combined to form ═O;

$R_5$ and $R_6$ are independently selected from H, D, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration; wherein $R_3$ is optionally substituted by one or more substituent groups selected from H, D, halogen, CN, OH, ═O, $NR_cR_d$, $C_{1-6}$ alkyl, $C_{1-6}$ haloalkyl, $C_{1-6}$ alkoxy, $C_{3-7}$ cycloalkyl, 4- to 7-membered heterocyclyl, $C_{6-10}$ aryl, 5- to 10-membered heteroaryl, —O—$C_{3-7}$ cycloalkyl, —O-4- to 7-membered heterocyclyl, —O—$C_{6-10}$ aryl, —O-5- to 10-membered heteroaryl, —C(O)—$C_{1-6}$ alkyl, —C(O)—$C_{1-6}$ haloalkyl, —C(O)—$C_{3-7}$ cycloalkyl, —C(O)-4- to 7-membered heterocyclyl, —C(O)—$C_{6-10}$ aryl, —C(O)-5- to 10-membered heteroaryl; wherein $R_c$ is selected from H, $C_{1-6}$ alkyl, $C_{1-6}$ haloalkyl, —C(O)—$C_{3-7}$ cycloalkyl, —C(O)-4- to 7-membered heterocyclyl, —C(O)—$C_{6-10}$ aryl or —C(O)-5- to 10-membered heteroaryl;

$R_d$ is selected from H, $C_{1-6}$ alkyl, $C_{1-6}$ haloalkyl, —C(O)—$C_{3-7}$ cycloalkyl, —C(O)-4- to 7-membered heterocyclyl, —C(O)—$C_{6-10}$ aryl or —C(O)-5- to 10-membered heteroaryl;

wherein the alkyl, haloalkyl, alkoxy, cycloalkyl, heterocyclyl, aryl and heteroaryl are optionally substituted with substituent groups selected from H, D, CN, OH, ═O, halogen, $C_{1-6}$ alkyl, $C_{1-6}$ haloalkyl, $C_{1-6}$ alkoxy, $C_{3-7}$ cycloalkyl, 4- to 7-membered heterocyclyl, $C_{6-10}$ aryl, 5- to 10-membered heteroaryl, —O—$C_{3-7}$ cycloalkyl, —O-4- to 7-membered heterocyclyl, —O—$C_{6-10}$ aryl, —O-5- to 10-membered heteroaryl, —C(O)—$C_{1-6}$ alkyl, —C(O)—$C_{1-6}$ haloalkyl, —C(O)—$C_{3-7}$ cycloalkyl, —C(O)-4- to 7-membered heterocyclyl, —C(O)—$C_{6-10}$ aryl, —C(O)-5- to 10-membered heteroaryl, or substituted with one or more D, up to complete deuteration.

In another more specific embodiment, the present disclosure relates to a compound of formula (VI), or a tautomer, stereoisomer, prodrug, crystal form, pharmaceutically acceptable salt, hydrate or solvate thereof: wherein $R_3$ is optionally substituted by one or more substituent groups selected from H, D, halogen, CN, OH, ═O, $NR_cR_d$, $C_{1-6}$ alkyl, $C_{1-6}$ haloalkyl, $C_{1-6}$ alkoxy, $C_{3-7}$ cycloalkyl, —C(O)—$C_{1-6}$ alkyl, —C(O)—$C_{3-7}$ cycloalkyl or —O—$C_{6-10}$ aryl;

wherein $R_c$ is selected from H, $C_{1-6}$ alkyl, $C_{1-6}$ haloalkyl or —C(O)—$C_{3-7}$ cycloalkyl;

$R_d$ is selected from H, $C_{1-6}$ alkyl, $C_{1-6}$ haloalkyl or —C(O)—$C_{3-7}$ cycloalkyl; wherein the alkyl, haloalkyl, alkoxy, cycloalkyl, heterocyclyl, aryl and heteroaryl are optionally substituted with substituent groups selected from H, D, CN, ═O, halogen, $C_{1-6}$ alkyl, $C_{1-6}$ haloalkyl, $C_{1-6}$ alkoxy or —C(O)—$C_{1-6}$ alkyl, or substituted with one or more D, up to complete deuteration.

In another more specific embodiment, the present disclosure relates to a compound of formula (VI), or a tautomer, stereoisomer, prodrug, crystal form, pharmaceutically acceptable salt, hydrate or solvate thereof:

wherein

X is $C(R_x)$;

wherein $R_x$ is selected from H or halogen;

R' is selected from H, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration;

$R_3$ is selected from $(CR_7R_8)_m$—$C_{1-6}$ alkyl, $(CR_7R_8)_m$—$C_{1-6}$ haloalkyl, $(CR_7R_8)_n$—$C_{3-7}$ cycloalkyl or $(CR_7R_8)_n$- 4- to 7-membered heterocyclyl only containing O as heteroatom;

wherein m is 0, 1, 2, 3, 4 or 5;

n is 0, 1, 2, 3, 4 or 5;

$R_7$ and $R_8$ are independently selected from H, D, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration;

$R_5$ and $R_6$ are independently selected from H, D, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration;

wherein $R_3$ is optionally substituted with a group selected from H, D, $C_{1-6}$ alkyl, $C_{1-6}$ haloalkyl or $C_{1-6}$ alkoxy.

In another more specific embodiment, the present disclosure relates to a compound of formula (VI), or a tautomer, stereoisomer, prodrug, crystal form, pharmaceutically acceptable salt, hydrate or solvate thereof: wherein X is $C(R_x)$;

wherein $R_x$ is selected from H or halogen;

R' is selected from H, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration;

$R_3$ is selected from $(CR_7R_8)_m$—$C_{1-6}$ alkyl, $(CR_7R_8)_m$—$C_{1-6}$ haloalkyl or $(CR_7R_8)_n$-4- to 7-membered heterocyclyl only containing O as heteroatom;

wherein m is 0, 1, 2, 3, 4 or 5;

n is 0, 1, 2, 3, 4 or 5;

$R_7$ and $R_8$ are independently selected from H, D, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration;

$R_5$ and $R_6$ are independently selected from H, D, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration;

wherein $R_3$ is optionally substituted with a group selected from H, D, $C_{1-6}$ alkyl, $C_{1-6}$ haloalkyl or $C_{1-6}$ alkoxy.

In another more specific embodiment, the present disclosure relates to a compound of formula (VII), or a tautomer, stereoisomer, prodrug, crystal form, pharmaceutically acceptable salt, hydrate or solvate thereof:

(VII)

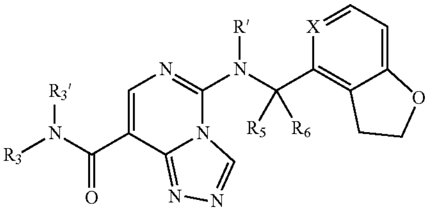

wherein

X is N or C($R_x$); alternatively, X is C($R_x$);

wherein $R_x$ is selected from H, halogen, $C_{1-6}$ alkyl, $C_{1-6}$ haloalkyl or $C_{1-6}$ alkoxy; alternatively, $R_x$ is selected from H or halogen;

R' is selected from H, $C_{1-6}$ alkyl or $C_{1-6}$ haloalkyl;

$R_3$ is selected from $(CR_7R_8)_m$—$C_{1-6}$ alkyl, $(CR_7R_8)_m$—$C_{1-6}$ haloalkyl, $(CR_7R_8)_n$—$C_{3-7}$ cycloalkyl, $(CR_7R_8)_n$-4- to 7-membered heterocyclyl, $(CR_7R_8)_n$—$C_{6-10}$ aryl or $(CR_7R_8)_n$-5- to 10-membered heteroaryl;

$R_3$' is selected from H, $(CR_7R_8)_m$—$C_{1-6}$ alkyl, $(CR_7R_8)_m$—$C_{1-6}$ haloalkyl or $(CR_7R_8)_n$—$C_{3-7}$ cycloalkyl; or, $R_3$, $R_3$' and the N atom to which they are attached together form a 4- to 7-membered heterocyclyl group;

wherein m is 0, 1, 2, 3, 4 or 5;

n is 0, 1, 2, 3, 4 or 5;

$R_7$ and $R_8$ are independently selected from H, D, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration; or $R_7$ and $R_8$ on the same carbon atom are combined to form =O;

$R_5$ and $R_6$ are independently selected from H, D, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration;

wherein $R_3$ is optionally substituted with one or more groups selected from H, D, halogen, $C_{1-6}$ alkyl, $C_{1-6}$ haloalkyl or $C_{1-6}$ alkoxy.

In another more specific embodiment, the present disclosure relates to a compound of formula (VII), or a tautomer, stereoisomer, prodrug, crystal form, pharmaceutically acceptable salt, hydrate or solvate thereof: wherein X is C($R_x$), wherein $R_x$ is selected from H or halogen;

R' is selected from H, $C_{1-6}$ alkyl or $C_{1-6}$ haloalkyl;

$R_3$ is selected from $(CR_7R_8)_m$—$C_{1-6}$ alkyl, $(CR_7R_8)_m$—$C_{1-6}$ haloalkyl or $(CR_7R_8)_n$—$C_{3-7}$ cycloalkyl;

$R_3$' is selected from H, $(CR_7R_8)_m$—$C_{1-6}$ alkyl, $(CR_7R_8)_m$—$C_{1-6}$ haloalkyl or $(CR_7R_8)_n$—$C_{3-7}$ cycloalkyl;

or, $R_3$, $R_3$' and the N atom to which they are attached together form a 4- to 7-membered heterocyclyl group;

m is 0, 1, 2, 3, 4 or 5;

n is 0, 1, 2, 3, 4 or 5;

$R_7$ and $R_8$ are independently selected from H, D, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration;

$R_5$ and $R_6$ are independently selected from H, D, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration;

wherein $R_3$ is optionally substituted with one or more groups selected from H, D, halogen, $C_{1-6}$ alkyl, $C_{1-6}$ haloalkyl or $C_{1-6}$ alkoxy.

In another more specific embodiment, the present disclosure relates to the following compounds, or a tautomer, stereoisomer, prodrug, crystal form, pharmaceutically acceptable salt, hydrate or solvate thereof:

HJM-001

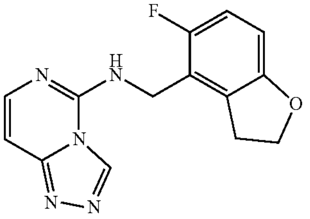

HJM-002

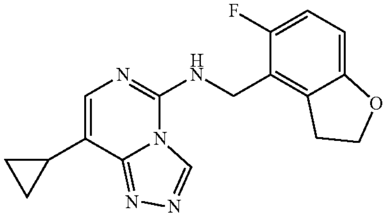

HJM-003

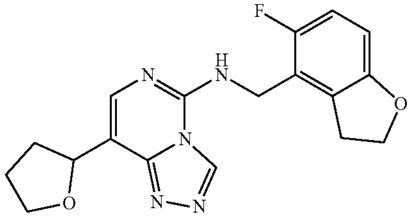

HJM-004

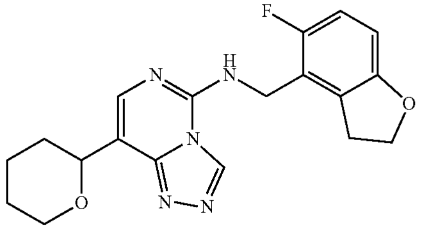

HJM-005

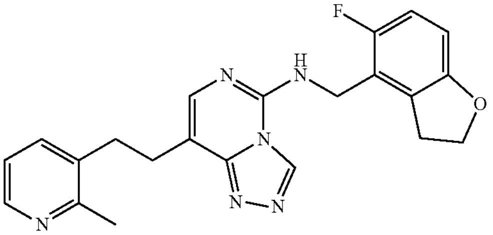

-continued
HJM-006
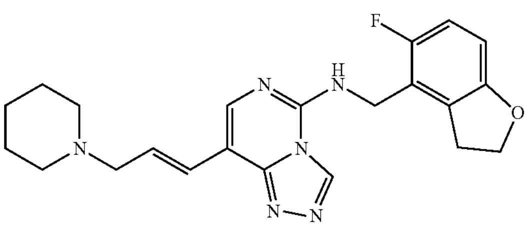
HJM-007
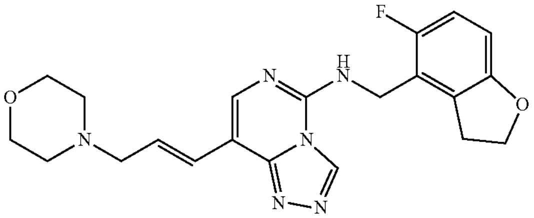
HJM-008
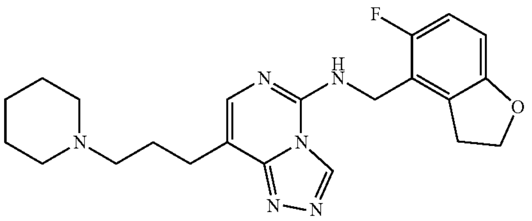
HJM-009
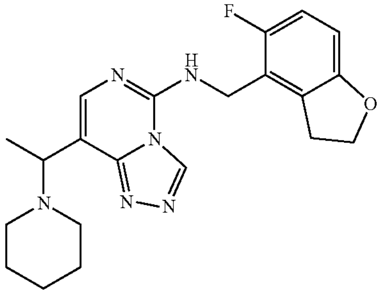
HJM-010
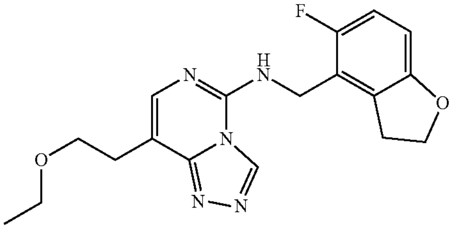
HJM-011
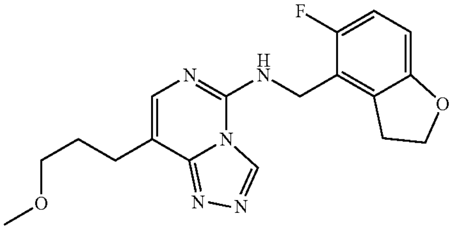
-continued
HJM-012
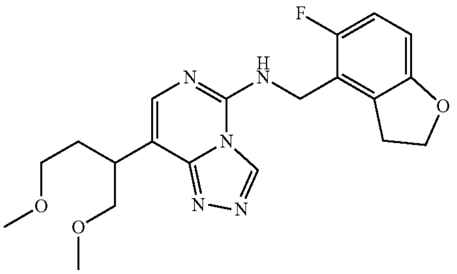
HJM-013
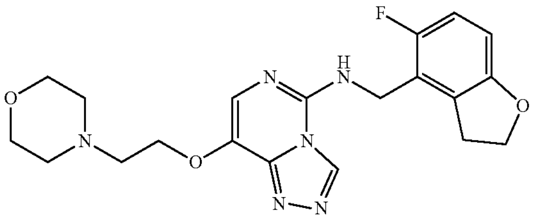
HJM-014
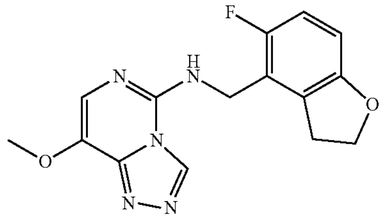
HJM-015
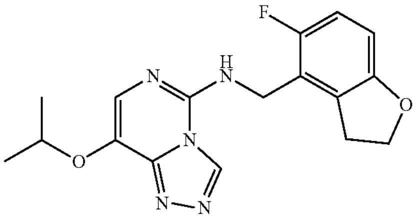
HJM-016
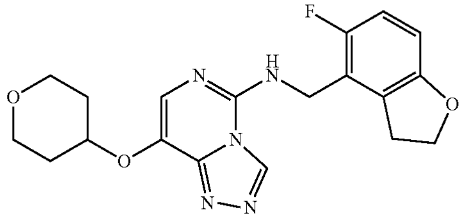
HJM-017
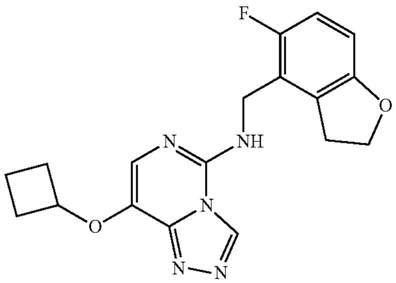

-continued
HJM-018
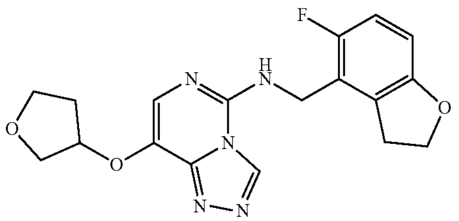
HJM-019
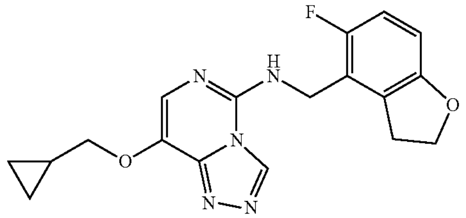
HJM-020
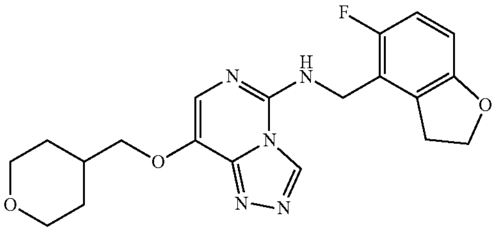
HJM-021
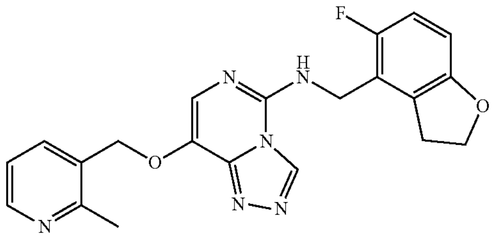
HJM-022
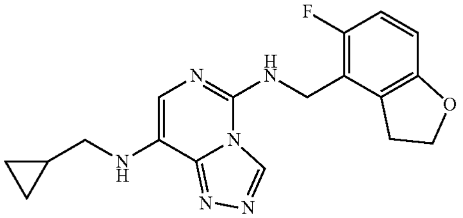
HJM-023
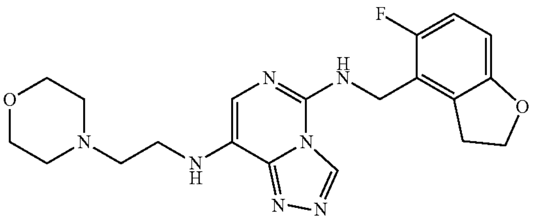
-continued
HJM-024
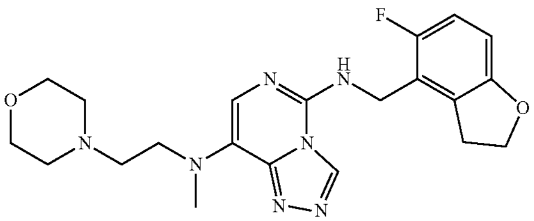
HJM-025
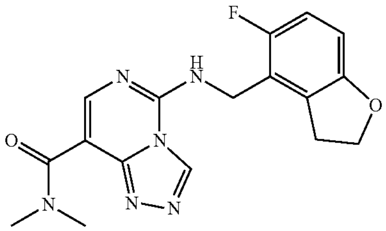
HJM-026
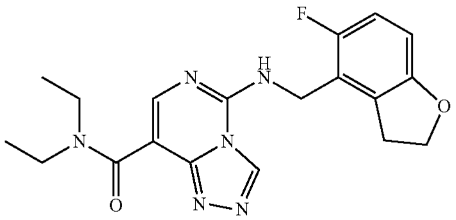
HJM-027
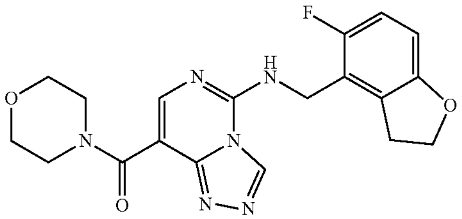
HJM-028
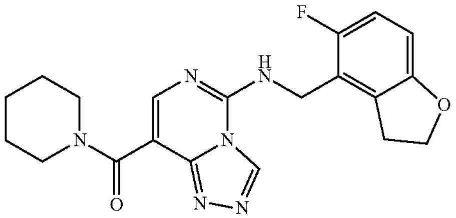
HJM-029
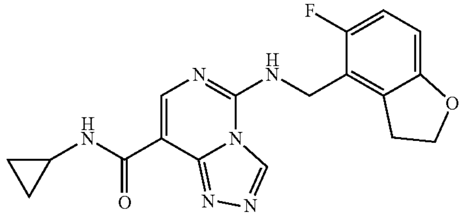

-continued
HJM-030
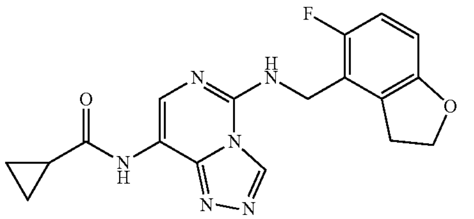
HJM-031
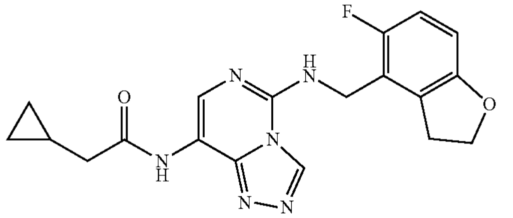
HJM-032
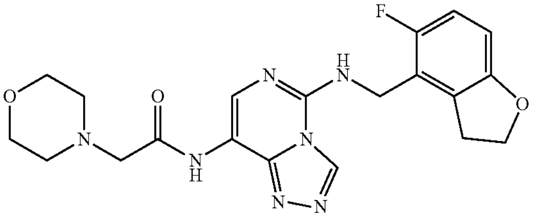
HJM-033
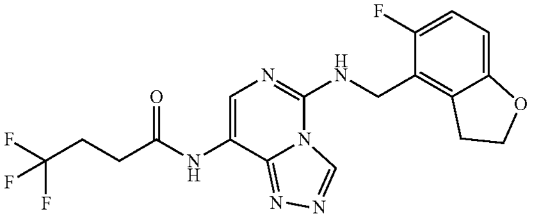
HJM-034
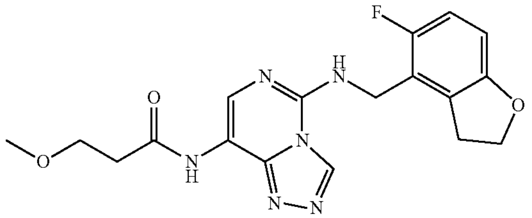
HJM-035
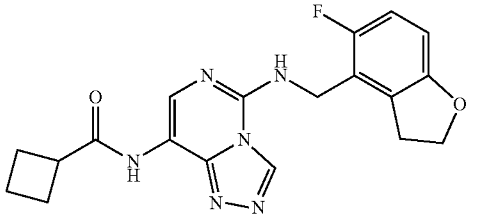
-continued
HJM-036
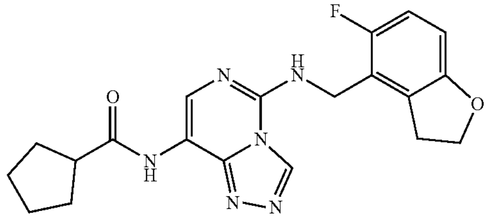
HJM-037
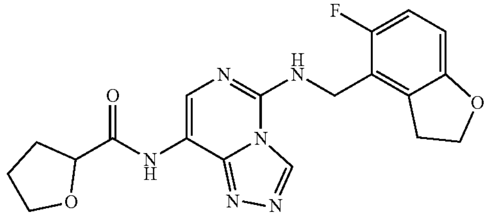
HJM-038
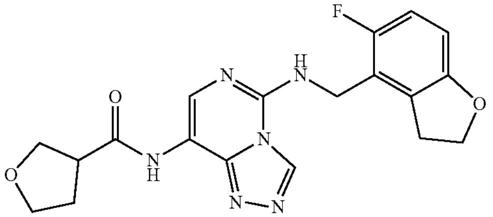
HJM-039
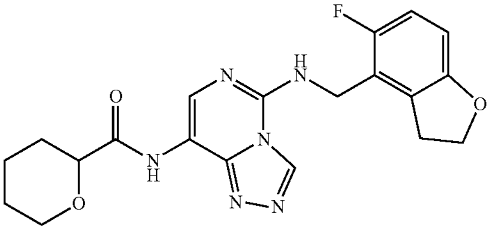
HJM-040
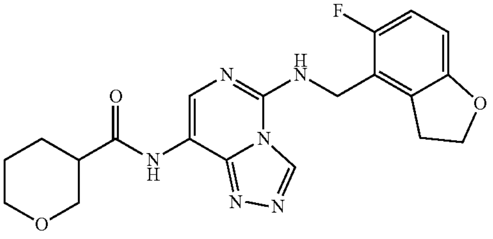
HJM-041
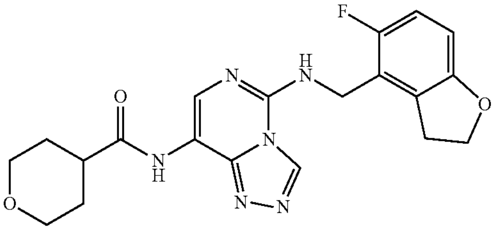

-continued
HJM-042
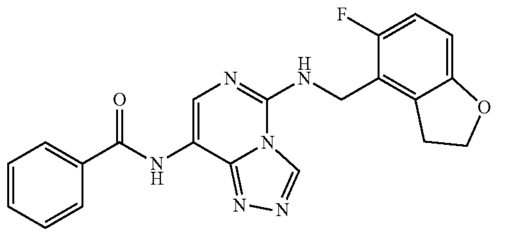
HJM-043
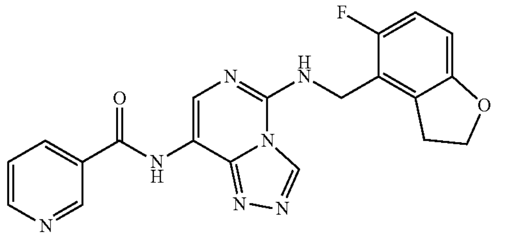
HJM-044
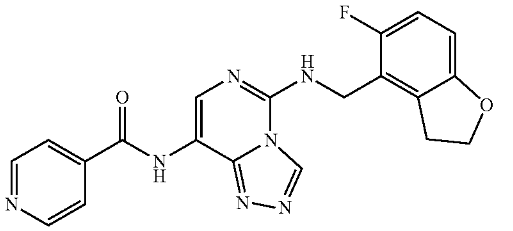
HJM-045
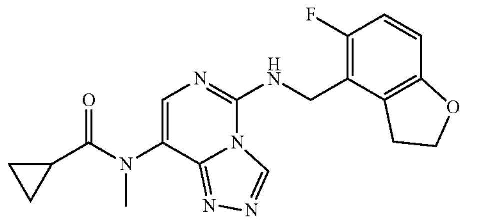
HJM-046
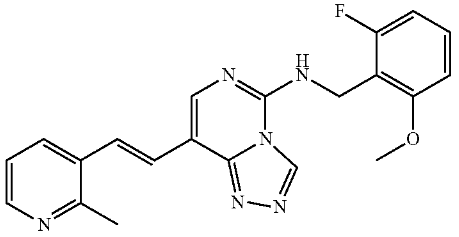
HJM-047
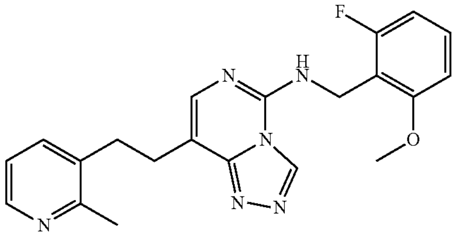
-continued
HJM-048
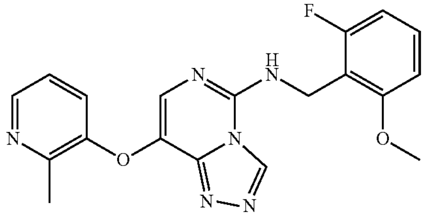
HJM-049
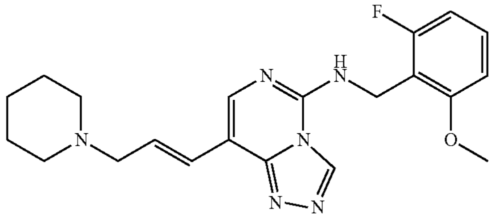
HJM-065
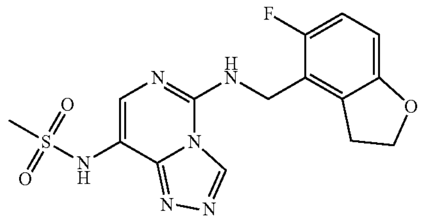
HJM-066
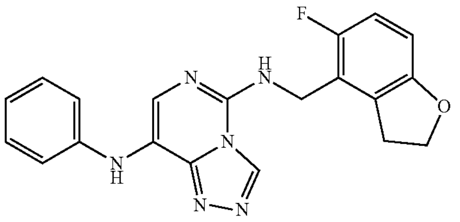
HJM-067
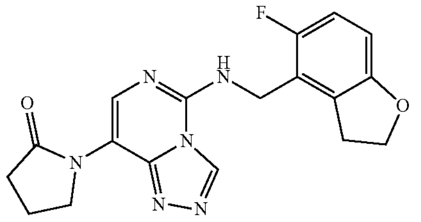
HJM-068
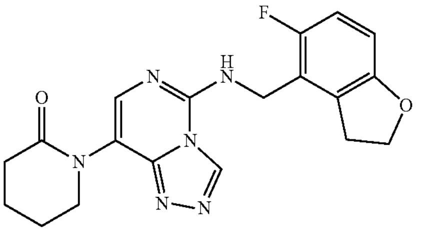
HJM-069
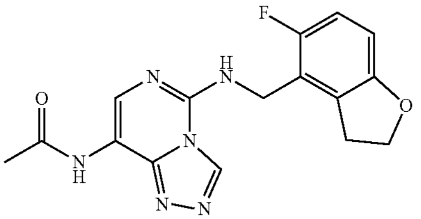

-continued
HJM-070
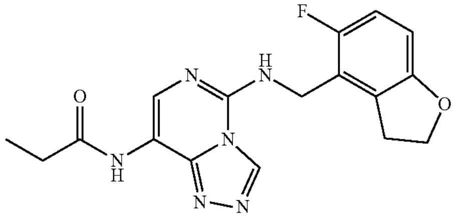
HJM-071
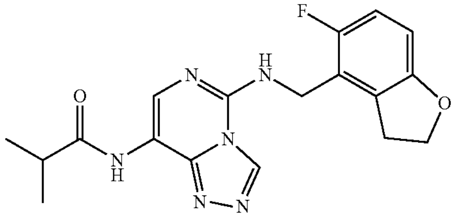
HJM-072
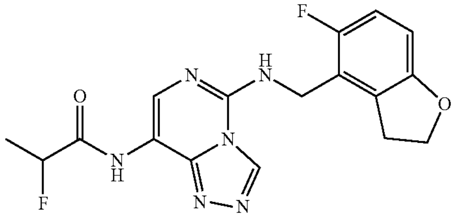
HJM-073
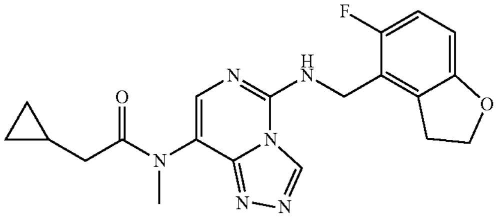
HJM-074
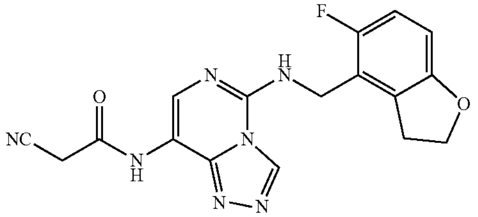
HJM-075
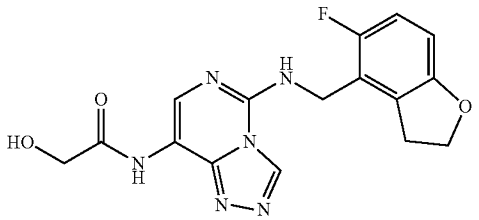
HJM-076
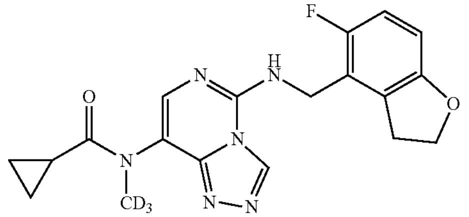
-continued
HJM-077
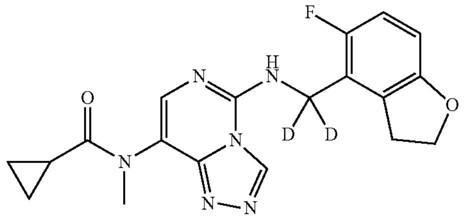
HJM-078
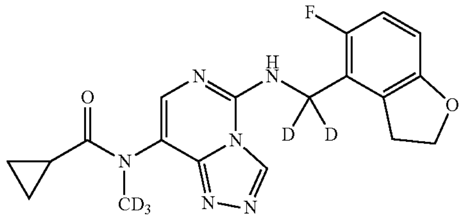
HJM-079
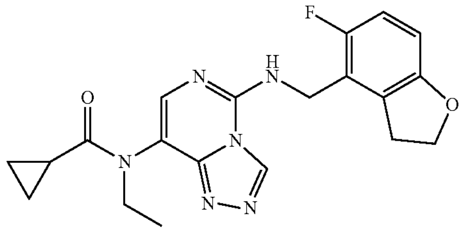
HJM-080
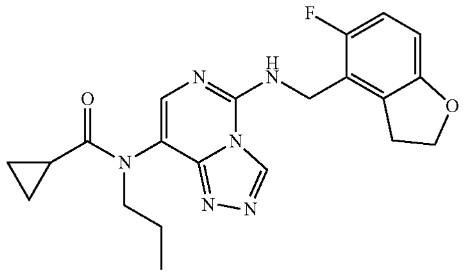
HJM-081
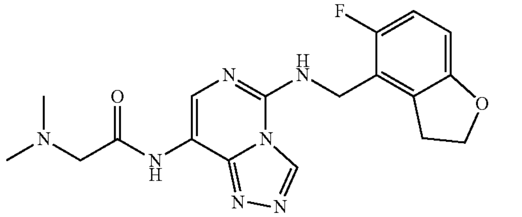
HJM-082
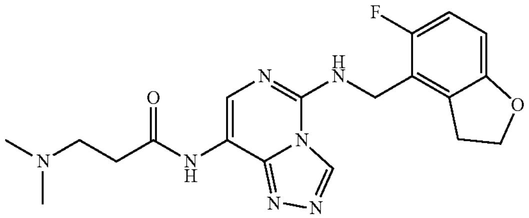

-continued
HJM-083
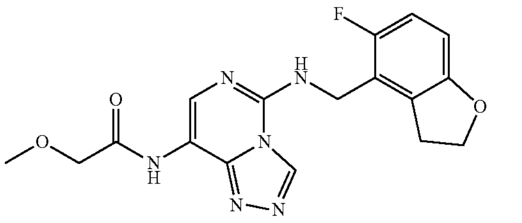
HJM-084
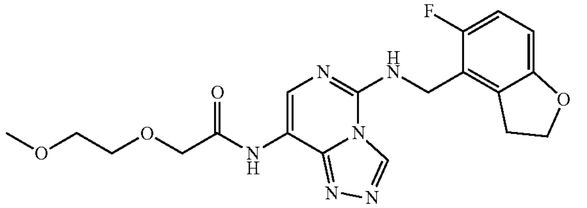
HJM-085
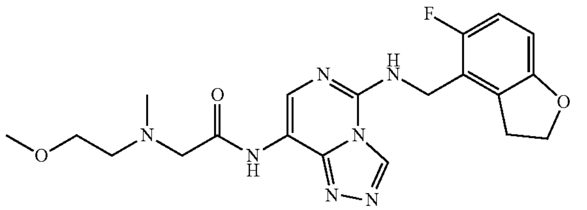
HJM-086
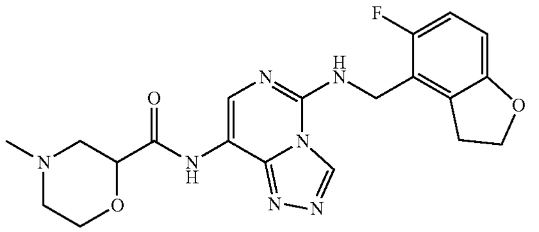
HJM-087
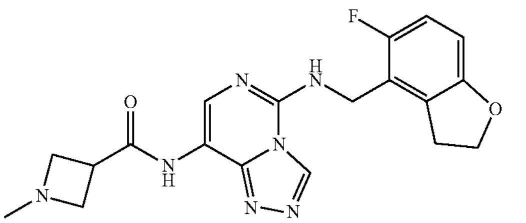
HJM-088
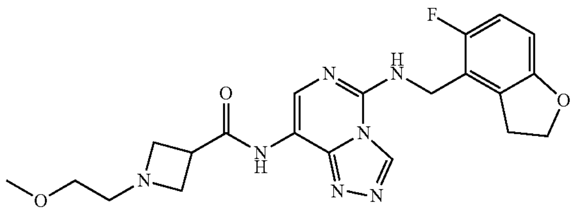
-continued
HJM-089
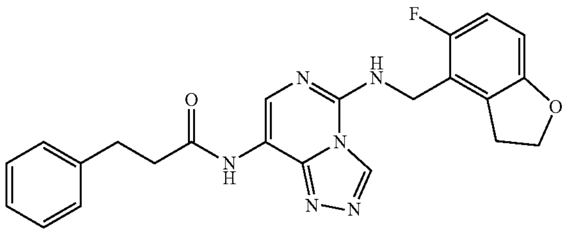
HJM-090
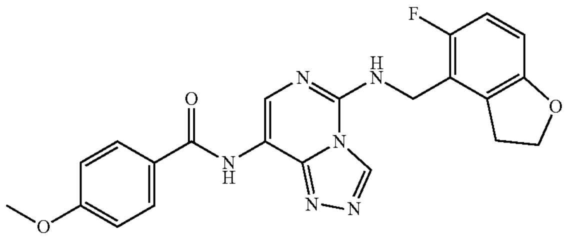
HJM-091
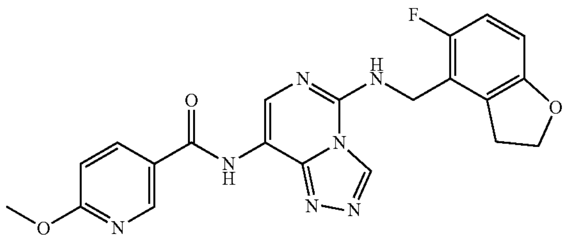
HJM-092
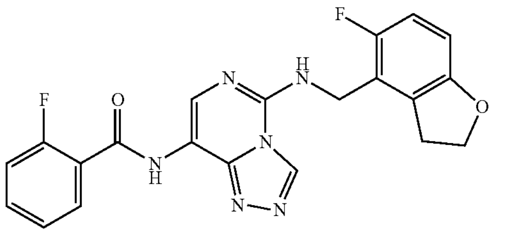
HJM-093
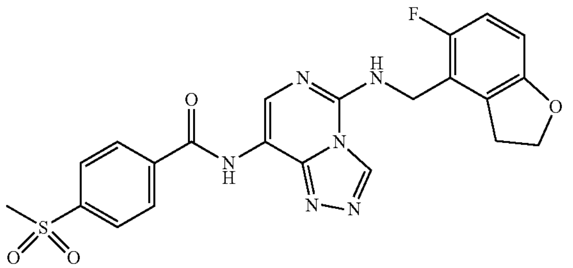
HJM-094
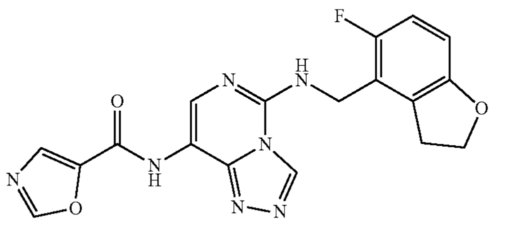

-continued
HJM-095
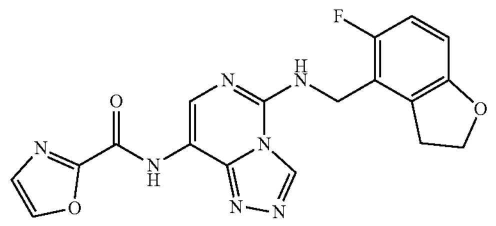
HJM-096
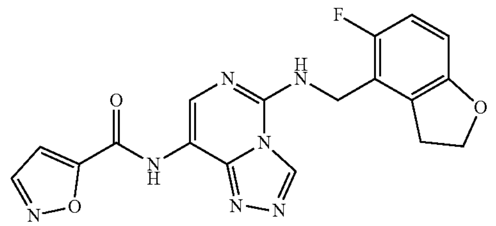
HJM-097
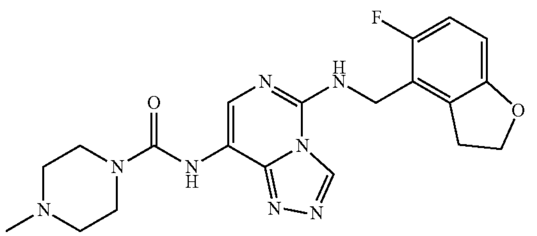
HJM-098
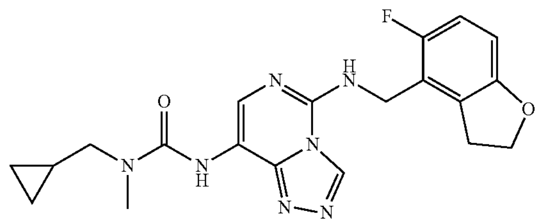
HJM-099
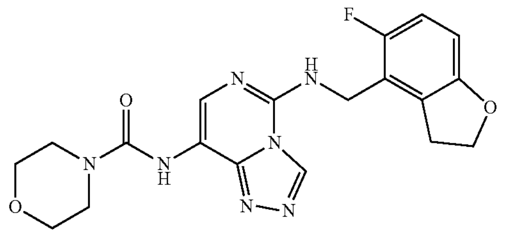
HJM-100
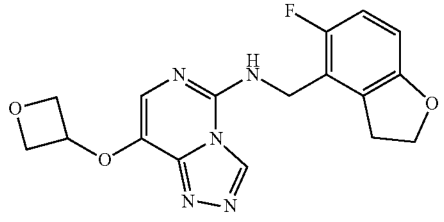
-continued
HJM-101
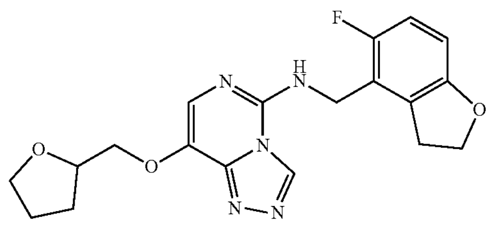
HJM-102
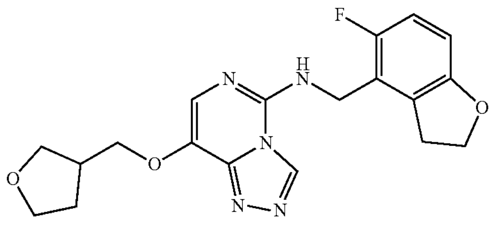
HJM-103
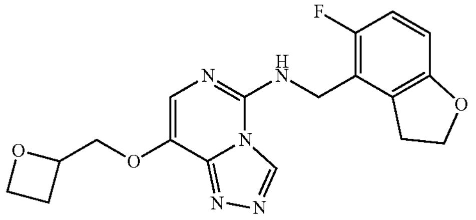
HJM-104
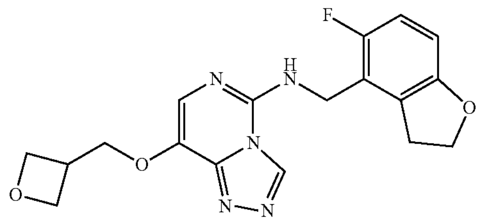
HJM-105
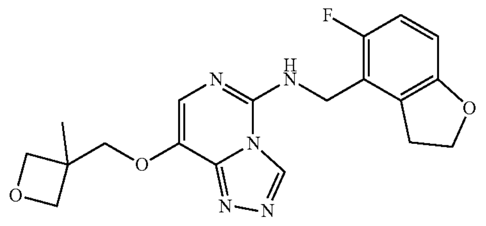
HJM-106
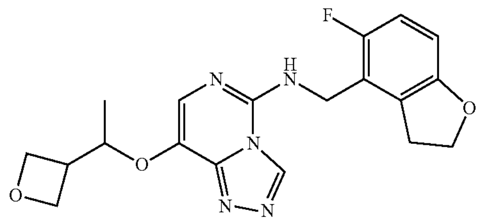

-continued
HJM-107
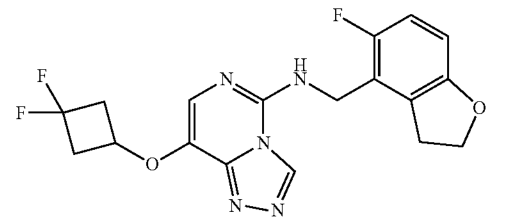
HJM-108
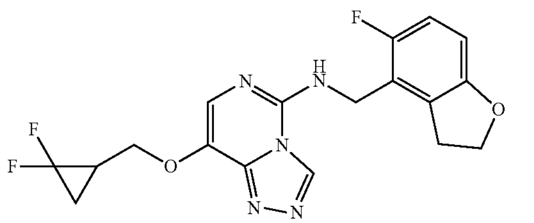
HJM-109
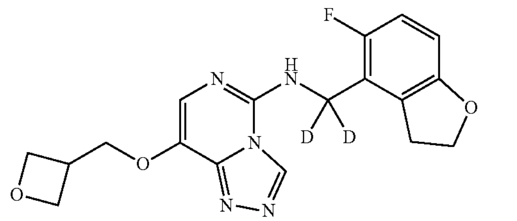
HJM-110
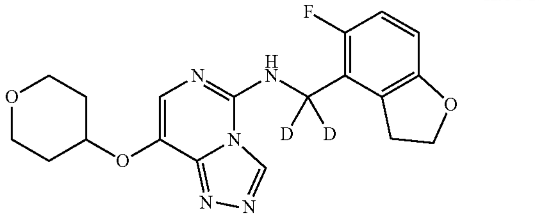
HJM-111
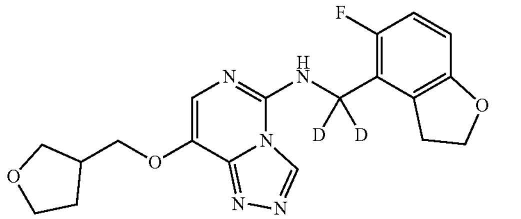
HJM-112
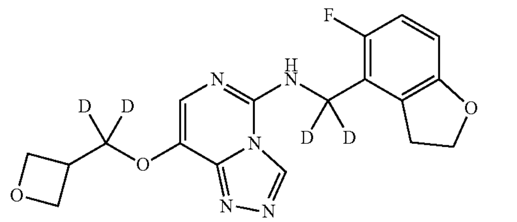
-continued
HJM-113
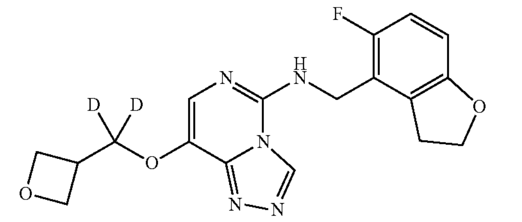
HJM-114
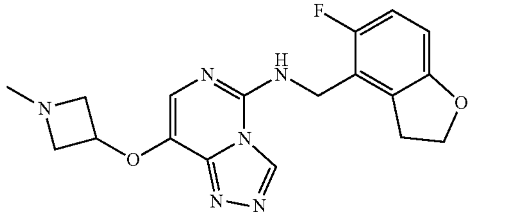
HJM-115
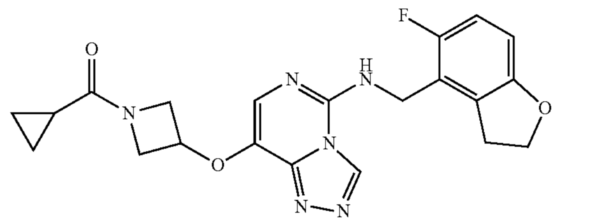
HJM-116
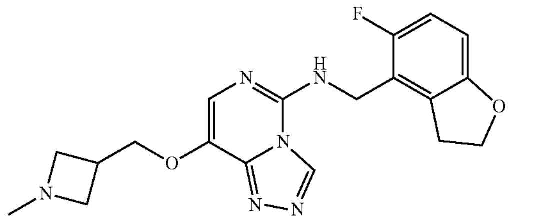
HJM-117
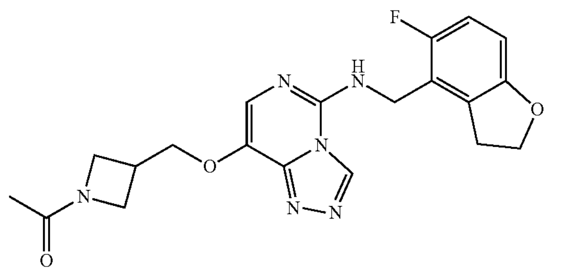
HJM-118
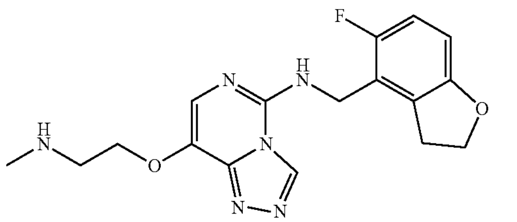

-continued
HJM-119
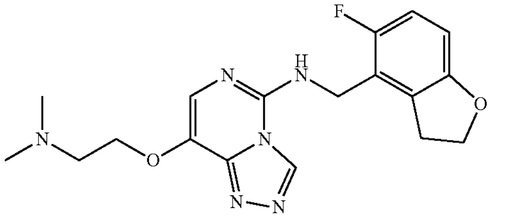
HJM-120
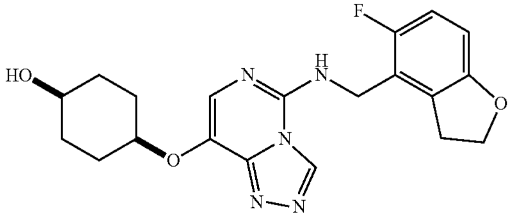
HJM-121
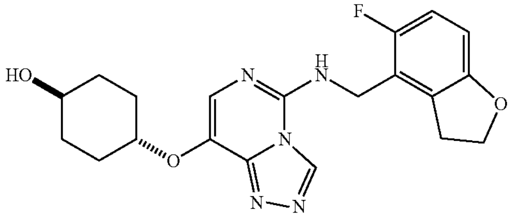
HJM-122
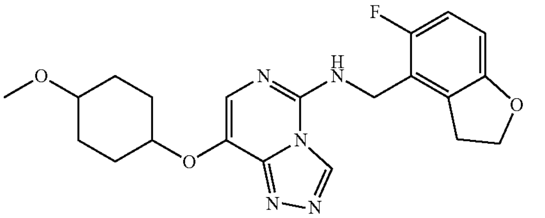
HJM-123
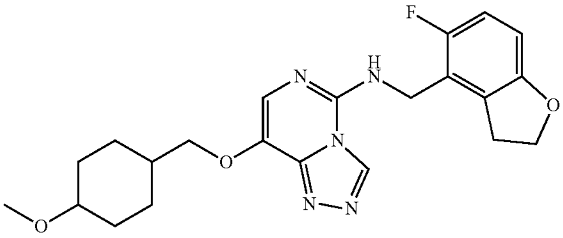
HJM-124
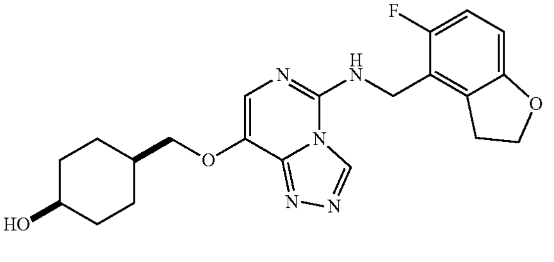
-continued
HJM-125
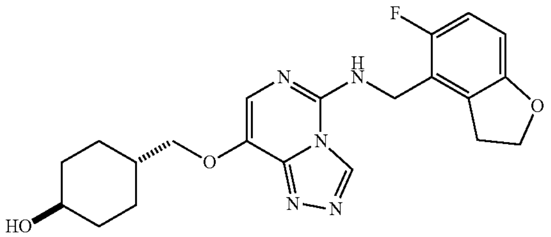
HJM-126
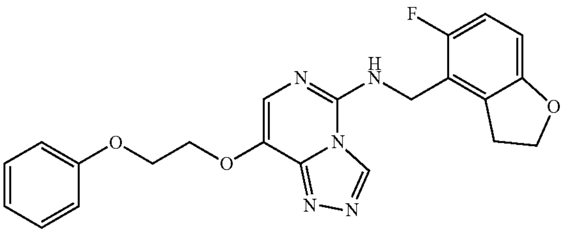
HJM-127
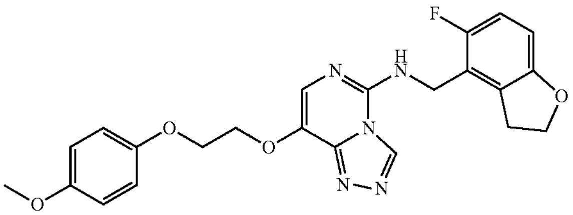
HJM-128
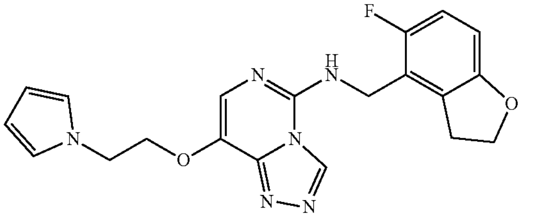
HJM-129
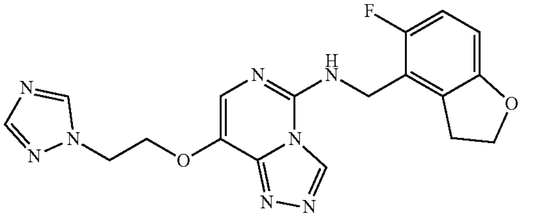
HJM-130
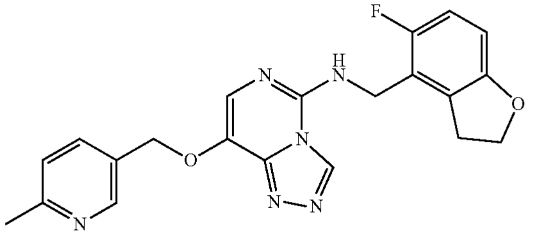

-continued
HJM-131
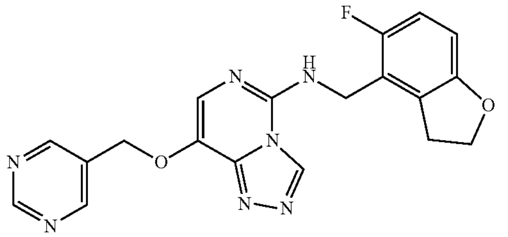
HJM-132
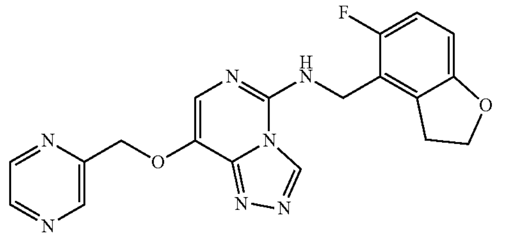
HJM-133
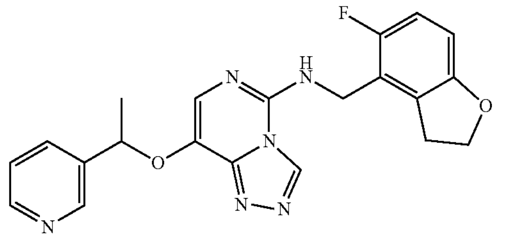
HJM-134
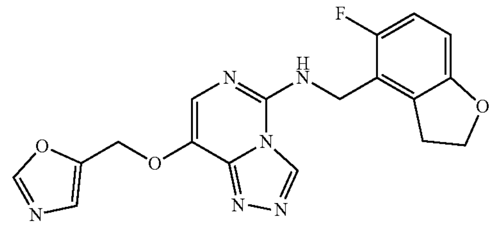
HJM-135
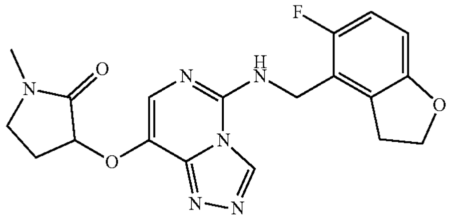
HJM-136
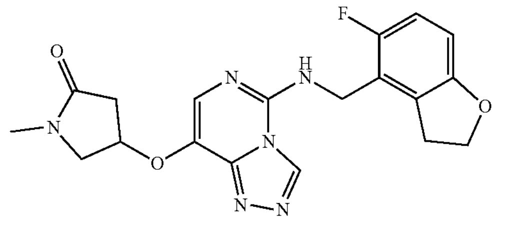
-continued
HJM-137
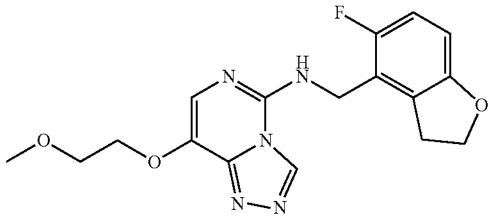
HJM-138
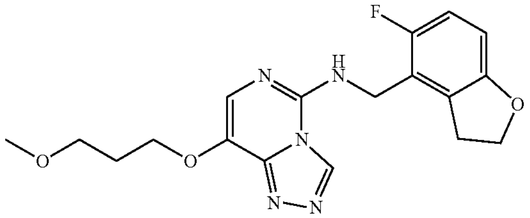
HJM-139
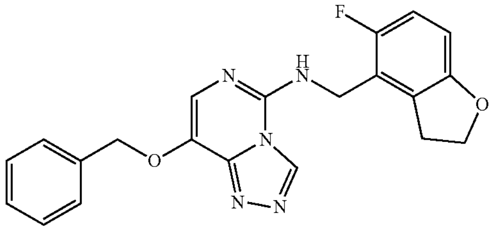
HJM-140
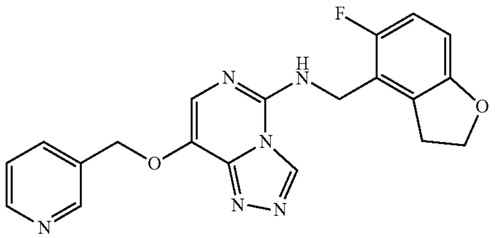
HJM-141
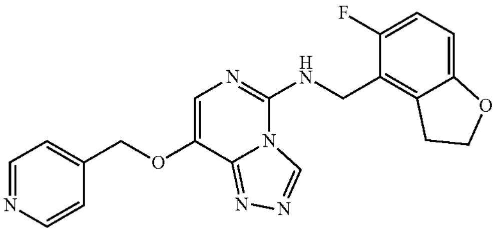
HJM-142
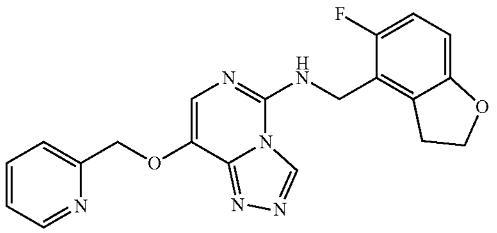

-continued

HJM-143

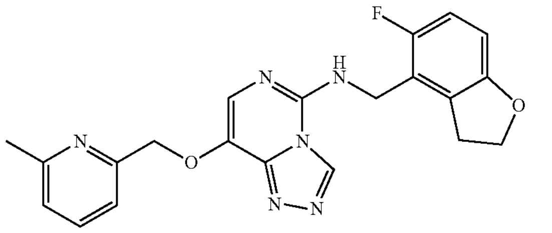

HJM-144

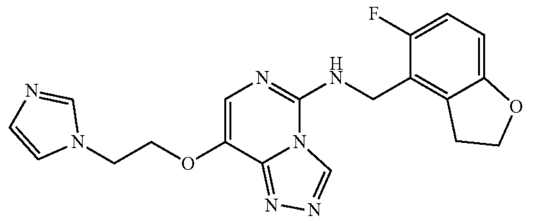

HJM-145

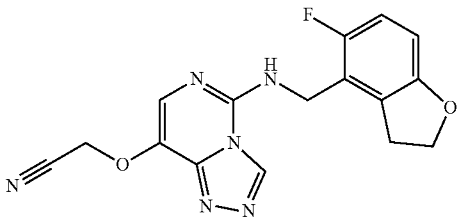

HJM-146

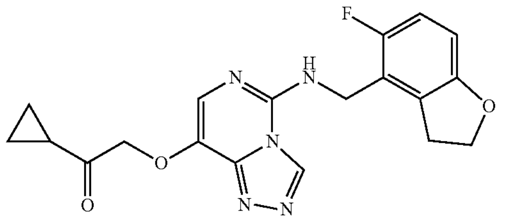

HJM-147

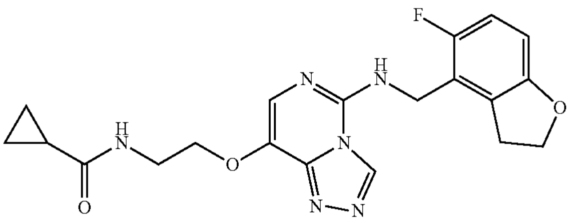

HJM-148

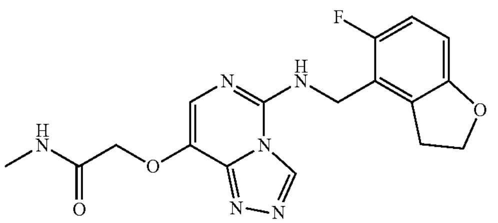

-continued

HJM-149

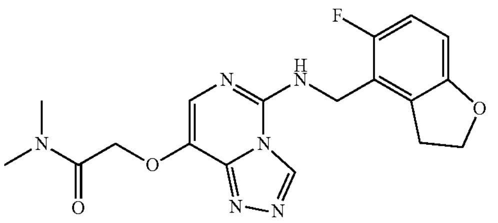

HJM-150

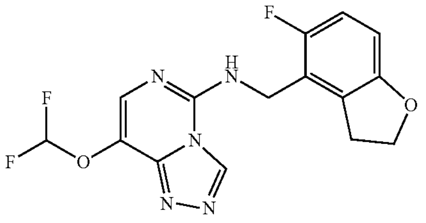

HJM-151

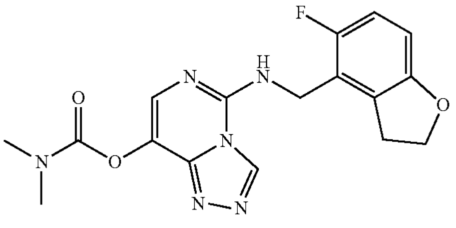

HJM-152

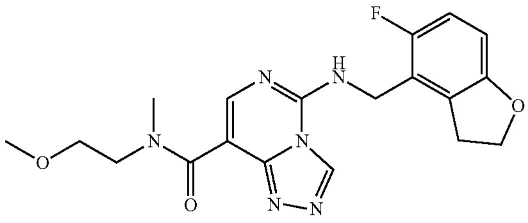

HJM-153

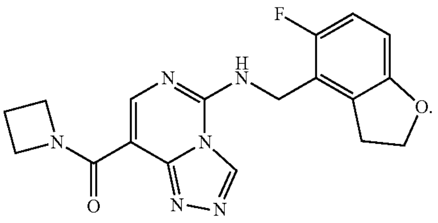

The compounds disclosed herein may include one or more asymmetric centers, and thus may exist in a variety of stereoisomeric forms, for example, enantiomers and/or diastereomers. For example, the compounds disclosed herein may be in the form of an individual enantiomer, diastereomer or geometric isomer (e.g., cis- and trans-isomers), or may be in the form of a mixture of stereoisomers, including racemic mixture and a mixture enriched in one or more stereoisomers. The isomers can be separated from the mixture by the methods known to those skilled in the art, including chiral high pressure liquid chromatography (HPLC) and the formation and crystallization of chiral salts; or alternative isomers can be prepared by asymmetric synthesis.

"Tautomer" refers to an isomer in which one functional group in a compound changes its structure into another functional group, wherein the compound and the isomer can quickly convert between each other, thus being in dynamic equilibrium; this two isomers are called tautomers.

It will be understood by those skilled in the art that the organic compounds can form complexes with solvents in which they are reacted or from which they are precipitated or crystallized. These complexes are known as "solvates." Where the solvent is water, the complex is known as "hydrate." The present disclosure encompasses all solvates of the compounds disclosed herein.

The term "solvate" refers to forms of a compound or a salt thereof, which are associated with a solvent, usually by a solvolysis reaction. This physical association may include hydrogen bonding. Conventional solvents include water, methanol, ethanol, acetic acid, DMSO, THF, diethyl ether, etc. The compounds described herein can be prepared, for example, in crystalline form, and can be solvated. Suitable solvates include pharmaceutically acceptable solvates and further include both stoichiometric solvates and non-stoichiometric solvates. In some cases, the solvates will be capable of isolation, for example, when one or more solvent molecules are incorporated into the crystal lattice of a crystalline solid. "Solvate" includes both solution-phase and isolatable solvates. Representative solvates include hydrates, ethanolates and methanolates.

The term "hydrate" refers to a compound that is associated with water. Generally, the number of water molecules contained in a hydrate of a compound is in a definite ratio to the number of the compound molecules in the hydrate. Therefore, hydrates of a compound can be represented, for example, by a general formula $R \cdot x\ H_2O$, wherein R is the compound, and x is a number greater than 0. Given compounds can form more than one type of hydrates, including, for example, monohydrates (x is 1), lower hydrates (x is a number greater than 0 and smaller than 1, for example, hemihydrates ($R \cdot 0.5H_2O$)) and polyhydrates (x is a number greater than 1, for example, dihydrates ($R \cdot 2H_2O$) and hexahydrates ($R \cdot 6H_2O$)).

Compounds disclosed herein may be in an amorphous or crystalline form (crystal form or polymorph). Furthermore, the compounds disclosed herein may exist in one or more crystalline forms. Therefore, the present disclosure includes all amorphous or crystalline forms of the compounds disclosed herein within its scope. The term "polymorph" refers to a crystalline form of a compound (or a salt, hydrate or solvate thereof) in a particular crystal packing arrangement. All polymorphs have the same elemental composition. Different crystalline forms generally have different X-ray diffraction patterns, infrared spectra, melting points, density, hardness, crystal shapes, optical and electrical properties, stability, and solubility. Recrystallization solvents, rate of crystallization, storage temperatures, and other factors may cause one crystalline form to dominate. Various polymorphs of a compound can be prepared by crystallization under different conditions.

The present disclosure also comprises compounds that are labeled with isotopes, which are equivalent to those described in formula (I), but one or more atoms are replaced by atoms having an atom mass or mass number that are different from that of atoms that are common in nature. Examples of isotopes which may be introduced into the compounds of the disclosure include isotopes of hydrogen, carbon, nitrogen, oxygen, phosphorus, sulfur, fluorine and chlorine, such as $^{2}H$, $^{3}H$, $^{13}C$, $^{11}C$, $^{14}C$, $^{15}N$, $^{18}O$, $^{17}O$, $^{31}P$, $^{32}P$, $^{35}S$, $^{18}F$ and $^{36}Cl$, respectively. Compounds disclosed herein that comprise the above isotopes and/or other isotopes of other atoms, prodrugs thereof and pharmaceutically acceptable salts of said compounds or prodrugs all are within the scope of the present disclosure. Certain isotope-labeled compounds disclosed herein, such as those incorporating radioactive isotopes (e.g., $^{3}H$ and $^{14}C$), can be used for the measurement of the distribution of drug and/or substrate in tissue. Tritium, which is 3H and carbon-14, which is $^{14}C$ isotope, are alternative, because they are easy to prepare and detect. Furthermore, replaced by heavier isotopes, such as deuterium, which is $^{2}H$, may provide therapeutic benefits due to the higher metabolic stability, such as prolonging the half-life in vivo or decreasing the dosage requirements, and thus may be alternative in some cases. Isotope-labeled compounds of formula (I) of the present disclosure and prodrugs thereof can be prepared generally by using readily available isotope-labeled reagents to replace non-isotope-labeled reagents in the following schemes and/or the procedures disclosed in the examples and preparation examples.

In addition, prodrugs are also included within the context of the present disclosure. The term "prodrug" as used herein refers to a compound that is converted in vivo into an active form that has medical effects by, for example, hydrolysis in blood. Pharmaceutically acceptable prodrugs are described in T. Higuchi and V. Stella, Prodrugs as Novel Delivery Systems, A.C.S. Symposium Series, Vol. 14, Edward B. Roche, ed., Bioreversible Carriers in Drug Design, American Pharmaceutical Association and Pergamon Press, 1987, and D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

The prodrugs are any covalently bonded compounds disclosed herein, which release the parent compound in vivo when the prodrug is administered to a patient. Prodrugs are typically prepared by modifying functional groups in such a way that the modifications can be cleaved either by routine manipulation or decompose in vivo to yield the parent compound. Prodrugs include, for example, compounds disclosed herein wherein the hydroxy, amino or sulfhydryl groups are bonded to any group that, when administered to a patient, cleaves to form the hydroxy, amino or sulfhydryl groups. Thus, representative examples of prodrugs include (but are not limited to) the acetate/acetamide, formate/formamide and benzoate/benzamide derivatives of the hydroxy, amino or sulfhydryl functional groups of the compounds of formula (I). Furthermore, in the case of carboxylic acid (—COOH), esters such as methyl esters and ethyl esters, etc. can be employed. The ester itself may be active in their own and/or hydrolyzable under in vivo conditions in the human body. Suitable pharmaceutically acceptable in vivo hydrolysable ester groups include those groups that can readily break down in the human body to release the parent acids or salts thereof.

Pharmaceutical Composition, Formulation, and Kit

In another aspect, the disclosure provides a pharmaceutical composition comprising a compound disclosed herein (also referred to as the "active ingredient") and a pharmaceutically acceptable excipient. In certain embodiments, the pharmaceutical composition comprises an effective amount of the active ingredient. In certain embodiments, the pharmaceutical composition comprises a therapeutically effective amount of the active ingredient. In certain embodiments, the pharmaceutical composition comprises a prophylactically effective amount of the active ingredient.

A pharmaceutically acceptable excipient for use in the present disclosure refers to a non-toxic carrier, adjuvant or vehicle which does not destroy the pharmacological activity of the compound formulated together. Pharmaceutically acceptable carriers, adjuvants, or vehicles that may be used in the compositions of the present disclosure include, but are not limited to, ion exchangers, alumina, aluminum stearate, lecithin, serum proteins (e.g., human serum albumin), buffer substances (such as phosphate), glycine, sorbic acid, potassium sorbate, a mixture of partial glycerides of saturated plant fatty acids, water, salt or electrolyte (such as protamine sulfate), disodium hydrogen phosphate, potassium hydrogen phosphate, sodium chloride, zinc salt, silica gel, magnesium trisilicate, polyvinyl pyrrolidone, cellulose-based materials, polyethylene glycol, sodium carboxymethyl cellulose, polyacrylate, wax, polyethylene-polyoxypropylene block polymers, polyethylene glycol and lanolin.

The present disclosure also includes kits (e.g., pharmaceutical packs). Kits provided may include a compound disclosed herein, other therapeutic agents, and a first and a second containers (e.g., vials, ampoules, bottles, syringes, and/or dispersible packages or other materials) containing the compound disclosed herein or other therapeutic agents. In some embodiments, kits provided can also optionally include a third container containing a pharmaceutically acceptable excipient for diluting or suspending the compound disclosed herein and/or other therapeutic agent. In some embodiments, the compound disclosed herein provided in the first container and the other therapeutic agents provided in the second container is combined to form a unit dosage form.

The pharmaceutical composition provided by the present disclosure may be administered by a variety of routes including, but not limited to, oral administration, parenteral administration, inhalation administration, topical administration, rectal administration, nasal administration, oral mucosal administration, vaginal administration, administration by implant or other means of administration. For example, parenteral administration as used herein includes subcutaneous administration, intradermal administration, intravenous administration, intramuscular administration, intra-articular administration, intraarterial administration, intrasynovial administration, intrasternal administration, intracerebroventricular administration, intralesional administration, and intracranial injection or infusion techniques.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

When used to prevent the disorder disclosed herein, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc., or may be continued indefinitely, for example, for the rest of the subject's life. In certain embodiments, the chronic administration is intended to provide a constant level of the compound in the blood, e.g., within the therapeutic window over the extended period of time.

The pharmaceutical compositions of the present disclosure may be further delivered using a variety of dosing methods. For example, in certain embodiments, the pharmaceutical composition may be given as a bolus, e.g., in order to raise the concentration of the compound in the blood to an effective level rapidly. The placement of the bolus dose depends on the desired systemic levels of the active ingredient, e.g., an intramuscular or subcutaneous bolus dose allows a slow release of the active ingredient, while a bolus delivered directly to the veins (e.g., through an IV drip) allows a much faster delivery which quickly raises the concentration of the active ingredient in the blood to an effective level. In other embodiments, the pharmaceutical composition may be administered as a continuous infusion, e.g., by IV drip, to provide maintenance of a steady-state concentration of the active ingredient in the subject's body. Furthermore, in still yet other embodiments, the pharmaceutical composition may be administered as first as a bolus dose, followed by continuous infusion.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or alternatively from about 1 to about 40% by weight) with the remainder being various vehicles or excipients and processing aids helpful for forming the desired dosing form.

With oral dosing, one to five and especially two to four and typically three oral doses per day are representative regimens. Using these dosing patterns, each dose provides from about 0.01 to about 20 mg/kg of the compound provided herein, with alternative doses each providing from about 0.1 to about 10 mg/kg, and especially about 1 to about 5 mg/kg.

Transdermal doses are generally selected to provide similar or lower blood levels than are achieved using injection doses, generally in an amount ranging from about 0.01 to about 20% by weight, alternatively from about 0.1 to about 20% by weight, alternatively from about 0.1 to about 10% by weight, and yet alternatively from about 0.5 to about 15% by weight.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

Liquid forms suitable for oral administration may include a suitable aqueous or nonaqueous vehicle with buffers, suspending and dispensing agents, colorants, flavours and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavouring agent such as peppermint, methyl salicylate, or orange flavouring.

Injectable compositions are typically based upon injectable sterile saline or phosphate-buffered saline or other injectable excipients known in the art. As before, the active compound in such compositions is typically a minor component, often being from about 0.05 to 10% by weight with the remainder being the injectable excipient and the like.

Transdermal compositions are typically formulated as a topical ointment or cream containing the active ingredient(s). When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or Formulation. All such known transdermal formulations and ingredients are included within the scope provided herein.

The compounds provided herein can also be administered by a transdermal device. Accordingly, transdermal administration may be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pennsylvania, which is incorporated herein by reference.

The compounds disclosed herein can also be administered in sustained release forms or from sustained release drug delivery systems. A description of representative sustained release materials may be found in Remington's Pharmaceutical Sciences.

The present disclosure also relates to the pharmaceutically acceptable formulations of a compound disclosed herein. In one embodiment, the formulation comprises water. In another embodiment, the formulation comprises a cyclodextrin derivative. The most common cyclodextrins are α-, β- and γ-cyclodextrins consisting of 6, 7 and 8 α-1,4-linked glucose units, respectively, optionally comprising one or more substituents on the linked sugar moieties, which include, but are not limited to, methylated, hydroxyalkylated, acylated, and sulfoalkylether substitution. In certain embodiments, the cyclodextrin is a sulfoalkyl ether β-cyclodextrin, e.g., for example, sulfobutyl ether β-cyclodextrin, also known as Captisol. See, e.g., U.S. Pat. No. 5,376,645. In certain embodiments, the formulation comprises hexapropyl-ρ-cyclodextrin (e.g., 10-50% in water).

Indication

Examples of EED- and/or PRC2-mediated diseases or disorders to be treated by the compounds of the present disclosure include, but are not limited to, diffuse Large B-Cell Lymphoma (DLBCL), follicular lymphoma, other lymphomas, leukemia, multiple myeloma, mesothelioma, gastric cancer, malignant rhabdomyoma, liver cancer, prostate cancer, breast cancer, bile duct and gallbladder cancer, bladder cancer, brain tumors (including neuroblastoma, schwannoma, glioma, glioblastoma and astrocytoma), cervical cancer, colon cancer, melanoma, endometrial cancer, esophageal cancer, head and neck cancer, lung cancer, nasopharyngeal cancer, ovarian cancer, pancreatic cancer, renal cell cancer, rectal cancer, thyroid cancer, parathyroid tumor, uterine tumor and soft tissue sarcomas such as rhabdomyosarcoma (RMS), Kaposi's sarcoma, synovial sarcoma, osteosarcoma and Ewing's sarcoma.

In addition, the compounds of the present disclosure can also be used for tumor immunization.

Drug Combination

The compound of the present disclosure can be used in combination with one or more other active ingredients in pharmaceutical compositions or methods to treat the diseases and conditions described herein. Other additional active ingredients include other therapeutic agents or medicines that mitigate adverse effects of the therapeutic agent on the intended disease target. The combination can be used to increase efficacy, improve other disease symptoms, reduce one or more negative effects, or reduce the required dosage of the compound of the present disclosure. The additional active ingredient may be formulated into a pharmaceutical composition separate from the compound of the present disclosure or may be included in a single pharmaceutical composition with the compound of the present disclosure. The additional active ingredient may be administered simultaneously with, before, or after the administration of the compound of the present disclosure.

Common chemotherapeutic agents considered for combination therapy include anastrozole, bicalutamide, bleomycin sulfate, busulfan, busulfan injection, capecitabine, N4-pentoxycarbonyl-5-deoxy-5-fluorocytidine, carboplatin, carmustine, chlorambucil, cisplatin, cladribine, cyclophosphamide, cytarabine, cytosine cytarabine, cytarabine liposome injection, dacarbazine, actinomycin (actinomycin D), daunorubicin hydrochloride, daunorubicin citrate liposome injection, dexamethasone, Docetaxel, doxorubicin hydrochloride, etoposide, fludarabine phosphate, 5-fluorouracil, flutamide, tezacitabine, Gemcitabine (difluorodeoxycytidine), hydroxyurea, idarubicin, ifosfamide, irinotecan, L-asparaginase, calcium leucovorin, melphalan, 6-mercaptopurine, methotrexate, mitoxantrone, mylotarg, paclitaxel, nab-paclitaxel, Phoenix (Yttrium90/MX-DTPA), pentostatin, carmustine implants with polybenzamide 20 as carrier, tamoxifen citrate, teniposide, 6-thioguanine, thiatepa, tirapazamine, topotecan hydrochloride for injection, vinblastine, vincristine and vinorelbine.

In addition, the compounds of the present disclosure can be used in combination with immune checkpoint inhibitors.

The present disclosure provides a method of treating a disease or condition mediated by EED and/or PRC2, comprising administering to a patient in need thereof a therapeutically effective amount of a first therapeutic agent and optionally a second therapeutic agent, wherein the first therapeutic agent is an EED inhibitor, and the second therapeutic agent is another type of therapeutic agent, wherein the disease or disorder is selected from diffuse large B-cell lymphoma (DLBCL), follicular lymphoma, other lymphomas, leukemia, multiple myeloma, gastric cancer, malignant rhabdomyoma and liver cancer.

DETAILED DESCRIPTION

The present disclosure is further described below in combination with specific examples, but the present disclosure is not limited to these examples.

EXAMPLES

Preparation of Compound of Formula (I)

The present disclosure also provides the preparation method of a compound as shown in formula (I) and an intermediate thereof, the method comprising:

Scheme 1

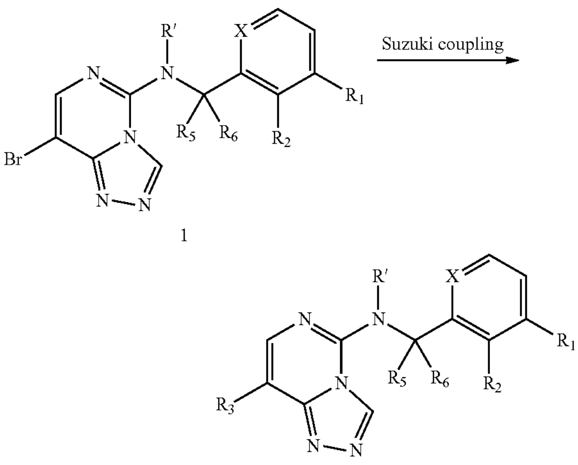

1

2

The target product 2 was afforded by Suzuki coupling reaction of bromide 1 with various boric acids with $R_3$ groups or their equivalents under the action of palladium catalyst.

In the Scheme, the definition of each group was the same as above.

Scheme 2

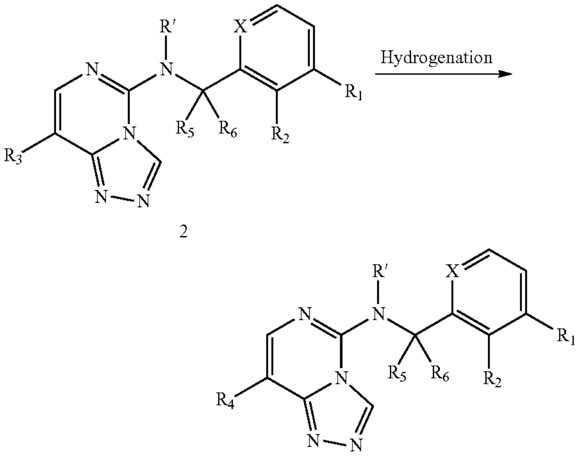

2

3

Compound 1 or compound 2 afforded from scheme 1 was dissolved in a solvent, such as but not limited to methanol, ethanol or tetrahydrofuran. A metal catalyst such as but not limited to 10% palladium/carbon, $Pd(OH)_2$ or $Al_2O_3$ was added. Hydrogen gas was introduced. The mixture was reacted at room temperature or under heating condition to afford the target product 3 in which the double bond was reduced.

In the Scheme, $R_4$ was the group in which the double bond in the $R_3$ group was reduced, and the definitions of other groups were the same as above.

Scheme 3

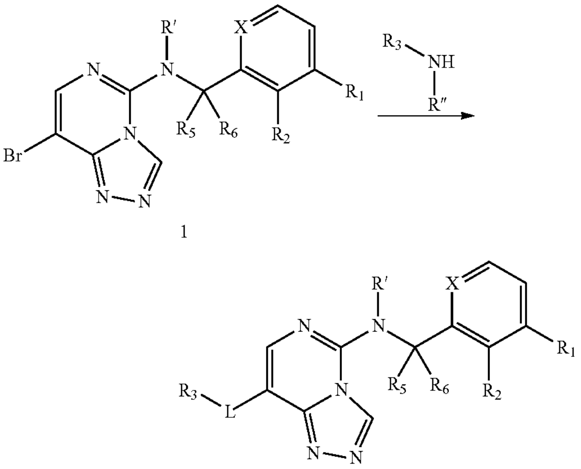

1

10

The bromide 1 was directly substituted by the amine $R_3R''NH$ to afford target product 10.

In the Scheme, L was N(R''), and the definitions of other groups were the same as above.

Scheme 4

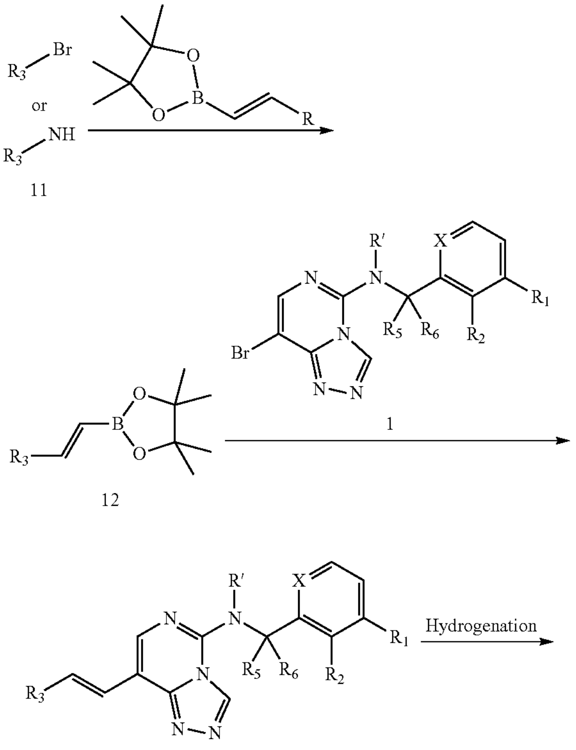

11

1

12

13

-continued

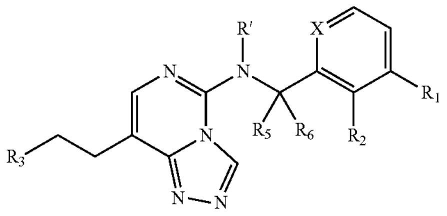

14

Firstly, halide or amine 11 was reacted with substituted or unsubstituted pinacol vinylboronate to afford borate ester 12; then, borate ester 12 was subjected to Suzuki reaction with bromide 1 to afford alkene 13; and finally, alkene 13 was hydrogenated to afford the target product 14 in which the double bond was reduced.

In the Scheme, the definition of each group was the same as above.

Scheme 5

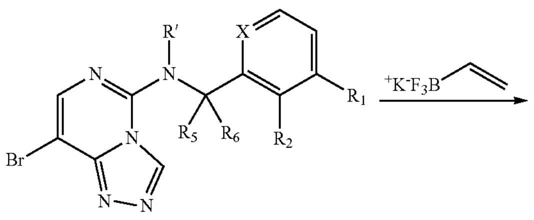

1

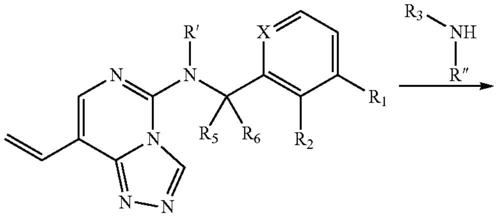

15

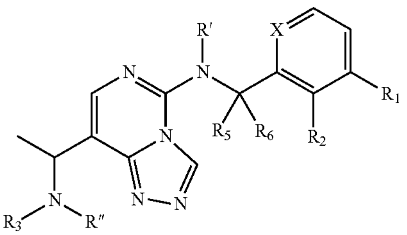

16

Firstly, bromide 1 was reacted with potassium vinyl trifluoroborate to afford alkene compound 15; and then alkene 15 was subjected to addition reaction with amine $R_3R''NH$ to afford target product 16.

In the Scheme, the definition of each group was the same as above.

Scheme 6

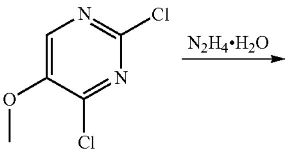

17

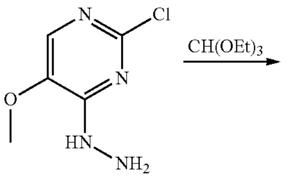

18

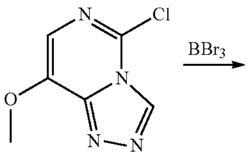

19

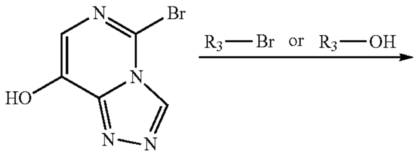

20

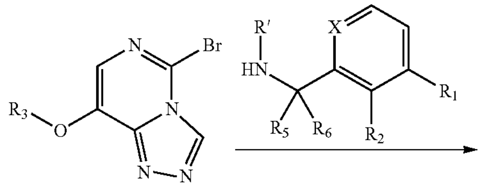

21

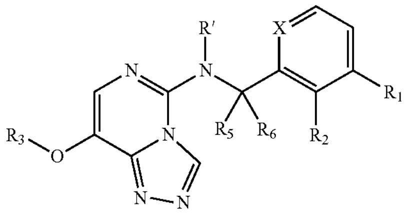

22

Firstly, 2,4-dichloro-5-methoxypyrimidine 17 was reacted with hydrazine hydrate to afford compound 18, and compound 18 was converted into triazole product 19 using triethyl orthoformate; then, boron tribromide was demethylated to afford compound 20, and compound 20 was subjected to substitution reaction with bromide $R_3Br$ or subjected to Mitusunobu reaction with alcohol $R_3OH$ to afford compound 21; and finally, triazole product 21 was substituted by amine to afford product 22.

In the Scheme, the definition of each group was the same as above.

Scheme 7

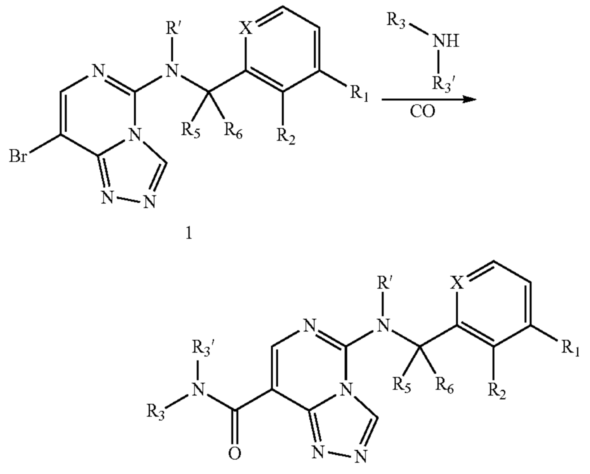

1

23

Bromide 1 was subjected to carbonyl insertion reaction with amine $R_3R_3$'NH in the presence of carbon monoxide to afford the target product 23.

In the Scheme, the definition of each group was the same as above.

Scheme 8

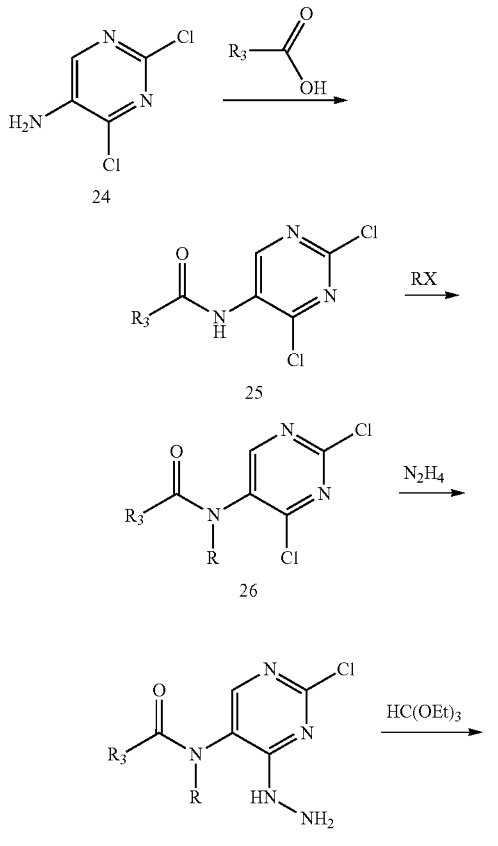

24

25

26

27

-continued

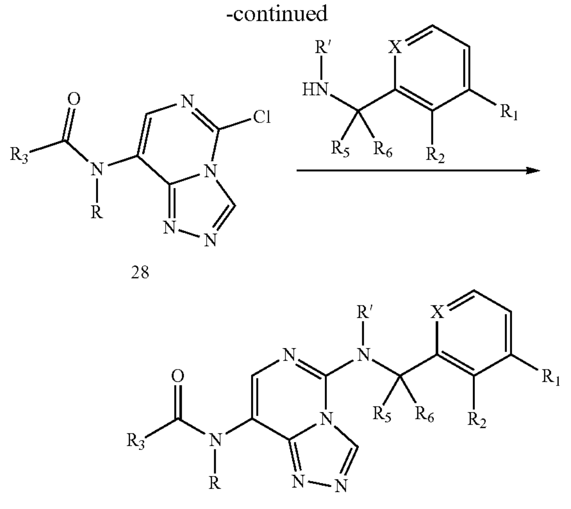

28

29

5-Amino-2,4-dichloropyrimidine 24 was condensed with carboxylic acid $R_3COOH$ in the presence of phosphorus oxychloride to afford compound 25, and compound 25 was subjected to substitution reaction with halide RX to afford substituted amide 26 (this step was not necessary); then, the amide compound 26 was treated with hydrazine hydrate to afford compound 27; compound 27 was then converted into triazole product 28 using triethyl orthoformate; and finally, triazole product 28 was substituted by amine to afford target product 29.

In the Scheme, the definition of each group was the same as above.

Scheme 9

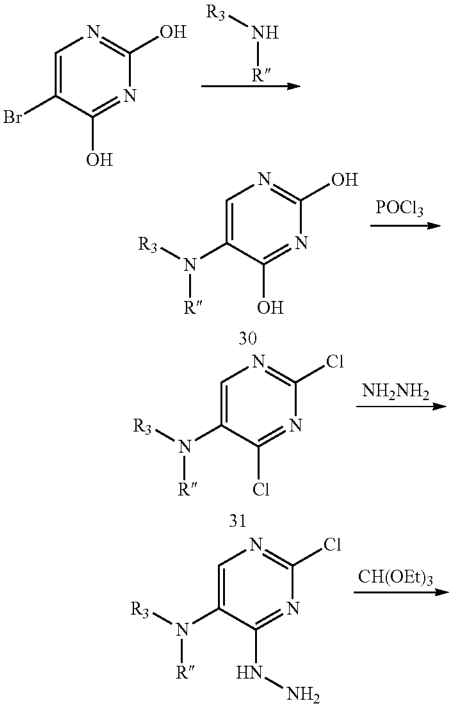

30

31

32

-continued

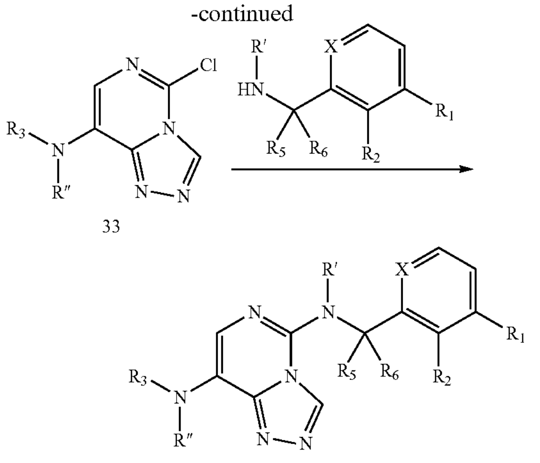

33

34

5-Bromouracil was reacted with amine $R_3R''NH$ to afford amino compound 30, and the amino compound 30 was treated with phosphorus oxychloride to afford compound 31; then, compound 31 was treated with hydrazine hydrate to afford compound 32, and compound 32 was converted into triazole product 33 using triethyl orthoformate; and finally, the triazole product 33 was substituted by amine to afford the target product 34.

In the Scheme, the definition of each group was the same as above.

All raw materials in Schemes 1 to 9 can be purchased from reagent companies or prepared according to conventional literature.

EXAMPLES OF COMPOUND PREPARATION

Preparation Example 1: Synthesis of Compound HJM-001

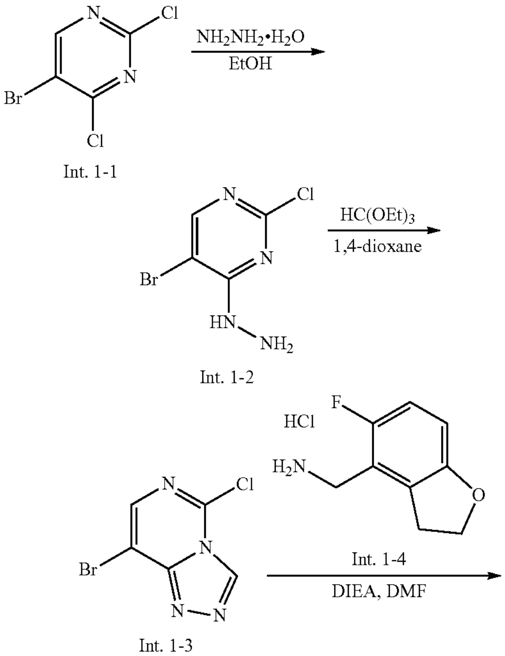

Int. 1-1

Int. 1-2

Int. 1-3

-continued

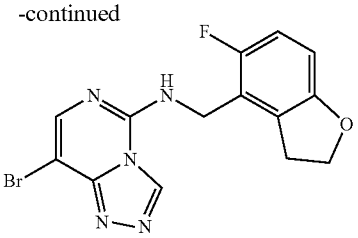

1

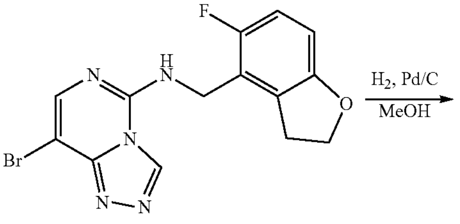

1

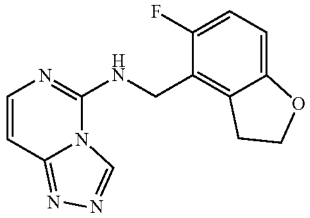

HJM-001

Step 1:

At room temperature, 5-bromo-2,4-dichloropyrimidine Int.1-1 (115 g, 504.66 mmol, 64.61 mL) was dissolved in EtOH (800 mL), then hydrazine hydrate (purity: 85%, 51.50 g, 874.45 mmol, 50 mL) was added, and the mixture was reacted with stirring at room temperature for 10 h. The mixture was filtered and the filter cake was washed with ethanol (3×800 mL) for three times. The resulting solid was dried in vacuum to afford compound 5-bromo-2-chloro-4-hydrazinylpyrimidine Int.1-2 (230 g, crude) as a white solid. The crude product was directly used in the next step.

Step 2:

At room temperature, 5-bromo-2-chloro-4-hydrazinylpyrimidine Int.1-2 (124 g, 554.91 mmol) was dissolved in dioxane (1 L) solvent, triethyl orthoformate (131.58 g, 887.86 mmol, 147.68 mL) was added, and the mixture was reacted with stirring at 75° C. for 2 h. Raw materials were completely reacted. The mixture was cooled to room temperature, and filtered. The filtrate was concentrated to afford a crude product. The crude product was purified by silica gel column chromatography (petroleum ether:ethyl acetate (V/V)=5:1-1:1) to afford compound 8-bromo-5-chloro-[1,2,4]triazolo[4,3-c]pyrimidine Int.1-3 (43 g, yield: 33.2%).

$^1H$ NMR (400 MHz, DMSO-$d_6$) δ 9.68 (s, 1H), 8.24 (s, 1H).

Step 3:

At room temperature, 8-bromo-5-chloro-[1,2,4]triazolo[4,3-c]pyrimidine Int.1-3 (2.00 g, 8.57 mmol) and (5-fluoro-2,3-dihydrobenzofuran-4-yl)methylamine Int.1-4 hydrochloride (1.92 g, 9.42 mmol) were added successively to N,N-dimethylformamide (15 mL), then N,N-diisopropylethylamine (3.32 g, 25.70 mmol, 4.48 mL) was added, and the mixture was reacted with stirring at 85° C. for 0.5 h. The mixture was cooled to room temperature, diluted with water (80 mL), and extracted with ethyl acetate (2×50 mL) for two times. The organic phases were combined. The organic phase was washed twice with water (2×50 mL) and once with saturated brine (50 mL), dried with anhydrous sodium sulfate, and filtered. The filtrate was concentrated to afford a crude product. The crude product was slurried with petroleum ether and ethyl acetate (20:1, 60 mL), and filtered to afford compound 8-bromo-N-((5-fluoro-2,3-dihydrobenzofuran-4-yl)methyl)-[1,2,4]triazolo[4,3-c]pyrimidine-5-amine 1 (2.50 g, yield: 80.1%).

$^1$H NMR (400 MHz, DMSO-$d_6$) δ 9.46 (s, 1H), 8.73 (br s, 1H), 7.84 (s, 1H), 6.92 (d, J=10.0 Hz, 1H), 6.69 (dd, J=3.9, 8.6 Hz, 1H), 4.64 (s, 2H), 4.52 (t, J=8.8 Hz, 2H), 3.26 (t, J=8.7 Hz, 2H).

Step 4:

8-Bromo-N-((5-fluoro-2,3-dihydrobenzofuran-4-yl)methyl)-[1,2,4]triazolo[4,3-c]pyrimidine-5-amine 1 (50 mg, 0.14 mmol) was dissolved in 20 mL of methanol, and the atmosphere was replaced with $N_2$. 10 mg of 10% Pd/C was added quickly, and the atmosphere was replaced with $H_2$. The mixture was reacted at room temperature under a hydrogen balloon for 2 days. The mixture was filtered, and the filter cake was washed twice with methanol. The filtrates were combined, concentrated, and purified by preparative HPLC to afford HJM-001 (13 mg, yield: 33.3%) as a yellow solid.

$^1$H NMR (400 MHz, DMSO-$d_6$) δ 9.40 (s, 1H), 8.62 (s, 1H), 7.68 (t, J=6.8 Hz, 1H), 7.04-6.81 (m, 2H), 6.71 (dd, J=8.8, 4.0 Hz, 1H), 4.68 (d, J=4.0 Hz, 2H), 4.54 (t, J=8.8 Hz, 2H), 3.28 (t, J=8.8 Hz, 2H). LCMS $[M+H]^+$=286.2.

Preparation Example 2: Synthesis of Compound HJM-002

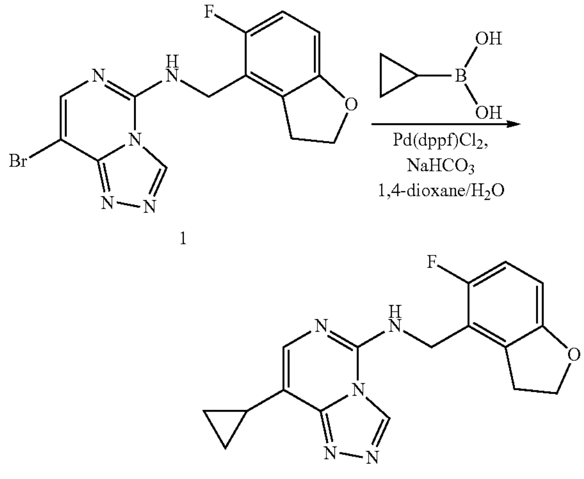

1

HJM-002

Under Ar protection, 8-bromo-N-((5-fluoro-2,3-dihydrobenzofuran-4-yl)methyl)-[1,2,4]triazolo[4,3-c]pyrimidine-5-amine 1 (300 mg, 0.83 mmol), cyclopropylboronic acid (710 mg, 8.26 mmol) and $NaHCO_3$ (264 mg, 2.49 mmol) were dissolved in 18 mL of a mixture of 1,4-dioxane and water (5:1), 1,1'-bis(diphenylphosphino)ferrocene-palladium(II)dichloride dichloromethane complex (59 mg, 0.08 mmol) was added at room temperature, and the mixture was heated to 100° C. and reacted for 16 h. TLC showed that the reaction was completed. The mixture was stopped from heating, naturally cooled to room temperature, and concentrated under reduced pressure. The residue was purified by preparative HPLC to afford HJM-002 (3.0 mg, yield: 1.1%) as a white solid.

$^1$H NMR (400 MHz, $CD_3OD$) δ 9.24 (s, 1H), 7.44 (d, J=0.8 Hz, 1H), 6.87-6.80 (m, 1H), 6.66-6.58 (m, 1H), 4.72 (s, 2H), 4.59-4.51 (m, 2H), 3.35-3.32 (m, 2H), 2.12-2.02 (m, 1H), 1.01-0.94 (m, 2H), 0.87-0.81 (m, 2H). LCMS $[M+H]^+$=326.3.

Preparation Example 3: Synthesis of Compound HJM-003

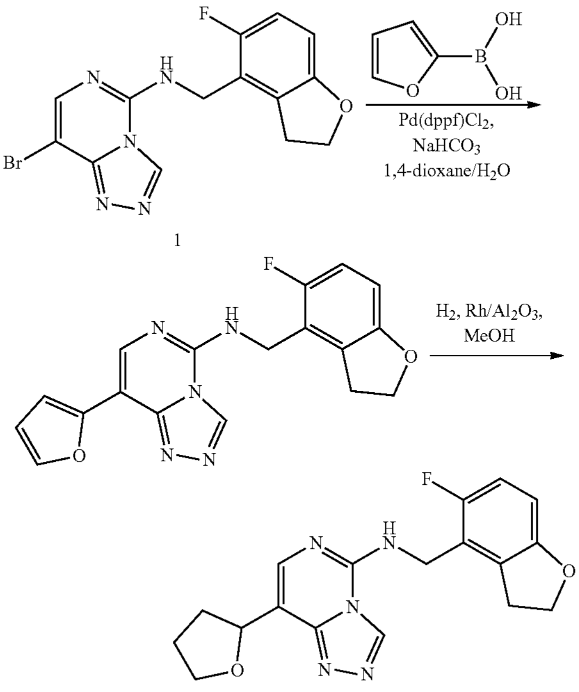

1

HJM-003

Step 1:

Under Ar protection, 8-bromo-N-((5-fluoro-2,3-dihydrobenzofuran-4-yl)methyl)-[1,2,4]triazolo[4,3-c]pyrimidine-5-amine 1 (400 mg, 1.09 mmol), furan-2-boric acid (123 mg, 1.09 mmol) and $NaHCO_3$ (369 mg, 4.39 mmol) were dissolved in a mixture (13 mL) of 1,4-dioxane and water (10:3), 1,1'-bis(diphenylphosphino)ferrocene-palladium(II)dichloride dichloromethane complex (86 mg, 0.11 mmol) was added at room temperature, and the mixture was heated to 105° C. and reacted for 2 h. TLC showed that the reaction was completed. The mixture was stopped from heating, naturally cooled to room temperature, and concentrated under reduced pressure. The residue was purified by silica gel column chromatography (DCM:MeOH=20:1) to afford N-((5-fluoro-2,3-dihydrobenzofuran-4-yl)methyl)-8-(furan-2-yl)-[1,2,4]triazolo[4,3-c]pyrimidin-5-amine (150 mg, yield: 39.0%) as a yellow solid, LCMS $[M+H]^+$=352.1.

Step 2:

Compound N-((5-fluoro-2,3-dihydrobenzofuran-4-yl)methyl)-8-(furan-2-yl)-[1,2,4]triazolo[4,3-c]pyrimidin-5-amine (150 mg, 0.42 mmol) was dissolved in methanol (10 mL), and the atmosphere was replaced with $N_2$. 30 mg of $Rh/Al_2O_3$ was added quickly, and the atmosphere was replaced with $H_2$ for three times. The mixture was heated to 40° C. and reacted under a hydrogen balloon for 3 days. The mixture was filtered, and the filter cake was washed twice with methanol. The filtrates were combined, concentrated, and purified by preparative HPLC to afford HJM-003 (12 mg, yield: 8.0%) as a yellow solid.

$^1$H NMR (400 MHz, $CD_3OD$) δ 9.32 (s, 1H), 7.89 (s, 1H), 8.87-8.82 (m, 1H), 6.66-6.62 (m, 1H), 5.16-5.14 (m, 1H), 4.78 (s, 2H), 4.57 (t, J=8.8 Hz, 2H), 4.15-4.14 (m, 1H), 3.94-3.92 (m, 1H), 3.37-3.35 (m, 2H), 2.42-2.41 (m, 1H), 2.10-2.04 (m, 3H). LCMS $[M+H]^+$=356.1.

Preparation Example 4: Synthesis of Compound HJM-004

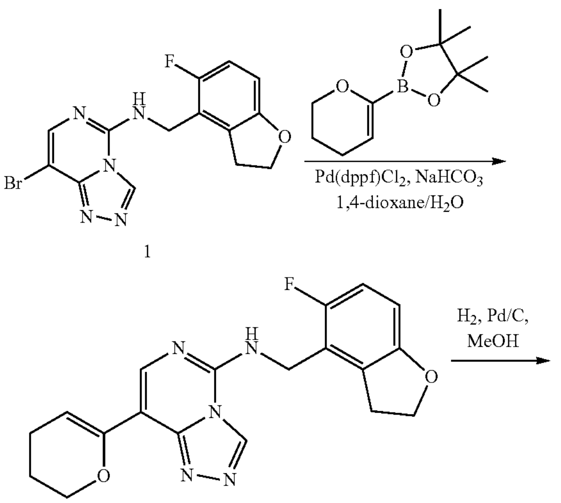

1

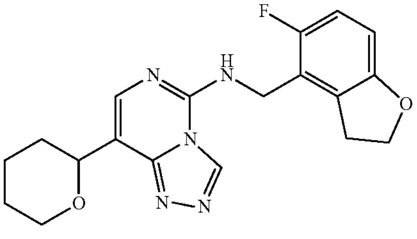

HJM-004

Compound N-((5-fluoro-2,3-dihydrobenzofuran-4-yl)methyl)-8-(tetrahydro-2H-pyran-2-yl)-[1,2,4]triazolo[4,3-c]pyrimidin-5-amine HJM-004 (9 mg, yield: 9.9%) was prepared as a white solid using 3,4-dihydro-2H-pyran-6-boronic acid pinacol ester as starting material according to the method similar to that for preparation example 3.

$^1$H NMR (400 MHz, DMSO-$d_6$) δ 9.41 (s, 1H), 8.57 (d, J=4.4 Hz, 1H), 7.62 (s, 1H), 6.96-6.91 (m, 1H), 6.71-6.68 (m, 1H), 4.66-4.63 (m, 3H), 4.55-4.51 (m, 2H), 4.04 (d, J=12.0 Hz, 1H), 3.60-3.56 (m, 1H), 3.30-3.26 (m, 2H), 2.03-2.01 (m, 1H), 1.88-1.87 (m, 1H), 1.69-1.57 (m, 4H). LCMS $[M+H]^+$=370.2.

Preparation Example 5: Synthesis of Compound HJM-005

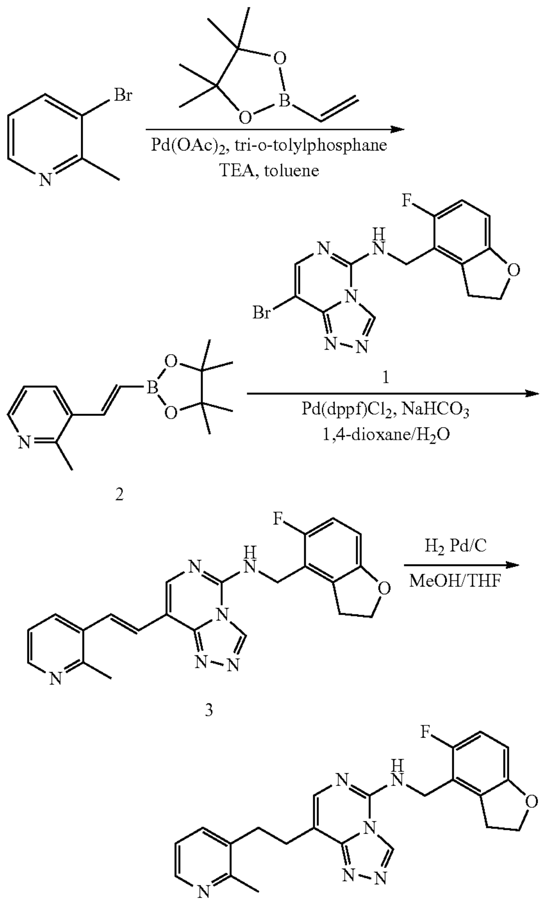

1

2

3

HJM-005

Step 1:

Under $N_2$ protection, 3-bromo-2-methylpyridine (1.0 g, 5.84 mmol), pinacol vinylboronate (2 mL, 11.7 mmol) and triethylamine (2.4 mL, 17.52 mmol) were dissolved in toluene (20 mL), and palladium acetate (129 mg, 0.58 mmol) and tris(o-methylphenyl)phosphine (176 mg, 0.58 mmol) were added at room temperature. The atmosphere was replaced three times with $N_2$, and the mixture was heated to 100° C. and reacted for 18 h. TLC showed that the reaction was completed. The mixture was stopped from heating, naturally cooled to room temperature, and concentrated under reduced pressure. The residue was purified by silica gel column chromatography (PE:EA=5:1) to afford brownish yellow liquid 2 (500 mg, yield: 35.0%), LCMS $[M+H]^+$=246.4.

Step 2:

Under $N_2$ protection, 8-bromo-N-((5-fluoro-2,3-dihydrobenzofuran-4-yl)methyl)-[1,2,4]triazolo[4,3-c]pyrimidine-5-amine 1 (200 mg, 0.55 mmol), pinacol borate 2 (405 mg, 1.65 mmol) and $NaHCO_3$ (292 mg, 2.75 mmol) were dissolved in a mixture (8 mL) of 1,4-dioxane and water (3:1), 1,1'-bis(diphenylphosphino)ferrocene-palladium(II) dichloride dichloromethane complex (36 mg, 0.05 mmol) was added at room temperature, and the mixture was heated to 100° C. and reacted for 2 h. TLC showed that the reaction was completed. The mixture was stopped from heating, naturally cooled to room temperature, and concentrated under reduced pressure. The residue was purified by silica gel column chromatography (DCM:MeOH=20:1) to afford 3 (150 mg, yield: 90.1%) as a white solid, LCMS $[M+H]^+$ =403.4.

Step 3:

Compound 3 (150 mg, 0.372 mmol) was dissolved in a mixture of tetrahydrofuran (30 mL) and methanol (30 mL), and the atmosphere was replaced with $N_2$. 30.0 mg of 10% Pd/C was added quickly, the atmosphere was replaced with $H_2$, and the mixture was stirred at room temperature under a hydrogen balloon for 2 h. The mixture was filtered, and the filter cake was washed twice with methanol. The filtrates were combined, concentrated, and purified by preparative HPLC to afford HJM-005 (29.0 mg, yield: 19.2%) as a white solid.

$^1$H NMR (400 MHz, DMSO-$d_6$) δ 9.44 (s, 1H), 8.66 (dd, J=5.6, 1.2 Hz, 1H), 8.56 (s, 1H), 8.29 (d, J=8.0 Hz, 1H), 7.80 (d, J=7.6, 6.0 Hz, 1H), 7.50 (s, 1H), 7.01-6.88 (m, 1H), 6.70 (dd, J=8.8, 4.0 Hz, 1H), 4.65 (s, 2H), 4.54 (t, J=8.8 Hz, 2H), 3.31-3.16 (m, 4H), 3.11-3.00 (m, 2H), 2.77 (s, 3H). LCMS $[M+H]^+$=405.2.

Preparation Example 6: Synthesis of Compound HJM-006

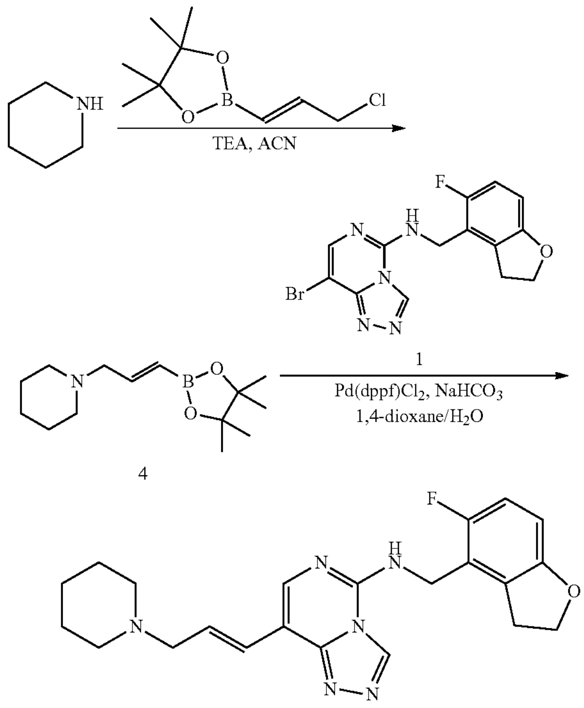

HJM-006

Step 1:

Under $N_2$ protection, piperidine (0.18 mL, 1.98 mmol) and triethylamine (0.27 mL, 1.98 mmol) were dissolved in acetonitrile (3 mL), 3-chloropropenyl-1-boric acid pinacol ester (200 mg, 0.99 mmol) was added at room temperature, the atmosphere was replaced three times with $N_2$, and the mixture was stirred at room temperature overnight. TLC showed that the reaction was completed. The mixture was concentrated under reduced pressure to afford crude product 4 (400 mg, quantitative yield), which was directly used in the next step without purification. LCMS $[M+H]^+$=252.3.

Step 2:

Under $N_2$ protection, pinacol borate 4 (205 mg, crude), 8-bromo-N-((5-fluoro-2,3-dihydrobenzofuran-4-yl) methyl)-[1,2,4]triazolo[4,3-c]pyrimidine-5-amine 1 (150 mg, 0.41 mmol) and $NaHCO_3$ (131 mg, 1.24 mmol) were dissolved in a mixture (8 mL) of 1,4-dioxane and water, 1,1'-bis(diphenylphosphino)ferrocene-palladium(II)dichloride dichloromethane complex (30 mg, 0.04 mmol) was added at room temperature, and the mixture was heated to 100° C. and reacted for 2 h. TLC showed that the reaction was completed. The mixture was stopped from heating, naturally cooled to room temperature, and concentrated under reduced pressure. The residue was purified by preparative HPLC to afford HJM-006 (70 mg, yield: 41.9%) as a brown viscous solid.

$^1$H NMR (400 MHz, DMSO-$d_6$) δ 9.53 (s, 1H), 8.98 (s, 1H), 7.80 (s, 1H), 7.13-7.02 (m, 1H), 6.98-6.91 (m, 1H), 6.85 (d, J=15.6 Hz, 1H), 6.71 (dd, J=8.8, 4.0 Hz, 1H), 4.73 (s, 2H), 4.55 (t, J=8.8 Hz, 2H), 3.99-3.87 (m, 2H), 3.46 (d, J=11.6 Hz, 2H), 3.29 (t, J=8.8 Hz, 2H), 2.97-2.82 (m, 2H), 1.92-1.78 (m, 2H), 1.77-1.57 (m, 3H), 1.48-1.30 (m, 1H). LCMS $[M+H]^+$=409.6.

Preparation Example 7: Synthesis of Compound HJM-007

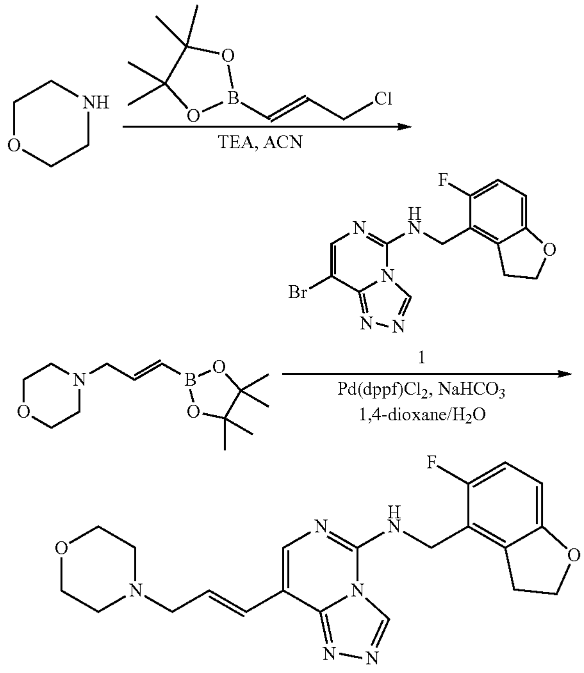

HJM-007

HJM-007 (30 mg, yield: 26.3%) was prepared as a white solid using morpholine as starting material according to the method similar to that for preparation example 6.

$^1$H NMR (400 MHz, DMSO-$d_6$) δ 9.44 (s, 1H), 8.66 (t, J=5.2 Hz, 1H), 7.68 (s, 1H), 7.15-7.00 (m, 1H), 6.99-6.90 (m, 1H), 6.70 (dd, J=8.8, 4.0 Hz, 1H), 6.57 (d, J=15.6 Hz, 1H), 4.69 (d, J=4.8 Hz, 2H), 4.53 (t, J=8.8 Hz, 2H), 3.63-3.56 (m, 4H), 3.26 (t, J=8.8 Hz, 2H), 3.15 (d, J=6.4 Hz, 2H), 2.43 (s, 4H). LCMS $[M+H]^+$=411.2.

Preparation Example 8: Synthesis of Compound HJM-008

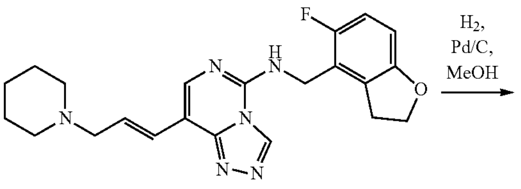

HJM-006

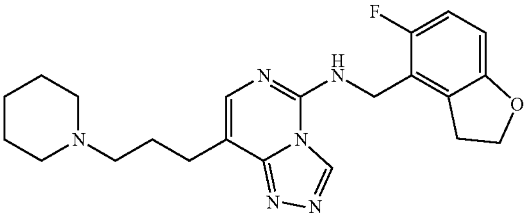

HJM-008

Compound HJM-006 (60 mg, 0.15 mmol) was dissolved in methanol (6 mL), and the atmosphere was replaced with $N_2$. 10.0 mg of 10% Pd/C was added quickly, the atmosphere was replaced with $H_2$, and the mixture was stirred at room temperature under a hydrogen balloon for 2 h. The mixture was filtered, and the filter cake was washed twice with methanol. The filtrates were combined, concentrated, and purified by preparative HPLC to afford HJM-008 (4.2 mg, yield: 7.0%) as a white solid.

$^1$H NMR (400 MHz, $CD_3OD$) δ 9.27 (s, 1H), 7.61 (s, 1H), 6.84 (t, J=9.6 Hz, 1H), 6.63 (dd, J=8.8, 4.0 Hz, 1H), 4.74 (s, 2H), 4.57 (t, J=8.8 Hz, 2H), 3.36 (t, J=8.8 Hz, 2H), 3.33-3.31 (m, 4H), 3.15-3.09 (m, 2H), 2.88 (t, J=7.2 Hz, 2H), 2.23-2.11 (m, 2H), 1.95-1.51 (m, 6H). LCMS $[M+H]^+$=411.4.

Preparation Example 9: Synthesis of Compound HJM-009

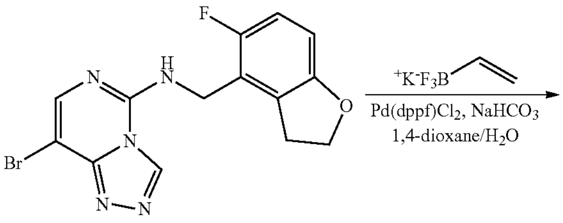

1

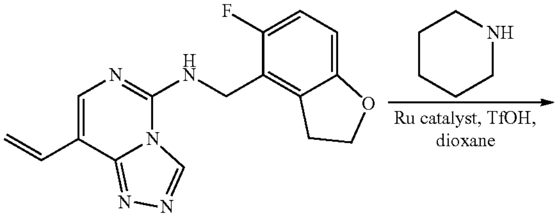

5

-continued

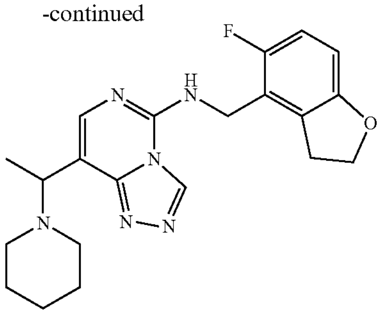

HJM-009

Step 1:

Under $N_2$ protection, 8-bromo-N-((5-fluoro-2,3-dihydrobenzofuran-4-yl)methyl)-[1,2,4]triazolo[4,3-c]pyrimidine-5-amine 1 (200 mg, 0.55 mmol), potassium vinyl trifluoroborate (148 mg, 1.10) and $NaHCO_3$ (175 mg, 1.65 mmol) were dissolved in a mixture (12 mL) of 1,4-dioxane and water (3:1), 1,1'-bis(diphenylphosphino)ferrocene-palladium(II)dichloride dichloromethane complex (37 mg, 0.05 mmol) was added at room temperature, and the mixture was heated to 100° C. and reacted for 2 h. TLC showed that the reaction was completed. The mixture was stopped from heating, naturally cooled to room temperature, and concentrated under reduced pressure. The residue was purified by silica gel column chromatography (DCM:MeOH=50:1) to afford 5 (150 mg, yield: 87.7%) as a yellow solid, LCMS $[M+H]^+$=312.3.

Step 2:

Under Ar protection, compound 5 (50 mg, 0.16 mmol) and piperidine (0.03 mL, 0.32 mmol) were dissolved in 1,4-dioxane (3 mL). Bis-(2-methylallyl)cyclooctyl-1,5-diene ruthenium (3 mg, 0.01 mmol), 1,5-bis(diphenylphosphino)pentane (4 mg, 0.01 mmol) and trifluoromethanesulfonic acid (0.01 mL) were added at room temperature, and the mixture was heated to 100° C. and reacted for 16 h. TLC showed that the reaction was completed. The mixture was stopped from heating, naturally cooled to room temperature, and concentrated under reduced pressure. The residue was purified by preparative HPLC to afford HJM-009 (6.0 mg, yield: 9.5%) as a white solid.

$^1$H NMR (400 MHz, DMSO-$d_6$) δ 9.39 (s, 1H), 8.49 (t, J=4.8 Hz, 1H), 7.57 (s, 1H), 7.03-6.85 (m, 1H), 6.76-6.64 (m, 1H), 4.65 (d, J=4.8 Hz, 2H), 4.55 (t, J=8.8 Hz, 2H), 4.08-4.00 (m, 1H), 3.34-3.26 (m, 6H), 1.52-1.45 (m, 7H), 1.37-1.27 (m, 2H). LCMS $[M+H]^+$=397.4.

Preparation Example 10: Synthesis of Compound HJM-010

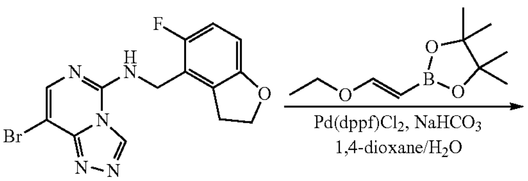

1

-continued

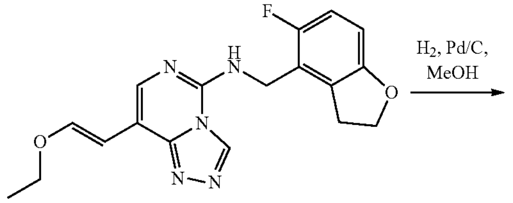

6

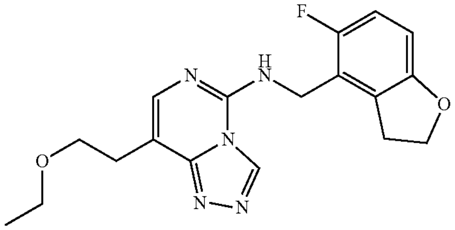

HJM-010

Step 1:

Under $N_2$ protection, 8-bromo-N-((5-fluoro-2,3-dihydrobenzofuran-4-yl)methyl)-[1,2,4]triazolo[4,3-c]pyrimidine-5-amine 1 (200 mg, 0.55 mmol), (E)-1-ethoxyvinyl-2-boronic acid pinacol ester (109 mg, 0.55 mmol) and $NaHCO_3$ (140 mg, 1.667 mmol) were dissolved in a mixture (10 mL) of 1,4-dioxane and water (4:1), 1,1'-bis(diphenylphosphino)ferrocene-palladium(II)dichloride dichloromethane complex (60 mg, 0.081 mmol) was added at room temperature, and the mixture was heated to 100° C. and reacted for 8 h. TLC showed that the reaction was completed. The mixture was stopped from heating, and naturally cooled to room temperature. Water and ethyl acetate were added, and the mixture was layered. The aqueous phase was extracted with ethyl acetate (2×20 mL). The organic phases were combined, and then washed successively with water (2×20 mL) and saturated brine. The organic layer was dried with $Na_2SO_4$, filtered, and concentrated. The residue was purified by silica gel column chromatography (DCM:MeOH=100:1) to afford 6 (50 mg, yield: 24.9%) as a yellow solid, LCMS $[M+H]^+$=356.1.

Step 2:

Compound 6 (50 mg, 0.14 mmol) was dissolved in methanol (10 mL), and the atmosphere was replaced with $N_2$. 50.0 mg of 10% Pd/C was added quickly, the atmosphere was replaced with $H_2$, and the mixture was stirred at room temperature under a hydrogen balloon for 6 h. The mixture was filtered, and the filter cake was washed twice with methanol. The filtrates were combined, concentrated, and purified by preparative HPLC to afford HJM-010 (7.0 mg, yield: 14.1%) as a yellow solid.

$^1H$ NMR (400 MHz, $CD_3OD$) δ 9.27 (s, 1H), 7.71 (s, 1H), 6.85-6.83 (d, J=9.6 Hz, 1H), 6.66-6.63 (m, 1H), 4.76 (s, 2H), 4.59-4.55 (m, 2H), 3.78-3.75 (m, 2H), 3.53-3.48 (m, 2H), 3.37-3.35 (m, 2H), 3.06-3.03 (m, 2H), 1.13-1.12 (m, 3H). LCMS $[M+H]^+$=358.4.

Preparation Example 11: Synthesis of Compound HJM-011

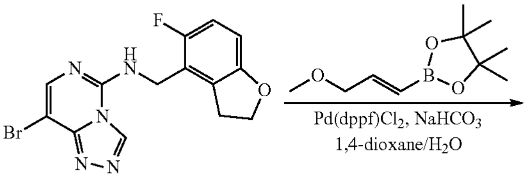

1

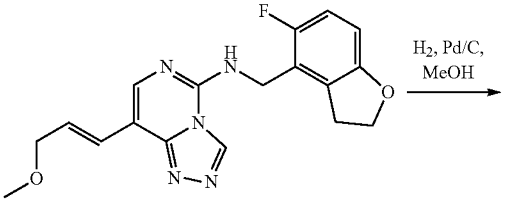

6

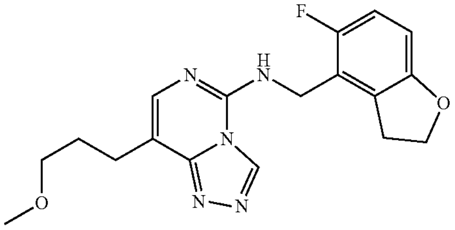

HJM-011

HJM-011 (90 mg, yield: 64.3%) was prepared as a yellow solid using trans-3-methoxy-1-propenylboronic acid pinacol ester as starting material according to the method similar to that for preparation example 10.

$^1H$ NMR (400 MHz, $CD_3OD$) δ 9.23 (s, 1H), 7.53 (s, 1H), 6.84-6.81 (d, J=9.2 Hz, 1H), 6.64-6.61 (m, 1H), 4.73 (s, 2H), 4.58-4.54 (m, 2H), 3.46-3.43 (m, 2H), 3.35-3.30 (m, 5H), 2.87-2.84 (m, 2H), 2.00-1.97 (m, 2H). LCMS: $[M+H]^+$=358.4.

Preparation Example 12: Synthesis of Compound HJM-012

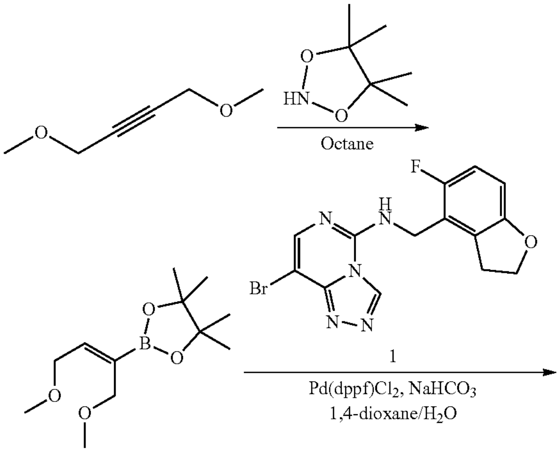

7

-continued

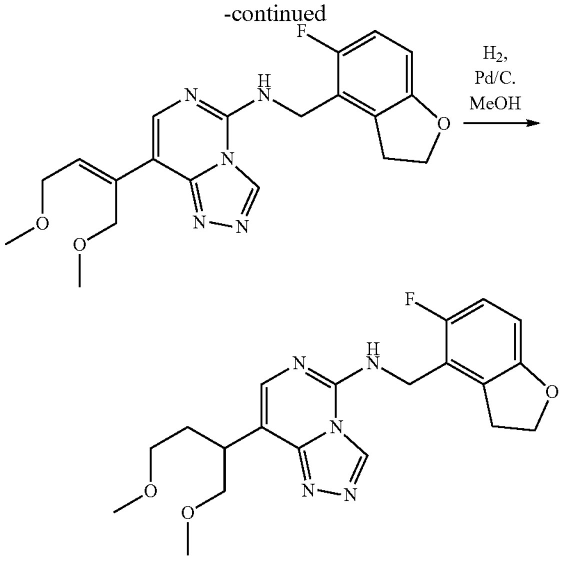

HJM-012

Step 1:

Under $N_2$ protection, 1,4-dimethoxy-2-butyne (500 mg, 4.38 mmol) and triethylamine (0.27 mL, 1.98 mmol) were dissolved in n-octane (5 mL). 4-Dimethylaminobenzoic acid (36 mg, 1.06 mmol) and pinacol borane (2.8 g, 21.90 mmol) were added at room temperature, and the mixture was heated to 100° C. and reacted for 12 h. TLC showed that the reaction was completed. The mixture was stopped from heating, naturally cooled to room temperature, and concentrated under reduced pressure to afford crude product 7 (quantitative yield) as a black oil, which was directly used in the next step without purification.

Steps 2-3:

HJM-012 (35 mg, yield: 22.9%) was prepared as a yellow solid using intermediate 7 as starting material according to the method similar to that for preparation example 10.

$^1H$ NMR (400 MHz, $CD_3OD$) δ 9.23 (s, 1H), 7.55 (s, 1H), 6.86-6.82 (m, 1H), 6.65-6.62 (m, 1H), 4.73 (s, 2H), 4.56 (t, J=8.8 Hz, 2H), 3.87-3.65 (m, 2H), 3.37-3.33 (m, 3H), 3.31-3.30 (m, 5H), 3.23 (s, 3H), 2.11-2.08 (m, 2H). LCMS $[M+H]^+$=402.2.

Preparation Example 13: Synthesis of Compound HJM-013

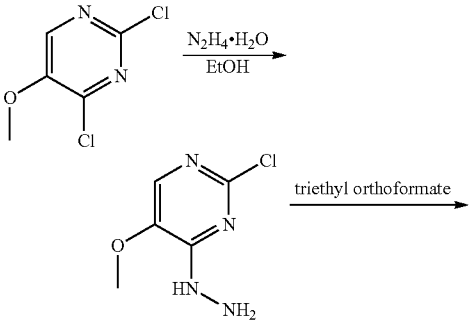

-continued

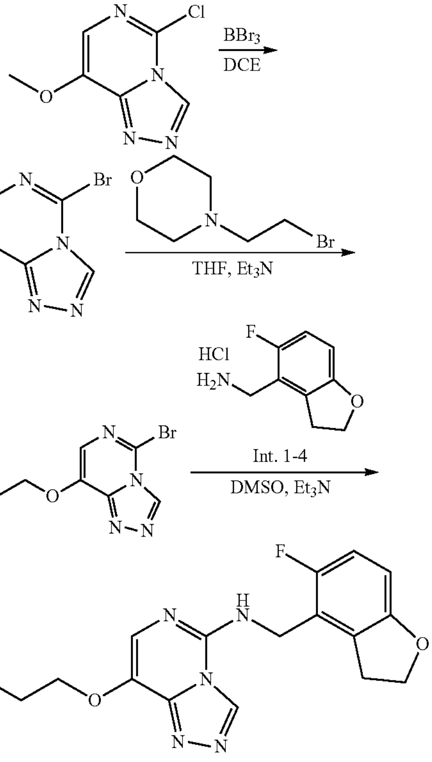

HJM-013

Step 1:

2,4-Dichloro-5-methoxypyrimidine (15 g, 83.8 mmol) was dissolved in 200 mL of ethanol, hydrazine hydrate (5.42 g, 92.18 mmol) was slowly added at room temperature, and the mixture was stirred at room temperature for 2 h. TLC showed that the reaction was completed. The mixture was allowed to stand, and filtered. The filter cake was dried in vacuum to afford compound 2-chloro-5-methoxy-4-hydrazino-pyrimidine (10.5 g, yield: 72.0%) as a solid, LCMS $[M+H]^+$=175.3.

Step 2:

Under $N_2$ protection, 2-chloro-5-methoxy-4-hydrazino-pyrimidine (10.5 g, 60.14 mmol) was dissolved in 100 mL of triethyl orthoformate, and the mixture was heated to 150° C. and stirred for 2 h. TLC showed that the reaction was completed. The mixture was stopped from heating, naturally cooled to room temperature, and filtered. The filter cake was dried in vacuum to afford compound 5-chloro-8-methoxy-[1,2,4]triazolo[4,3-c]pyrimidine (7 g, yield: 63.6%) as a solid, LCMS $[M+H]^+$=185.3.

Step 3:

Under $N_2$ protection, 5-chloro-8-methoxy-[1,2,4]triazolo[4,3-c]pyrimidine (184 mg, 1.0 mmol) was dissolved in 10 mL of 1,2-dichloroethane, boron tribromide (10 mL, 10 mmol) was slowly added under an ice-water bath, and the mixture was heated to 85° C. and stirred overnight. TLC showed that the reaction was completed. The mixture was stopped from heating, and naturally cooled to room temperature. 1M $Na_2CO_3$ solution was added under an ice-water bath to quench the reaction, and the mixture was stirred at room temperature for 1 h. The mixture was acidified with saturated $NH_4Cl$ solution and acetic acid to a pH of 6-7, and layered. The aqueous phase was extracted with ethyl acetate (2×20 mL). The organic phases were combined, washed with saturated brine (2×20 mL), dried with $Na_2SO_4$, and filtered. The filtrate was concentrated to afford 5-bromo-[1,2,4]triazolo[4,3-c]pyrimidine-8-ol (100 mg, yield: 47.0%), LCMS $[M+H]^+$=215.2. (Note: 5-chloro-[1,2,4]triazolo[4,3-c]pyrimidine-8-ol was afforded sometimes)

Step 4:

Under $N_2$ protection, 5-bromo-[1,2,4]triazolo[4,3-c]pyrimidine-8-ol (100 mg, 0.47 mmol) was dissolved in 5 mL of tetrahydrofuran. Triethylamine (119 mg, 1.176 mmol) and 4-(2-bromoethyl)morpholine (228 mg, 1.176 mmol) were added successively, and the mixture was heated to 75° C. and stirred overnight. TLC showed that the reaction was completed. The mixture was stopped from heating, naturally cooled to room temperature, and concentrated under reduced pressure. The residue was purified by preparative TLC to afford compound 4-(2-((5-bromo-[1,2,4]triazolo[4,3-c]pyrimidine-8-yl)oxy)ethyl)morpholine (70 mg, yield: 46.1%) as a solid, LCMS $[M+H]^+$=328.0.

Step 5:

Under $N_2$ protection, compound 4-(2-((5-bromo-[1,2,4]triazolo[4,3-c]pyrimidine-8-yl)oxy)ethyl)morpholine (70 mg, 0.213 mmol) was dissolved in 3 mL of dimethyl sulfoxide. 5-Fluoro-2,3-dihydrobenzofuran-4-methylamine Int.1-4 hydrochloride (86 mg, 0.427 mmol) and triethylamine (86 mg, 0.853 mmol) were added successively, and the mixture was heated to 75° C. and stirred overnight. The next day, TLC showed that the reaction was completed. The mixture was stopped from heating, naturally cooled to room temperature, and concentrated under reduced pressure. The residue was purified by preparative TLC to afford HJM-013 (20 mg, yield: 22.6%) as a white solid.

$^1$H NMR (400 MHz, $CD_3OD$) δ 9.28 (s, 1H), 7.49 (s, 1H), 6.87-6.79 (m, 1H), 6.63 (dd, J=8.4, 3.6 Hz, 1H), 4.71 (s, 2H), 4.60-4.51 (m, 4H), 4.13-3.96 (m, 4H), 3.72-3.68 (m, 2H), 3.38-3.33 (m, 6H).

$^1$H NMR (400 MHz, DMSO-$d_6$) δ 9.45 (s, 1H), 8.38 (t, J=4.8 Hz, 1H), 7.47 (s, 1H), 6.94 (t, J=9.6 Hz, 1H), 6.70 (dd, J=8.4, 3.6 Hz, 1H), 4.62 (t, J=4.8 Hz, 2H), 4.56-4.52 (m, 4H), 4.37-3.95 (m, 4H), 3.62 (t, J=4.4 Hz, 4H), 3.29 (t, J=8.4 Hz, 4H). LCMS $[M+H]^+$=415.2.

Preparation Example 14: Synthesis of Compound HJM-014

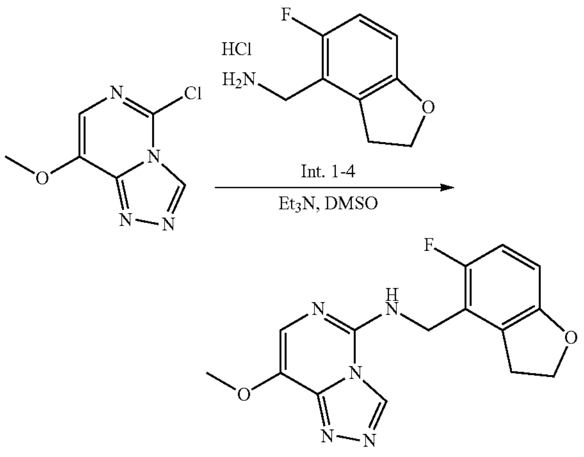

HJM-014

Under $N_2$ protection, 5-fluoro-2,3-dihydrobenzofuran-4-methylamine Int.1-4 hydrochloride (131 mg, 0.65 mmol) and triethylamine (0.15 mL, 1.08 mmol) were dissolved in 3 mL of dimethyl sulfoxide, 5-chloro-8-methoxy-[1,2,4]triazolo[4,3-c]pyrimidine 1 (100 mg, 0.54 mmol) was added at room temperature, and the mixture was stirred at room temperature for 16 h. TLC showed that the reaction was completed. The mixture was concentrated under reduced pressure, and purified by preparative HPLC to afford HJM-014 (63 mg, yield: 36.8%) as a white solid.

$^1$H NMR (400 MHz, DMSO-$d_6$) δ 9.39 (s, 1H), 8.11 (t, J=5.2 Hz, 1H), 7.28 (s, 1H), 6.99-6.87 (m, 1H), 6.69 (dd, J=8.8, 4.0 Hz, 1H), 4.61 (d, J=4.8 Hz, 2H), 4.54 (t, J=8.8 Hz, 2H), 3.28 (t, J=8.8 Hz, 2H), 2.56-2.43 (m, 3H). LCMS $[M+H]^+$=316.1.

Preparation Example 15: Synthesis of Compound HJM-015

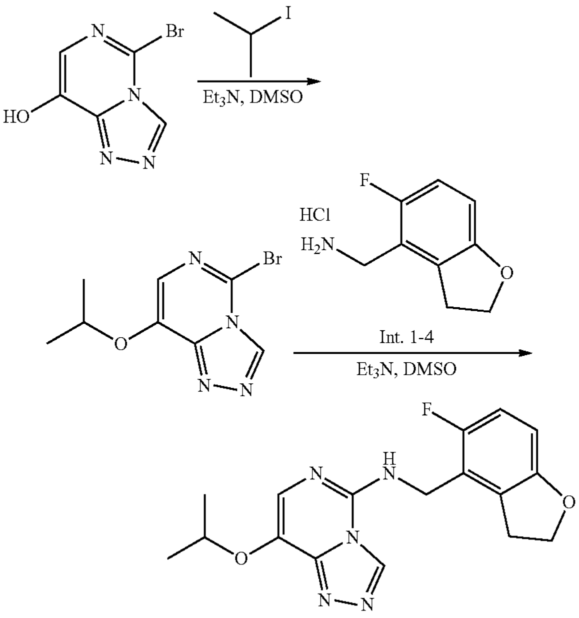

HJM-015

Step 1:

Under $N_2$ protection, 5-bromo-[1,2,4]triazolo[4,3-c]pyrimidin-8-ol (100 mg, 0.47 mmol) was dissolved in dimethyl sulfoxide (3 mL). Triethylamine (94 mg, 0.93 mmol) and isopropyl iodide (158 mg, 0.93 mmol) were added successively, and the mixture was heated to 75° C. and stirred overnight. TLC showed that the reaction was completed. The mixture was stopped from heating, and naturally cooled to room temperature. The mixture was poured into water to quench the reaction, and the aqueous phase was extracted with ethyl acetate (2×20 mL). The organic phases were combined, washed with saturated brine (2×5 mL), dried with $Na_2SO_4$, filtered, and concentrated. The residue was purified by silica gel column chromatography (PE:EA=2:1) to afford compound 5-bromo-8-isopropyl-[1,2,4]triazolo[4,3-c]pyrimidine (30 mg, yield: 25.2%) as a white solid, LCMS $[M+H]^+$=257.1.

Step 2:

Under $N_2$ protection, 5-fluoro-2,3-dihydrobenzofuran-4-methylamine Int.1-4 hydrochloride (48 mg, 0.23 mmol) and triethylamine (23 mg, 0.23 mmol) were dissolved in dimethyl sulfoxide (2 mL), 5-bromo-8-isopropyl-[1,2,4]triazolo[4,3-c]pyrimidine (30 mg, 0.12 mmol) was added at room temperature, and the mixture was heated to 75° C. and stirred for 2 h. TLC showed that the reaction was completed. The mixture was stopped from heating, naturally cooled to room temperature, and concentrated under reduced pressure. The residue was purified by preparative HPLC to afford HJM-015 (5 mg, yield: 12.5%) as a white solid.

$^1$H NMR (400 MHz, DMSO-$d_6$) δ 9.39 (s, 1H), 8.16 (t, J=4.8 Hz, 1H), 7.31 (s, 1H), 7.01-6.87 (m, 1H), 6.70 (dd, J=8.6, 3.9 Hz, 1H), 4.83-4.77 (m, 1H), 4.60 (d, J=4.8 Hz, 2H), 4.54 (t, J=8.8 Hz, 2H), 3.28 (t, J=8.7 Hz, 2H), 1.29 (s, 3H), 1.27 (s, 3H). LCMS $[M+H]^+$=344.1.

Preparation Example 16: Synthesis of Compound HJM-016

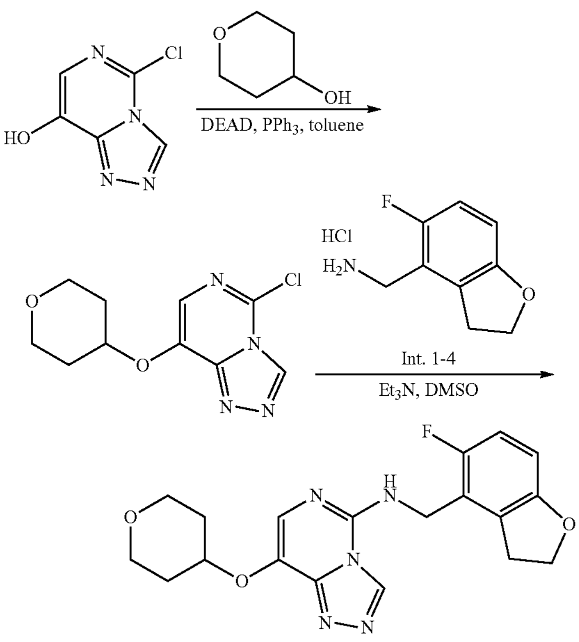

HJM-016

Step 1:

Under $N_2$ protection, 5-chloro-[1,2,4]triazolo[4,3-c]pyrimidin-8-ol (50 mg, 0.29 mmol) and tetrahydropyran-4-ol (44 mg, 0.44 mmol) were dissolved in anhydrous toluene (5 mL). Diethyl azodicarboxylate DEAD (102 mg, 0.59 mmol) and triphenyl phosphine (154 mg, 0.59 mmol) were added successively, and the mixture was heated to 110° C. and stirred overnight. The next day, TLC showed that the reaction was completed. The mixture was stopped from heating, naturally cooled to room temperature, and concentrated under reduced pressure. The residue was purified by preparative TLC to afford compound 5-chloro-8-(tetrahydro-2H-pyran-4-yl)-[1,2,4]triazolo[4,3-c]pyrimidine (30 mg, yield: 41.1%) as a yellow solid, LCMS $[M+H]^+$=255.1.

Step 2:

Under $N_2$ protection, compound 5-fluoro-2,3-dihydrobenzofuran-4-methylamine Int.1-4 hydrochloride (48 mg, 0.236 mmol) and triethylamine (0.05 mL, 0.36 mmol) were dissolved in dimethyl sulfoxide (5 mL), compound 5-chloro-8-(tetrahydro-2H-pyran-4-yl)[1,2,4]triazolo[4,3-c]pyrimidine (30 mg, 0.12 mmol) was slowly added, and the mixture was heated to 50° C. and stirred for 2 h. TLC showed that the reaction was completed. The mixture was stopped from heating, naturally cooled to room temperature, and concentrated under reduced pressure. The residue was purified by preparative HPLC to afford HJM-016 (3.3 mg, yield: 7.3%) as a white solid.

$^1$H NMR (400 MHz, DMSO-$d_6$) δ 9.43 (s, 1H), 8.31 (s, 1H), 7.40 (s, 1H), 6.98-6.89 (m, 1H), 6.70 (dd, J=8.8, 4.0 Hz, 1H), 4.78-4.69 (m, 1H), 4.61 (d, J=4.4 Hz, 2H), 4.54 (t, J=8.8 Hz, 2H), 3.92-3.83 (m, 2H), 3.45-3.40 (m, 2H), 3.32-3.25 (m, 2H), 2.05-1.90 (m, 2H), 1.71-1.56 (m, 2H). LCMS $[M+H]^+$=386.3.

Preparation Example 17: Synthesis of Compound HJM-017

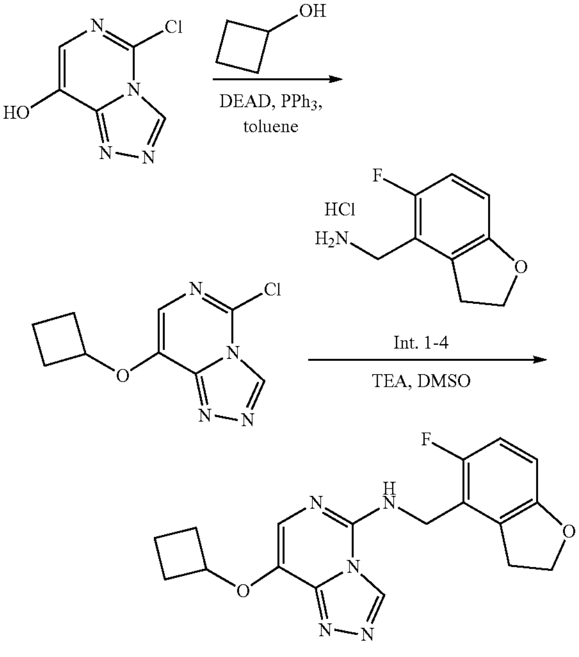

HJM-017

HJM-017 (32 mg) was prepared as a white solid using cyclobutanol as starting material according to the method similar to that for preparation example 16.

$^1$H NMR (400 MHz, DMSO-$d_6$) δ 9.39 (s, 1H), 8.17-8.09 (m, 1H), 7.16 (s, 1H), 6.98-6.89 (m, 1H), 6.69 (dd, J=8.8, 4.0 Hz, 1H), 4.82 (q, J=7.2 Hz, 1H), 4.62-4.49 (m, 4H), 3.27 (t, J=8.8 Hz, 2H), 2.47-2.36 (m, 2H), 2.18-2.03 (m, 2H), 1.84-1.75 (m, 1H), 1.66-1.59 (m, 1H). LCMS $[M+H]^+$=356.2.

Preparation Example 18: Synthesis of Compound HJM-018

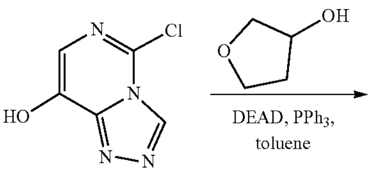

-continued

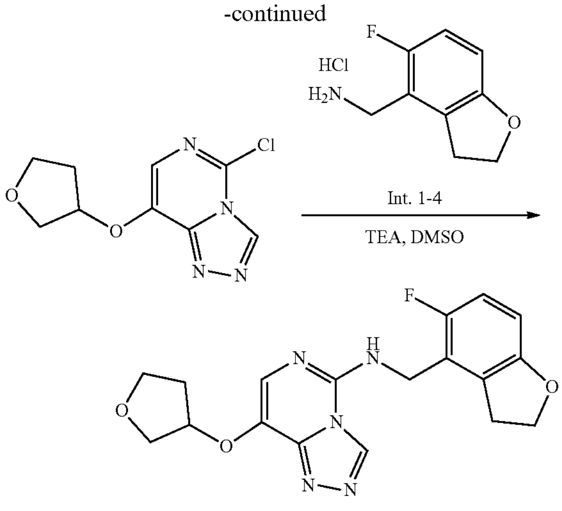

HJM-018

HJM-018 (39 mg) was prepared as a white solid using 3-hydroxymethyl tetrahydrofuran as starting material according to the method similar to that for preparation example 16.

$^1H$ NMR (400 MHz, DMSO-$d_6$) δ 9.40 (s, 1H), 8.19 (t, J=5.2 Hz, 1H), 7.31 (s, 1H), 6.94 (t, J=9.6 Hz, 1H), 6.70 (dd, J=8.4, 3.6 Hz, 1H), 5.28-5.22 (m, 1H), 4.60 (d, J=4.8 Hz, 2H), 4.54 (t, J=8.8 Hz, 2H), 3.94-3.81 (m, 3H), 3.76 (td, J=8.0, 4.4 Hz, 1H), 3.28 (t, J=8.4 Hz, 2H), 2.22-1.96 (m, 2H). LCMS $[M+H]^+$=372.1.

Preparation Example 19: Synthesis of Compound HJM-019

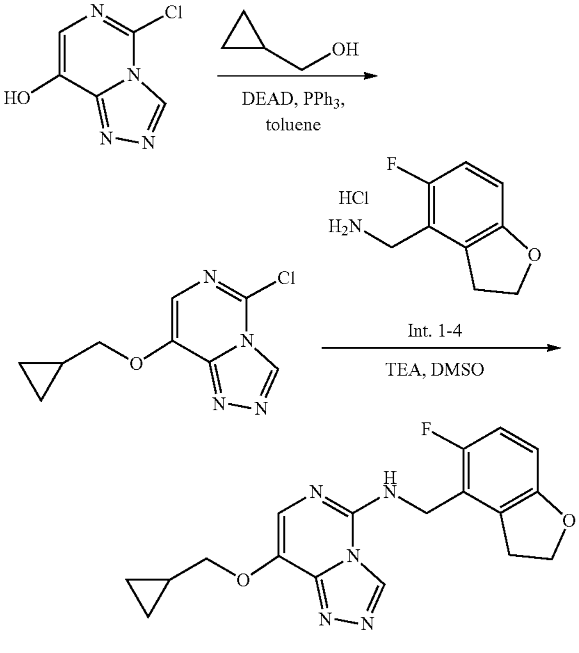

HJM-019

HJM-019 (21 mg) was prepared as a white solid using hydroxymethylcyclopropane as starting material according to the method similar to that for preparation example 16.

$^1H$ NMR (400 MHz, DMSO-$d_6$) δ 9.39 (s, 1H), 8.14 (t, J=5.2 Hz, 1H), 7.28 (s, 1H), 6.93 (t, J=9.6 Hz, 1H), 6.69 (dd, J=8.4, 4.0 Hz, 1H), 4.60 (d, J=4.8 Hz, 2H), 4.53 (t, J=8.8 Hz, 2H), 3.97 (d, J=7.2 Hz, 2H), 3.27 (t, J=8.8 Hz, 2H), 1.33-1.23 (m, 1H), 0.63-0.54 (m, 2H), 0.35-0.31 (m, 2H). LCMS $[M+H]^+$=356.1.

Preparation Example 20: Synthesis of Compound HJM-020

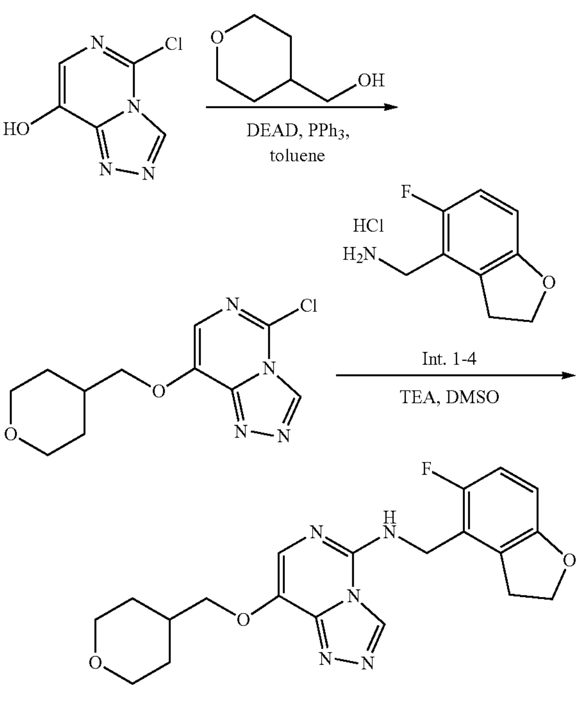

HJM-020

HJM-020 (23 mg) was prepared as a white solid using 4-hydroxymethyltetrahydropyran as starting material according to the method similar to that for preparation example 16.

$^1H$ NMR (400 MHz, DMSO-$d_6$): δ 9.38 (s, 1H), 8.13 (t, J=5.2 Hz, 1H), 7.29 (s, 1H), 6.93 (t, J=8.8 Hz, 1H), 6.70-6.67 (m, 1H), 4.60 (d, J=5.2 Hz, 2H), 4.53 (t, J=8.8 Hz, 2H), 3.99 (d, J=6.4 Hz, 2H), 3.89 (dd, J=3.2, 11.2 Hz, 2H), 3.31-3.25 (m, 4H), 2.00-1.97 (m, 1H), 1.71-1.68 (m, 2H), 1.38-1.28 (m, 2H). LCMS $[M+H]^+$=400.0.

Preparation Example 21: Synthesis of Compound HJM-021

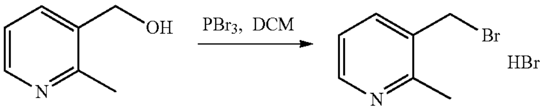

-continued

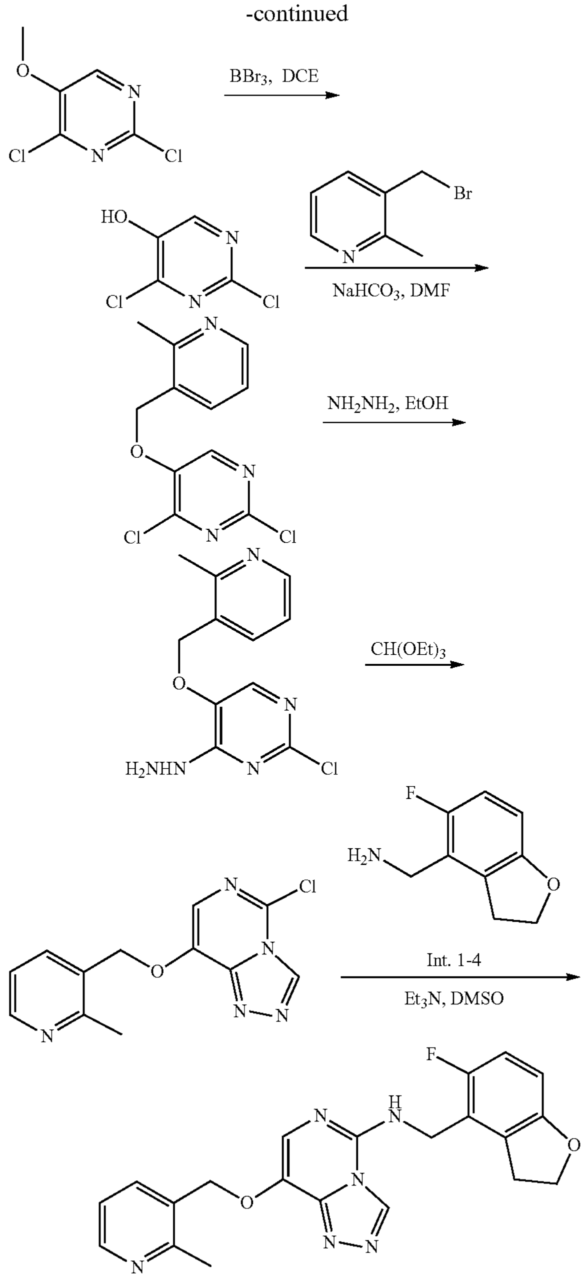

HJM-021

Step 1:

Compound 3-hydroxymethyl-2-methylpyridine (1.6 g, 13.0 mmol) was dissolved in dichloromethane (20 mL), phosphorus tribromide (1.5 mL, 15.6 mmol) was slowly added under an ice-water bath and $N_2$ protection, and the mixture was stirred at room temperature overnight. TLC showed that the reaction was completed. The mixture was concentrated under reduced pressure to afford 3-bromomethyl-2-methylpyridine hydrobromide (3.5 g, yield: 99.0%) as a yellow solid, LCMS $[M+H]^+$=186.1.

Step 2:

2,4-Dichloro-5-methoxypyrimidine (5.0 g, 27.9 mmol) was dissolved in 1,2-dichloroethane (75 mL), boron tribromide (13.5 mL, 140 mmol) was slowly added under an ice-water bath and $N_2$ protection, and the mixture was heated to 80° C. and stirred overnight. TLC showed that the reaction was completed. The mixture was stopped from heating, and naturally cooled to room temperature. 1M NaOH solution was added under an ice-water bath to quench the reaction, and the mixture was stirred at room temperature for 1 h. The mixture was acidified with saturated $NH_4Cl$ solution and acetic acid to a pH of 6-7. The mixture was layered, and the aqueous phase was extracted with ethyl acetate (2×20 mL). The organic phases were combined, washed with saturated brine (2×20 mL), dried with $Na_2SO_4$, filtered, and concentrated. The residue was purified by silica gel column chromatography (PE:EA=5:1) to afford compound 2,4-dichloropyrimidine-5-ol (4.0 g, yield: 86.9%) as a solid, LCMS $[M+H]^+$=162.8.

Step 3:

Under $N_2$ protection, compound 2,4-dichloropyrimidine-5-ol (1.8 g, 10.9 mmol) was dissolved in N,N-dimethylformamide (20 mL), 3-bromomethyl-2-methylpyridine hydrobromide (1.5 mL, 13.1 mmol) and $NaHCO_3$ (1.1 g, 13.1 mmol) were added successively, and the mixture was stirred at room temperature overnight. TLC showed that the reaction was completed. Water was added to quench the reaction, and the aqueous phase was extracted with ethyl acetate (2×20 mL). The organic phases were combined, washed with saturated brine (2×20 mL), dried with $Na_2SO_4$, and filtered. The filtrate was concentrated to afford 2,4-dichloro-5-((2-methylpyridin-3-yl)methoxy)pyrimidine (1.75 g, yield: 59.4%) as a yellow solid, LCMS: $[M+H]^+$=269.9.

Step 4:

Compound 2,4-dichloro-5-((2-methylpyridin-3-yl)methoxy)pyrimidine (1.75 g, 6.48 mmol) was dissolved in ethanol (30 mL), 85% hydrazine hydrate (457.4 mg, 7.78 mmol) was slowly added at room temperature, and the mixture was stirred at room temperature overnight. TLC showed that the reaction was completed. The mixture was concentrated under reduced pressure to afford crude compound 2-chloro-4-hydrazinyl-5-((2-methylpyridin-3-yl)methoxy)pyrimidine (2.0 g, yield: 99.0%), LCMS $[M+H]^+$=266.2.

Step 5:

Under $N_2$ protection, the crude compound 2-chloro-4-hydrazinyl-5-((2-methylpyridin-3-yl)methoxy)pyrimidine (2.0 g, 7.51 mmol) was dissolved in 15 mL of triethyl orthoformate, and the mixture was heated to 150° C. and stirred overnight. TLC showed that the reaction was completed. The mixture was stopped from heating, naturally cooled to room temperature, and concentrated under reduced pressure. The residue was purified by silica gel column chromatography to afford 5-chloro-8-((2-methylpyridin-3-yl)methoxy)-[1,2,4]triazolo[4,3-c]pyrimidine (600 mg, yield: 33.7%) as a yellow solid, LCMS $[M+H]^+$=276.2.

Step 6:

Under $N_2$ protection, compound 5-chloro-8-((2-methylpyridin-3-yl)methoxy)-[1,2,4]triazolo[4,3-c]pyrimidine (150 mg, 0.545 mmol) was dissolved in dimethyl sulfoxide (5 mL), 5-fluoro-2,3-dihydrobenzofuran-4-methylamine Int.1-4 (273 mg, 1.636 mmol) and triethylamine (276 mg, 2.727 mmol) were added successively, and the mixture was heated to 75° C. and stirred overnight. TLC showed that the reaction was completed. The mixture was stopped from heating, and naturally cooled to room temperature. Water and ethyl acetate were added, and the mixture was layered. The aqueous phase was extracted with ethyl acetate (2×20 mL). The organic phases were combined, and then washed successively with water (2×20 mL) and saturated brine. The organic layer was dried with $Na_2SO_4$, filtered, and concentrated. The residue was purified by silica gel column chromatography (DCM:MeOH=20:1) to afford HJM-021 (160 mg, yield: 72.2%) as a white solid.

$^1$H NMR (400 MHz, DMSO-$d_6$) δ 9.45 (s, 1H), 8.75 (d, J=5.2 Hz, 1H), 8.47 (d, J=7.6 Hz, 1H), 8.34 (s, 1H), 7.89-7.78 (m, 1H), 7.50 (s, 1H), 6.94 (t, J=9.6 Hz, 1H), 6.70 (dd, J=8.4, 3.2 Hz, 1H), 5.45 (s, 2H), 4.61 (d, J=3.2 Hz, 2H), 4.54 (t, J=8.4 Hz, 2H), 3.28 (t, J=8.4 Hz, 2H), 2.76 (s, 3H). LCMS $[M+H]^+$=407.3.

Preparation Example 22: Synthesis of Compound HJM-022

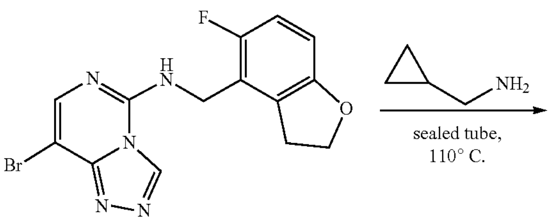

1

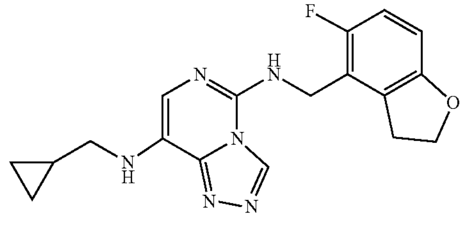

HJM-022

Under $N_2$ protection, 8-bromo-N-((5-fluoro-2,3-dihydrobenzofuran-4-yl)methyl)-[1,2,4]triazolo[4,3-c]pyrimidine-5-amine 1 (83 mg, 0.23 mmol) and cyclopropylmethylamine (3 mL) were placed in a sealed tube, and the mixture was heated to 110° C. and stirred for 1.5 h. TLC showed that the reaction was completed. The mixture was stopped from heating, naturally cooled to room temperature, and concentrated under reduced pressure. The residue was purified by preparative HPLC to afford HJM-022 (16 mg, yield: 20%) as a white solid.

$^1$H NMR (400 MHz, DMSO-$d_6$) δ 9.32 (s, 1H), 7.66 (t, J=5.6 Hz, 1H), 6.92 (t, J=9.2 Hz, 1H), 6.83 (s, 1H), 6.69 (q, J=4.0 Hz, 1H), 5.14 (t, J=5.6 Hz, 1H), 4.56-4.50 (m, 4H), 3.27 (t, J=8.8 Hz, 2H), 3.00 (t, J=6.4 Hz, 2H), 1.15-1.11 (m, 1H), 0.48-0.44 (m, 2H), 0.25-0.21 (m, 2H). LCMS $[M+H]^+$=355.4.

Preparation Example 23: Synthesis of Compound HJM-023

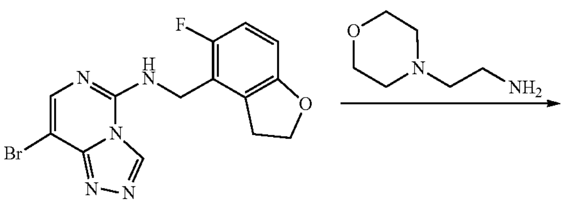

1

-continued

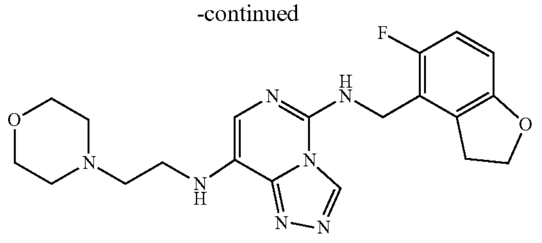

HJM-023

HJM-023 (105 mg, yield: 46.5%) was prepared as a solid using N-(2-aminoethyl)morpholine as starting material according to the method similar to that for preparation example 22.

$^1$H NMR (400 MHz, $CD_3OD$) δ 9.28 (s, 1H), 8.50 (s, 1H), 7.07 (s, 1H), 6.95-6.78 (m, 1H), 6.68-6.65 (m, 1H), 4.65 (s, 2H), 4.60 (t, J=8.7 Hz, 2H), 3.94-3.81 (m, 4H), 3.52 (t, J=6.2 Hz, 2H), 3.38-3.29 (m, 4H), 3.09 (t, J=5.7 Hz, 2H), 3.03-2.97 (m, 4H). LCMS $[M+H]^+$=414.2.

Preparation Example 24: Synthesis of Compound HJM-024

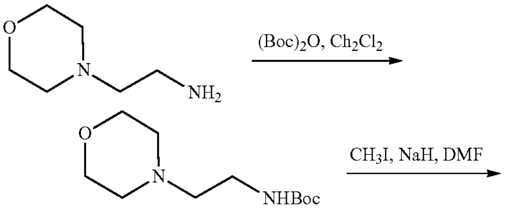

8

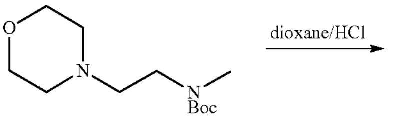

9

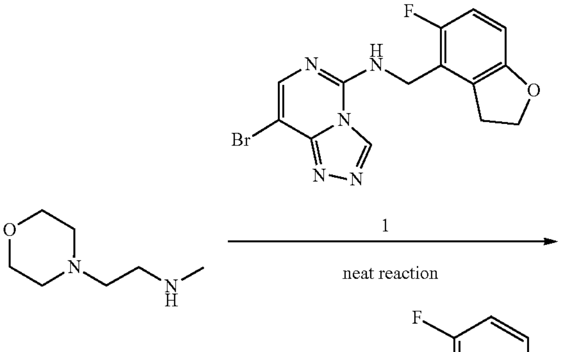

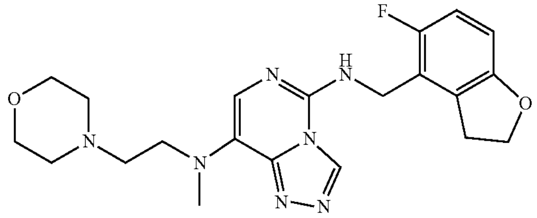

HJM-024

Step 1:

N-(2-aminoethyl)morpholine (2 g, 15.38 mmol) was dissolved in dichloromethane (30 mL), di-tert-butyl dicarbonate (6.7 g, 30.77 mmol) was slowly added at room temperature, and the mixture was stirred at room temperature for 2 h. TLC showed that the reaction was completed. The mixture was concentrated under reduced pressure, and purified by silica gel column chromatography (PE:EA=3.3:1) to afford compound 8 (2.4 g, yield: 67.0%) as a solid, LCMS $[M+H]^+$=231.2.

Step 2:

Under $N_2$ protection, compound 8 (2.4 g, 10.43 mmol) was dissolved in anhydrous N,N-dimethylformamide (20 mL), 60% sodium hydride (626 mg, 15.65 mmol) was slowly added under an ice-water bath, and the mixture was stirred in the ice-water bath for 30 min. Iodomethane (1.3 mL, 20.86 mmol) was then added dropwise, and the mixture was kept at 0° C. and further stirred for 2 h. TLC showed that the reaction was completed. The mixture was poured into water to quench the reaction, and the aqueous phase was extracted with ethyl acetate (20 mL×2). The organic phases were combined, washed with saturated brine (5 mL×2), dried with $Na_2SO_4$, filtered, and concentrated. The residue was purified by silica gel column chromatography (PE: EA=3.3:1) to afford compound 9 (1.5 g, yield: 59.1%) as a solid, LCMS $[M+H]^+$=245.2.

Step 3:

Compound 9 (1.5 g, 15.38 mmol) was dissolved in a solution of hydrochloric acid in 1,4-dioxane (2 M, 4 mL), and the mixture was stirred at room temperature for 2 h. TLC showed that the reaction was completed. The mixture was concentrated, and the resulting crude was washed with ethyl acetate to afford solid compound N-methyl-2-morpholinylethylamine (500 mg, yield: 56.5%), which was directly used in the next step without purification.

Step 4:

HJM-024 (16 mg, yield: 13.7%) was prepared as a solid using N-methyl-2-morpholinylethylamine as starting material according to the method similar to that for preparation example 22.

$^1$H NMR (400 MHz, $CD_3OD$) δ 9.28 (s, 1H), 7.11 (s, 1H), 6.88-6.75 (m, 1H), 6.62 (dd, J=8.4, 3.6 Hz, 1H), 4.69 (s, 2H), 4.56 (t, J=8.8 Hz, 2H), 3.70 (t, J=6.8 Hz, 2H), 3.55-3.47 (m, 4H), 3.35 (t, J=8.8 Hz, 2H), 2.95 (s, 3H), 2.59 (t, J=6.8 Hz, 2H), 2.50-2.40 (m, 4H). LCMS $[M+H]^+$=428.4.

Preparation Example 25: Synthesis of Compound HJM-025

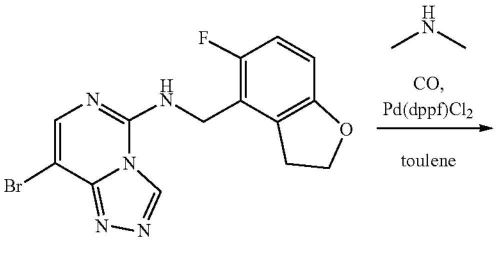

1

-continued

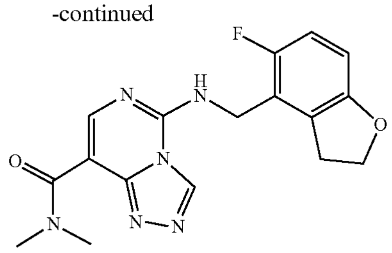

HJM-025

Under $N_2$ protection, a solution of 8-bromo-N-((5-fluoro-2,3-dihydrobenzofuran-4-yl)methyl)-[1,2,4]triazolo[4,3-c] pyrimidine-5-amine 1 (150 mg, 0.41 mmol) and dimethylamine in tetrahydrofuran (1M, 4.0 mL) was dissolved in anhydrous toluene (10 mL). 1,1'-Bis(diphenylphosphino) ferrocene-palladium(II)dichloride dichloromethane complex (60 mg, 0.08 mmol) was added at room temperature, the atmosphere was replaced three times with CO, and the mixture was heated to 110° C. under a CO balloon overnight (2 MP). TLC showed that the reaction was completed. The mixture was stopped from heating, naturally cooled to room temperature, and purified by preparative HPLC to afford HJM-025 (7 mg, yield: 4.8%) as a white solid.

$^1$H NMR (400 MHz, DMSO-$d_6$) δ 9.42 (s, 1H), 8.85 (s, 1H), 7.74 (s, 1H), 6.97-6.93 (m, 1H), 6.72-6.69 (m, 1H), 4.70 (s, 2H), 4.54 (t, J=8.8 Hz, 2H), 3.29-3.27 (m, 2H), 2.99-2.90 (m, 6H). LCMS $[M+H]^+$=357.2.

Preparation Example 26: Synthesis of Compound HJM-026

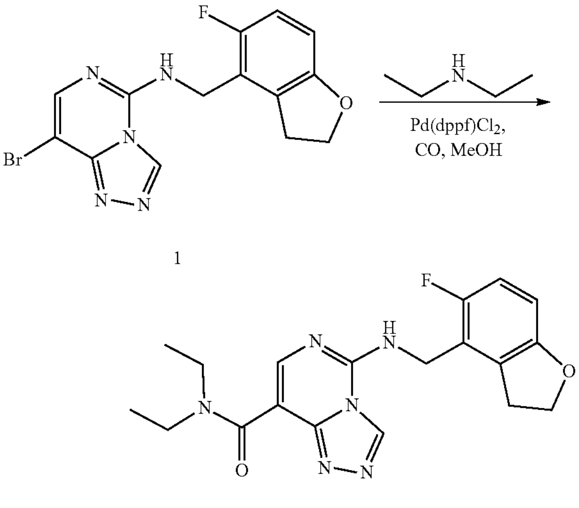

1

HJM-026

HJM-026 (6.5 mg) was prepared as a white solid using diethylamine as starting material according to the method similar to that for preparation example 25.

$^1$H NMR (400 MHz, $CD_3OD$) δ 9.29 (s, 1H), 7.79 (s, 1H), 6.85 (t, J=9.2 Hz, 1H), 6.64 (dd, J=8.8, 4.0 Hz, 1H), 4.80 (s, 2H), 4.57 (t, J=8.8 Hz, 2H), 3.64-3.56 (m, 2H), 3.37 (t, J=8.4 Hz, 4H), 1.36-1.30 (m, 3H), 1.29-1.11 (m, 3H). LCMS $[M+H]^+$=385.1.

Preparation Example 27: Synthesis of Compound HJM-027

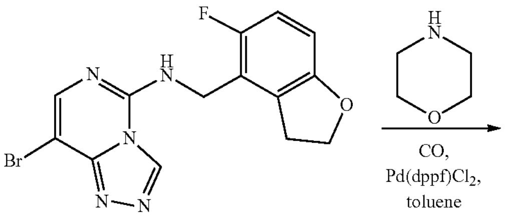

1

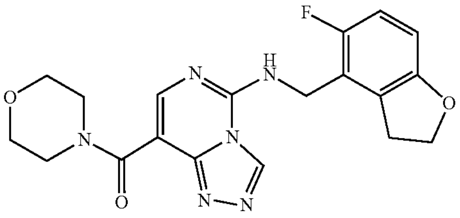

HJM-027

HJM-027 (62 mg, yield: 18.3%) was prepared as a yellow solid using morpholine as starting material according to the method similar to that for preparation example 25.

$^1$H NMR (400 MHz, DMSO-$d_6$) δ 9.36 (s, 1H), 8.89-8.88 (m, 1H), 7.78 (s, 1H), 6.98-6.91 (m, 1H), 6.71-6.68 (m, 1H), 4.69 (s, 2H), 4.53 (t, J=8.8 Hz, 2H), 3.60-3.59 (m, 4H), 3.50-3.46 (m, 2H), 3.29-3.27 (m, 2H), 2.67-2.66 (m, 2H). LCMS $[M+H]^+$=399.2.

Preparation Example 28: Synthesis of Compound HJM-028

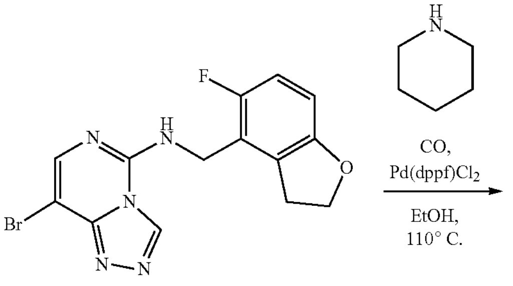

1

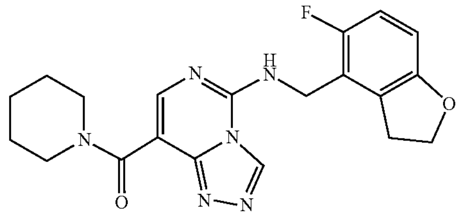

HJM-028

HJM-028 (9 mg, yield: 4.3%) was prepared as a white solid using piperidine as starting material according to the method similar to that for preparation example 25.

$^1$H NMR (400 MHz, $CD_3OD$) δ 9.33 (s, 1H), 7.85 (s, 1H), 6.84-6.82 (m, 1H), 6.65-6.61 (m, 1H), 4.80 (s, 2H), 4.57 (t, J=8.8 Hz, 2H), 3.76-3.78 (m, 2H), 3.39-3.34 (m, 4H), 1.69-1.58 (m, 6H). LCMS $[M+H]^+$=397.4.

Preparation Example 29: Synthesis of Compound HJM-029

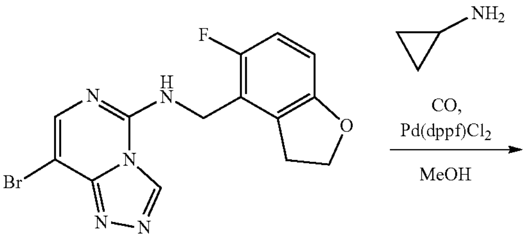

1

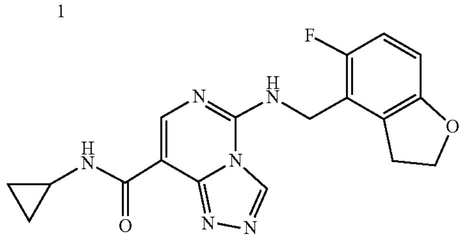

HJM-029

HJM-029 (16 mg) was prepared as a white solid using cyclopropylamine as starting material according to the method similar to that for preparation example 25.

$^1$H NMR (400 MHz, DMSO-$d_6$) δ 9.49 (s, 1H), 9.20 (t, J=5.2 Hz, 1H), 8.76 (d, J=4.0 Hz, 1H), 8.30 (s, 1H), 6.95 (dd, J=10.2, 8.8 Hz, 1H), 6.71 (dd, J=8.8, 4.0 Hz, 1H), 4.75 (d, J=5.2 Hz, 2H), 4.54 (t, J=8.8 Hz, 2H), 3.29 (t, J=8.8 Hz, 2H), 2.94-2.87 (m, 1H), 0.82-77 (m, 2H), 0.62-0.53 (m, 2H). LCMS $[M+H]^+$=369.1.

Preparation Example 30: Synthesis of Compound HJM-030

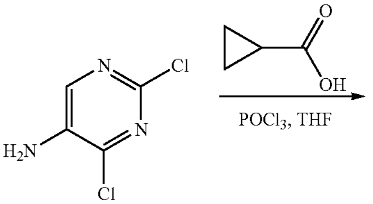

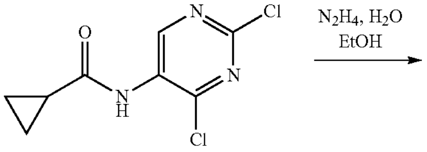

-continued

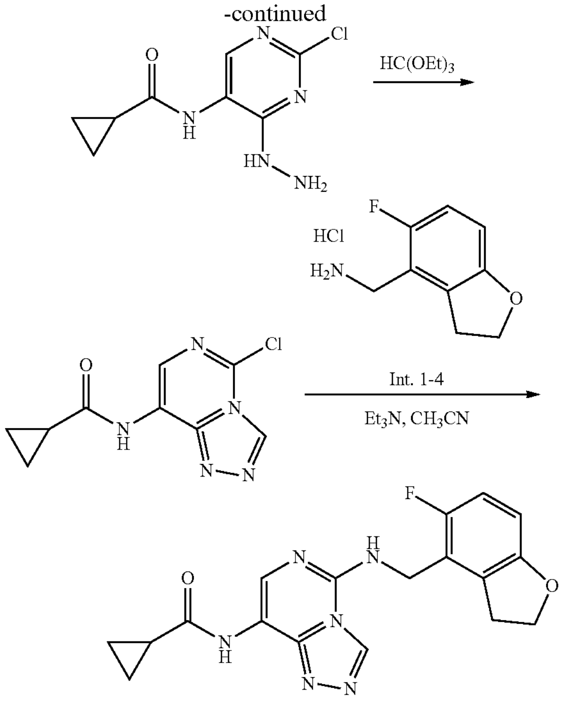

HJM-030

Step 1:

5-Amino-2,4-dichloropyrimidine (1.0 g, 6.13 mmol) and cyclopropanecarboxylic acid (1.5 mL, 18.4 mmol) were dissolved in anhydrous tetrahydrofuran (20 mL), phosphorus oxychloride (0.2 mL, 2.18 mmol) was slowly added under $N_2$ protection, and the mixture was heated to 70° C. and stirred overnight. TLC showed that the reaction was completed. The mixture was stopped from heating, and naturally cooled to room temperature. Saturated $NaHCO_3$ solution was added to quench the reaction, and the aqueous phase was extracted with ethyl acetate (2×20 mL). The organic phases were combined, washed with saturated brine (2×20 mL), dried with $Na_2SO_4$, filtered, and concentrated. The residue was purified by silica gel column chromatography (PE:EA=5:1) to afford compound N-(2,4-dichloropyrimidin-5-yl)cyclopropanecarboxamide (1.2 g, yield: 84.7%) as a white solid, LCMS $[M+H]^+$=232.1.

Step 2:

Compound N-(2,4-dichloropyrimidin-5-yl)cyclopropanecarboxamide (600 mg, 2.60 mmol) was dissolved in ethanol (20 mL), hydrazine hydrate (0.18 mL, 3.12 mmol) was slowly added at room temperature, and the mixture was stirred at room temperature overnight. TLC showed that the reaction was completed. The mixture was concentrated under reduced pressure to afford crude compound N-(2-chloro-4-hydrazinopyrimidin-5-yl)cyclopropanecarboxamide (590 mg, quantitative yield), LCMS $[M+H]^+$=228.2.

Step 3:

Under $N_2$ protection, compound N-(2-chloro-4-hydrazinopyrimidin-5-yl)cyclopropanecarboxamide (590 mg, 2.60 mmol) was dissolved in 20 mL of triethyl orthoformate, and the mixture was heated to 150° C. and stirred for 3 h. TLC showed that the reaction was completed. The mixture was stopped from heating, naturally cooled to room temperature, and concentrated under reduced pressure. The residue was purified by silica gel column chromatography (PE:EA=5:1) to afford compound N-(5-chloro-[1,2,4]triazolo[4,3-c]pyrimidin-8-yl)cyclopropanecarboxamide (120 mg, yield: 19.2%), LCMS $[M+H]^+$=238.1.

Step 4:

Under $N_2$ protection, 5-fluoro-2,3-dihydrobenzofuran-4-methylamine Int.1-4 hydrochloride (153 mg, 0.75 mmol) and triethylamine (0.2 mL, 1.51 mmol) were dissolved in acetonitrile (5 mL), compound N-(5-chloro-[1,2,4]triazolo[4,3-c]pyrimidin-8-yl)cyclopropanecarboxamide (120 mg, 0.51 mmol) was added, and the mixture was heated to 50° C. and stirred for 2 h. TLC showed that the reaction was completed. The mixture was stopped from heating, naturally cooled to room temperature, and concentrated under reduced pressure. The residue was purified by preparative HPLC to afford HJM-030 (50 mg, yield: 26.7%) as a white solid.

$^1H$ NMR (400 MHz, DMSO-$d_6$) δ 10.19 (s, 1H), 9.43 (s, 1H), 8.41 (t, J=4.4 Hz, 1H), 8.08 (s, 1H), 7.02-6.85 (m, 1H), 6.70 (dd, J=8.8, 4.0 Hz, 1H), 4.65 (d, J=4.4 Hz, 2H), 4.54 (t, J=8.8 Hz, 2H), 3.29 (t, J=8.8 Hz, 2H), 2.17-2.06 (m, 1H), 0.79 (d, J=6.0 Hz, 4H). LCMS $[M+H]^+$=369.1.

Preparation Example 31: Synthesis of Compound HJM-031

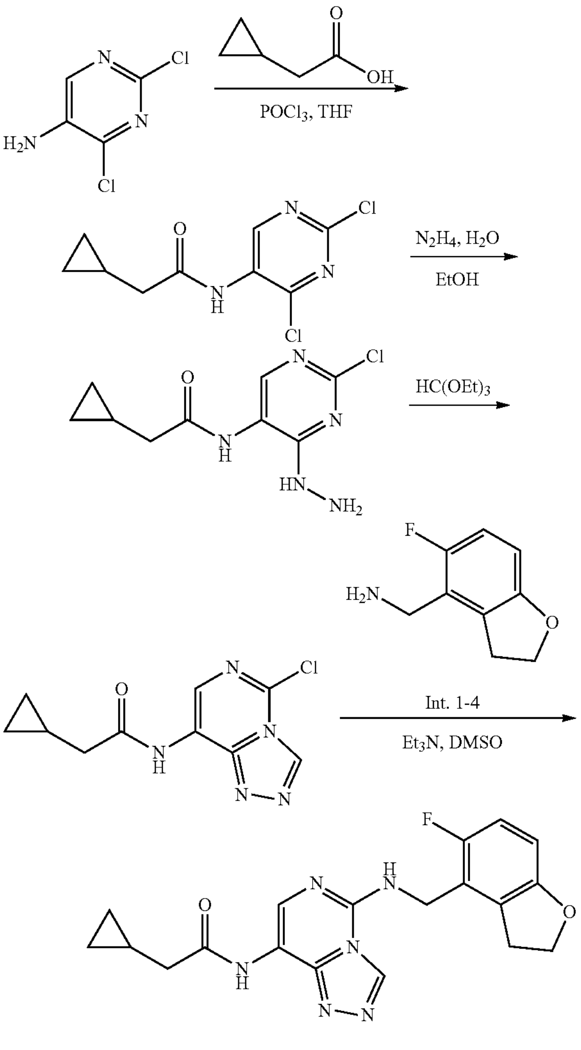

HJM-031

HJM-031 (9 mg, yield: 7.6%) was prepared as a white solid using cyclopropane acetic acid as starting material according to the method similar to that for preparation example 30.

$^1H$ NMR (400 MHz, DMSO-$d_6$) δ 10.19 (s, 1H), 9.43 (s, 1H), 8.41 (t, J=4.4 Hz, 1H), 8.08 (s, 1H), 7.02-6.85 (m, 1H), 6.70 (dd, J=8.8, 4.0 Hz, 1H), 4.65 (d, J=4.4 Hz, 2H), 4.54 (t, J=8.8 Hz, 2H), 3.29 (t, J=8.8 Hz, 2H), 2.17-2.06 (m, 1H), 0.79 (d, J=6.0 Hz, 4H). LCMS $[M+H]^+$=383.2.

Preparation Example 32: Synthesis of Compound HJM-032

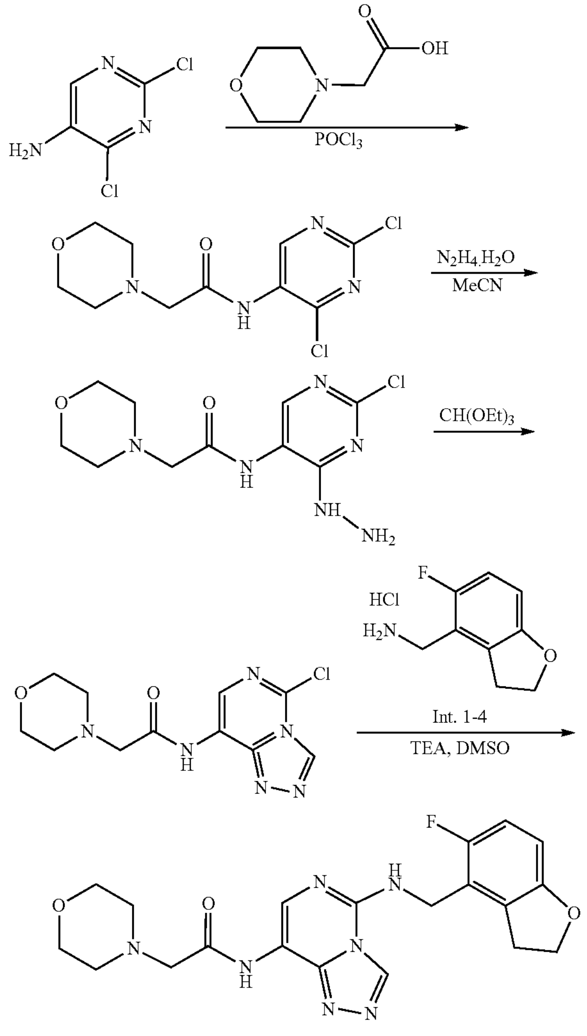

HJM-032

HJM-032 (10 mg, yield: 5.8%) was prepared as a white solid using 2-morpholinoacetic acid as starting material according to the method similar to that for preparation example 30.

$^1H$ NMR (400 MHz, $CD_3OD$) δ 9.29 (s, 1H), 8.08 (s, 1H), 6.89-6.75 (m, 1H), 6.65-6.52 (m, 1H), 4.76 (s, 2H), 4.57 (t, J=6.8 Hz, 2H), 3.99-3.86 (m, 6H), 3.35 (t, J=8.8 Hz, 2H), 3.22-3.17 (m, 4H). LCMS $[M+H]^+$=428.1.

Preparation Example 33: Synthesis of Compound HJM-033

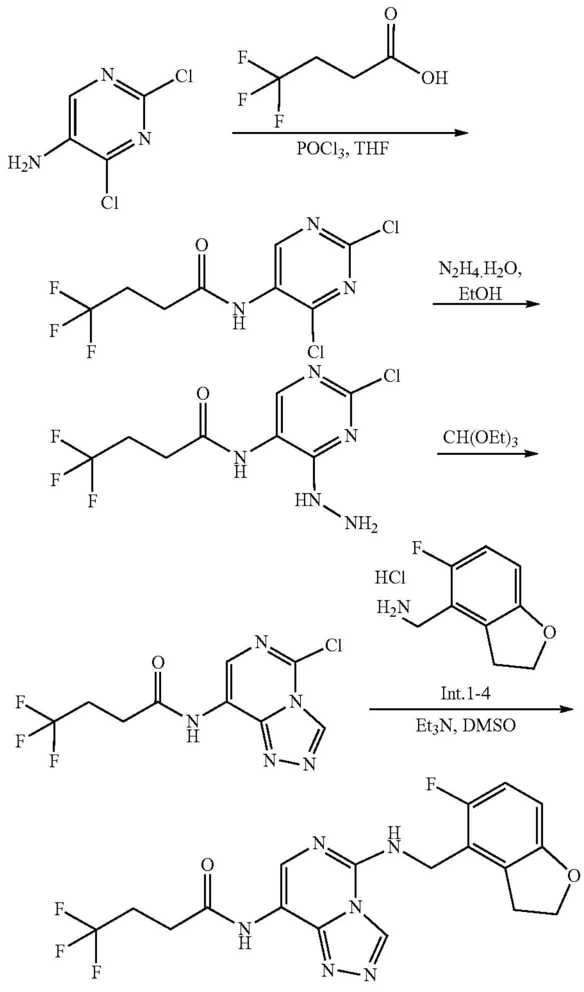

HJM-033

HJM-033 (20 mg, yield: 23.1%) was prepared as a white solid using 4,4,4-trifluorobutyric acid as starting material according to the method similar to that for preparation example 30.

$^1H$ NMR (400 MHz, DMSO-$d_6$) δ 10.1 (s, 1H), 9.42 (s, 1H), 8.43 (s, 1H), 8.11 (s, 1H), 6.94-6.92 (m, 1H), 6.71-6.89 (m, 1H), 4.66-4.64 (m, 2H), 4.56-4.52 (m, 2H), 3.33-3.22 (m, 2H), 2.76-2.72 (m, 2H), 2.58-2.57 (m, 2H). LCMS $[M+H]^+$=425.3.

Preparation Example 34: Synthesis of Compound HJM-034

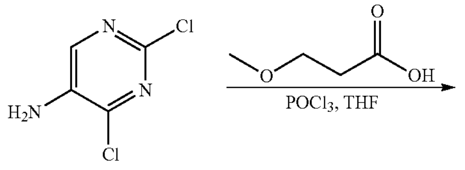

-continued

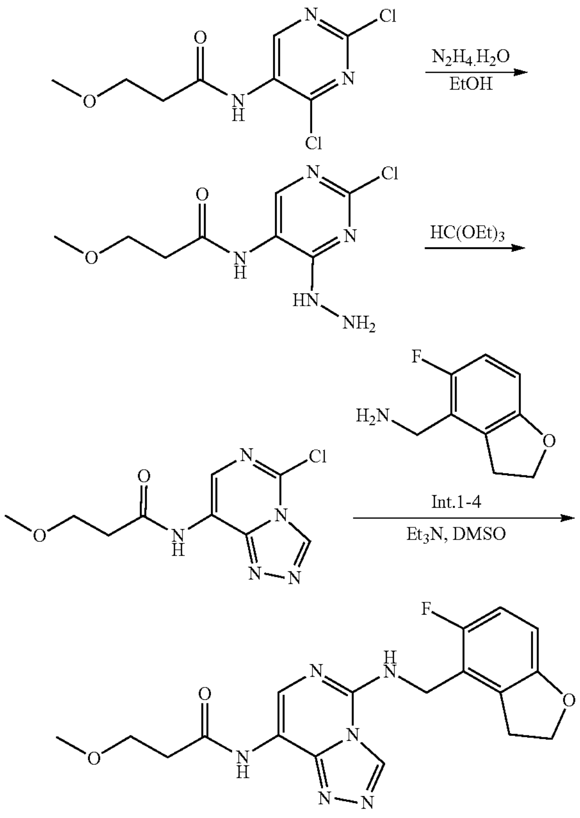

HJM-034

HJM-034 (37 mg, yield: 50%) was prepared as a white solid using 3-methoxypropionic acid as starting material according to the method similar to that for preparation example 30.

$^1H$ NMR (400 MHz, DMSO-$d_6$) δ 9.93 (s, 1H), 9.42 (s, 1H), 8.41 (t, J=4.8 Hz, 1H), 8.13 (s, 1H), 6.94 (t, J=9.2 Hz, 1H), 6.71-6.68 (m, 1H), 4.64 (d, J=4.8 Hz, 2H), 4.53 (t, J=8.8 Hz, 2H), 3.61 (t, J=6.4 Hz, 2H), 3.31-3.27 (m, 2H), 3.26 (s, 3H), 2.67 (t, J=6.4 Hz, 2H). LCMS $[M+H]^+$=387.1.

Preparation Example 35: Synthesis of Compound HJM-035

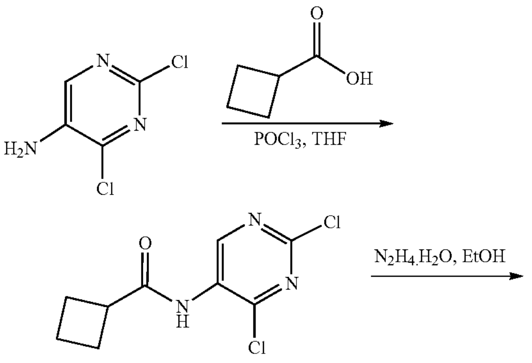

-continued

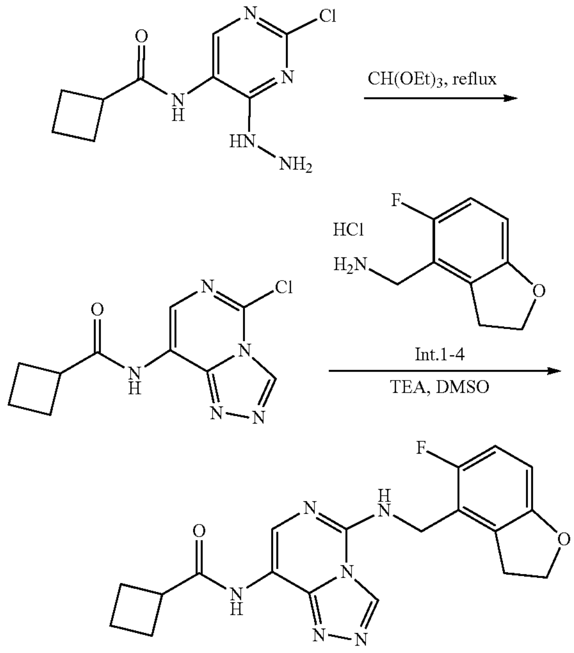

HJM-035

HJM-035 (13 mg) was prepared as a white solid using cyclobutanecarboxylic acid as starting material according to the method similar to that for preparation example 30.

$^1H$ NMR (400 MHz, DMSO-$d_6$) δ 9.67 (s, 1H), 9.41 (s, 1H), 8.40 (t, J=5.2 Hz, 1H), 8.07 (s, 1H), 6.94 (t, J=9.6 Hz, 1H), 6.70 (dd, J=8.8, 4.0 Hz, 1H), 4.65 (d, J=4.8 Hz, 2H), 4.54 (t, J=8.8 Hz, 2H), 3.56-3.25 (m, 3H), 2.27-2.17 (m, 2H), 2.16-2.06 (m, 2H), 1.98-1.89 (m, 1H), 1.86-1.77 (m, 1H). LCMS $[M+H]^+$=383.2.

Preparation Example 36: Synthesis of Compound HJM-036

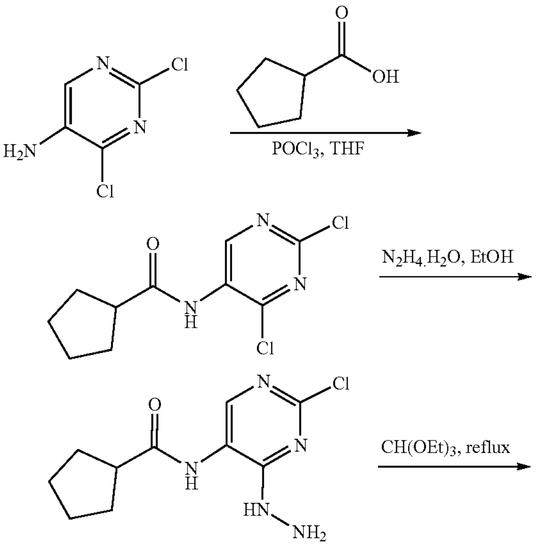

-continued

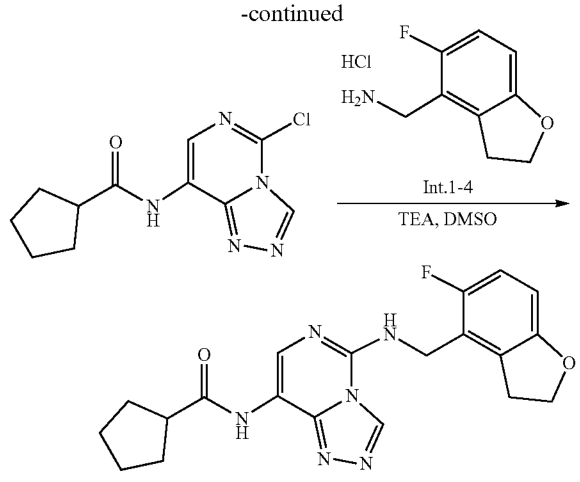

HJM-036

HJM-036 (40 mg) was prepared as a white solid using cyclopentanecarboxylic acid as starting material according to the method similar to that for preparation example 30.

$^1$H NMR (400 MHz, DMSO-$d_6$) δ 9.80 (s, 1H), 9.42 (s, 1H), 8.41 (t, J=5.2 Hz, 1H), 8.06 (s, 1H), 6.94 (t, J=9.2 Hz, 1H), 6.70 (dd, J=8.4, 3.6 Hz, 1H), 4.65 (d, J=4.8 Hz, 2H), 4.54 (t, J=8.8 Hz, 2H), 3.29 (t, J=8.8 Hz, 2H), 3.05-2.97 (m, 1H), 1.91-1.79 (m, 2H), 1.79-1.60 (m, 4H), 1.60-1.49 (m, 2H). LCMS $[M+H]^+$=397.1.

Preparation Example 37: Synthesis of Compound HJM-037

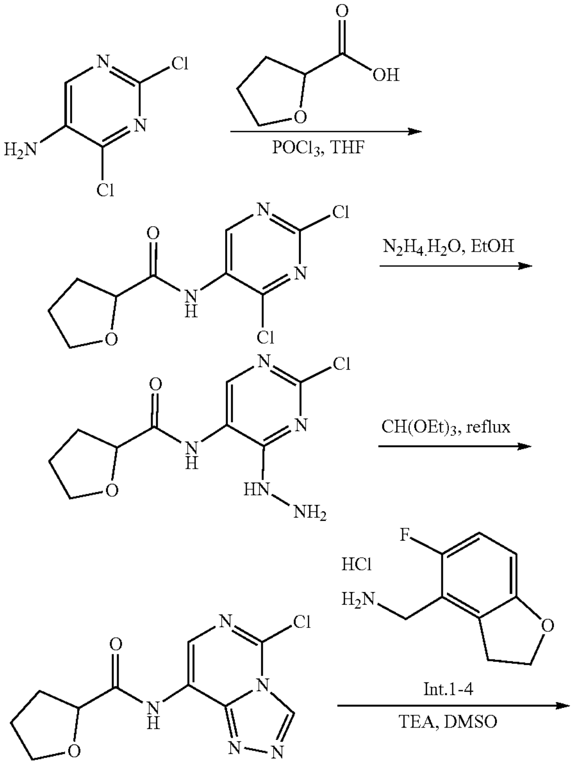

-continued

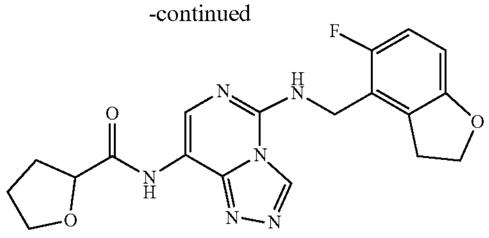

HJM-037

HJM-037 (46 mg, yield: 42.7%) was prepared as a white solid using 2-tetrahydrofuroic acid as starting material according to the method similar to that for preparation example 30.

$^1$H NMR (400 MHz, DMSO-$d_6$) δ 9.42 (s, 1H), 9.33 (s, 1H), 8.49-8.48 (m, 1H), 8.07 (s, 1H), 6.95-6.91 (m, 1H), 6.71-6.68 (m, 1H), 4.65 (d, J=4.4 Hz, 2H), 4.56-4.48 (m, 3H), 4.02-3.86 (m, 2H), 3.31-3.26 (m, 2H), 2.23-2.18 (m, 2H), 1.92-1.87 (m, 2H). LCMS $[M+H]^+$=399.4.

Preparation Example 38: Synthesis of Compound HJM-038

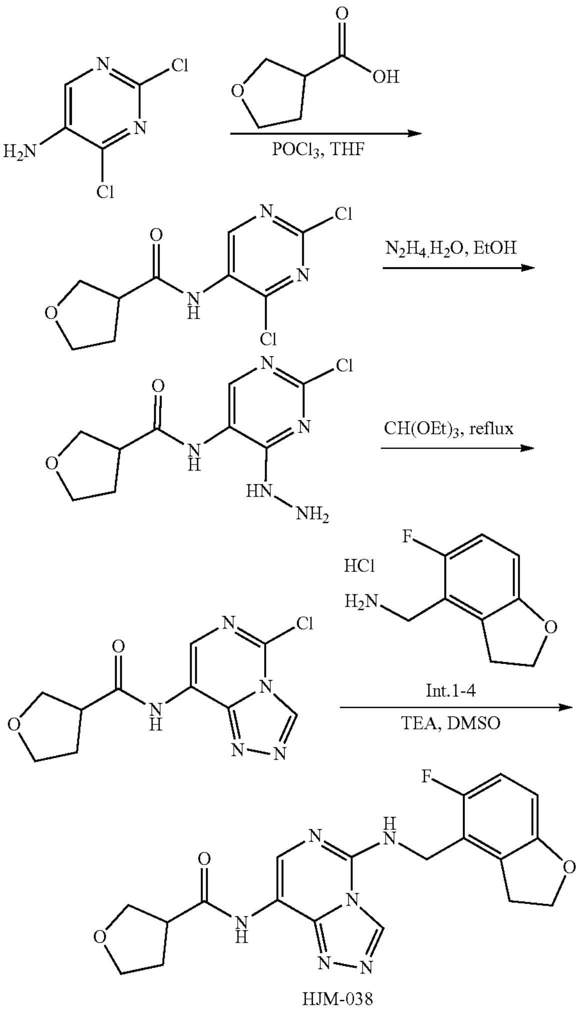

HJM-038

HJM-038 (45 mg) was prepared as a white solid using tetrahydrofuran-3-carboxylic acid as starting material according to the method similar to that for preparation example 30.

$^1H$ NMR (400 MHz, DMSO-$d_6$) δ 10.01 (s, 1H), 9.42 (s, 1H), 8.42 (t, J=5.2 Hz, 1H), 8.08 (s, 1H), 6.94 (dd, J=10.4, 8.8 Hz, 1H), 6.70 (dd, J=8.8, 4.0 Hz, 1H), 4.65 (d, J=4.8 Hz, 2H), 4.54 (t, J=8.8 Hz, 2H), 3.94 (t, J=8.0 Hz, 1H), 3.83-3.65 (m, 3H), 341-3.35 (m, 1H), 3.30-0.27 (m, 2H), 2.12-2.06 (m, 2H). LCMS $[M+H]^+$=399.4.

Preparation Example 39: Synthesis of Compound HJM-039

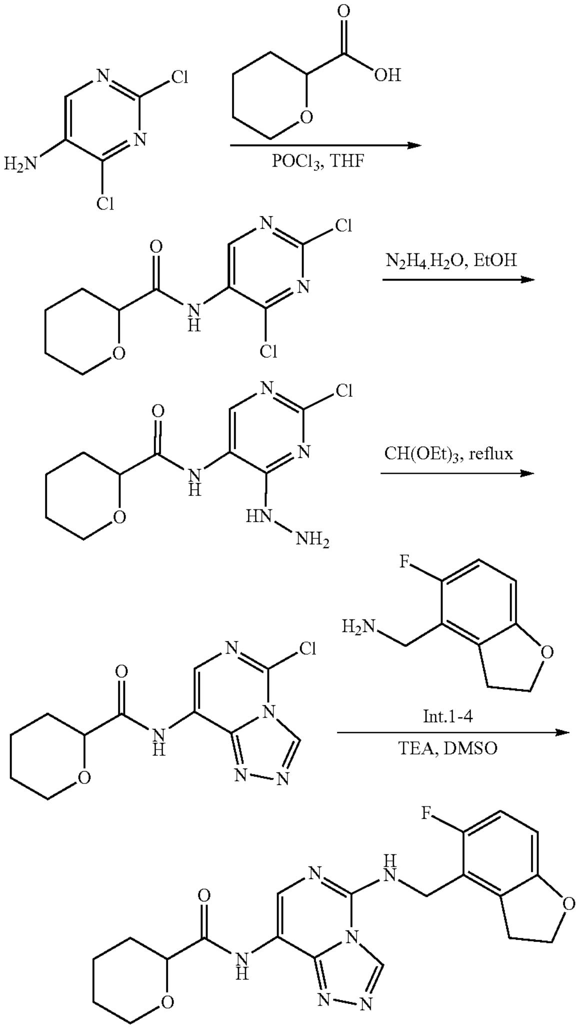

HJM-039

HJM-039 (33 mg, yield: 44.5%) was prepared as a white solid using tetrahydropyran-2-carboxylic acid as starting material according to the method similar to that for preparation example 30.

$^1H$ NMR (400 MHz, $CD_3OD$) δ 9.26 (s, 1H), 8.17 (s, 1H), 6.86-6.81 (m, 1H), 6.64-6.61 (m, 1H), 4.87 (s, 2H), 4.56 (t, J=8.8 Hz, 2H), 4.17-4.01 (m, 2H), 3.61-3.60 (m, 1H), 3.34 (t, J=8.8 Hz, 2H), 2.15-1.98 (m, 2H), 1.67-1.60 (m, 4H). LCMS $[M+H]^+$=413.2.

Preparation Example 40: Synthesis of Compound HJM-040

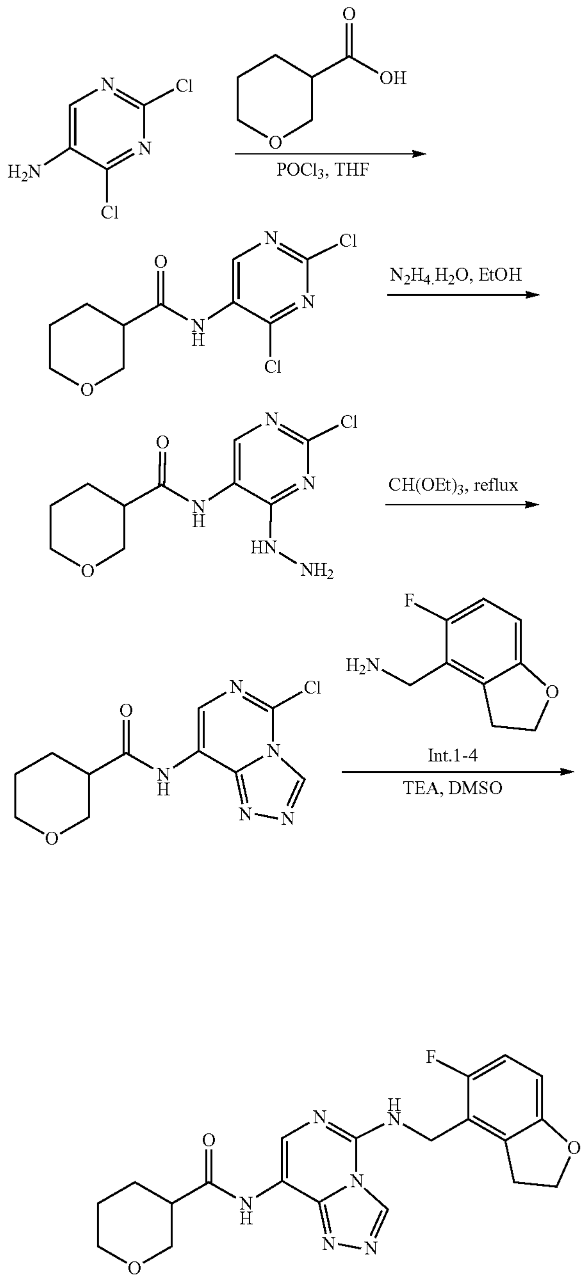

HJM-040

HJM-040 (69 mg, yield: 47.8%) was prepared as a white solid using tetrahydropyran-3-carboxylic acid as starting material according to the method similar to that for preparation example 30.

$^1H$ NMR (400 MHz, DMSO-$d_6$) δ 9.93 (s, 1H), 9.42 (s, 1H), 8.45-8.43 (m, 1H), 8.03 (s, 1H), 6.96-6.91 (m, 1H), 6.71-6.68 (m, 1H), 4.65-4.64 (m, 2H), 4.53 (t, J=8.8 Hz, 2H), 3.96-3.78 (m, 2H), 3.41 (t, J=6.8 Hz, 1H), 3.32-3.26 (m, 3H), 3.26-3.25 (m, 1H), 1.94-1.93 (m, 1H), 1.68-1.61 (m, 3H). LCMS $[M+H]^+$=413.4.

Preparation Example 41: Synthesis of Compound HJM-041

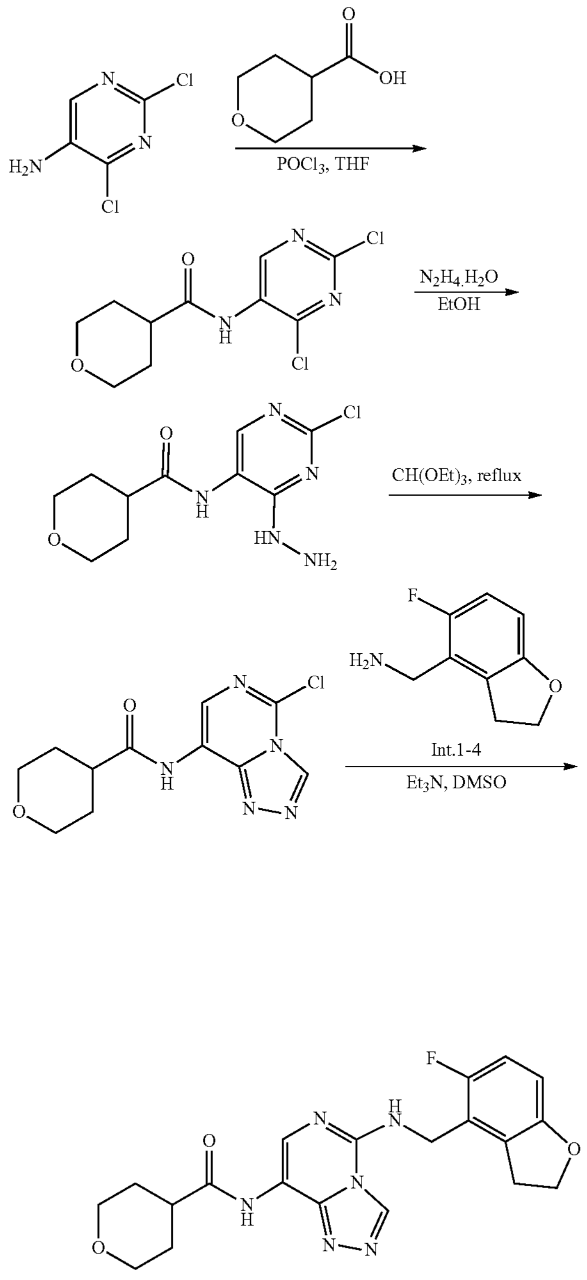

HJM-041

HJM-041 (25 mg, yield: 28.0%) was prepared as a white solid using tetrahydropyran-4-carboxylic acid as starting material according to the method similar to that for preparation example 30.

$^1$H NMR (400 MHz, DMSO-$d_6$) δ 9.86 (s, 1H), 9.42 (s, 1H), 8.42 (t, J=4.8 Hz, 1H), 8.06 (s, 1H), 6.94 (t, J=9.2 Hz, 1H), 6.71-6.68 (m, 1H), 4.64 (d, J=4.8 Hz, 2H), 4.53 (t, J=8.8 Hz, 2H), 3.89 (d, J=11.2 Hz, 2H), 3.37-3.34 (m, 2H), 3.28-3.26 (m, 2H), 2.84-2.82 (m, 1H), 1.72-1.63 (m, 4H). LCMS $[M+H]^+$=413.2.

Preparation Example 42: Synthesis of Compound HJM-042

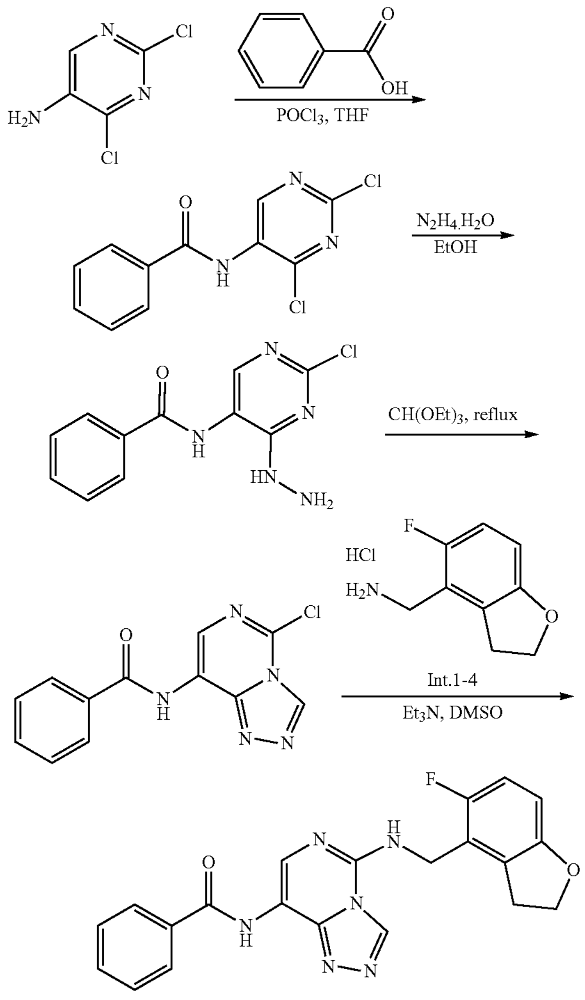

HJM-042

HJM-042 (15 mg, yield: 25.8%) was prepared as a blue solid using benzoic acid as starting material according to the method similar to that for preparation example 30.

$^1$H NMR (400 MHz, $CD_3OD$) δ 9.31 (s, 1H), 8.12 (s, 1H), 8.06-8.04 (m, 2H), 7.63-7.55 (m, 3H), 6.89 (t, J=8.8 Hz, 1H), 6.66-6.64 (m, 1H), 4.82-4.80 (m, 2H), 4.61 (t, J=8.4 Hz, 2H), 3.41 (t, J=8.4 Hz, 2H). LCMS $[M+H]^+$=405.1.

Preparation Example 43: Synthesis of Compound HJM-043

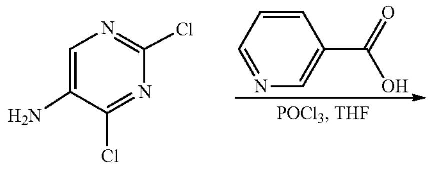

-continued

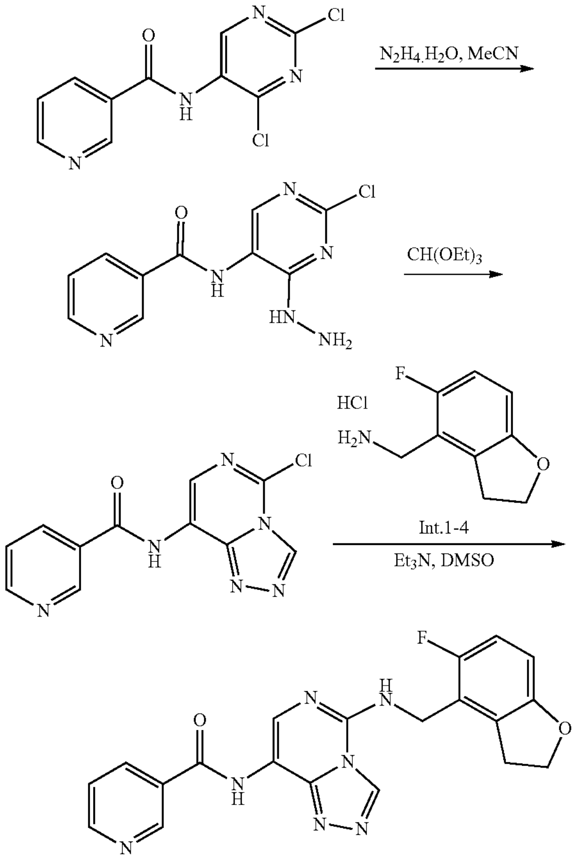

HJM-043

HJM-043 (87 mg) was prepared as a white solid using nicotinic acid as starting material according to the method similar to that for preparation example 30.

$^{1}$H NMR (400 MHz, DMSO-d$_6$) δ 10.48 (s, 1H), 9.48 (s, 1H), 9.16 (s, 1H), 8.79 (dd, J=4.8, 1.6 Hz, 1H), 8.64 (t, J=5.2 Hz, 1H), 8.36 (d, J=8.0 Hz, 1H), 7.90 (s, 1H), 7.60 (dd, J=8.0, 4.8 Hz, 1H), 7.03-6.89 (m, 1H), 6.75-6.70 (m, 1H), 4.70 (d, J=4.8 Hz, 2H), 4.56 (t, J=8.8 Hz, 2H), 3.32 (t, J=8.8 Hz, 2H). LCMS [M+H]$^+$=406.1.

Preparation Example 44: Synthesis of Compound HJM-044

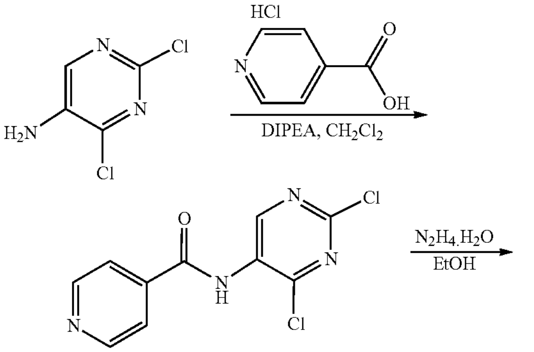

-continued

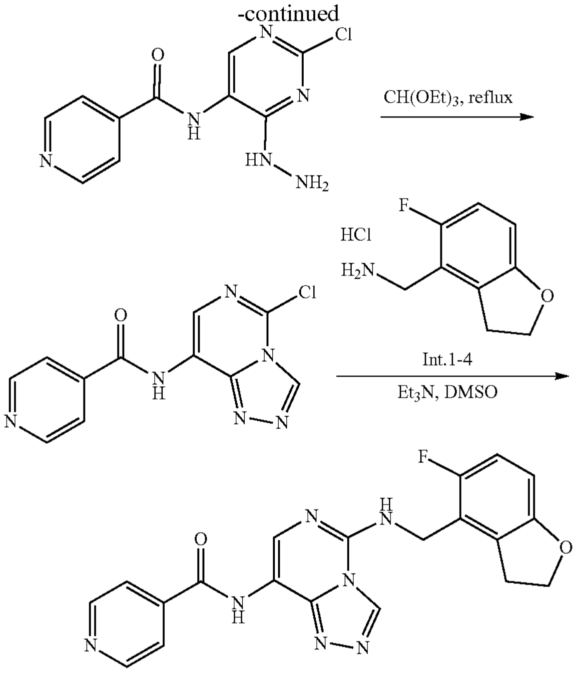

HJM-044

HJM-044 (7.0 mg) was prepared as a white solid using isonicotinic acid chloride as starting material according to the method similar to that for preparation example 30.

$^{1}$H NMR (400 MHz, DMSO-d$_6$) δ 10.54 (s, 1H), 9.46 (s, 1H), 8.81-8.80 (m, 2H), 8.64 (t, J=5.2 Hz, 1H), 7.91-7.90 (m, 2H), 7.88 (s, 1H), 6.98 (t, J=8.8 Hz, 1H), 6.73-6.68 (m, 1H), 4.70 (d, J=4.8 Hz, 2H), 4.55 (t, J=8.8 Hz, 2H), 3.41-3.29 (m, 2H). LCMS [M+H]$^+$=406.1.

Preparation Example 45: Synthesis of Compound HJM-045

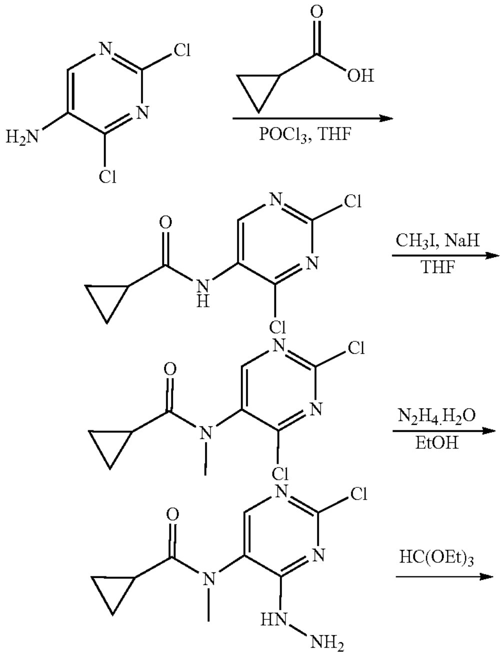

-continued

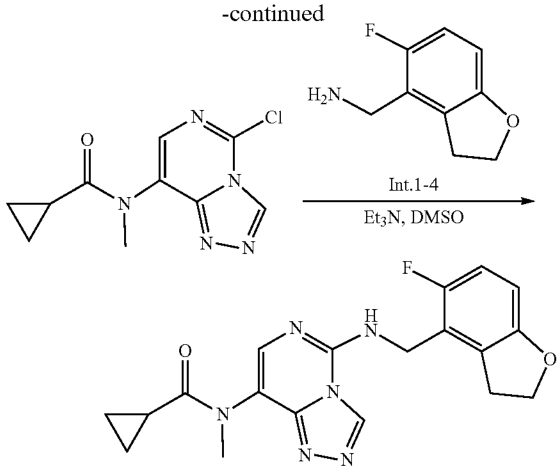

HJM-045

Steps 1-2:

Under $N_2$ protection, compound N-(2,4-dichloropyrimidin-5-yl)cyclopropanecarboxamide (See Step 1 of preparation example 30, 700 mg, 3.0 mmol) was dissolved in anhydrous tetrahydrofuran (10 mL), 60% sodium hydride (145 mg, 3.6 mmol) was slowly added under an ice-water bath, and the mixture was stirred in an ice-water bath for 16 min. Iodomethane (1.28 g, 9.0 mmol) was then slowly added dropwise. After the dropwise addition, the ice-water bath was removed, and the mixture was stirred at room temperature for 2 h. TLC showed that the reaction was completed. The mixture was concentrated under reduced pressure, and purified by silica gel column chromatography (PE:EA=2:1) to afford compound N-(2,4-dichloropyrimidin-5-yl)-N-methylcyclopropanecarboxamide (350 mg, yield: 47%) as a white solid, LCMS $[M+H]^+$=246.1.

Steps 3-5:

HJM-045 (12 mg, yield: 26%) was prepared as a white solid using compound N-(2,4-dichloropyrimidin-5-yl)-N-methylcyclopropanecarboxamide as starting material according to the method similar to that for preparation example 30.

$^1$H NMR (400 MHz, DMSO-$d_6$) δ 9.47 (s, 1H), 8.81 (s, 1H), 7.73 (s, 1H), 6.95 (t, J=9.2 Hz, 1H), 6.72-6.69 (m, 1H), 4.67 (s, 2H), 4.55 (t, J=8.8 Hz, 2H), 3.32 (t, J=8.8 Hz, 2H), 3.17 (s, 3H), 1.54-1.50 (m, 1H), 0.82-70 (m, 2H), 0.65-0.47 (m, 2H). LCMS $[M+H]^+$=383.2.

Preparation Example 46: Synthesis of Compound HJM-046

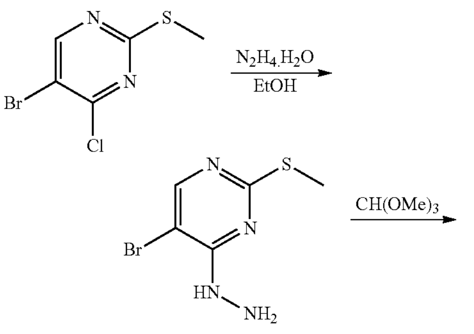

-continued

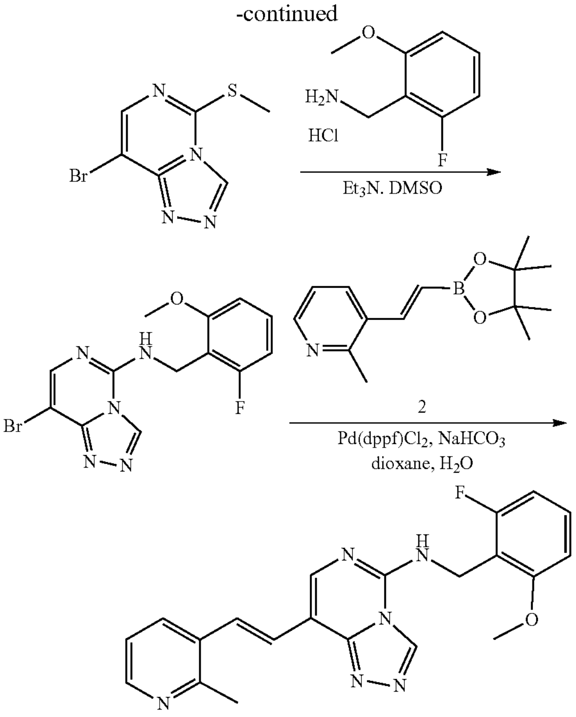

HJM-046

Step 1:

2-Methylthio-4-chloro-5-bromopyrimidine (33.0 g, 0.138 mol) was dissolved in ethanol (350 mL), 85% hydrazine hydrate (13.8 g, 0.235 mol) was slowly added at room temperature, and the mixture was stirred at room temperature for 4 h. TLC showed that the reaction was completed. The mixture was concentrated under reduced pressure to afford crude compound 2-methylthio-4-hydrazinyl-5-bromopyrimidine (32.0 g, yield: 99.0%), which was directly used in the next step without purification.

$^1$H NMR (400 MHz, DMSO-$d_6$) δ 8.07 (s, 1H), 2.45 (s, 3H). LCMS $[M+CH_3CN]^+$=275.0.

Step 2:

Under $N_2$ protection, the crude compound 2-methylthio-4-hydrazinyl-5-bromopyrimidine (32.0 g, 0.138 mol) was dissolved in 150 mL of triethyl orthoformate, and the mixture was heated to 150° C. and stirred for 3 h. TLC showed that the reaction was completed. The mixture was stopped from heating, and naturally cooled to room temperature. The mixture was concentrated under reduced pressure, slurried with ethyl acetate, and filtered to afford 8-bromo-5-(methylthio)-[1,2,4]triazolo[4,3-c]pyrimidine (27.0 g, yield: 80.0%) as a grayish white solid.

$^1$H NMR (400 MHz, DMSO-$d_6$) δ9.58 (s, 1H), 8.19 (s, 1H), 2.75 (s, 3H). LCMS $[M+H]^+$=245.1.

Step 3:

Under $N_2$ protection, compound 8-bromo-5-(methylthio)-[1,2,4]triazolo[4,3-c]pyrimidine (1.0 g, 4.08 mmol) was dissolved in dimethyl sulfoxide (10 mL), 2-fluoro-6-methoxybenzylamine hydrochloride (3.9 g, 20.40 mmol) and triethylamine (4.1 g, 40.80 mmol) were added successively, and the mixture was heated to 70° C. and stirred overnight. TLC showed that the reaction was completed. The mixture was stopped from heating, and naturally cooled to room temperature. Water and ethyl acetate were added, and the mixture was layered. The aqueous phase was extracted with ethyl acetate (2×50 mL). The organic phases were combined, and then washed successively with water (2×20 mL) and saturated brine. The organic layer was dried with $Na_2SO_4$, filtered, and concentrated. The residue was purified by silica gel column chromatography (DCM: MeOH=20:1) to afford 8-bromo-N-(2-fluoro-6-methoxybenzyl)-[1,2,4]triazolo[4,3-c]pyrimidin-5-amine (550 mg, yield: 38.0%) as a white solid.

$^1H$ NMR (400 MHz, DMSO-$d_6$) δ 9.50 (s, 1H), 8.49 (s, 1H), 7.86 (s, 1H), 7.38-7.40 (m, 1H), 6.93 (d, J=7.2 Hz, 1H), 6.86 (t, J=8.8 Hz, 1H), 4.66 (s, 2H), 3.83 (s, 3H). LCMS $[M+H]^+$=352.1.

Step 4:

Under $N_2$ protection, 8-bromo-N-(2-fluoro-6-methoxybenzyl)-[1,2,4]triazolo[4,3-c]pyrimidin-5-amine (200 mg, 0.57 mmol), pinacol borate 2 (418 mg, 1.71 mmol) and $NaHCO_3$ (181 mg, 1.71 mmol) were dissolved in a mixture (8 mL) of 1,4-dioxane and water (3:1), and 1,1'-bis(diphenylphosphino)ferrocene-palladium(II)dichloride dichloromethane complex (37 mg, 0.05 mmol) was added at room temperature. The atmosphere was replaced three times with $N_2$, and the mixture was heated to 100° C. and reacted for 2 h. TLC showed that the reaction was completed. The mixture was stopped from heating, naturally cooled to room temperature, and concentrated under reduced pressure. The residue was purified by silica gel column chromatography (DCM:MeOH=12:1) to afford HJM-046 (200 mg, yield: 90.1%) as a yellow solid.

$^1H$ NMR (400 MHz, DMSO-$d_6$) δ 9.52 (s, 1H), 8.52 (t, J=4.4 Hz, 1H), 8.33 (d, J=4.4 Hz, 1H), 8.25 (d, J=16.0 Hz, 1H), 8.06 (d, J=8.0 Hz, 1H), 7.89 (s, 1H), 7.40 (dd, J=16.0, 8.0 Hz, 1H), 7.30-7.25 (m, 2H), 6.95 (d, J=8.0 Hz, 1H), 6.88 (t, J=8.8 Hz, 1H), 4.73 (d, J=4.0 Hz, 2H), 3.84 (s, 3H), 2.61 (s, 3H). LCMS $[M+H]^+$=391.4.

Preparation Example 47: Synthesis of Compound HJM-047

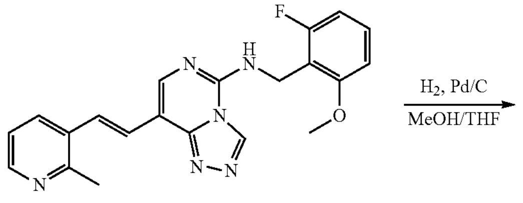

HJM-046

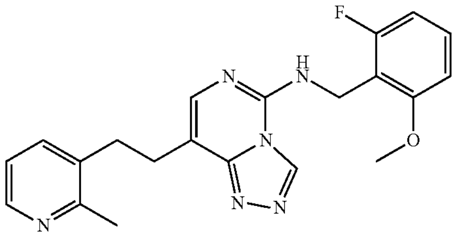

HJM-047

Compound HJM-046 (150 mg, 0.38 mmol) was dissolved in a mixture of tetrahydrofuran (7 mL) and methanol (7 mL), and the atmosphere was replaced with $N_2$. 30.0 mg of 10% Pd/C was added quickly, the atmosphere was replaced with $H_2$, and the mixture was stirred at room temperature under a hydrogen balloon for 2 h. The mixture was filtered, and the filter cake was washed twice with methanol. The filtrates were combined, concentrated, and purified by preparative HPLC to afford HJM-047 (65 mg, yield: 43.0%) as a white solid.

$^1H$ NMR (400 MHz, DMSO-$d_6$) δ 9.43 (s, 1H), 8.28 (dd, J=4.8, 1.6 Hz, 1H), 8.11 (t, J=4.4 Hz, 1H), 7.54-7.48 (m, 1H), 7.44 (s, 1H), 7.38 (dd, J=15.2, 8.4 Hz, 1H), 7.13 (dd, J=7.6, 4.8 Hz, 1H), 6.93 (d, J=8.4 Hz, 1H), 6.86 (t, J=8.8 Hz, 1H), 4.64 (d, J=3.6 Hz, 2H), 3.82 (s, 3H), 3.08-2.93 (m, 4H), 2.49 (s, 3H). LCMS $[M+H]^+$=393.6.

Preparation Example 48: Synthesis of Compound HJM-048

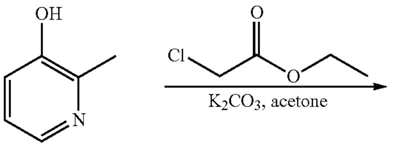

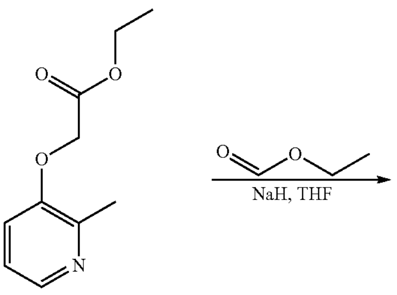

10

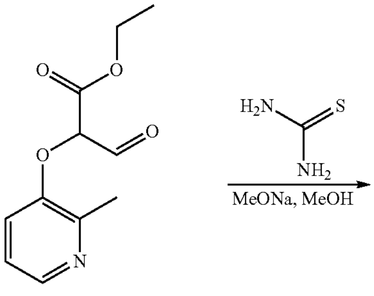

11

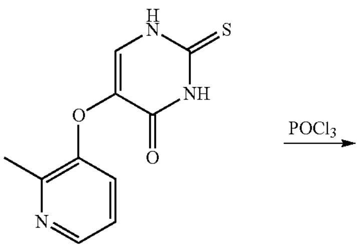

12

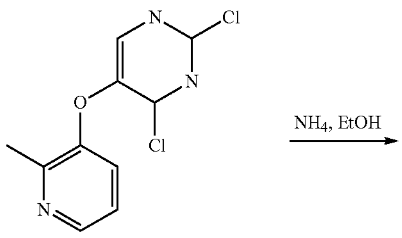

13

-continued

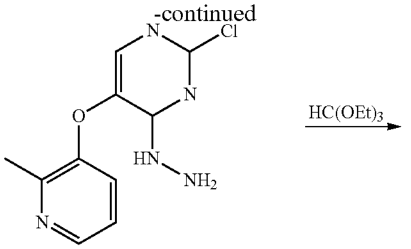

14

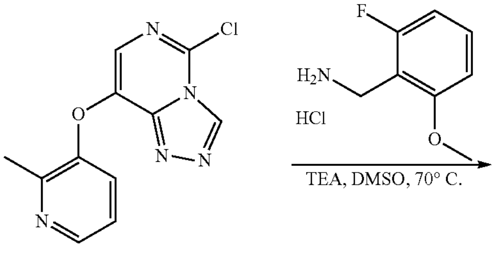

15

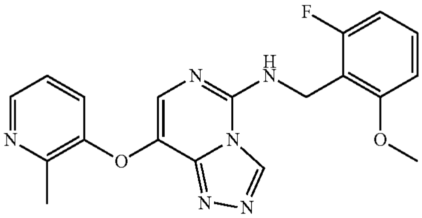

HJM-048

Step 1:

3-Hydroxy-2-methylpyridine (4.7 g, 0.043 mol) and $K_2CO_3$ (8.9 g, 0.065 mol) were dissolved in anhydrous acetone (100 mL), ethyl chloroacetate (6.9 mL, 0.065 mol) was slowly added under $N_2$ protection, and the mixture was heated to 80° C. and stirred for 16 h. TLC showed that the reaction was completed. The mixture was stopped from heating, naturally cooled to room temperature, and filtered. The filtrate was concentrated under reduced pressure, and purified by silica gel column chromatography (PE:EA=20:1) to afford compound 10 (3.0 g, yield: 36.4%) as a brown liquid, LCMS $[M+H]^+$=196.2.

Step 2:

Compound 10 (3.0 g, 0.015 mol) was dissolved in anhydrous tetrahydrofuran (50 mL), NaH (0.92 g, 0.023 mol, w/w 60%) was added under an ice-water bath and $N_2$ protection, and the mixture was stirred at room temperature for 1 h. The mixture was then cooled to 0° C., and ethyl formate (1.8 mL, 0.023 mol) was slowly added dropwise. After the dropwise addition, the mixture was stirred at room temperature overnight. TLC showed that the reaction was completed. The mixture was poured into ice water to quench the reaction, and the aqueous phase was extracted with ethyl acetate (2×100 mL). The organic phases were combined, washed with saturated brine (2×20 mL), dried with $Na_2SO_4$, and filtered. The filtrate was concentrated to afford crude compound 11 (3.3 g, quantitative yield), which was directly used in the next step without purification, LCMS $[M+H]^+$ =224.3.

Step 3:

Compound 11 (3.3 g, 15 mol) and thiourea (2.2 g, 30 mol) were dissolved in methanol (200 mL), sodium methoxide (1.6 g, 30 mmol) was slowly added under $N_2$ protection, and the mixture was heated to 80° C. and stirred for 16 h. TLC showed that the reaction was completed. The mixture was stopped from heating, and naturally cooled to room temperature. The mixture was poured into ice water to quench the reaction, and the aqueous phase was extracted with ethyl acetate (2×100 mL). The organic phases were combined, washed with saturated brine (2×20 mL), dried with $Na_2SO_4$, filtered, and concentrated. The residue was purified by silica gel column chromatography (DCM:MeOH=20:1) to afford compound 12 (1.2 g, yield: 34.3%) as a yellow solid, LCMS $[M+H]^+$=236.1.

Step 4:

Under $N_2$ protection, compound 12 (700 mg, 2.98 mmol) was dissolved in phosphorus oxychloride (10 mL), and the mixture was heated to 90° C. and stirred for 48 h. TLC showed that the reaction was completed. The mixture was stopped from heating, naturally cooled to room temperature, and concentrated under reduced pressure to remove most of the solvent. The residue was adjusted to weak alkalinity with saturated $NaHCO_3$ solution, and the aqueous phase was extracted with ethyl acetate (2×50 mL). The organic phases were combined, washed with saturated brine (2×20 mL), dried with $Na_2SO_4$, filtered, and concentrated. The residue was purified by silica gel column chromatography (DCM: MeOH=100:1) to afford compound 13 (350 mg, yield: 46.1%) as a white solid, LCMS $[M+H]^+$=256.1.

Step 5:

Compound 13 (350 mg, 1.39 mmol) was dissolved in ethanol (5 mL), hydrazine hydrate (0.1 mL, 1.67 mmol) was slowly added at room temperature, and the mixture was stirred at room temperature for 2 h. TLC showed that the reaction was completed. The mixture was concentrated under reduced pressure to afford crude compound 14 (350 mg, quantitative yield), LCMS $[M+H]^+$=252.1.

Step 6:

Under $N_2$ protection, compound 14 (300 mg, 1.20 mmol) was dissolved in 30 mL of triethyl orthoformate, and the mixture was heated to 150° C. and reacted for 4 h. TLC showed that the reaction was completed. The mixture was stopped from heating, naturally cooled to room temperature, and concentrated under reduced pressure. The residue was purified by silica gel column chromatography (DCM: MeOH=50:1) to afford 15 (150 mg, yield: 48.1%) as a yellow solid, LCMS $[M+H]^+$=262.3.

Step 7:

Under $N_2$ protection, 2-fluoro-6-methoxybenzylamine hydrochloride (330 mg, 1.72 mmol) and triethylamine (0.40 mL, 2.85 mmol) were dissolved in dimethyl sulfoxide (5 mL), compound 15 (150 mg, 0.57 mmol) was added, and the mixture was heated to 80° C. and stirred for 2 h. TLC showed that the reaction was completed. The mixture was stopped from heating, naturally cooled to room temperature, and poured into ice water. Solid was precipitated, and filtered. The filter cake was purified by preparative HPLC to afford HJM-048 (85 mg, yield: 39.3%) as a white solid.

$^1H$ NMR (400 MHz, DMSO-$d_6$) δ 9.48 (s, 1H), 8.32-8.16 (s, 1H), 7.69 (s, 1H), 7.45-7.32 (m, 2H), 7.24 (dd, J=8.4, 4.8 Hz, 1H), 6.96 (d, J=8.4 Hz, 1H), 6.89 (t, J=8.8 Hz, 1H), 4.67 (d, J=3.2 Hz, 2H), 3.85 (s, 3H), 2.63 (s, 3H). LCMS $[M+H]^+$=381.2.

Preparation Example 49: Synthesis of Compound HJM-049

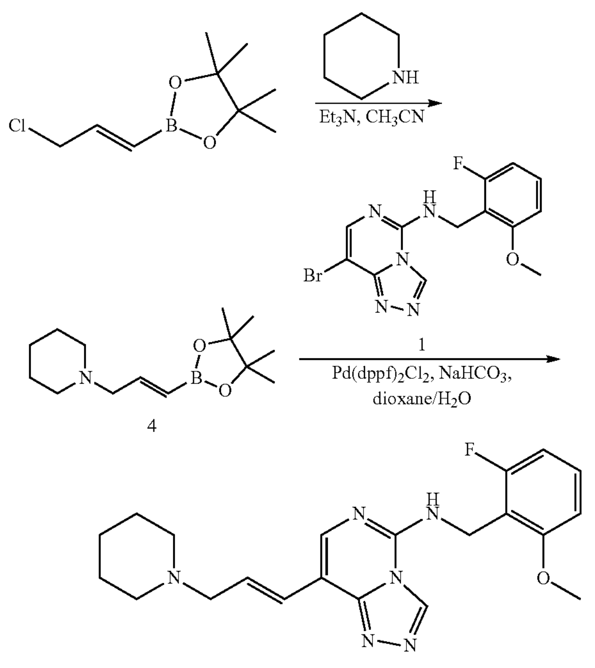

HJM-049

Step 1:

Under $N_2$ protection, piperidine (0.1 mL, 0.99 mmol) and triethylamine (0.2 mL, 1.49 mmol) were dissolved in acetonitrile (3 mL), and 3-chloropropenyl-1-boric acid pinacol ester (100 mg, 0.50 mmol) was added at room temperature. The atmosphere was replaced three times with $N_2$, and the mixture was stirred at room temperature overnight. TLC showed that the reaction was completed. The mixture was concentrated under reduced pressure to afford crude compound 2 (120 mg, quantitative yield), which was directly used in the next step without purification. LCMS $[M+H]^+=252.3$.

Step 2:

Under $N_2$ protection, pinacol borate 4 (100 mg, 0.40 mmol), 8-bromo-N-((2-fluoro-6-methoxybenzyl)-[1,2,4]triazolo[4,3-c]pyrimidin-5-amine 1 (140 mg, 0.40 mmol) and $NaHCO_3$ (127 mg, 1.20 mmol) were dissolved in a mixture (8 mL) of 1,4-dioxane and water (3:1), 1,1'-bis(diphenylphosphino)ferrocene-palladium(II)dichloride dichloromethane complex (30 mg, 0.04 mmol) was added at room temperature, and the mixture was heated to 100° C. and reacted for 2 h. TLC showed that the reaction was completed. The mixture was stopped from heating, naturally cooled to room temperature, and concentrated under reduced pressure. The residue was purified by preparative HPLC to afford HJM-049 (12 mg, yield: 7.6%) as a white solid.

$^1$H NMR (400 MHz, DMSO-$d_6$) δ 9.48 (s, 1H), 8.39 (t, J=4.4 Hz, 1H), 7.70 (s, 1H), 7.39 (dd, J=15.6, 8.4 Hz, 1H), 7.13-7.02 (m, 1H), 6.93 (d, J=8.4 Hz, 1H), 6.86 (t, J=8.4 Hz, 1H), 6.58 (d, J=15.6 Hz, 1H), 4.69 (d, J=3.6 Hz, 2H), 3.83 (s, 3H), 3.21 (d, J=6.8 Hz, 2H), 2.52-2.49 (m, 4H), 1.59-1.51 (m, 4H), 1.46-1.35 (m, 2H). LCMS $[M+H]^+=397.4$.

Preparation Example 50: Synthesis of Compound HJM-050

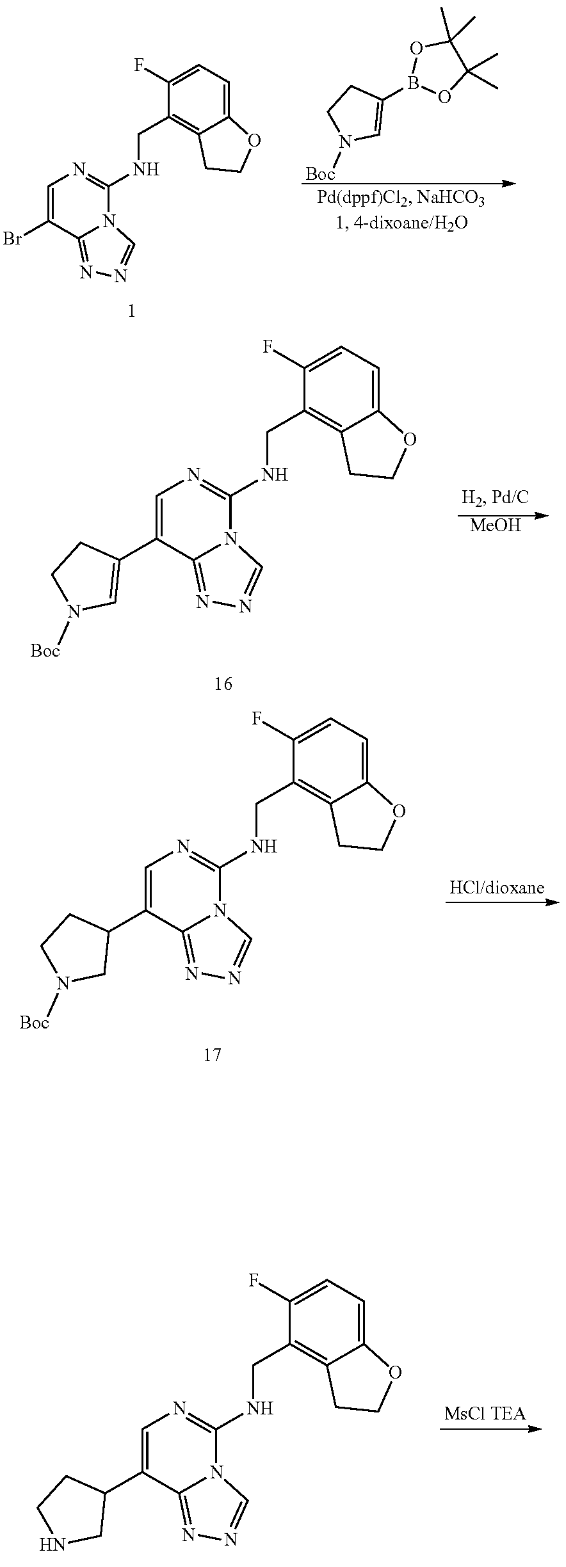

18

-continued

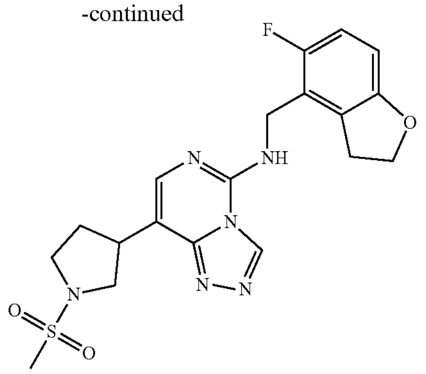

HJM-050

Step 1:

Under $N_2$ protection, 8-bromo-N-((5-fluoro-2,3-dihydrobenzofuran-4-yl)methyl)-[1,2,4]triazolo[4,3-c]pyrimidine-5-amine 1 (200 mg, 0.55 mmol), N-tert-butoxycarbonyl-2,3-dihydro-1H-pyrrole-4-boronic acid pinacol ester (325 mg, 1.10 mmol) and $NaHCO_3$ (175 mg, 1.65 mmol) were dissolved in a mixture (12 mL) of 1,4-dioxane and water (3:1), 1,1'-bis(diphenylphosphino)ferrocene-palladium(II)dichloride dichloromethane complex (36 mg, 0.05 mmol) was added at room temperature, and the mixture was heated to 100° C. and reacted for 2 h. TLC showed that the reaction was completed. The mixture was stopped from heating, naturally cooled to room temperature, and concentrated under reduced pressure. The residue was purified by silica gel column chromatography (DCM:MeOH=20:1) to afford 16 (200 mg, yield: 80.6%) as a brown solid, LCMS $[M+H]^+$=453.1.

Step 2:

Compound 16 (200 mg, 0.44 mmol) was dissolved in methanol (20 mL), and the atmosphere was replaced with $N_2$. 20 mg of 10% Pd/C was added quickly, the atmosphere was replaced with $H_2$ for three times, and the mixture was stirred at room temperature under a hydrogen balloon for 2 h. The mixture was filtered, and the filter cake was washed twice with methanol. The filtrates were combined and concentrated to afford crude product compound 17 (200 mg, quantitative yield), which was directly used in the next step without purification. LCMS $[M+H]^+$=455.2.

Step 3:

Compound 17 (200 mg, 0.44 mmol) was dissolved in ethanol (5 mL), and the mixture was slowly added to a solution of hydrochloric acid in 1,4-dioxane (4 M, 5 mL) at room temperature. The mixture was stirred at room temperature for 4 h. TLC showed that the reaction was completed. The mixture was concentrated to afford crude compound 18 (150 mg, quantitative yield), which was directly used in the next step without purification. LCMS $[M+H]^+$=355.4.

Step 4:

Under $N_2$ protection, compound 18 (150 mg, 0.42 mmol) and triethylamine (0.18 mL, 1.27 mmol) were dissolved in dichloromethane (5 mL), methanesulfonyl chloride (0.06 mL, 0.85 mmol) was slowly added dropwise at room temperature, and the mixture was stirred at room temperature for 30 min. TLC showed that the reaction was completed. The mixture was poured into water to quench the reaction, and the aqueous phase was extracted with dichloromethane (2×50 mL). The organic phases were combined, washed with saturated brine (2×5 mL), dried with $Na_2SO_4$, and filtered. The filtrate was concentrated and purified by preparative HPLC to afford HJM-050 (39 mg, yield: 21.5%) as a white solid.

$^1$H NMR (400 MHz, DMSO-$d_6$) δ 9.41 (s, 1H), 8.53 (t, J=5.2 Hz, 1H), 7.57 (s, 1H), 7.03-6.87 (m, 1H), 6.70 (dd, J=8.4, 4.0 Hz, 1H), 4.65 (d, J=4.8 Hz, 2H), 4.54 (t, J=8.8 Hz, 2H), 3.76-3.67 (m, 1H), 3.67-3.57 (m, 1H), 3.56-3.44 (m, 2H), 3.42-3.36 (m, 1H), 3.30-3.26 (m. 2H), 2.98 (s, 3H), 2.39-2.21 (m, 2H). LCMS $[M+H]^+$=433.3.

Preparation Example 51: Synthesis of Compound HJM-051

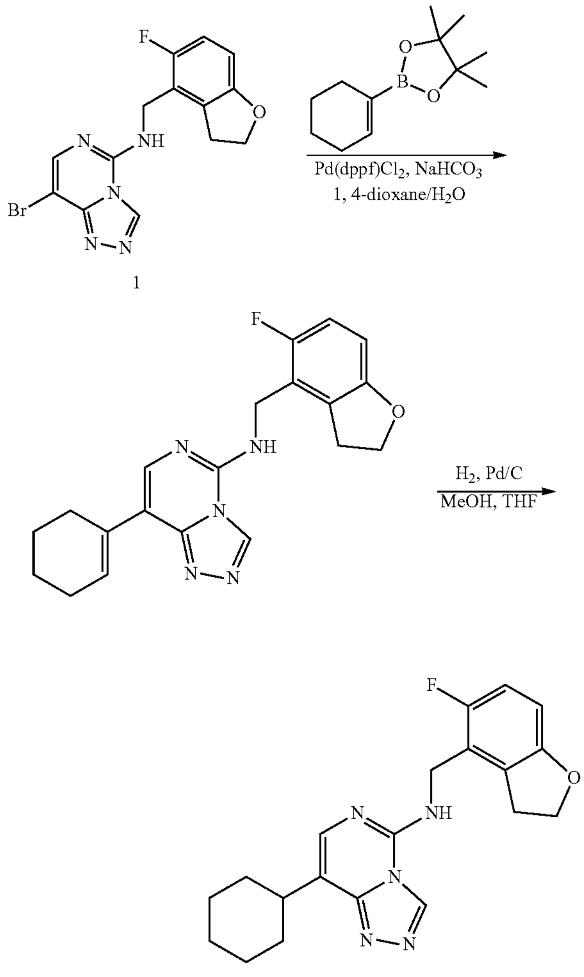

1

HJM-051

HJM-051 (9 mg, yield: 9.9%) was prepared as a white solid using cyclohexene-1-boronic acid pinacol ester as starting material according to the method similar to that for preparation example 3.

$^1$H NMR (400 MHz, DMSO-$d_6$) δ 9.38 (s, 1H), 8.37 (s, 1H), 7.44 (s, 1H), 6.94 (t, J=9.2 Hz, 1H), 6.70 (d, J=5.2 Hz, 1H), 4.63 (s, 2H), 4.54 (t, J=8.4 Hz, 2H), 3.28 (t, J=8.4 Hz, 2H), 2.92-2.75 (m, 1H), 1.95-1.85 (m, 2H), 1.85-1.76 (m, 2H), 1.74-1.61 (m, 3H), 1.48-1.17 (m, 3H). LCMS $[M+H]^+$=368.4.

Preparation Example 52: Synthesis of Compound HJM-052

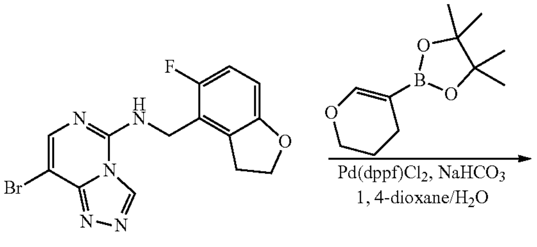

1

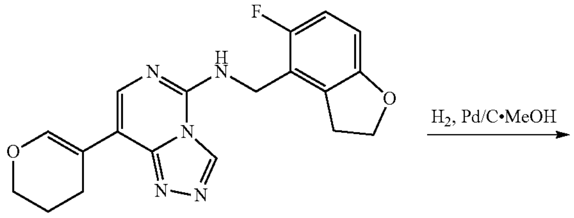

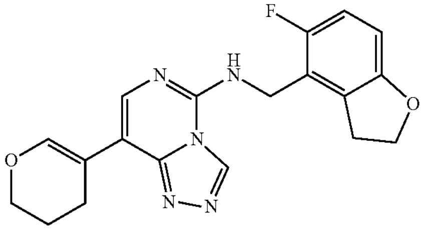

HJM-052

HJM-052 (10 mg, yield: 14.1%) was prepared as a yellow solid using 2-(3,4-dihydro-2H-pyran-5-yl)-4,4,5,5-tetramethyl-1,3,2-dioxaborolane as starting material according to the method similar to that for preparation example 3.

$^1$H NMR (400 MHz, $CD_3OD$) δ 9.24 (s, 1H), 7.63 (s, 1H), 6.84 (t, J=9.2 Hz, 1H), 6.63 (dd, J=8.4, 4.0 Hz, 1H), 4.74 (s, 2H), 4.56 (t, J=8.4 Hz, 2H), 4.10-4.06 (m, 1H), 3.96-3.93 (m, 1H), 3.73-3.66 (m, 1H), 3.60-3.54 (m, 1H), 3.38-3.35 (m, 1H), 3.34-3.31 (m, 2H), 2.08-2.02 (m, 2H), 1.83-1.72 (m, 2H). LCMS $[M+H]^+$=370.3.

Preparation Example 53: Synthesis of Compound HJM-053

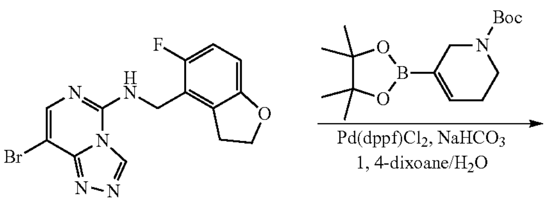

1

-continued

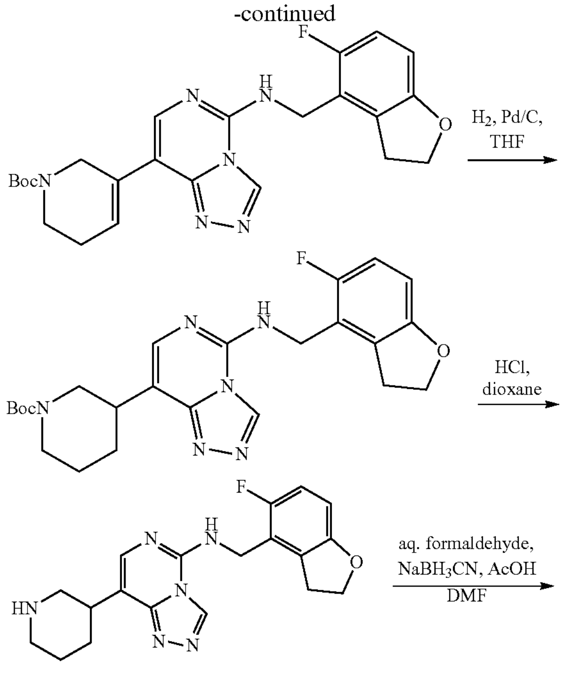

19

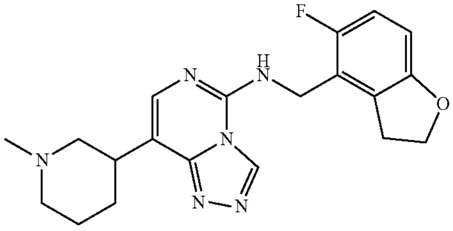

HJM-053

Steps 1-3:

Compound 19 (200 mg) was prepared as a white solid using N-tert-butoxycarbonyl-1,2,5,6-tetrahydropyridine-3-boronic acid pinacol ester as starting material according to the method similar to that for preparation example 50.

Step 4:

Under $N_2$ protection, compound 19 (40 mg, 0.38 mmol) was dissolved in N,N-dimethylformamide (3 mL), 37% formaldehyde aqueous solution (0.7 mL) and a drop of glacial acetic acid were slowly added at room temperature, and the mixture was stirred at 0° C. for 30 min. Sodium cyanobohydride (27 mg, 0.42 mmol) was added, and the mixture was further stirred at 0° C. for 30 min. TLC showed that the reaction was completed. The reaction mixture was poured into saturated $NaHCO_3$ solution to quench the reaction, and the aqueous phase was extracted with ethyl acetate (50 mL×2). The organic phases were combined, washed with saturated brine (2×5 mL), dried with $Na_2SO_4$, and filtered. The filtrate was concentrated and purified by preparative HPLC to afford HJM-053 (33 mg, yield: 22.76%) as a white solid.

$^1$H NMR (400 MHz, DMSO-$d_6$) δ 9.64 (s, 1H), 9.43 (s, 1H), 8.63 (s, 1H), 7.55 (s, 1H), 6.99-6.86 (m, 1H), 6.70 (dd, J=8.4, 3.6 Hz, 1H), 4.65 (s, 2H), 4.54 (t, J=8.8 Hz, 2H), 3.62 (d, J=11.2 Hz, 1H), 3.50 (d, J=11.2 Hz, 1H), 3.43-3.24 (m, 4H), 3.04-2.92 (m, 1H), 2.83 (d, J=4.4 Hz, 3H), 2.06-1.73 (m, 4H). LCMS $[M+H]^+$=383.3.

Preparation Example 54: Synthesis of Compound HJM-054

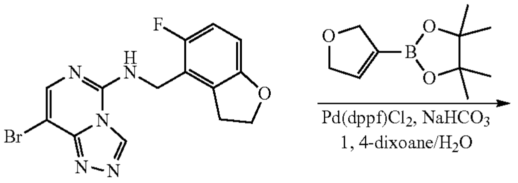

1

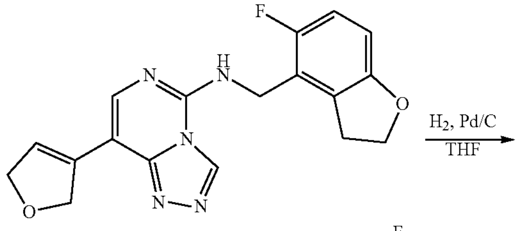

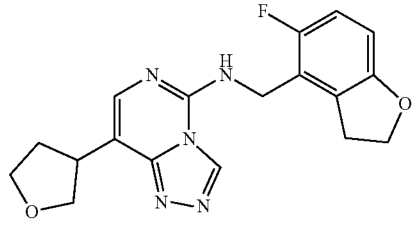

HJM-054

HJM-054 (7 mg, yield: 8.7%) was prepared as a white solid using 2-(2,5-dihydrofuran-3-yl)-4,4,5,5-tetramethyl-1,3,2-dioxaborolane as starting material according to the method similar to that for preparation example 3.

$^1$H NMR (400 MHz, $CD_3OD$) δ 9.28 (s, 1H), 7.68 (s, 1H), 6.88-6.79 (m, 1H), 6.63 (dd, J=8.8, 4.0 Hz, 1H), 4.75 (s, 2H), 4.57 (t, J=8.8 Hz, 2H), 4.18-4.12 (m, 1H), 4.11-4.05 (m, 1H), 3.98-3.88 (m, 2H), 3.76-3.69 (m, 1H), 3.38-3.32 (m, 2H), 2.41-2.35 (m, 1H), 2.32-2.23 (m, 1H). LCMS $[M+H]^+$=356.3.

Preparation Example 55: Synthesis of Compound HJM-055

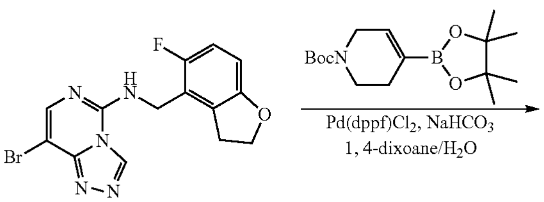

1

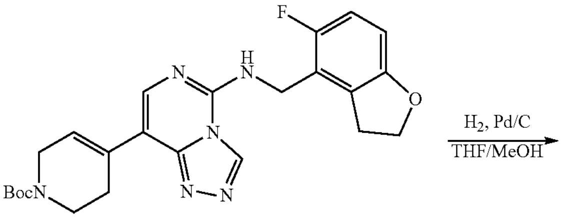

-continued

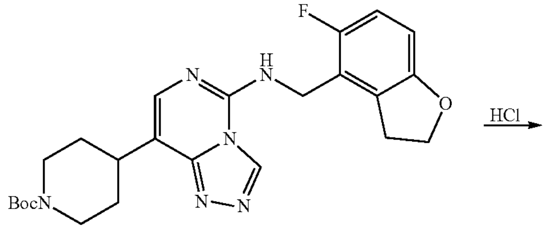

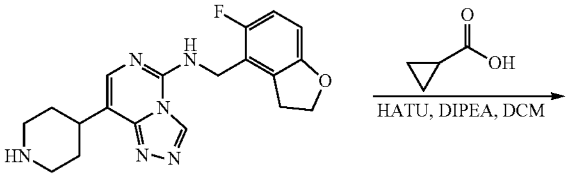

20

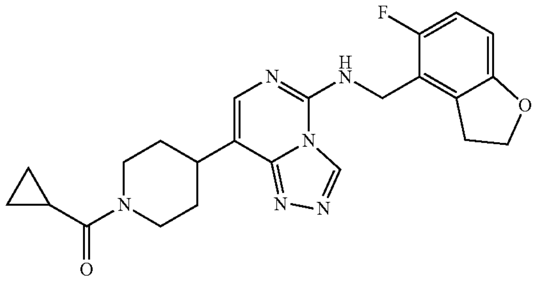

HJM-055

Steps 1-3:

Compound 20 (200 mg) was prepared as a white solid using N-tert-butoxycarbonyl-1,2,5,6-tetrahydropyridine-4-boronic acid pinacol ester as starting material according to the method similar to that for preparation example 50.

Step 4:

Under $N_2$ protection, compound 20 (100 mg, 0.25 mmol) and cyclopropanecarboxylic acid (43 mg, 0.50 mmol) were dissolved in dichloromethane (4 mL), HATU (141 mg, 0.37 mmol) and N,N-diisopropylethylamine (160 mg, 1.24 mmol) were slowly added at room temperature, and the mixture was stirred at room temperature for 2 h. TLC showed that the reaction was completed. The mixture was concentrated under reduced pressure, and purified by preparative HPLC to afford HJM-055 (18 mg, yield: 15.25%) as a white solid.

$^1$H NMR (400 MHz, DMSO-$d_6$) δ 9.39 (s, 1H), 8.41 (t, J=5.2 Hz, 1H), 7.48 (s, 1H), 7.00-6.86 (m, 1H), 6.69 (dd, J=8.4, 4.0 Hz, 1H), 4.64 (d, J=4.8 Hz, 2H), 4.54 (t, J=8.8 Hz, 4H), 4.40 (d, J=12.0 Hz, 1H), 3.29 (t, J=8.8 Hz, 2H), 3.16-3.05 (m, 1H), 2.71-2.65 (m, 1H), 2.07-1.94 (m, 2H), 1.91-1.85 (m, 2H), 1.75-1.68 (m, 1H), 0.76-0.69 (m, 4H). LCMS $[M+H]^+$=437.2.

Preparation Example 56: Synthesis of Compound HJM-056

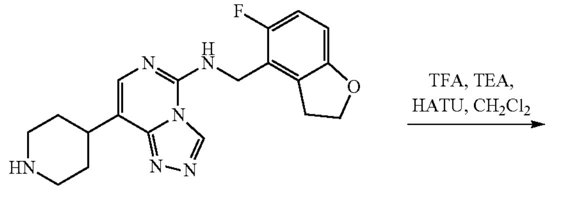

20

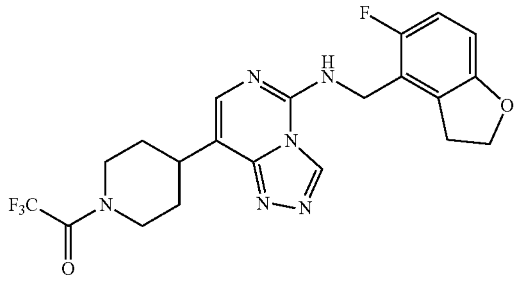

HJM-056

HJM-056 (3.1 mg, yield: 2.5%) was prepared as a white solid using trifluoroacetic acid as starting material according to the method similar to that for preparation example 55.

$^1H$ NMR (400 MHz, DMSO-$d_6$) δ 9.39 (s, 1H), 8.47 (s, 1H), 7.50 (s, 1H), 6.99-6.87 (m, 1H), 6.69 (dd, J=8.8, 4.0 Hz, 1H), 4.64 (d, J=4.8 Hz, 2H), 4.53 (t, J=8.8 Hz, 2H), 4.44 (d, J=13.2 Hz, 1H), 3.98 (d, J=13.2 Hz, 1H), 3.46-3.42 (m, 1H), 3.30-3.26 (m, 2H), 3.23-3.16 (m, 1H), 3.03 (t, J=12.0 Hz, 1H), 2.09-1.86 (m, 4H). LCMS $[M+H]^+$=465.2.

Preparation Example 57: Synthesis of Compound HJM-057

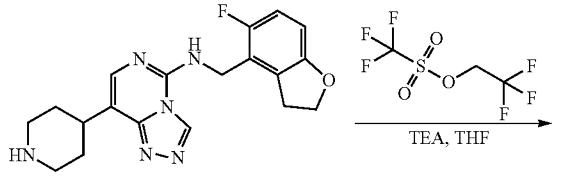

20

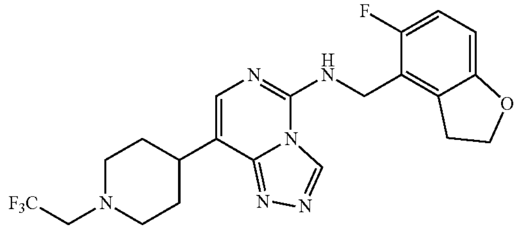

HJM-057

Under $N_2$ protection, compound 20 (100 mg, 0.25 mmol) and triethylamine (0.11 mL, 0.81 mmol) were dissolved in tetrahydrofuran (5 mL), trifluoroethyl trifluoromethanesulfonate (0.08 mL, 0.54 mmol) was slowly added at room temperature, and the mixture was stirred at room temperature for 16 h. TLC showed that the reaction was completed. The mixture was concentrated under reduced pressure, and purified by preparative HPLC to afford HJM-057 (28 mg, yield: 23.1%) as a white solid.

$^1H$ NMR (400 MHz, DMSO-$d_6$) δ 9.39 (s, 1H), 8.45 (s, 1H), 7.47 (s, 1H), 6.97-6.88 (m, 1H), 6.69 (dd, J=8.8, 4.0 Hz, 1H), 4.63 (d, J=4.4 Hz, 2H), 4.53 (t, J=8.8 Hz, 2H), 3.28 (t, J=8.8 Hz, 2H), 3.19 (dd, J=20.4, 10.0 Hz, 2H), 3.02 (d, J=11.2 Hz, 2H), 2.88-2.77 (m, 1H), 2.50-2.42 (m, 2H), 2.00-1.79 (m, 4H). LCMS $[M+H]^+$=451.2.

Preparation Example 58: Synthesis of Compound HJM-058

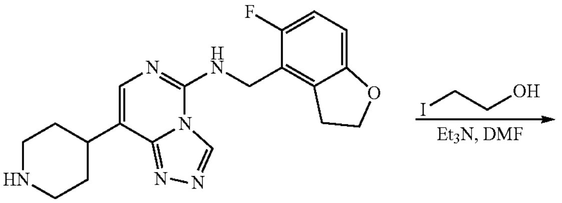

20

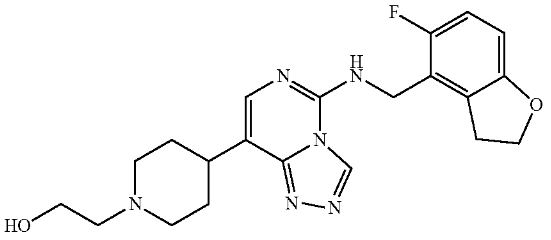

HJM-058

Under $N_2$ protection, compound 20 (100 mg, 0.25 mmol) and triethylamine (125 mg, 1.24 mmol) were dissolved in N,N-dimethylformamide (4 mL), 2-iodoethanol (0.08 mL, 0.54 mmol) was slowly added at room temperature, and the mixture was stirred at room temperature for 16 h. TLC showed that the reaction was completed. The mixture was concentrated under reduced pressure, and purified by preparative HPLC to afford HJM-058 (9 mg, yield: 8.8%) as a white solid.

$^1H$ NMR (400 MHz, DMSO-$d_6$) δ 9.40 (s, 1H), 8.47 (s, 1H), 8.26 (s, 1H), 7.45 (s, 1H), 6.93 (t, J=9.2 Hz, 1H), 6.70-6.67 (m, 1H), 4.64 (s, 2H), 4.53 (t, J=8.4 Hz, 2H), 3.60 (s, 2H), 3.28 (t, J=8.4 Hz, 2H), 3.21-3.15 (m, 2H), 2.94-2.87 (m, 1H), 2.69-2.65 (m, 2H), 2.45 (d, J=10.0 Hz, 2H), 2.17-1.83 (m, 4H). LCMS $[M+H]^+$=413.3.

Preparation Example 59: Synthesis of Compound HJM-059

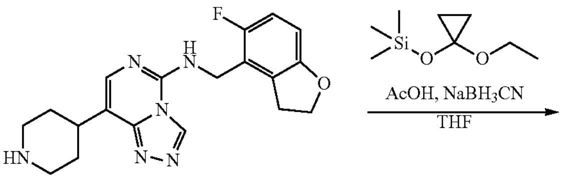

20

-continued

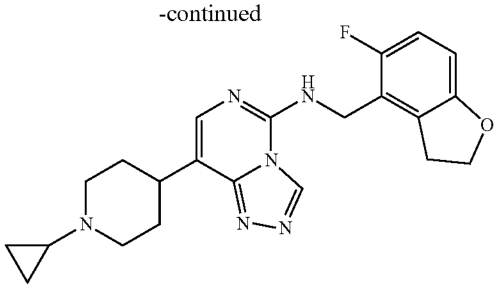

HJM-059

Under $N_2$ protection, compound 20 (100 mg, 0.25 mmol) and (1-ethoxycyclopropyloxy)trimethylsilane (0.27 mL, 1.36 mmol) were dissolved in tetrahydrofuran (10 mL), glacial acetic acid (1 mL) and sodium cyanobohydride (85 mg, 1.36 mmol) were slowly added at room temperature, and the mixture was stirred at 70° C. for 16 h. TLC showed that the reaction was completed. The mixture was concentrated under reduced pressure, and purified by preparative HPLC to afford HJM-059 (3.1 mg, yield: 2.8%) as a yellow solid.

$^1$H NMR (400 MHz, DMSO-$d_6$) δ 9.38 (s, 1H), 8.39 (t, J=4.8 Hz, 1H), 7.44 (s, 1H), 6.97-6.89 (m, 1H), 6.69 (dd, J=8.8, 4.0 Hz, 1H), 4.63 (d, J=4.8 Hz, 2H), 4.53 (t, J=8.8 Hz, 2H), 3.28 (t, J=8.8 Hz, 2H), 3.05 (d, J=11.6 Hz, 2H), 2.89-2.78 (m, 1H), 2.35-2.23 (m, 2H), 1.90-1.76 (m, 4H), 1.68-1.62 (m, 1H), 0.47-0.40 (m, 2H), 0.34-0.28 (m, 2H). LCMS $[M+H]^+$=409.2.

Preparation Example 60: Synthesis of Compound HJM-060

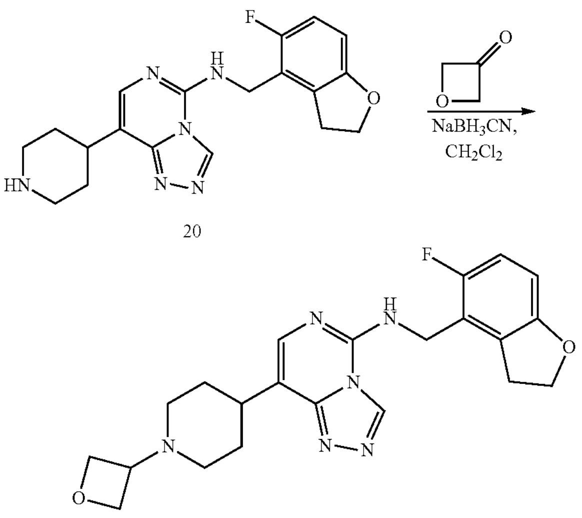

20

HJM-060

Under $N_2$ protection, compound 20 (100 mg, 0.25 mmol) and oxetan-3-one (0.08 mL, 1.36 mmol) were dissolved in dichloromethane (5 mL), sodium cyanobohydride (85 mg, 1.36 mmol) was slowly added at room temperature, and the mixture was stirred at room temperature for 16 h. TLC showed that the reaction was completed. The mixture was concentrated under reduced pressure, and purified by preparative HPLC to afford HJM-060 (11 mg, yield: 9.6%) as a yellow solid.

$^1$H NMR (400 MHz, DMSO-$d_6$) δ 9.39 (s, 1H), 8.42 (s, 1H), 7.47 (s, 1H), 6.93 (t, J=9.2 Hz, 1H), 6.69 (dd, J=8.8, 4.0 Hz, 1H), 4.64 (d, J=4.0 Hz, 2H), 4.58-4.51 (m, 4H), 4.45 (t, J=6.0 Hz, 2H), 3.44-3.40 (m, 1H), 3.28 (t, J=8.8 Hz, 2H), 2.91-2.74 (m, 3H), 1.99-1.78 (m, 6H). LCMS $[M+H]^+$=425.2.

Preparation Example 61: Synthesis of Compound HJM-061

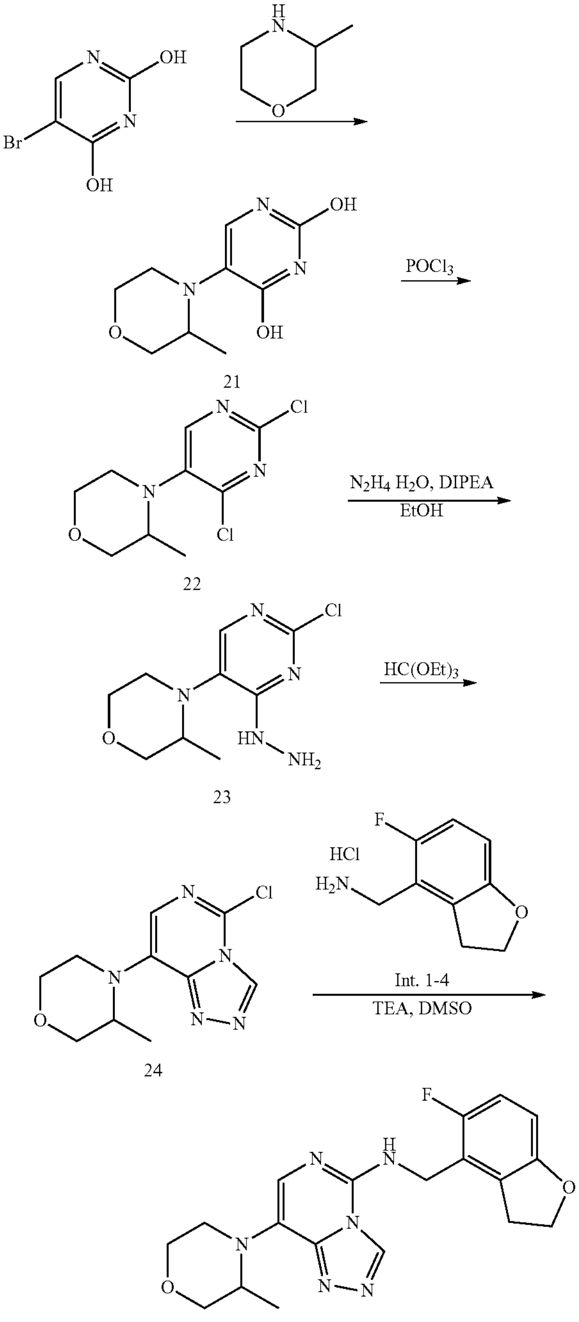

21

22

23

24

HJM-061

Step 1:

Under $N_2$ protection, a solution of 5-bromo-uracil (2.0 g, 10.5 mmol) and 3-methylmorpholine (5.32 g, 52.5 mmol)

was heated to 135° C. and stirred for 2 h. TLC showed that the reaction was completed. The mixture was stopped from heating, and naturally cooled to room temperature. The mixture was concentrated under reduced pressure, and the solid was washed twice with dichloromethane to afford 21 (2.0 g, yield: 90%) as a white solid, LCMS $[M+H]^+$=212.2.

Step 2:

Under $N_2$ protection, compound 21 (2.0 g, 9.48 mmol) was dissolved in phosphorus oxychloride (12 mL), and the mixture was heated to 110° C. and stirred for 96 h. TLC showed that the reaction was completed. The mixture was stopped from heating, naturally cooled to room temperature, and concentrated under reduced pressure to remove most of the solvent. The residue was adjusted to weak alkalinity with saturated $NaHCO_3$ solution, and the aqueous phase was extracted with ethyl acetate (2×50 mL). The organic phases were combined, washed with saturated brine (2×20 mL), dried with $Na_2SO_4$, filtered, and concentrated. The residue was purified by silica gel column chromatography (PE: EA=2:1) to afford 22 (800 mg, yield: 34%) as a white solid, LCMS $[M+H]^+$=248.1.

Step 3:

Compound 22 (200 mg, 0.81 mmol) and N,N-diisopropylethylamine (209 mg, 1.62 mmol) were dissolved in ethanol (3 mL), 85% hydrazine hydrate (58 mg, 0.98 mmol) was slowly added at room temperature, and the mixture was stirred at room temperature for 16 h. TLC showed that the reaction was completed. The mixture was concentrated under reduced pressure, and purified by reversed silica gel column chromatography ($CH_3CN/H_2O$=30/70) to afford 23 (100 mg, yield: 50%) as a white solid, LCMS $[M+H]^+$=244.1.

Step 4:

Under $N_2$ protection, compound 23 (100 mg, 0.41 mmol) was dissolved in 9 mL of triethyl orthoformate, and the mixture was heated to 150° C. and stirred for 4 h. TLC showed that the reaction was completed. The mixture was stopped from heating, naturally cooled to room temperature, and concentrated under reduced pressure. The residue was purified by silica gel column chromatography (PE:EA=5:4) to afford 24 (100 mg, yield: 96%) as a white solid, LCMS $[M+H]^+$=254.1.

Step 5:

Under $N_2$ protection, 5-fluoro-2,3-dihydrobenzofuran-4-methylamine Int.1-4 hydrochloride (120 mg, 0.59 mmol) and triethylamine (79 mg, 0.78 mmol) were dissolved in dimethyl sulfoxide (3 mL), compound 24 (100 mg, 0.39 mmol) was added, and the mixture was stirred at room temperature for 4 h. TLC showed that the reaction was completed. The mixture was stopped from heating, and naturally cooled to room temperature. Water and ethyl acetate were added, and the mixture was layered. The aqueous phase was extracted with ethyl acetate (3×5 mL). The organic phases were combined, and then washed successively with water and saturated brine. The organic layer was dried with $Na_2SO_4$, and filtered. The filtrate was concentrated and purified by preparative HPLC to afford HJM-061 (50 mg, yield: 33.0%) as a white solid.

$^1H$ NMR (400 MHz, DMSO-$d_6$) δ 9.39 (s, 1H), 8.13 (t, J=4.8 Hz, 1H), 7.126 (s, 1H), 6.94 (t, J=8.8 Hz, 1H), 6.67-6.68 (m, 1H), 4.61 (d, J=4.8 Hz, 2H), 4.54 (t, J=8.8 Hz, 2H), 4.31-4.27 (m, 1H), 3.84-3.79 (m, 2H), 3.71-3.65 (m, 1H), 3.52-3.48 (m, 1H), 3.31 (d, J=4.4 Hz, 2H), 3.17-3.06 (m, 2H), 0.85 (d, J=6.4 Hz, 3H). LCMS $[M+H]^+$=385.2.

Preparation Example 62: Synthesis of Compound HJM-062

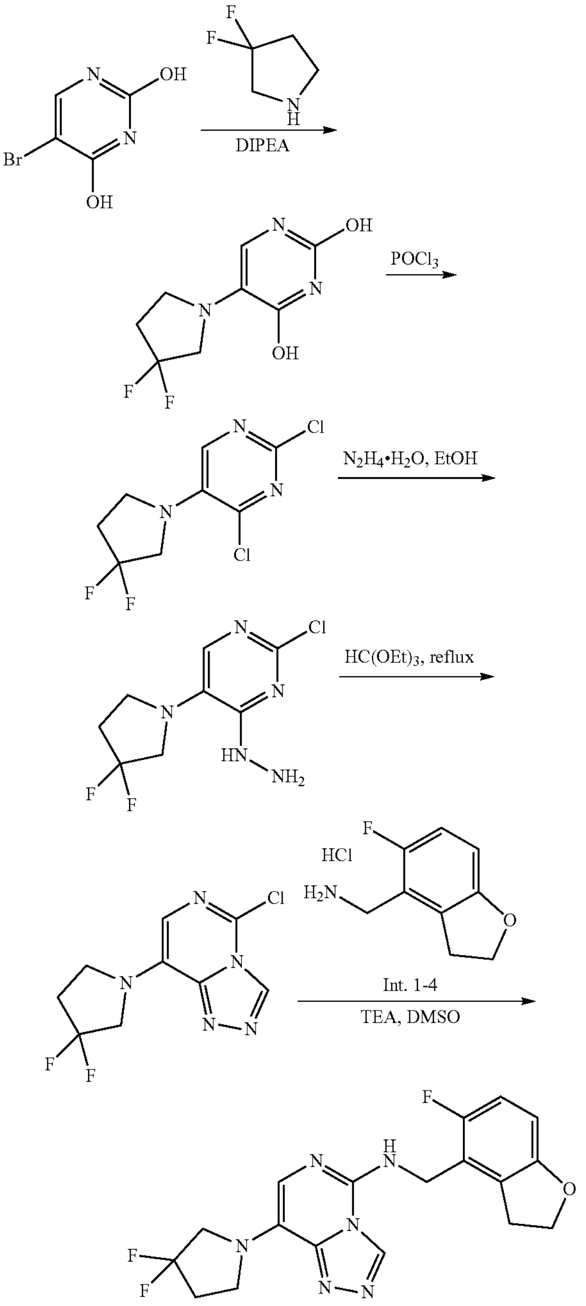

HJM-062

HJM-062 (100 mg, yield: 46.0%) was prepared as a white solid using 3,3-difluoropyrrolidine as starting material according to the method similar to that for preparation example 61.

$^1H$ NMR (400 MHz, DMSO-$d_6$) δ 9.39 (s, 1H), 8.00 (t, J=5.2 Hz, 1H), 6.92 (t, J=9.2 Hz, 2H), 6.70-6.67 (m, 1H), 4.59 (d, J=4.8 Hz, 2H), 4.53 (t, J=8.4 Hz, 2H), 3.86 (t, J=13.2 Hz, 2H), 3.64 (t, J=7.2 Hz, 2H), 3.27 (t, J=8.8 Hz, 2H), 2.54 (d, J=7.2 Hz, 2H). LCMS $[M+H]^+$=391.1.

Preparation Example 63: Synthesis of Compound HJM-063

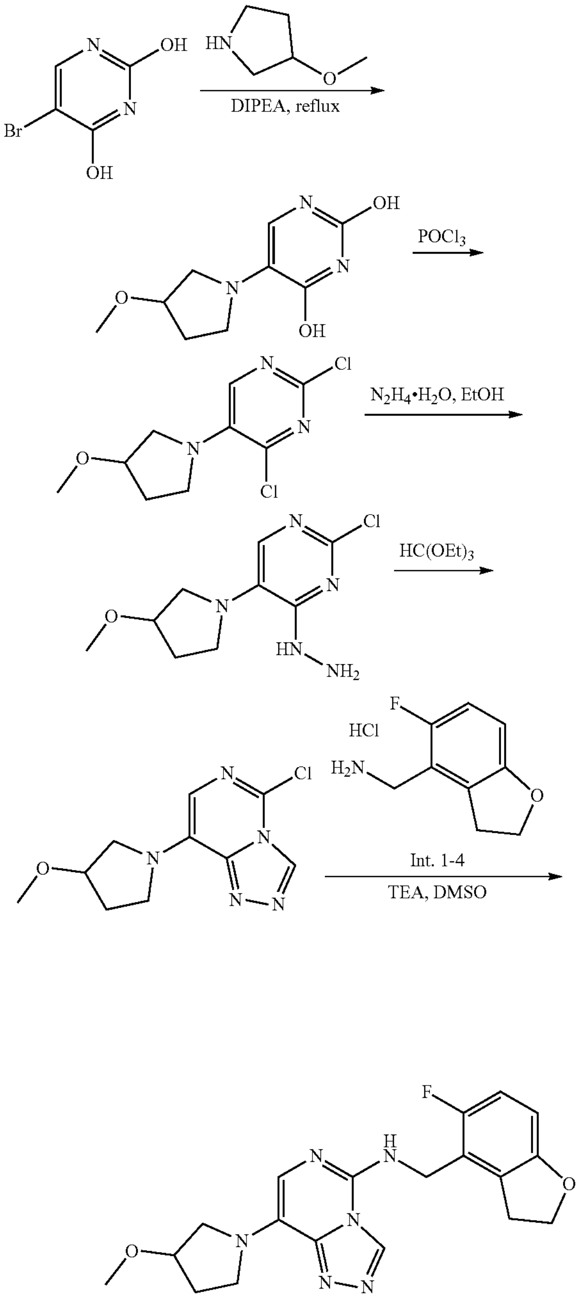

HJM-063

HJM-063 (10 mg, yield: 4.0%) was prepared as a white solid using 3-methoxypyrrolidine as starting material according to the method similar to that for preparation example 61.

$^1$H NMR (400 MHz, DMSO-$d_6$) δ 9.36 (s, 1H), 7.79 (t, J=5.2 Hz, 1H), 6.92 (t, J=8.8 Hz, 1H), 6.77 (s, 1H), 6.70-6.67 (m, 1H), 4.58-4.50 (m, 4H), 4.08-4.05 (m, 1H), 3.64-3.60 (m, 1H), 3.54-3.43 (m, 3H), 3.29-3.25 (m, 5H), 2.11-2.07 (m, 1H), 1.99-1.97 (m, 1H). LCMS $[M+H]^+$=385.1.

Preparation Example 64: Synthesis of Compound HJM-064

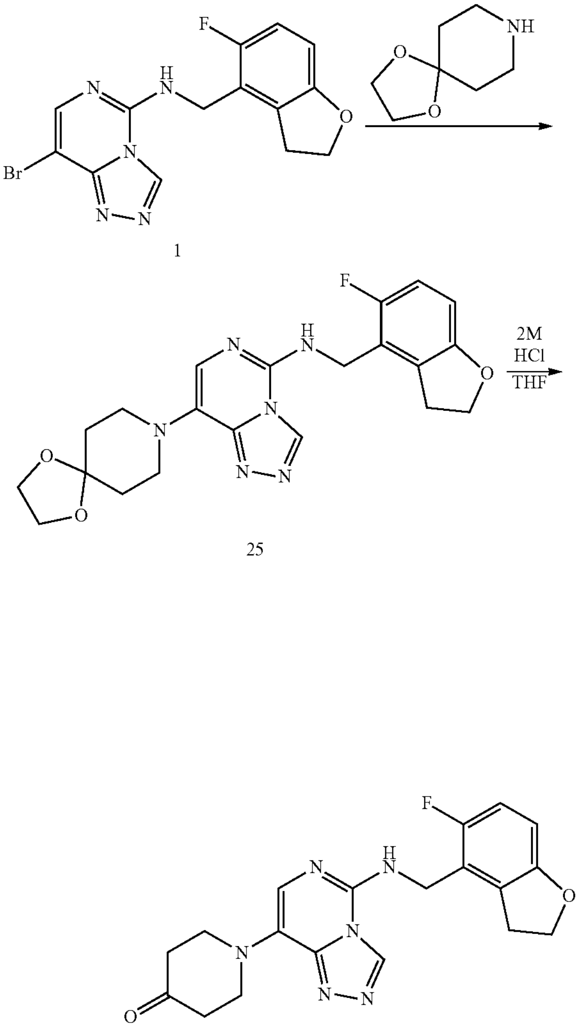

HJM-064

Step 1:

Compound 25 (200 mg) was prepared as a white solid using 4-piperidone ethylene glycol acetal as starting material according to the method similar to that for preparation example 22. LCMS: $[M+H]^+$=427.1.

Step 2:

Compound 25 (100 mg, 0.23 mmol) was dissolved in tetrahydrofuran (2 mL), 2M HCl aqueous solution (0.5 mL) was added, and the mixture was stirred at room temperature overnight. The mixture was concentrated to afford a crude product. The crude product was purified by preparative HPLC to afford compound HJM-064 (20 mg, yield: 22.3%) as a white solid.

$^1$H NMR (400 MHz, DMSO-$d_6$) δ 9.41 (s, 1H), 8.11 (t, J=5.2 Hz, 1H), 7.18 (s, 1H), 6.93 (t, J=9.6 Hz, 1H), 6.69 (dd, J=8.4, 3.6 Hz, 1H), 4.61 (d, J=4.8 Hz, 2H), 4.54 (t, J=8.8 Hz, 2H), 3.65 (t, J=6.0 Hz, 4H), 3.29 (t, J=8.8 Hz, 2H), 2.55-2.48 (m, 4H). LCMS $[M+H]^+$=383.3.

Preparation Example 65: Synthesis of Compound HJM-065

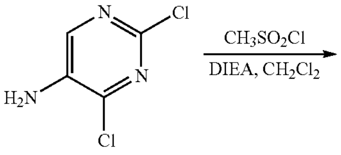

24

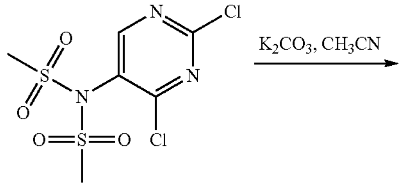

35

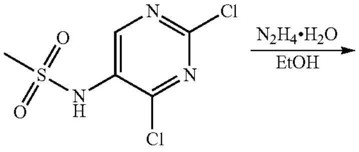

36

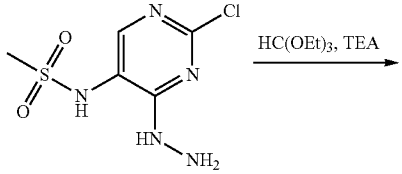

37

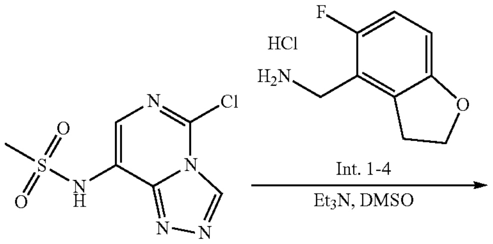

38

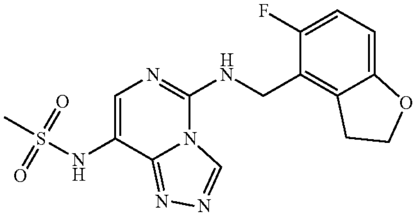

HJM-065

Step 1:

5-Amino-2,4-dichloropyrimidine 24 (944 mg, 5.75 mmol) and N,N-diisopropylethylamine (2.96 g, 23 mmol) were dissolved in dichloromethane (25 mL), methanesulfonyl chloride (2.62 g, 23 mmol) was added dropwise, and the mixture was stirred at room temperature overnight. The mixture was concentrated to afford a crude product. The crude product was purified by silica gel column chromatography (petroleum ether/ethyl acetate, ethyl acetate: 0-20%) to afford compound 35 (455 mg, yield: 24.8%) as a white solid.

$^1$H NMR (400 MHz, $CDCl_3$) δ 8.54 (s, 1H), 3.51 (s, 6H). LCMS $[M+H]^+$=320.1.

Step 2:

Compound 35 (455 mg, 1.42 mmol) was dissolved in acetonitrile (30 mL), potassium carbonate (1.95 g, 14.2 mmol) was added, and the mixture was stirred at room temperature overnight. The mixture was filtered, and the filtrate was concentrated to afford crude compound 36 (310 mg, yield: 91%) as a white solid.

$^1$H NMR (400 MHz, DMSO-$d_6$) δ 8.35 (s, 1H), 2.67 (s, 3H). LCMS $[M-H^-]$=239.9.

Step 3:

Compound 36 (260 mg, 1.07 mmol) was dissolved in ethanol (5 mL), hydrazine hydrate (76 mg, 1.29 mmol) was added, and the mixture was stirred at room temperature for 2 h. The mixture was concentrated to afford a crude product. The crude product was purified by silica gel column chromatography (dichloromethane/methanol, methanol: 0-10%) to afford compound 37 (190 mg, yield: 75%) as a brown oil. LCMS $[M+H]^+$=238.1.

Step 4:

Compound 37 (190 mg, 0.86 mmol) was dissolved in triethyl orthoformate (8 mL), trifluoroacetic acid (1 mL) was added, and the mixture was stirred at 120° C. for 2 h. The mixture was cooled, and concentrated to afford a crude product. The crude product was purified by preparative TLC to afford compound 38 (12 mg, yield: 5.6%) as a white solid. LCMS $[M+H]^+$=248.1.

Step 5:

Compound 38 (12 mg, 0.048 mmol), (5-fluoro-2,3-dihydrobenzofuran-4-yl)methylamine Int.1-4 hydrochloride (12 mg, 0.057 mmol) and triethylamine (10 mg, 0.096 mmol) were dissolved in dimethyl sulfoxide (3 mL), and the mixture was stirred at room temperature for 1 h. The mixture was purified by preparative HPLC to afford compound HJM-065 (2 mg, yield: 11.1%) as a white solid.

$^1$H NMR (400 MHz, $CD_3OD$) δ 9.28 (s, 1H), 7.72 (s, 1H), 6.85 (t, J=9.5 Hz, 1H), 6.65 (dd, J=8.6, 3.8 Hz, 1H), 4.77 (s, 2H), 4.58 (t, J=8.7 Hz, 2H), 3.36 (t, J=8.7 Hz, 1H), 3.09 (s, 1H). LCMS $[M+H]^+$=379.2.

Preparation Example 66: Synthesis of Compound HJM-066

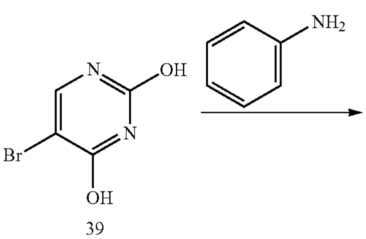

39

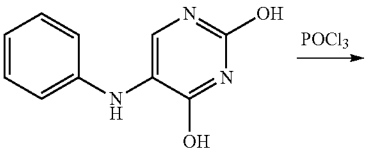

40

-continued

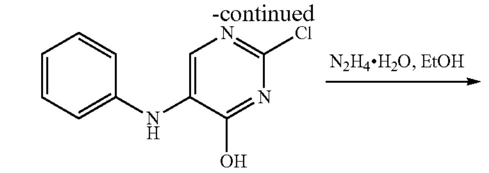

41

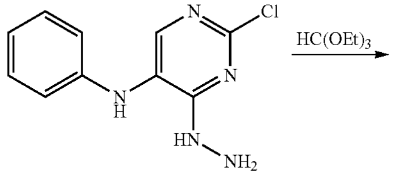

42

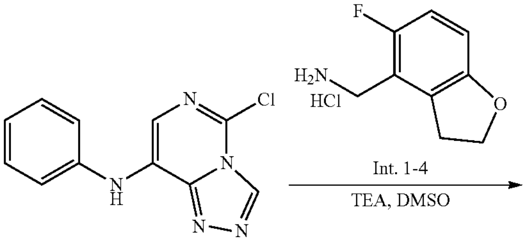

43

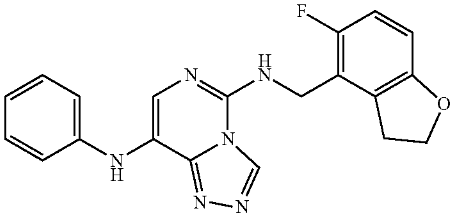

HJM-066

Step 1:

Compound 2,4-dihydroxy-5-bromopyrimidine 39 (5 g, 26.2 mmol) was added to aniline (50 mL, 547.6 mmol), and the mixture was heated at 135° C. and stirred overnight. The mixture was cooled, and filtered to afford a solid. The solid was washed with 1 N HCl, and dried in vacuum to afford compound 40 (2 g, yield: 37.6%) as a white solid. LCMS $[M+H]^+$=204.2.

Step 2:

Compound 40 (1.0 g, 4.92 mmol) was added to $POCl_3$ (10 mL), and the mixture was heated at 100° C. and stirred overnight. The mixture was cooled, and concentrated to afford a crude product. The crude product was purified by silica gel column chromatography (petroleum ether/ethyl acetate, ethyl acetate: 0-50%) to afford compound 41 (500 mg, yield: 42.3%) as a yellow solid. LCMS $[M+H]^+$=240.1.

Step 3:

Compound 41 (200 mg, 0.83 mmol) was dissolved in ethanol (5 mL), 85% hydrazine hydrate (51.8 mg, 0.88 mmol) was added, and the mixture was stirred at room temperature for 6 h. The mixture was concentrated to afford a crude product. The crude product was purified by reversed-phase column chromatography (acetonitrile:water=20:80) to afford compound 42 (150 mg, yield: 76.4%) as a white solid. LCMS $[M+H]^+$=236.2.

Step 4:

Compound 42 (100 mg, 0.42 mmol) was added to triethyl orthoformate (2 mL), and the mixture was heated at 120° C. and stirred for 3 h. The mixture was cooled, and concentrated to afford a crude product. The crude product was purified by preparative TLC to afford compound 43 (70 mg, yield: 67.1%) as a white solid. LCMS $[M+H]^+$=246.3.

Step 5:

Compound 43 (70 mg, 0.28 mmol), Int. 1-4 hydrochloride (87 mg, 0.43 mmol) and triethylamine (62 mg, 0.6 mmol) were dissolved in dimethyl sulfoxide (2 mL), and the mixture was stirred at room temperature for 4 h. The mixture was purified by preparative HPLC to afford compound HJM-066 (9 mg, yield: 8.4%) as a white solid.

$^1$H NMR (400 MHz, $CD_3OD$) δ 9.27 (s, 1H), 7.65 (s, 1H), 7.23-7.14 (m, 2H), 6.96-6.88 (m, 2H), 6.90-6.76 (m, 2H), 6.64 (dd, J=8.7, 3.9 Hz, 1H), 4.74 (s, 2H), 4.57 (t, J=8.7 Hz, 2H), 3.35 (t, J=8.7 Hz, 2H). LCMS $[M+H]^+$=377.1.

Preparation Example 67: Synthesis of Compound HJM-067

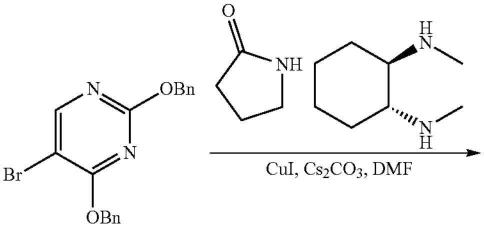

44

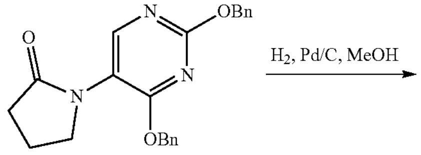

45

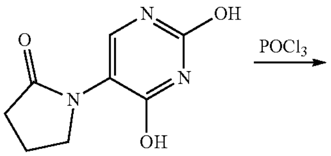

46

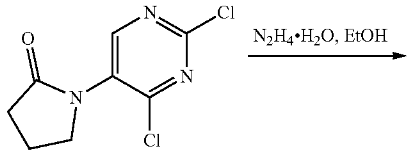

47

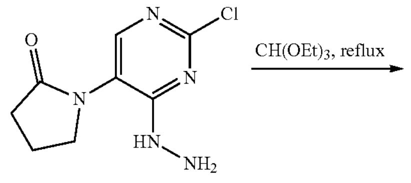

48

-continued

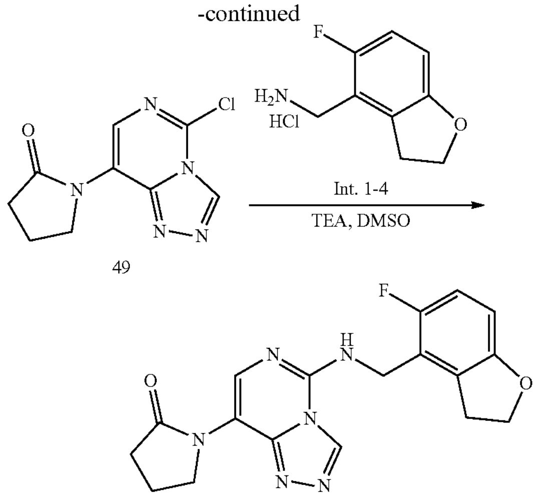

49

HJM-067

Step 1:

Compound 2,4-dibenzyloxy-5-bromopyrimidine 44 (6.0 g, 16.16 mmol) and pyrrolidone (1.5 g, 17.78 mmol) were dissolved in N,N-dimethylformamide (100 mL), cesium carbonate (10.5 g, 32.32 mmol), (1R,2R)—N1,N2-dimethylcyclohexyl-1,2-diamine (690 mg, 4.84 mmol) and cuprous iodide (4.0 g, 21.01 mmol) were added successively, and the mixture was heated under nitrogen atmosphere at 85° C. for 2 h. The mixture was cooled, and concentrated to afford a residue. The residue was purified by silica gel column chromatography (petroleum ether/ethyl acetate, ethyl acetate: 0-30%) to afford compound 45 (3.0 g, yield: 49.4%) as a white solid. LCMS $[M+H]^+$=376.3.

Step 2:

Compound 45 (3.0 g, 8.0 mmol) was dissolved in methanol (50 mL), and 5% Pd/C (500 mg) was added under nitrogen protection. The atmosphere was replaced three times with hydrogen gas, and the mixture was stirred at room temperature under a hydrogen balloon for 16 h. The mixture was filtered, and the filter cake was washed with methanol for three times. The filtrate was concentrated to afford compound 46 (1.2 g, yield: 76.9%) as a yellow solid. LCMS $[M+H]^+$=196.2.

Step 3:

Compound 46 (1.2 g, 6.24 mmol) was added to $POCl_3$ (10 mL), and the mixture was heated at 100° C. overnight. The mixture was cooled, and concentrated to afford a crude product. The crude product was purified by silica gel column chromatography (petroleum ether/ethyl acetate, ethyl acetate: 0-30%) to afford compound 47 (700 mg, yield: 48.3%) as a yellow solid. LCMS $[M+H]^+$=232.1.

Step 4:

Compound 47 (700 mg, 3.02 mmol) and 85% hydrazine hydrate (213 mg, 3.62 mmol) were added to ethanol (5 mL), and the mixture was stirred at room temperature for 2 h. The reaction mixture was concentrated to afford crude compound 48 (400 mg, yield: 58.2%) as a yellow solid. LCMS $[M+H]^+$=228.1.

Step 5:

Compound 48 (400 mg, 1.76 mmol) was added to triethyl orthoformate (10 mL), and the mixture was heated at 120° C. and refluxed with stirring for 2 h. The mixture was cooled, and concentrated to afford a crude product. The crude product was purified by preparative HPLC to afford compound 49 (40 mg, yield: 9.6%) as a yellow solid. LCMS $[M+H]^+$=238.1.

Step 6:

Compound 49 (40 mg, 0.17 mmol), Int. 1-4 hydrochloride (34 mg, 0.17 mmol) and triethylamine (51 mg, 0.51 mmol) were dissolved in dimethyl sulfoxide (3 mL), and the mixture was stirred at room temperature for 2 h. The mixture was purified by preparative HPLC to afford compound HJM-067 (25 mg, yield: 40.0%) as a white solid.

$^1H$ NMR (400 MHz, $CD_3OD$) δ 9.32 (s, 1H), 7.87 (s, 1H), 6.86 (t, J=9.4 Hz, 1H), 6.65 (dd, J=8.7, 3.9 Hz, 1H), 4.80 (s, 2H), 4.58 (t, J=8.7 Hz, 2H), 3.94 (t, J=7.1 Hz, 2H), 3.37 (t, J=8.7 Hz, 2H), 2.62 (t, J=8.1 Hz, 2H), 2.30 (p, J=7.6 Hz, 2H). LCMS $[M+H]^+$=369.4.

Preparation Example 68: Synthesis of Compound HJM-068

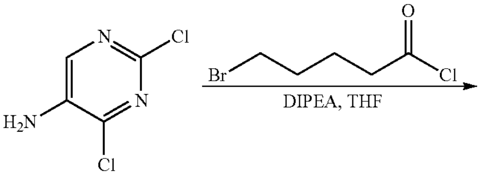

24

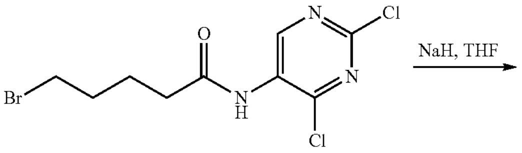

50

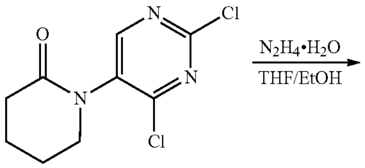

51

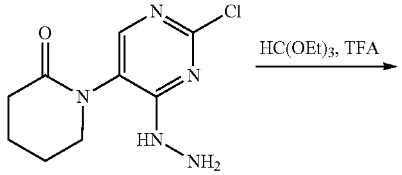

52

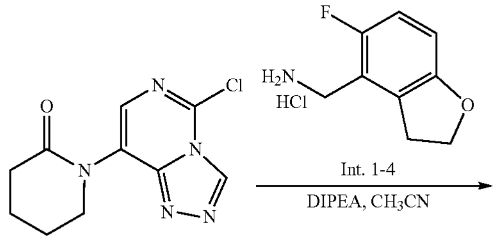

53

-continued

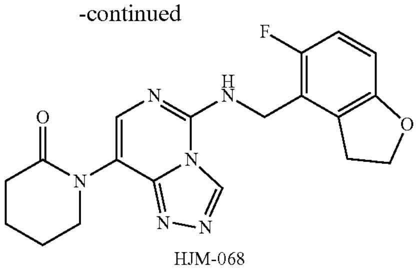

HJM-068

Step 1:

5-Amino-2,4-dichloropyrimidine 24 (1.64 g, 10 mmol) and N,N-diisopropylethylamine (5 mL, 30 mmol) were dissolved in tetrahydrofuran (25 mL), 5-bromovaleryl chloride (2.4 mL, 18 mmol) was added dropwise at 0° C., and the mixture was warmed to room temperature and stirred overnight. The mixture was concentrated to afford a crude product. The crude product was purified by silica gel column chromatography (petroleum ether/ethyl acetate, ethyl acetate: 0-50%) to afford compound 50 (290 mg, yield: 8.9%) as a white solid. LCMS $[M+H]^+$=324.2.

Step 2:

Compound 50 (290 mg, 0.88 mmol) was dissolved in anhydrous tetrahydrofuran (12 mL), and sodium hydride (75 mg, 1.87 mmol, purity: 60%) was added at 0° C. After the addition, the mixture was warmed to room temperature and stirred overnight. The mixture was cooled to 0° C., quenched with saturated aqueous ammonium chloride, and extracted with ethyl acetate (25 mL). The organic phases were combined, washed with saturated brine, dried with anhydrous sodium sulfate, and filtered. The filtrate was rotary evaporated to dryness to afford a crude product. The crude product was purified by silica gel column chromatography (petroleum ether/ethyl acetate, ethyl acetate: 30-70%) to afford compound 51 (135 mg, yield: 62%) as a white solid. LCMS $[M+H]^+$=246.2.

Step 3:

85% Hydrazine hydrate (47 mg, 0.82 mmol) was dissolved in a mixture of tetrahydrofuran (2.5 mL) and ethanol (0.5 mL), compound 51 (135 mg, 0.55 mmol) was added at 0° C., and the mixture was stirred at 0° C. for 1 h. The reaction was stopped, and ethyl acetate and water were added. The mixture was extracted, and layered. The organic layers were combined, washed with saturated brine, dried with anhydrous sodium sulfate, and filtered. The filtrate was concentrated to afford crude compound 52 (60 mg, yield: 45%) as a white solid, which was directly used in the next step.

Step 4:

Compound 52 (60 mg, 0.25 mmol) was suspended in triethyl orthoformate (2.5 mL), a catalytic amount of trifluoroacetic acid (12 uL) was added, and the mixture was heated to 80° C. and stirred for 1.5 h. The mixture was cooled and concentrated to afford a residue. The residue was purified by silica gel column chromatography (ethyl acetate/methanol, methanol: 0-5%) to afford compound 53 (30 mg, yield: 48%) as an off-white solid. LCMS $[M+H]^+$=252.2.

Step 5:

Compound 53 (30 mg, 0.12 mmol), Int. 1-4 hydrochloride (30 mg, 0.15 mmol) and N,N-diisopropylethylamine (0.064 mL, 0.38 mmol) were dissolved in acetonitrile (4 mL), and the mixture was stirred at room temperature for 16 h. The mixture was purified by preparative HPLC to afford compound HJM-068 (17 mg, yield: 37%) as a white solid.

$^1H$ NMR (500 MHz, DMSO-$d_6$) δ 9.91 (s, 1H), 9.61 (s, 1H), 7.97 (s, 1H), 6.93 (t, J=9.4 Hz, 1H), 6.69 (dd, J=9.4, 3.7 Hz, 1H), 4.69 (s, 2H), 4.54 (t, J=8.6 Hz, 2H), 3.62 (t, J=5.5 Hz, 2H), 3.35 (t, J=8.7 Hz, 2H), 2.44 (t, J=6.2 Hz, 2H), 1.96-1.83 (m, 4H). LCMS $[M+H]^+$=383.3.

Preparation Example 69: Synthesis of Compound HJM-069

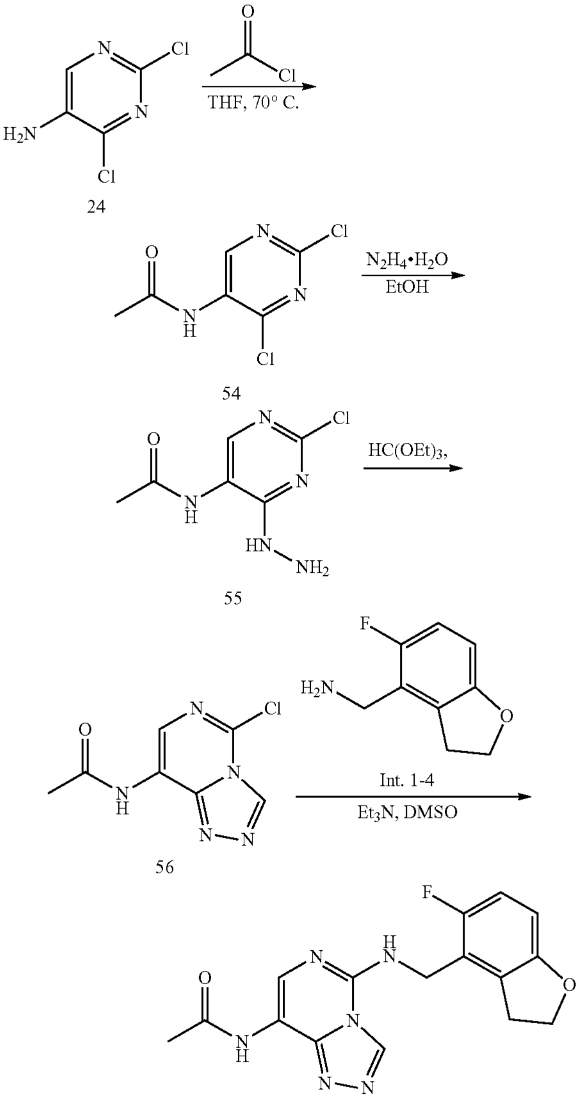

24

54

55

56

HJM-069

Step 1:

5-Amino-2,4-dichloropyrimidine 24 (300 mg, 1.83 mmol) and acetyl chloride (287 mg, 3.66 mmol) were dissolved in tetrahydrofuran (10 mL), and the mixture was heated at 70° C. for 4 h. The mixture was cooled, diluted with water, and extracted twice with ethyl acetate (2×30 mL). The organic phases were combined, washed once with saturated brine, dried with anhydrous sodium sulfate, and filtered. The filtrate was concentrated to afford crude compound 54 (220 mg, yield: 58.4%) as a yellow oil. LCMS $[M+H]^+$=206.0.

Step 2:

Compound 54 (220 mg, 1.07 mmol) was dissolved in ethanol (2 mL), a solution of 85% hydrazine hydrate (188.2 mg, 3.20 mmol) in ethanol (2 mL) was added at room temperature, and the mixture was reacted at room temperature for 1 h. The reaction mixture was diluted with water, and extracted twice with ethyl acetate. The organic phases were combined, washed once with saturated brine, dried with anhydrous sodium sulfate, and filtered. The filtrate was concentrated to afford crude compound 55 (160 mg, yield: 74.2%) as a yellow oil. LCMS $[M+H]^+$=202.1.

Step 3:

Compound 55 (160 mg, 0.79 mmol) was added to triethyl orthoformate (5 mL), and the mixture was heated at 120° C. for 2 h. The mixture was cooled, and concentrated to afford crude compound 56, which was directly used in the next step.

Step 4:

Above compound 56, Int.1-4 (132 mg, 0.79 mmol) and triethylamine (240 mg, 2.38 mmol) were dissolved in dimethyl sulfoxide (3 mL), and the mixture was stirred at room temperature for 1 h. The mixture was diluted with water, and extracted twice with ethyl acetate. The organic phases were combined, dried with anhydrous sodium sulfate, and filtered. The filtrate was concentrated to afford a crude product. The crude product was slurried with methanol. The resulting solid was filtered, and dried to afford compound HJM-069 (40 mg, two-step yield: 14.8%) as a white solid.

$^1$H NMR (400 MHz, DMSO-$d_6$) δ 9.91 (s, 1H), 9.41 (s, 1H), 8.39 (t, J=4.9 Hz, 1H), 8.06 (s, 1H), 6.97-6.91 (m, 1H), 6.70 (dd, J=8.7, 3.9 Hz, 1H), 4.65 (d, J=5.0 Hz, 2H), 4.54 (t, J=8.7 Hz, 2H), 3.28 (t, J=8.7 Hz, 2H), 2.11 (s, 3H). LCMS $[M+H]^+$=343.2.

Preparation Example 70: Synthesis of Compound HJM-070

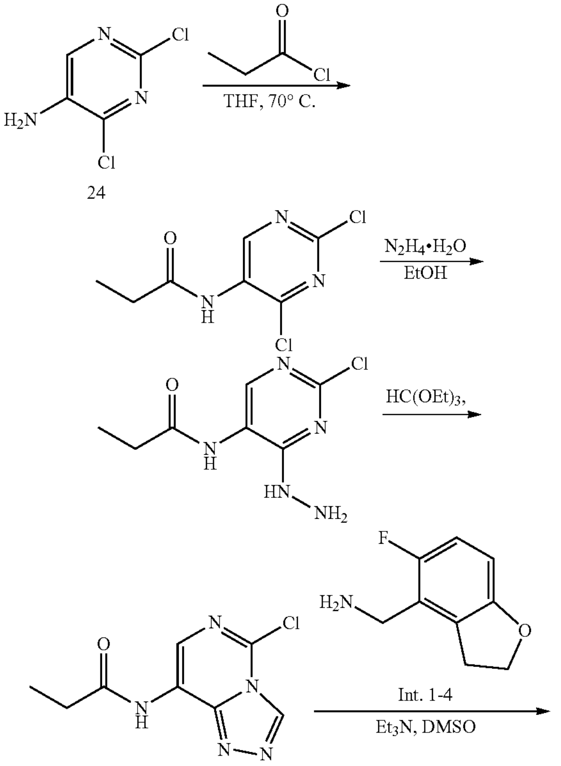

24

-continued

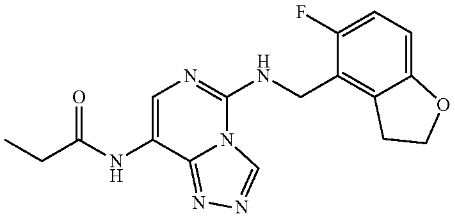

HJM-070

HJM-070 (78 mg) was prepared as a white solid using propionyl chloride as starting material according to the method similar to that for preparation example 69.

$^1$H NMR (400 MHz, DMSO-$d_6$) δ 9.82 (s, 1H), 9.41 (s, 1H), 8.38 (t, J=5.2 Hz, 1H), 8.08 (s, 1H), 6.94 (t, J=9.5 Hz, 1H), 6.70 (dd, J=8.6, 3.9 Hz, 1H), 4.65 (d, J=4.9 Hz, 2H), 4.54 (t, J=8.7 Hz, 2H), 3.28 (t, J=8.7 Hz, 2H), 2.43 (q, J=7.6 Hz, 2H), 1.08 (t, J=7.5 Hz, 3H). LCMS $[M+H]^+$=357.2.

Preparation Example 71: Synthesis of Compound HJM-071

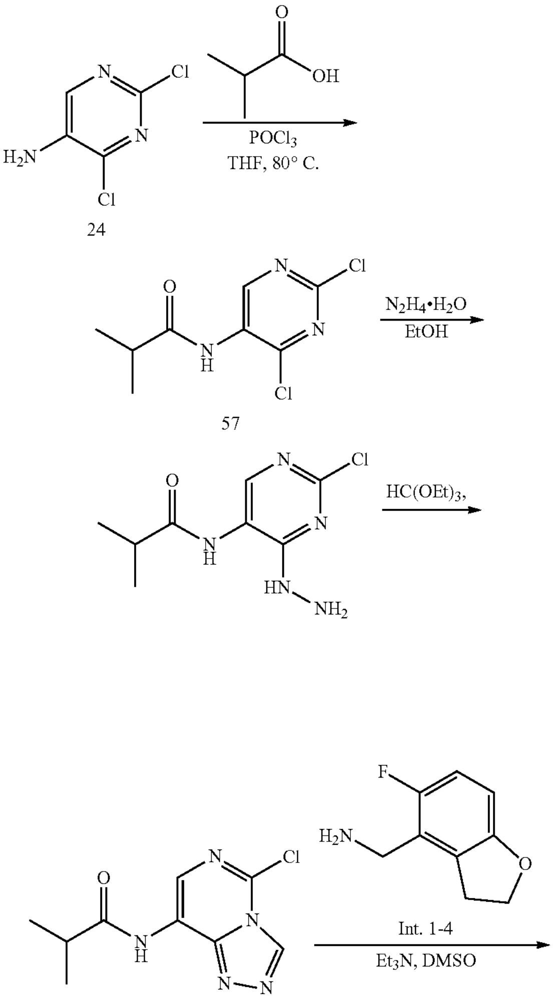

24

57

-continued

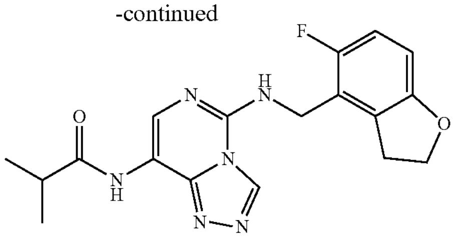

HJM-071

Step 1:

5-Amino-2,4-dichloropyrimidine 24 (600 mg, 3.66 mmol) and isobutyric acid (322 mg, 3.66 mmol) were dissolved in tetrahydrofuran (10 mL), phosphorus oxychloride (0.3 mL) was added dropwise, and the mixture was heated at 80° C. for 2 h. The mixture was cooled, and concentrated to afford a crude product. The crude product was purified by silica gel column chromatography (petroleum ether/ethyl acetate, ethyl acetate: 0-20%) to afford compound 57 (500 mg, yield: 58.4%) as a yellow solid. LCMS $[M+H]^+$=234.0.

In the following steps, HJM-071 (60 mg) was prepared as a white solid according to the method similar to that for preparation example 69.

$^1$H NMR (400 MHz, $CD_3OD$) δ 9.26 (s, 1H), 8.04 (s, 1H), 6.89-6.80 (m, 1H), 6.64 (dd, J=8.6, 3.9 Hz, 1H), 4.76 (s, 2H), 4.57 (t, J=8.7 Hz, 2H), 3.35 (t, J=8.7 Hz, 2H), 2.76 (p, J=6.9 Hz, 1H), 1.26 (d, J=6.8 Hz, 6H). LCMS $[M+H]^+$=371.2.

Preparation Example 72: Synthesis of Compound HJM-072

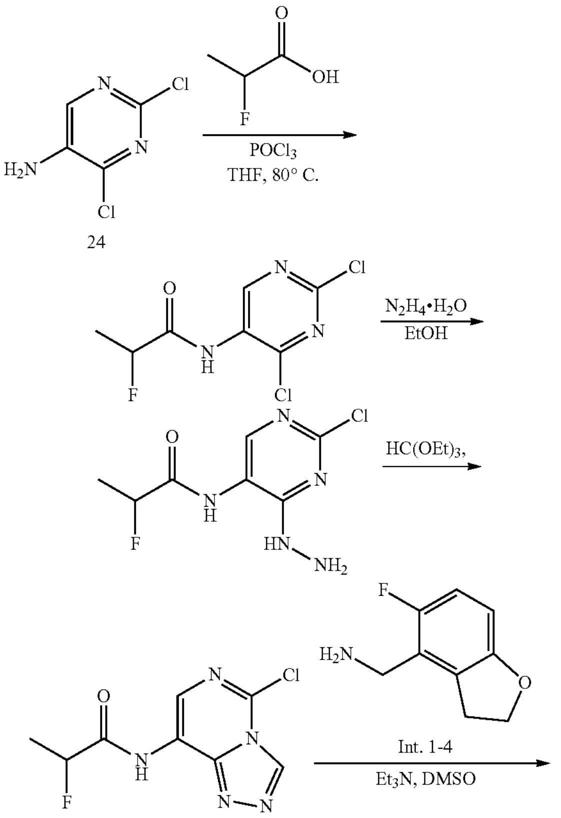

-continued

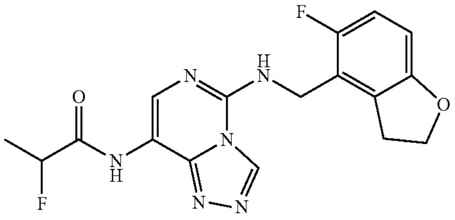

HJM-072

HJM-072 (31 mg) was prepared as a white solid using 2-fluoropropionic acid as starting material according to the method similar to that for preparation example 71.

$^1$H NMR (400 MHz, $CD_3OD$) δ 9.28 (s, 1H), 7.99 (s, 1H), 6.85 (t, J=9.4 Hz, 1H), 6.64 (dd, J=8.7, 3.9 Hz, 1H), 5.25 (dq, J=48.8, 6.8 Hz, 1H), 4.77 (s, 2H), 4.57 (t, J=8.7 Hz, 2H), 3.36 (t, J=8.8 Hz, 2H), 1.67 (dd, J=24.3, 6.8 Hz, 3H). LCMS $[M+H]^+$=375.1.

Preparation Example 73: Synthesis of Compound HJM-073

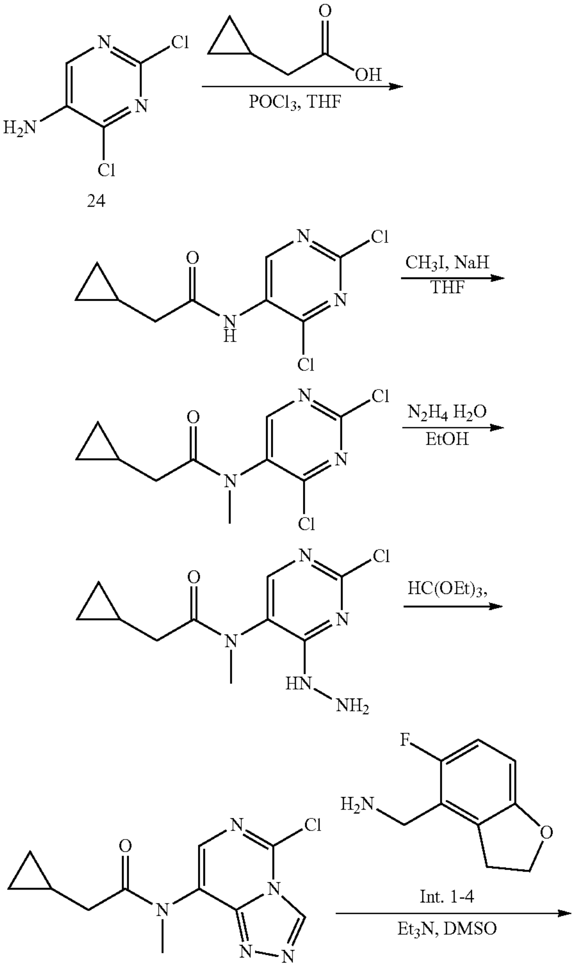

-continued

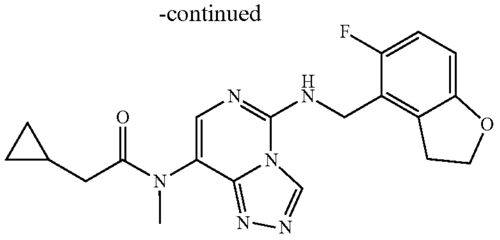

HJM-073

HJM-073 (9 mg) was prepared as a white solid using 2-cyclopropylacetic acid as starting material according to the method similar to that for preparation example 45.

$^1$H NMR (400 MHz, $CD_3OD$) δ 9.30 (s, 1H), 7.76 (s, 1H), 6.89-6.83 (m, 1H), 6.65 (dd, J=8.7, 3.9 Hz, 1H), 4.79 (d, J=6.8 Hz, 2H), 4.58 (t, J=8.7 Hz, 2H), 3.38 (t, J=8.6 Hz, 2H), 3.29 (s, 3H), 2.27-2.15 (m, 1H), 2.07-1.97 (m, 1H), 0.99-0.90 (m, 1H), 0.46-0.36 (m, 2H), −0.03 (d, J=5.0 Hz, 2H). LCMS $[M+H]^+$=397.5.

Preparation Example 74: Synthesis of Compound HJM-074

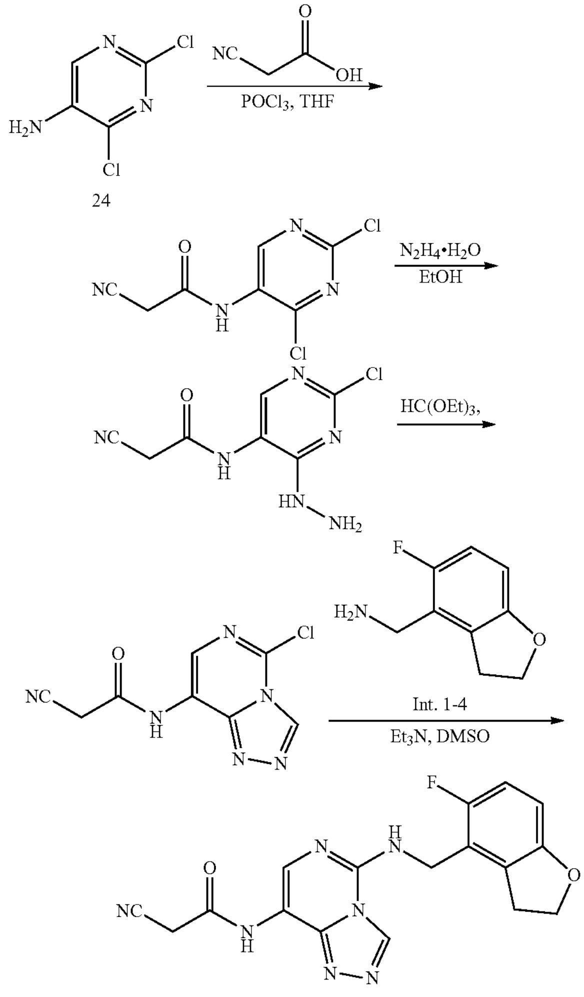

24

HJM-074

HJM-074 (31 mg) was prepared as a white solid using cyanoacetic acid as starting material according to the method similar to that for preparation example 71.

$^1$H NMR (400 MHz, DMSO-$d_6$) δ 10.43 (s, 1H), 9.44 (s, 1H), 8.52 (t, J=5.1 Hz, 1H), 8.12 (s, 1H), 6.94 (dd, J=10.3, 8.7 Hz, 1H), 6.70 (dd, J=8.7, 3.9 Hz, 1H), 4.66 (d, J=4.5 Hz, 2H), 4.54 (t, J=8.7 Hz, 2H), 4.03 (s, 2H), 3.29 (t, J=8.7 Hz, 2H). LCMS $[M+H]^+$=368.0.

Preparation Example 75: Synthesis of Compound HJM-075

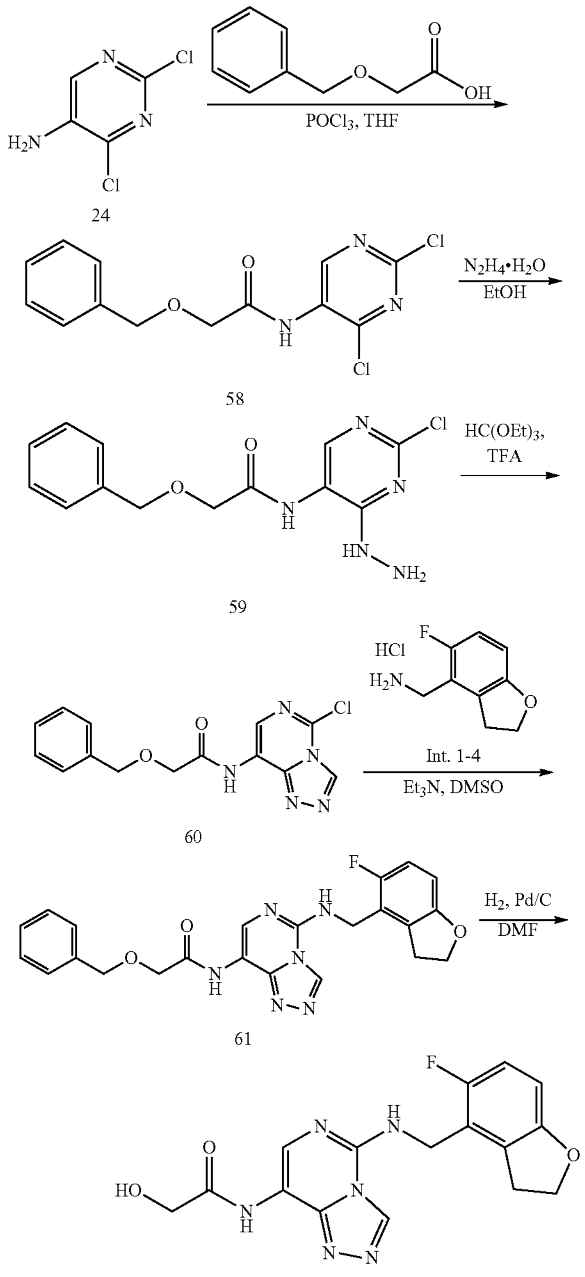

24

58

59

60

61

HJM-075

Step 1:

5-Amino-2,4-dichloropyrimidine 24 (800 mg, 4.88 mmol) and 2-benzyloxyacetic acid (890 mg, 5.36 mmol)

were dissolved in tetrahydrofuran (10 mL), phosphorus oxychloride (0.2 mL) was added dropwise, and the mixture was heated at 70° C. under nitrogen atmosphere for 16 h. The mixture was cooled, and concentrated to afford a crude product. The crude product was purified by silica gel column chromatography (petroleum ether/ethyl acetate, ethyl acetate: 0-20%) to afford compound 58 (820 mg, yield: 49%) as a white solid. LCMS [M+H]$^+$=312.1.

Step 2:

Compound 58 (800 mg, 2.56 mmol) was dissolved in ethanol (15 mL), 85% hydrazine hydrate (181.2 mg, 3.08 mmol) was added, and the mixture was reacted at room temperature for 1 h. The mixture was concentrated to afford crude compound 59, which was directly used in the next step. LCMS [M+H]$^+$=308.1.

Step 3:

The above compound 59 was added to triethyl orthoformate (10 mL), 2 drops of trifluoroacetic acid were added dropwise, and the mixture was heated at 120° C. for 1 h. The mixture was cooled, and concentrated to afford a crude product. The crude product was purified by silica gel column chromatography (petroleum ether/ethyl acetate, ethyl acetate: 0-100%) to afford compound 60 (250 mg, two-step yield: 31%) as a yellow oil.

$^{1}$H NMR (400 MHz, DMSO-$d_6$) δ 10.25 (s, 1H), 9.59 (s, 1H), 8.61 (s, 1H), 7.45-7.30 (m, 5H), 4.66 (s, 2H), 4.33 (s, 2H). LCMS [M+H]$^+$=318.1.

Step 4:

Compound 60 (250 mg, 0.79 mmol), Int.1-4 hydrochloride (174 mg, 0.87 mmol) and triethylamine (96 mg, 0.95 mmol) were dissolved in dimethyl sulfoxide (10 mL), and the mixture was stirred at room temperature for 2 h. The mixture was diluted with water, and extracted twice with ethyl acetate. The organic phases were combined, dried with anhydrous sodium sulfate, and filtered. The filtrate was concentrated to afford a crude product. The crude product was purified by silica gel column chromatography (dichloromethane/methanol, methanol: 0-5%) to afford compound 61 (301 mg, yield: 85%) as a white solid. LCMS [M+H]$^+$=449.3.

Step 5:

Compound 61 (100 mg, 0.22 mmol) was dissolved in N,N-dimethylformamide (6 mL), and 10% Pd/C (30 mg) was added under nitrogen atmosphere. The atmosphere was replaced three times with hydrogen gas, and the mixture was hydrogenated at ambient pressure at room temperature for 16 h. The mixture was filtered, and the filter cake was washed twice with methanol. The filtrates were combined, concentrated, and purified by preparative HPLC to afford compound HJM-075 (33 mg, yield: 41%) as a white solid.

$^{1}$H NMR (400 MHz, DMSO-$d_6$) δ 9.43 (s, 1H), 9.34 (s, 1H), 8.45 (t, J=5.0 Hz, 1H), 8.21 (s, 1H), 6.98-6.91 (m, 1H), 6.70 (dd, J=8.7, 3.9 Hz, 1H), 6.03 (t, J=5.7 Hz, 1H), 4.65 (d, J=5.0 Hz, 2H), 4.54 (t, J=8.7 Hz, 2H), 4.06 (d, J=5.7 Hz, 2H), 3.28 (t, J=8.8 Hz, 2H). LCMS [M+H]$^+$=359.4.

Preparation Example 76: Synthesis of Compound HJM-076

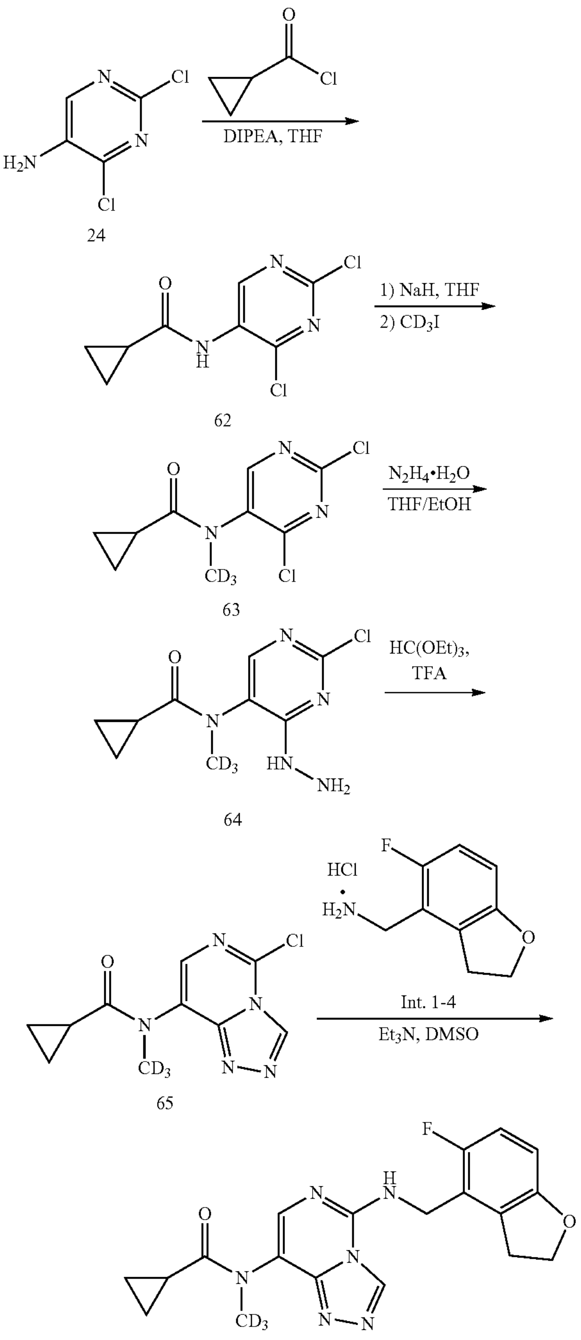

24

62

63

64

65

HJM-076

Step 1:

5-Amino-2,4-dichloropyrimidine 24 (20.1 g, 0.12 mol) and N,N-diisopropylethylamine (28.3 g, 0.22 mol) were dissolved in tetrahydrofuran (450 mL), and cyclopropyl chloride (17.9 g, 0.17 mol) was added dropwise at 0° C. After the addition, the mixture was warmed to room temperature and stirred for 6 h. The mixture was quenched with saturated aqueous ammonium chloride, and extracted with ethyl acetate (300 mL). The organic layer was washed with saturated brine, dried with anhydrous sodium sulfate, and filtered. The filtrate was concentrated to afford a residue. The residue was slurried with methyl tert-butyl ether, and filtered. The filter cake was dried to afford compound 62 (21 g, yield: 74%) as a white solid. LCMS $[M+H]^+$=232.0.

Step 2:

Compound 62 (2.55 g, 12.3 mmol) was dissolved in anhydrous tetrahydrofuran (35 mL), sodium hydride (575 mg, 1.42 mmol, purity: 60%) was added portionwise at 0° C., and the mixture was reacted with stirring at 0-5° C. for 1 h. Deuterated iodomethane (4.4 g, 30.3 mmol) was added dropwise, and the mixture was warmed to room temperature and stirred for 3 h. The mixture was cooled to 0° C., quenched with saturated aqueous ammonium chloride, and extracted with ethyl acetate (50 mL). The organic layer was washed with saturated brine, dried with anhydrous sodium sulfate, and filtered. The filtrate was concentrated to afford a crude product. The crude product was purified by silica gel column chromatography (petroleum ether/ethyl acetate, ethyl acetate: 20%-50%) to afford compound 63 (2.6 g, yield: 85%) as a colorless oil. LCMS $[M+H]^+$=249.0.

Step 3:

Compound 63 (2.6 g, 10.5 mmol) was dissolved in a mixture of tetrahydrofuran (12 mL) and dioxane (3 mL), and 85% hydrazine hydrate (1.05 mL, 21.0 mmol) was added at 0° C. After the addition, the mixture was warmed to room temperature and stirred for 1.5 h. Ethyl acetate and water were added to the reaction mixture, and the mixture was layered to afford an organic phase. The organic layer was washed with saturated brine, dried with anhydrous sodium sulfate, and filtered. The filtrate was concentrated to afford crude compound 64 (2.2 g, crude yield: 89%) as a white solid, which was directly used in the next step.

Step 4:

Compound 64 (2.2 g, 8.98 mmol) was suspended in triethyl orthoformate (12 mL), a catalytic amount of trifluoroacetic acid (90 uL) was added, and the mixture was heated to 85° C. and stirred for 45 min. The mixture was cooled, and concentrated to afford a crude product. The crude product was purified by silica gel column chromatography (ethyl acetate/methanol, methanol: 0-5%) to afford compound 65 (750 mg, yield: 32%) as a yellow oil. LCMS $[M+H]^+$=255.1.

Step 5:

Compound 65 (370 mg, 1.45 mmol) and Int.1-4 hydrochloride (320 mg, 1.57 mmol) were dissolved in acetonitrile (8 mL), N,N-diisopropylethylamine (0.58 mL, 3.5 mmol) was added, and the mixture was stirred at room temperature overnight. The mixture was concentrated to afford a crude product. The crude product was purified by preparative HPLC to afford compound HJM-076 (64 mg, yield: 11.5%) as a white solid.

$^1$H NMR (500 MHz, DMSO-$d_6$) δ 9.57 (s, 1H), 8.93 (t, J=5.0 Hz, 1H), 7.74 (s, 1H), 6.94 (t, J=9.4 Hz, 1H), 6.70 (dd, J=8.6, 3.8 Hz, 1H), 4.67 (s, 2H), 4.54 (t, J=8.7 Hz, 2H), 3.33 (t, J=8.8 Hz, 2H), 1.60-1.44 (m, 1H), 0.88-0.41 (m, 4H). LCMS $[M+H]^+$=386.5.

Preparation Example 77: Synthesis of Compound HJM-077

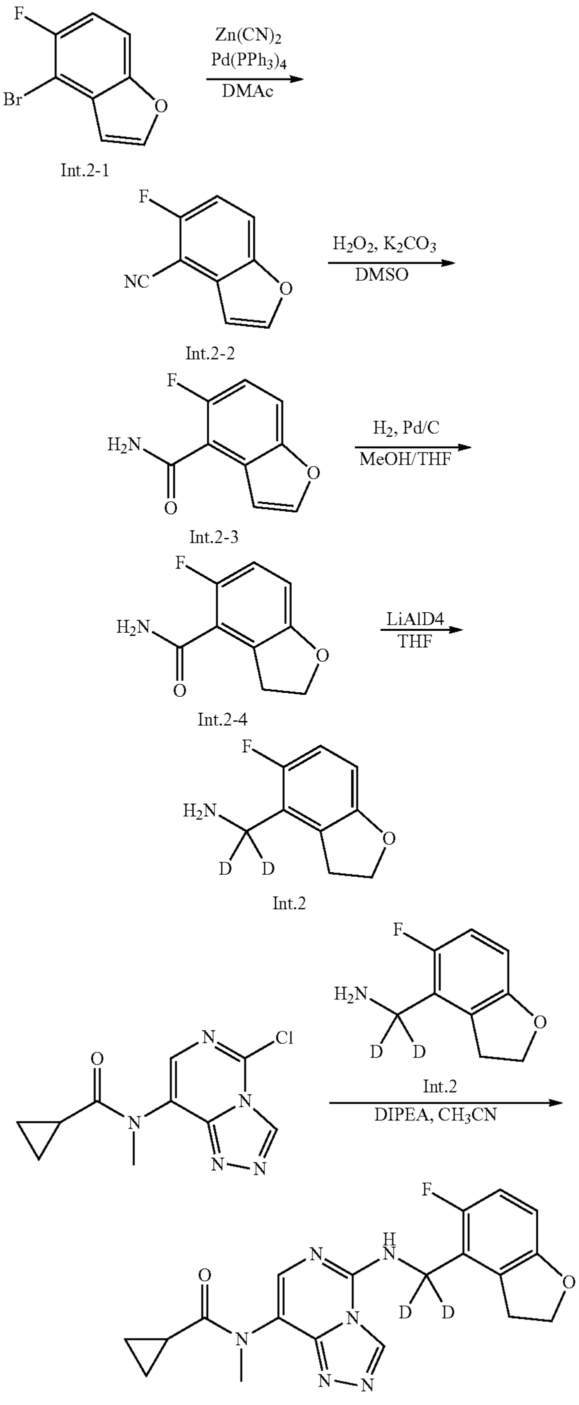

Int.2-1, Int.2-2, Int.2-3, Int.2-4, Int.2, HJM-077

Step 1:

Compound 4-bromo-5-fluorobenzofuran Int.2-1 (60 g, 279 mmol) was dissolved in N,N-dimethylacetamide (600 mL), zinc cyanide (130.6 g, 1.116 mol) and $Pd(PPh_3)_4$ (32.23 g, 27.9 mmol) were added under nitrogen atmosphere, and the mixture was heated at 110° C. and stirred for 12 h. The mixture was cooled to room temperature, diluted with ethyl acetate (500 mL), and washed with saturated brine for 5 times (5×400 mL). The organic phases were combined, dried with anhydrous sodium sulfate, and filtered. The filtrate was concentrated to afford a crude product. The resulting crude product was purified by silica gel column chromatography (petroleum ether:ethyl acetate (V/V)=100: 0-50:1) to afford compound 4-cyano-5-fluorobenzofuran Int.2-2 (12 g, yield: 26.7%) as a white solid.

Step 2:

Compound 4-cyano-5-fluorobenzofuran Int.2-2 (12 g, 74.5 mmol) was dissolved in dimethyl sulfoxide (150 mL), and potassium carbonate (10.28 g, 74.5 mmol) was added. Hydrogen peroxide (30%, 42.2 g, 372.7 mmol) was added dropwise, and the mixture was stirred at room temperature under nitrogen atmosphere for 1 h. The reaction mixture was poured into ice water and stirred for 20 min. The mixture was filtered, and the solid was dried to afford compound 5-fluorobenzofuran-4-formamide Int.2-3 (11 g, yield: 81.5%) as a white solid. LCMS $[M+H]^+$=180.1.

Step 3:

Under nitrogen protection, wet palladium on carbon (10% Pd/C, 6 g) was added to a mixture of 5-fluorobenzofuran-4-formamide Int.2-3 (6.4 g, 35.7 mmol) in methanol (60 mL) and tetrahydrofuran (20 mL). The atmosphere was replaced three times with hydrogen gas, and the mixture was stirred at 40° C. under the pressure of hydrogen gas (50 psi) for 8 h. LCMS showed that the reaction was completed. The mixture was filtered through diatomite, and the filter cake was washed with methanol (10 mL) for three times. The filtrates were combined and concentrated under reduced pressure to afford compound 5-fluoro-2,3-dihydrobenzofuran-4-carboxamide Int.2-4 (6.36 g, yield: 99.4%). LCMS $[M+H]^+$=182.1.

Step 4:

At 0° C., under nitrogen protection, a solution of 5-fluoro-2,3-dihydrobenzofuran-4-carboxamide Int.2-4 (5.0 g, 27.6 mmol) in anhydrous tetrahydrofuran (50 mL) was added dropwise to a solution of deuterated lithium aluminum hydride (2.1 g, 55.2 mmol) in anhydrous tetrahydrofuran (50 mL), and the mixture was heated to 100° C. and stirred for 1 h. LCMS showed that the reaction was completed. At 0° C., water (2.1 mL) was added dropwise to the mixture to quench the reaction, and the mixture was stirred for 10 min. Then 15% sodium hydroxide solution (2.1 mL) was added dropwise to the mixture, and the mixture was stirred for 10 min. Finally, water (6.3 mL) was added dropwise to the mixture, and the mixture was stirred for 10 min. The mixture was filtered through diatomite, and the filter cake was washed with dichloromethane (50 mL) for three times. The filtrates were combined, and concentrated under reduced pressure to afford a crude product. The crude product was purified by reversed-phase medium pressure column to afford compound (5-fluoro-2,3-dihydrobenzofuran-4-yl)dideuteromethylamine Int.2 (2.5 g, yield: 53.5%) as a brown oil.

$^1H$ NMR (400 MHz, $CDCl_3$) δ 6.82-6.76 (m, 1H), 6.59 (dd, J=8.6, 3.9 Hz, 1H), 4.59 (t, J=8.7 Hz, 2H), 3.23 (t, J=8.7 Hz, 2H). LCMS $[M+H]^+$=170.1.

Step 5:

Compound N-(5-chloro-[1,2,4]triazolo[4,3-c]pyrimidin-8-yl)-N-methylcyclopropanecarboxamide (see preparation example 45 for the synthesis procedure, 80 mg, 0.32 mmol) and Int.2 (60 mg, 0.35 mmol) were dissolved in acetonitrile (4 mL), N,N-diisopropylethylamine (80 mg, 0.62 mmol) was added, and the mixture was stirred at room temperature overnight. The mixture was concentrated to afford a crude product. The crude product was purified by preparative HPLC to afford compound HJM-077 (32 mg, yield: 26%) as a white solid.

$^1H$ NMR (500 MHz, DMSO-$d_6$) δ 9.51 (s, 1H), 8.82 (s, 1H), 7.75 (s, 1H), 6.95 (dd, J=10.2, 8.7 Hz, 1H), 6.71 (dd, J=8.6, 3.8 Hz, 1H), 4.55 (t, J=8.7 Hz, 2H), 3.32 (t, J=8.8 Hz, 2H), 3.17 (s, 3H), 1.58-1.47 (m, 1H), 0.87-0.42 (m, 4H). LCMS $[M+H]^+$=385.6.

Preparation Example 78: Synthesis of Compound HJM-078

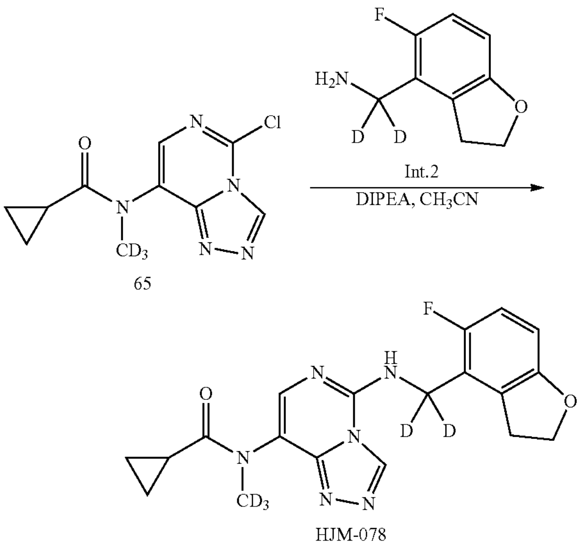

65

HJM-078

Compound 65 (80 mg, 0.32 mmol) and Int.2 (58 mg, 0.34 mmol) were dissolved in acetonitrile (4 mL), N,N-diisopropylethylamine (80 mg, 0.62 mmol) was added, and the mixture was stirred at room temperature overnight. The mixture was concentrated to afford a crude product. The crude product was purified by preparative HPLC to afford compound HJM-078 (18 mg, yield: 15%) as a white solid.

$^1H$ NMR (500 MHz, DMSO-$d_6$) δ 9.75 (s, 1H), 9.27 (s, 1H), 7.85 (s, 1H), 6.96-6.91 (m, 1H), 6.70 (dd, J=8.6, 3.9 Hz, 1H), 4.54 (t, J=8.7 Hz, 2H), 3.34 (t, J=8.7 Hz, 2H), 1.60-1.50 (m, 1H), 0.88-0.43 (m, 4H). LCMS $[M+H]^+$=388.6.

Preparation Example 79: Synthesis of Compound HJM-079

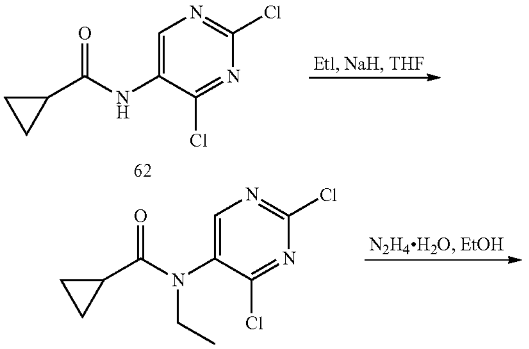

62

-continued

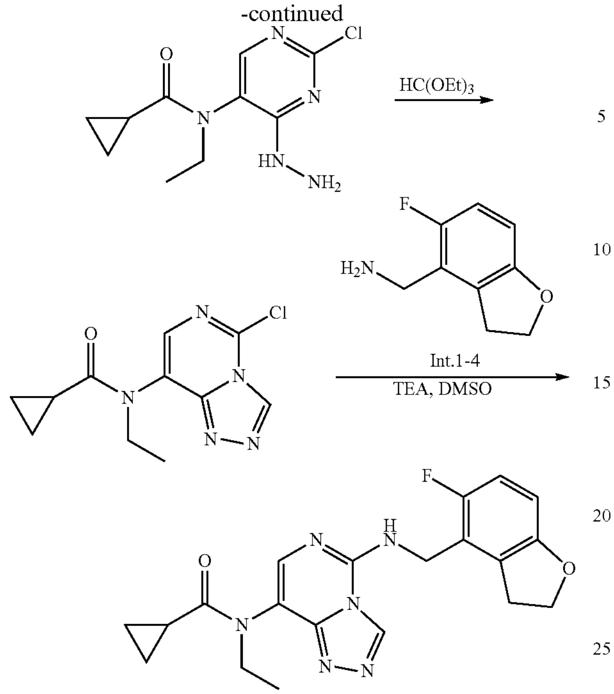

HJM-079

HJM-079 (4 mg) was prepared as a white solid using iodoethane instead of iodomethane according to the method similar to that for preparation example 45.

$^{1}H$ NMR (400 MHz, $CD_3OD$) δ 9.32 (s, 1H), 7.75 (s, 1H), 6.86 (dd, J=10.2, 8.7 Hz, 1H), 6.65 (dd, J=8.7, 3.9 Hz, 1H), 4.79 (s, 2H), 4.59 (t, J=8.7 Hz, 2H), 4.14-4.03 (m, 1H), 3.54-3.44 (m, 1H), 3.39 (t, J=8.7 Hz, 2H), 1.56-1.48 (m, 1H), 1.15 (t, J=7.1 Hz, 3H), 1.03-0.82 (m, 2H), 0.77-0.54 (m, 2H). LCMS $[M+H]^+$=397.1.

Preparation Example 80: Synthesis of Compound HJM-080

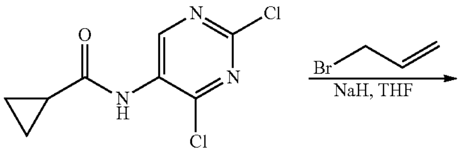

62

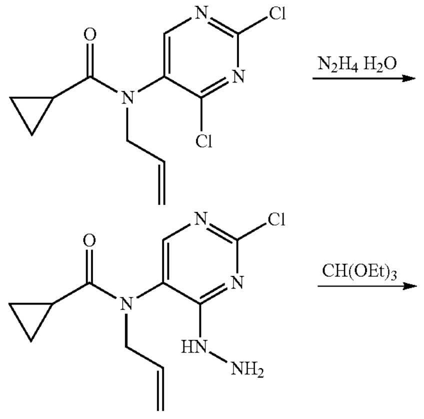

-continued

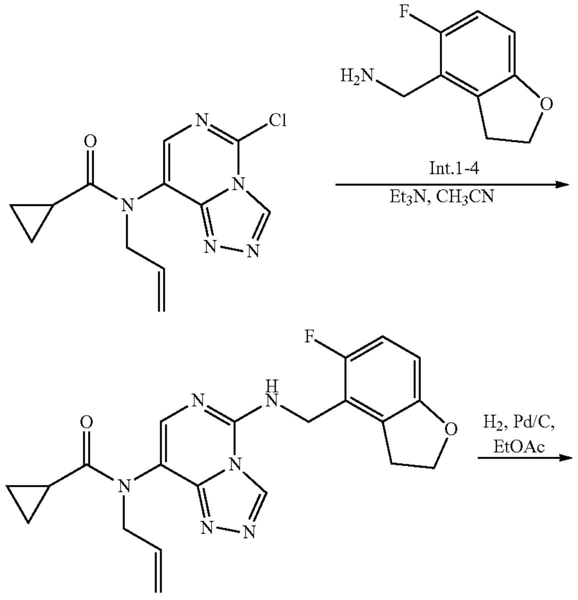

66

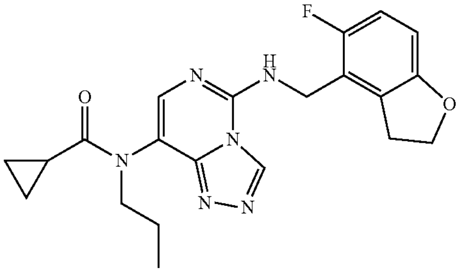

HJM-080

Steps 1-4:

Compound 66 (60 mg) was prepared using allyl bromide instead of iodomethane according to the method similar to that for preparation example 45. LCMS $[M+H]^+$=409.1.

Step 5:

Compound 66 (60 mg, 0.14 mmol) was dissolved in ethyl acetate (3 mL), and 10% Pd/C (10 mg) was added under nitrogen atmosphere. The atmosphere was replaced three times with hydrogen gas, and the mixture was hydrogenated at ambient pressure at room temperature for 16 h. The mixture was filtered, and the filter cake was washed twice with methanol. The filtrates were combined, concentrated, and purified by preparative HPLC to afford compound HJM-080 (15 mg, yield: 26%) as a white solid.

$^{1}H$ NMR (400 MHz, DMSO-$d_6$) δ 9.45 (s, 1H), 8.73 (s, 1H), 7.67 (s, 1H), 6.96 (dd, J=10.2, 8.6 Hz, 1H), 6.72 (dd, J=8.6, 3.8 Hz, 1H), 4.67 (s, 2H), 4.56 (t, J=8.7 Hz, 2H), 3.81 (brs, 1H), 3.38 (brs, 1H), 3.33 (t, J=8.6 Hz, 2H), 1.50-1.38 (m, 3H), 0.80 (t, J=7.4 Hz, 3H), 0.80-0.68 (m, 2H), 0.66-0.42 (m, 2H). LCMS $[M+H]^+$=411.2.

Preparation Example 81: Synthesis of Compound HJM-081

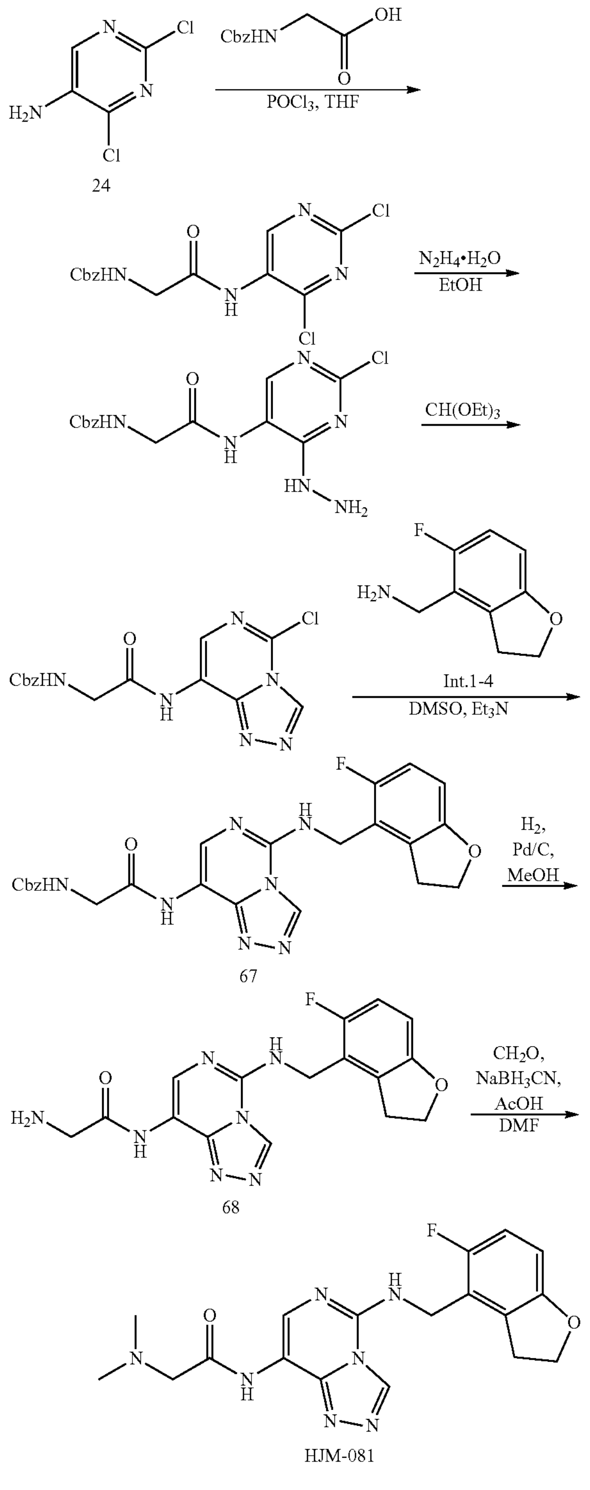

24

67

68

HJM-081

Steps 1-4:

Compound 67 (700 mg) was prepared using benzyloxycarbonylglycine as starting material according to the method similar to that for preparation example 71. LCMS $[M+H]^+$=492.2.

Step 5:

Compound 67 (700 mg, 1.425 mmol) was dissolved in methanol (20 mL), and 10% Pd/C (100 mg) was added under nitrogen atmosphere. The atmosphere was replaced three times with hydrogen gas, and the mixture was hydrogenated at ambient pressure at room temperature for 16 h. The mixture was filtered, and the filter cake was washed twice with methanol. The filtrates were combined, and concentrated to afford compound 68 (400 mg, yield: 78.6%). LCMS $[M+H]^+$=358.1.

Step 6:

Compound 68 (100 mg, 0.28 mmol) was dissolved in N,N-dimethylformamide (3 mL), and 37% formaldehyde aqueous solution (1 mL) was added. A drop of acetic acid was added dropwise, and the mixture was stirred at 0° C. for 10 min. Sodium cyanobohydride (53 mg, 0.84 mmol) was added, and the mixture was stirred at 0° C. for 2 h. The mixture was quenched with saturated sodium bicarbonate solution, and extracted twice with ethyl acetate. The organic phases were combined, dried with anhydrous sodium sulfate, and filtered. The filtrate was concentrated to afford a crude product. The crude product was purified by preparative HPLC to afford compound HJM-081 (22 mg, yield: 20.4%) as a white solid.

$^1$H NMR (400 MHz, DMSO-$d_6$) δ 10.73 (s, 1H), 9.45 (s, 1H), 8.57 (t, J=5.1 Hz, 1H), 8.11 (s, 1H), 7.01-6.90 (m, 1H), 6.71 (dd, J=8.7, 3.9 Hz, 1H), 4.66 (d, J=4.9 Hz, 2H), 4.54 (t, J=8.7 Hz, 2H), 4.23 (s, 2H), 3.29 (t, J=8.7 Hz, 2H), 2.88 (s, 6H). LCMS $[M+H]^+$=386.2.

Preparation Example 82: Synthesis of Compound HJM-082

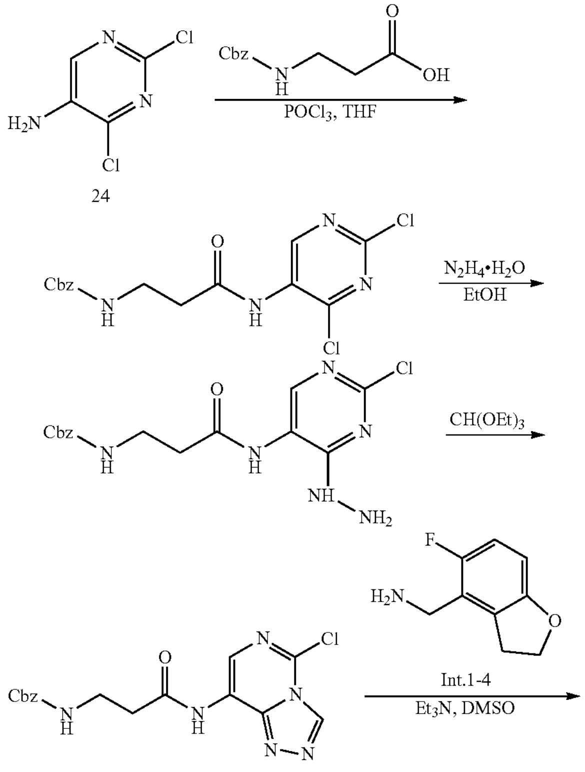

24

-continued

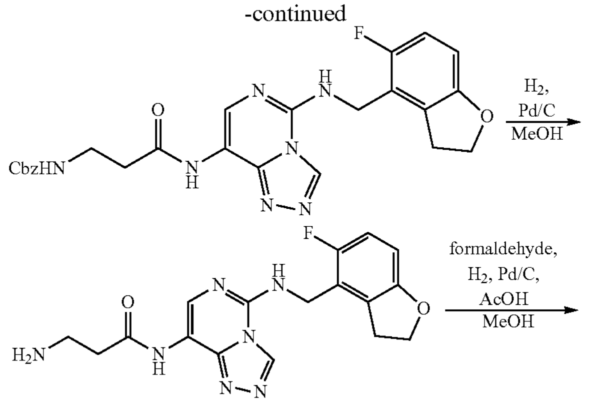

69

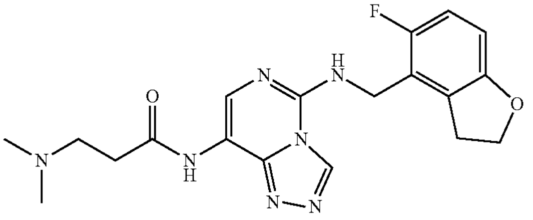

HJM-082

Steps 1-5:

Compound 69 (80 mg) was prepared as a yellow solid using benzyloxycarbonylglycine as starting material according to the method similar to that for compound 68 in preparation example 81. LCMS $[M+H]^+$=372.1.

Step 6:

Compound 69 (40 mg, 0.11 mmol) was dissolved in methanol (2 mL), and 37% formaldehyde aqueous solution (0.5 mL) was added. A drop of acetic acid was added dropwise, and 10% Pd/C (10 mg) was added under nitrogen atmosphere. The atmosphere was replaced three times with hydrogen gas, and the mixture was hydrogenated at ambient pressure at room temperature for 2 h. The mixture was filtered, and the filter cake was washed twice with methanol. The filtrates were combined, and concentrated to afford a crude product. The crude product was purified by preparative HPLC to afford compound HJM-082 (2 mg, yield: 4.6%) as a white solid.

$^1$H NMR (400 MHz, $CD_3OD$) δ 9.28 (s, 1H), 7.96 (s, 1H), 6.84 (t, J=9.4 Hz, 1H), 6.64 (dd, J=8.6, 3.9 Hz, 1H), 4.76 (s, 2H), 4.57 (t, J=8.7 Hz, 2H), 3.39-3.32 (m, 4H), 2.95 (t, J=6.5 Hz, 2H), 2.83 (s, 6H). LCMS $[M+H]^+$=400.1.

Preparation Example 83: Synthesis of Compound HJM-083

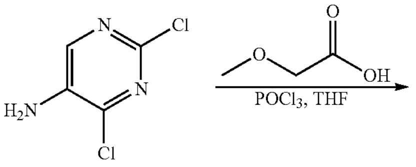

24

-continued

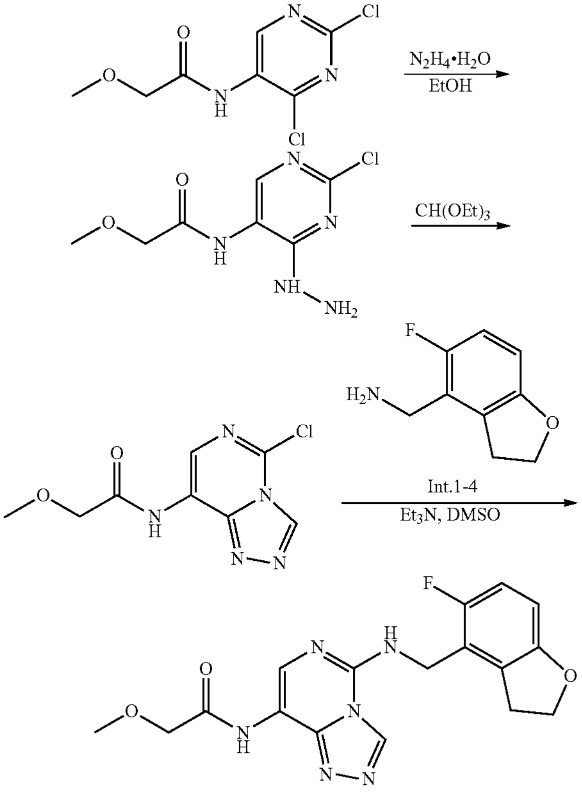

HJM-083

HJM-083 (13 mg) was prepared as a white solid using 2-methoxyacetic acid as starting material according to the method similar to that for preparation example 71.

$^1$H NMR (400 MHz, DMSO-$d_6$) δ 9.43 (s, 1H), 8.49 (t, J=4.9 Hz, 1H), 8.07 (s, 1H), 6.94 (t, J=9.5 Hz, 1H), 6.70 (dd, J=8.7, 3.8 Hz, 1H), 4.65 (d, J=4.9 Hz, 2H), 4.54 (t, J=8.7 Hz, 2H), 4.08 (s, 2H), 3.42 (s, 3H), 3.29 (t, J=8.7 Hz, 3H). LCMS $[M+H]^+$=373.3.

Preparation Example 84: Synthesis of Compound HJM-084

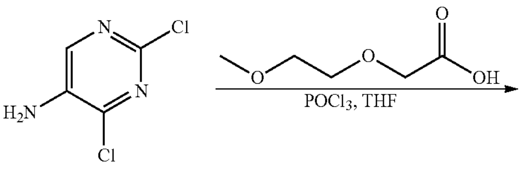

24

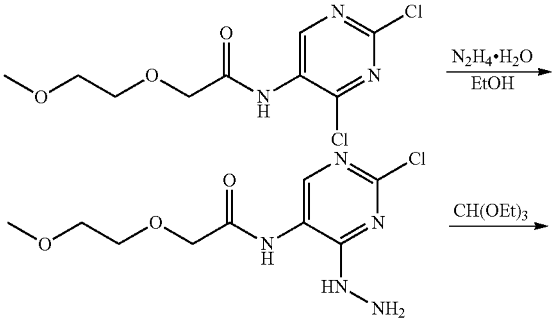

-continued

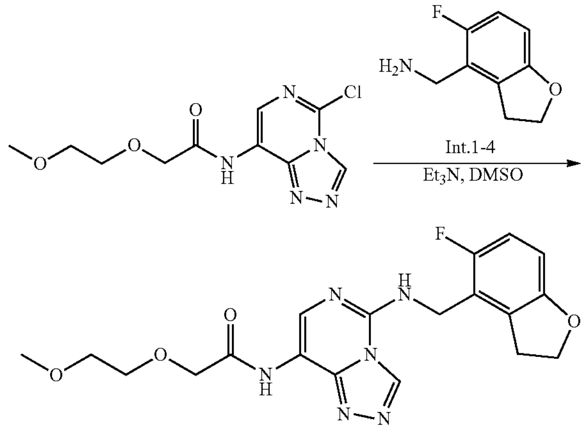

HJM-084

HJM-084 (75 mg) was prepared as a white solid using 2-(2-methoxyethoxy)acetic acid as starting material according to the method similar to that for preparation example 71.

$^1$H NMR (400 MHz, DMSO-$d_6$) δ 9.44 (s, 1H), 8.52 (t, J=5.2 Hz, 1H), 8.13 (s, 1H), 6.94 (dd, J=10.3, 8.7 Hz, 1H), 6.70 (dd, J=8.7, 3.8 Hz, 1H), 4.65 (d, J=4.6 Hz, 2H), 4.54 (t, J=8.7 Hz, 2H), 4.16 (s, 2H), 3.75-3.67 (m, 2H), 3.57-3.50 (m, 2H), 3.29 (t, J=8.8 Hz, 2H), 3.28 (s, 3H). LCMS $[M+H]^+$=417.3.

Preparation Example 85: Synthesis of Compound HJM-085

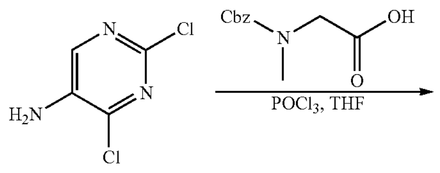

24

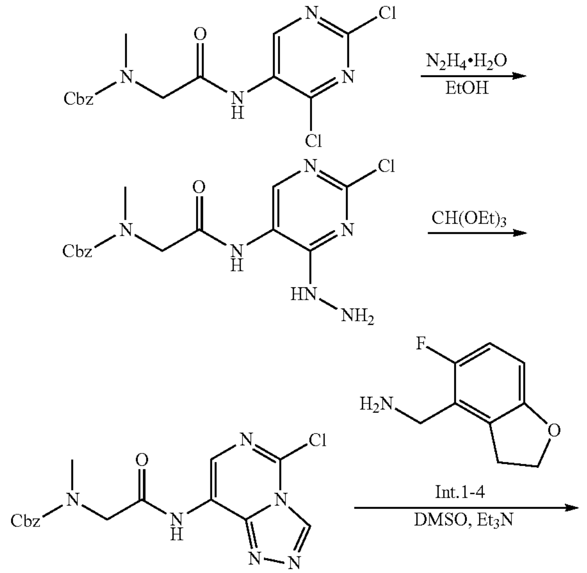

-continued

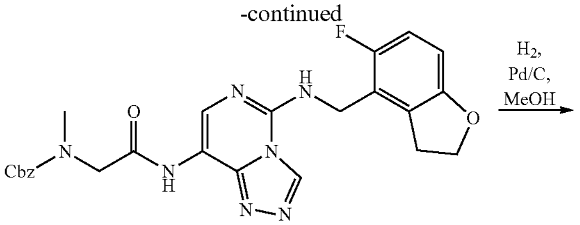

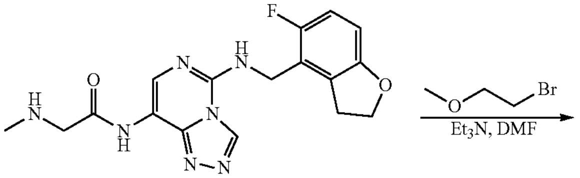

70

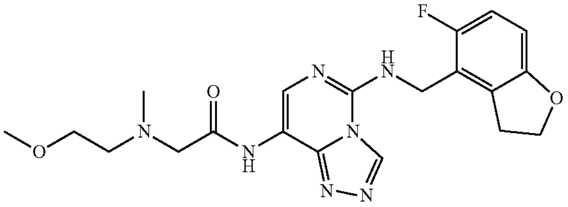

HJM-085

Steps 1-5:

Compound 70 (240 mg) was prepared as a white solid using N-benzyloxycarbonyl-N-methylglycine as starting material according to the method similar to that for compound 68 in preparation example 81. LCMS $[M+H]^+$=372.0.

Step 6:

Compound 70 (120 mg, 0.323 mmol), 1-bromo-2-methoxyethane (67 mg, 0.484 mmol) and triethylamine (65 mg, 0.646 mmol) were dissolved in N,N-dimethylformamide (3 mL), and the mixture was heated at 80° C. for 4 h. The mixture was cooled, and filtered. The filtrate was purified by preparative HPLC to afford compound HJM-085 (85 mg, yield: 61.5%) as a white solid.

$^1$H NMR (400 MHz, $CD_3OD$) δ 9.30 (s, 1H), 8.04 (s, 1H), 6.85 (dd, J=10.2, 8.7 Hz, 1H), 6.64 (dd, J=8.7, 3.9 Hz, 1H), 4.77 (s, 2H), 4.57 (t, J=8.7 Hz, 2H), 4.31 (brs, 2H), 3.78 (t, J=4.9 Hz, 2H), 3.53 (brs, 2H), 3.42 (s, 3H), 3.35 (t, J=8.7 Hz, 2H), 3.07 (s, 3H). LCMS $[M+H]^+$=430.5.

Preparation Example 86: Synthesis of Compound HJM-086

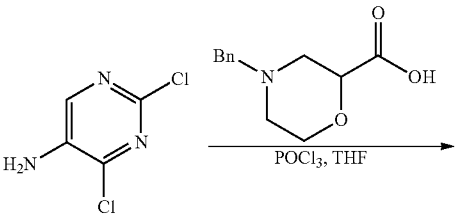

24

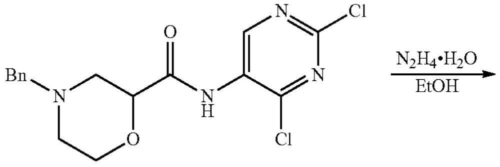

-continued

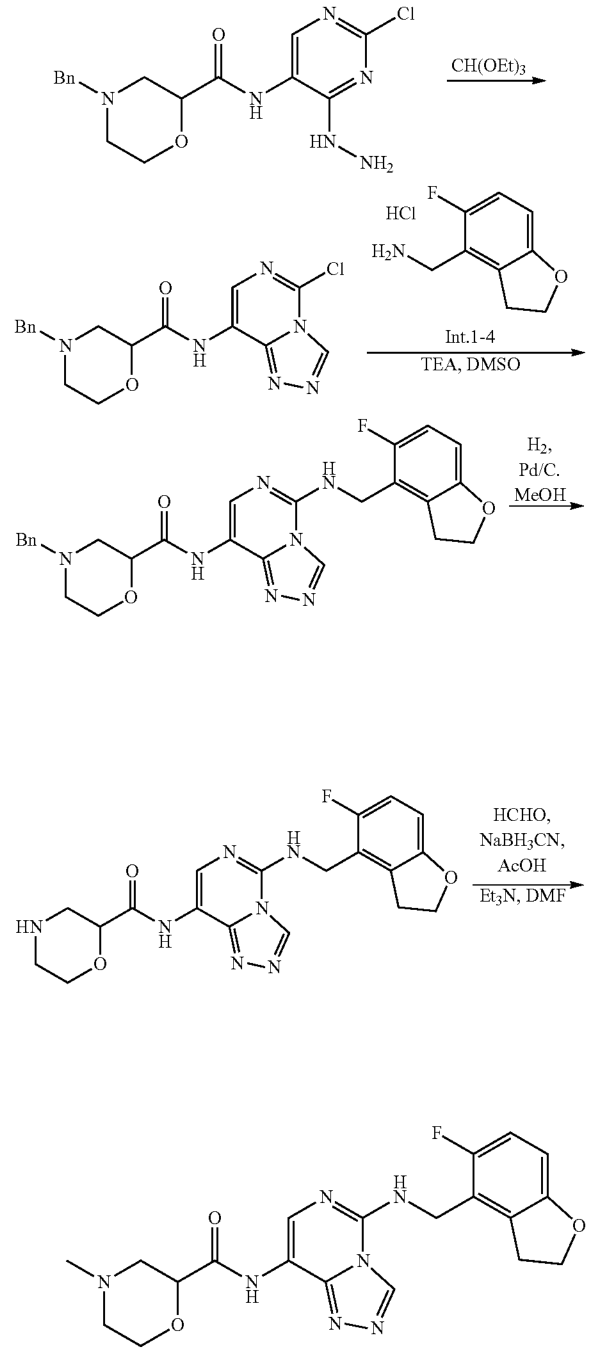

HJM-086

HJM-086 (9 mg) was prepared as a white solid using 4-benzylmorpholine-2-carboxylic acid as starting material according to the method similar to that for preparation example 81.

$^1$H NMR (400 MHz, $CD_3OD$) δ 9.27 (s, 1H), 8.13 (s, 1H), 6.85 (t, J=9.9, 8.7 Hz, 1H), 6.64 (dd, J=8.6, 3.8 Hz, 1H), 4.76 (s, 2H), 4.57 (t, J=8.7 Hz, 2H), 4.26 (dd, J=10.5, 2.8 Hz, 1H), 4.13-4.08 (m, 1H), 3.79 (td, J=11.5, 2.6 Hz, 1H), 3.36 (t, J=8.8 Hz, 2H), 3.20-3.14 (m, 1H), 2.78-2.72 (m, 1H), 2.36 (s, 3H), 2.26 (td, J=11.6, 3.5 Hz, 1H), 2.23-2.15 (m, 1H). LCMS $[M+H]^+$=428.1.

Preparation Example 87: Synthesis of Compound HJM-087

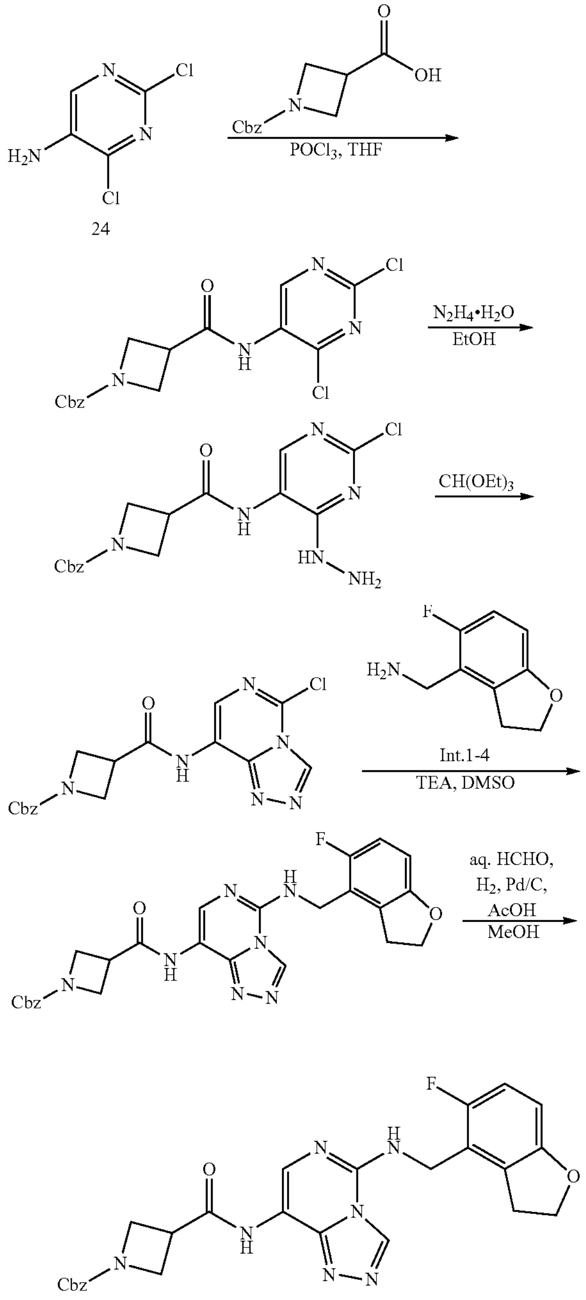

HJM-087

HJM-087 (9.9 mg) was prepared as a white solid using 1-benzyloxycarbonylazetidine-3-carboxylic acid as starting material according to the method similar to that for preparation example 82.

$^1$H NMR (400 MHz, $CD_3OD$) δ 9.29 (s, 1H), 8.00 (s, 1H), 6.85 (t, J=9.5 Hz, 1H), 6.64 (dd, J=8.8, 3.8 Hz, 1H), 4.77 (s, 2H), 4.57 (t, J=8.7 Hz, 2H), 4.35-4.24 (m, 4H), 3.82 (p, J=7.8 Hz, 1H), 3.35 (t, J=9.0 Hz, 2H), 2.89 (s, 3H). LCMS $[M+H]^+$=398.2.

Preparation Example 88: Synthesis of Compound HJM-088

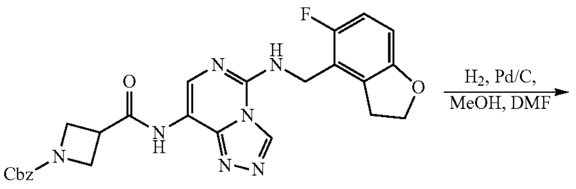

71

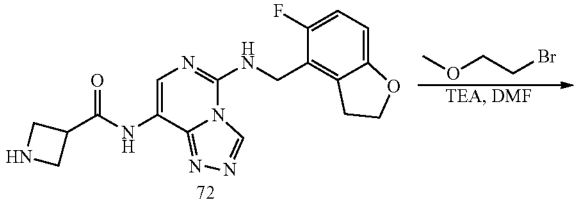

72

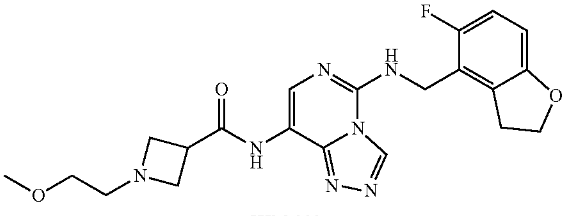

HJM-088

Step 1:

Compound 71 (an intermediate in preparation example 87, 100 mg, 0.19 mmol) was dissolved in a mixture of methanol (7 mL)/N,N-dimethylformamide (2 mL), and 10% Pd/C (20 mg) was added under nitrogen atmosphere. The atmosphere was replaced three times with hydrogen gas, and the mixture was hydrogenated at ambient pressure at room temperature for 16 h. The mixture was filtered, and the filter cake was washed twice with methanol. The filtrates were combined, and concentrated to afford crude compound 72 (50 mg, yield: 69%), which was directly used in the next step. LCMS $[M+H]^+$=384.1.

Step 2:

Compound 72 (45 mg, 0.11 mmol), 1-bromo-2-methoxy-ethane (17 mg, 0.11 mmol) and triethylamine (22 mg, 0.22 mmol) were dissolved in N,N-dimethylformamide (3 mL), and the mixture was heated at 70° C. and stirred for 3 h. The mixture was cooled and purified by preparative HPLC to afford compound HJM-088 (6 mg, yield: 12%) as a white solid.

$^1$H NMR (400 MHz, $CD_3OD$) δ 9.30 (s, 1H), 7.99 (s, 1H), 6.85 (t, J=9.5 Hz, 1H), 6.65 (dd, J=8.7, 3.9 Hz, 1H), 4.77 (s, 2H), 4.57 (t, J=8.7 Hz, 2H), 4.58-4.43 (m, 2H), 4.43-4.33 (m, 2H), 3.99-3.87 (m, 1H), 3.66-3.60 (m, 2H), 3.51-3.47 (m, 2H), 3.40 (s, 3H), 3.36 (t, J=8.8 Hz, 2H). LCMS $[M+H]^+$=442.2.

Preparation Example 89: Synthesis of Compound HJM-089

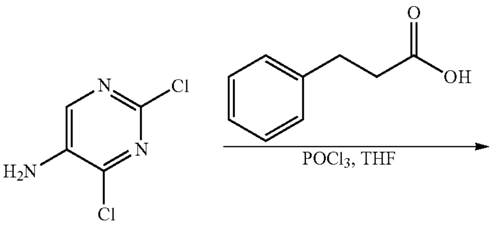

24

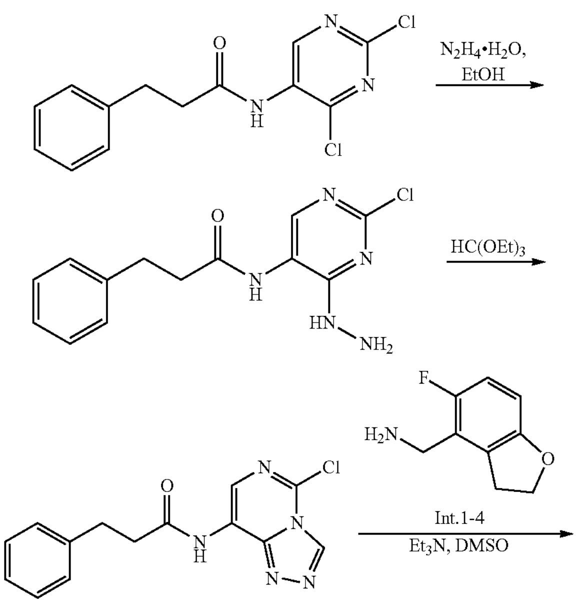

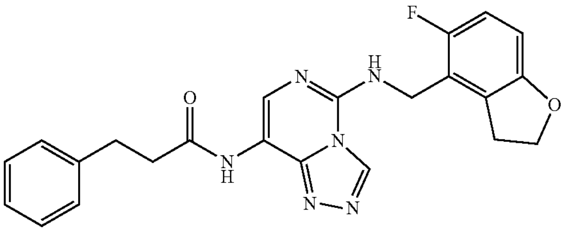

HJM-089

HJM-089 (28 mg) was prepared as a white solid using phenylpropionic acid as starting material according to the method similar to that for preparation example 71.

$^1$H NMR (400 MHz, DMSO-$d_6$) δ 9.95 (s, 1H), 9.41 (s, 1H), 8.40 (t, J=5.0 Hz, 2H), 8.09 (s, 1H), 7.33-7.15 (m, 5H), 7.00-6.89 (m, 1H), 6.70 (dd, J=8.7, 3.9 Hz, 1H), 4.65 (d, J=4.9 Hz, 2H), 4.54 (t, J=8.7 Hz, 2H), 3.28 (t, J=8.7 Hz, 2H), 2.91 (t, J=7.7 Hz, 2H), 2.74 (t, J=7.8 Hz, 2H). LCMS $[M+H]^+$=433.5.

Preparation Example 90: Synthesis of Compound HJM-090

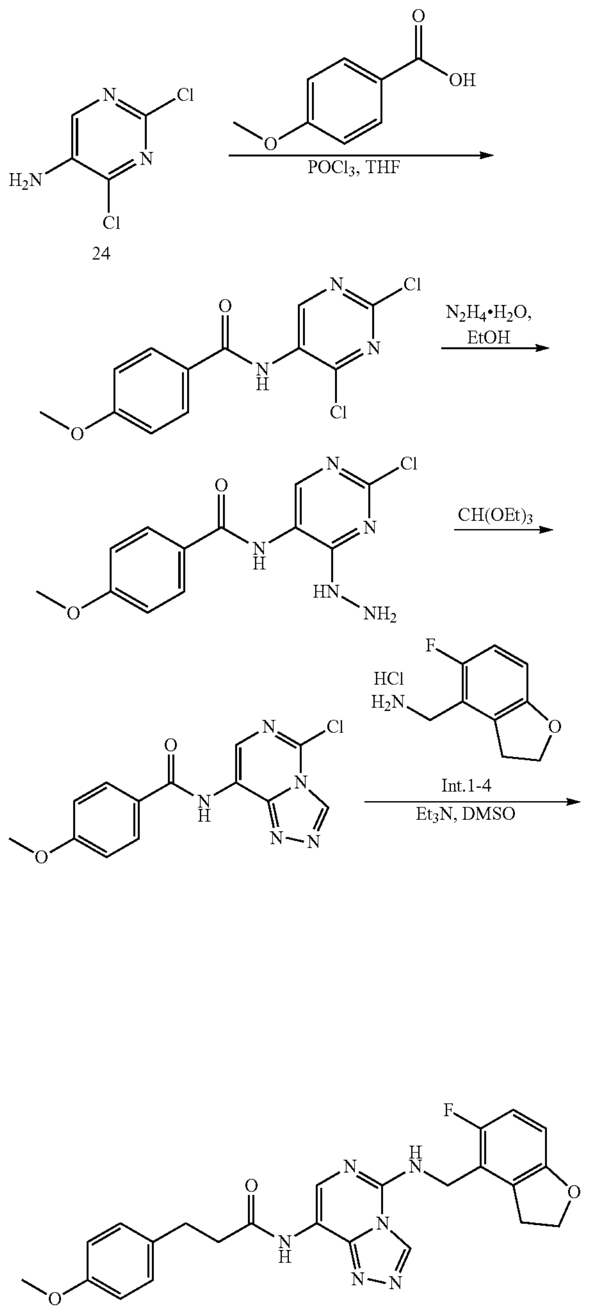

HJM-090

HJM-090 (9.5 mg) was prepared as a white solid using 4-methoxybenzoic acid as starting material according to the method similar to that for preparation example 71.

$^1$H NMR (400 MHz, DMSO-$d_6$) δ 9.98 (s, 1H), 9.45 (s, 1H), 8.56 (t, J=5.2 Hz, 1H), 8.00 (d, J=8.7 Hz, 2H), 7.82 (s, 1H), 7.07 (d, J=8.8 Hz, 2H), 7.00-6.91 (m, 1H), 6.71 (dd, J=8.5, 3.9 Hz, 1H), 4.69 (d, J=4.9 Hz, 2H), 4.55 (t, J=8.7 Hz, 2H), 3.85 (s, 3H), 2.54 (t, J=8.7 Hz, 1H). LCMS $[M+H]^+$=435.3.

Preparation Example 91: Synthesis of Compound HJM-091

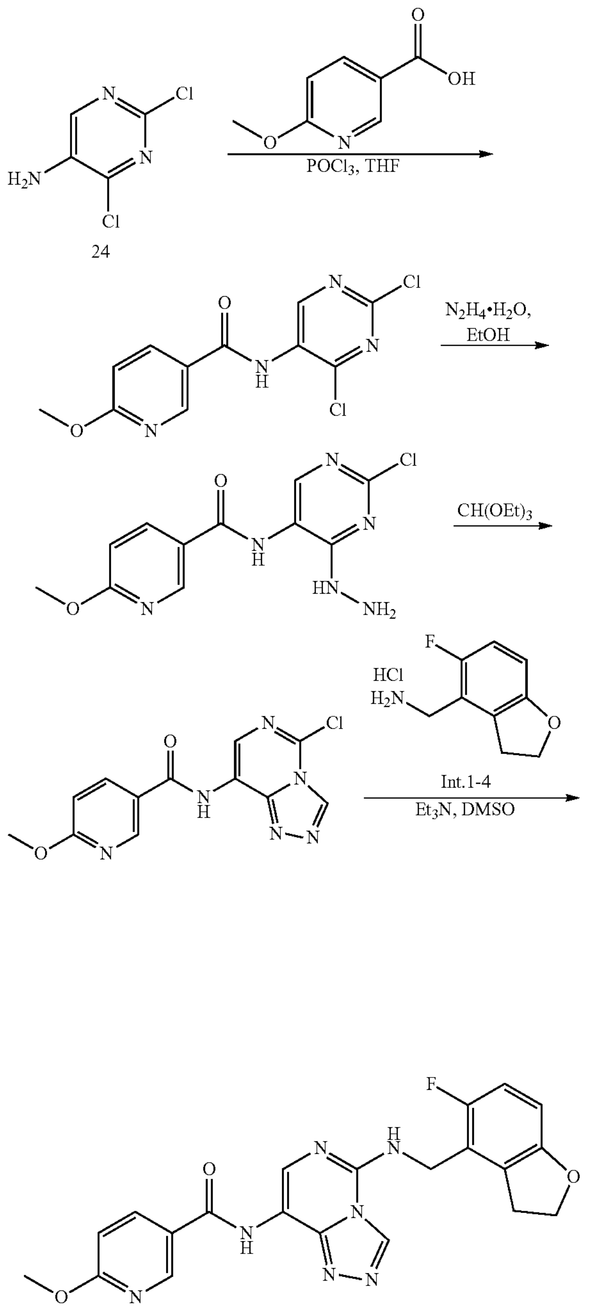

HJM-091

HJM-091 (45 mg) was prepared as a white solid using 6-methoxynicotinic acid as starting material according to the method similar to that for preparation example 71.

$^1$H NMR (400 MHz, DMSO-$d_6$) δ 10.24 (s, 1H), 9.47 (s, 1H), 8.83 (d, J=2.6 Hz, 1H), 8.61 (t, J=5.0 Hz, 1H), 8.27 (dd, J=8.7, 2.5 Hz, 1H), 7.85 (s, 1H), 7.01-6.90 (m, 2H), 6.71 (dd, J=8.6, 3.9 Hz, 1H), 4.69 (d, J=5.1 Hz, 2H), 4.55 (t, J=8.7 Hz, 2H), 3.95 (s, 3H), 3.30 (t, J=8.7 Hz, 2H). LCMS $[M+H]^+$=436.4.

Preparation Example 92: Synthesis of Compound HJM-092

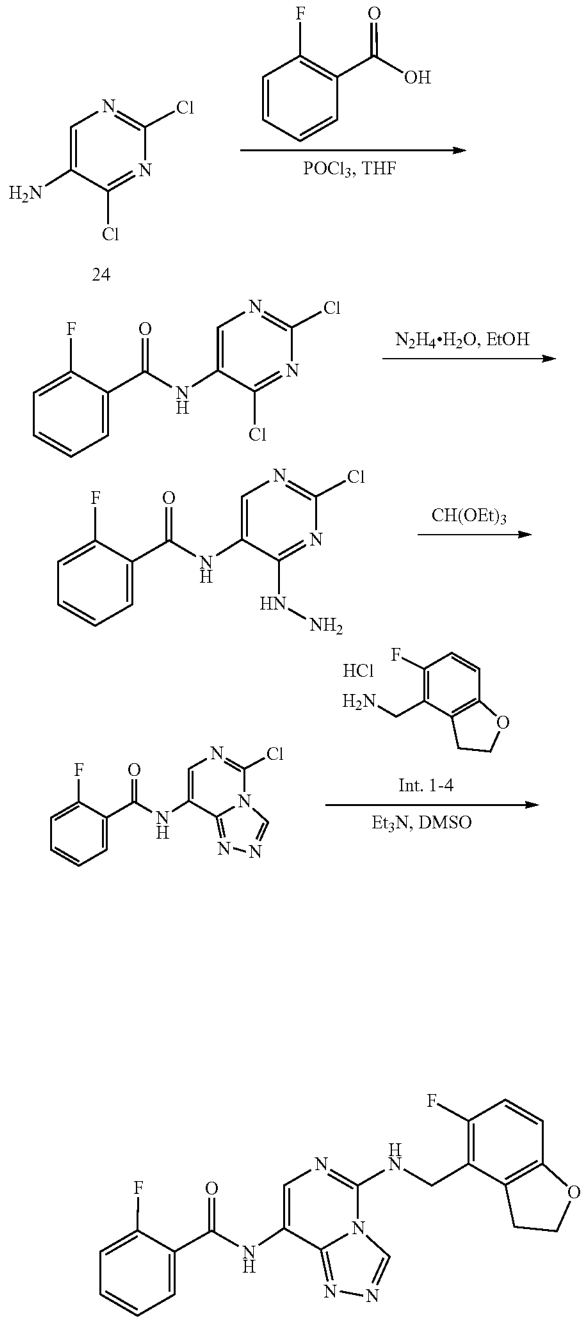

24

HJM-092

HJM-092 (35 mg) was prepared as a white solid using 2-fluorobenzoic acid as starting material according to the method similar to that for preparation example 71.

$^1$H NMR (400 MHz, DMSO-$d_6$) δ 10.10 (s, 1H), 9.45 (s, 1H), 8.56 (s, 1H), 8.10 (s, 1H), 7.82-7.75 (m, 1H), 7.69-7.57 (m, 1H), 7.46-7.29 (m, 2H), 6.95 (t, J=9.4 Hz, 1H), 6.78-6.65 (m, 1H), 4.68 (s, 2H), 4.55 (t, J=8.7 Hz, 2H), 3.30 (t, J=8.7 Hz, 2H). LCMS $[M+H]^+$=423.2.

Preparation Example 93: Synthesis of Compound HJM-093

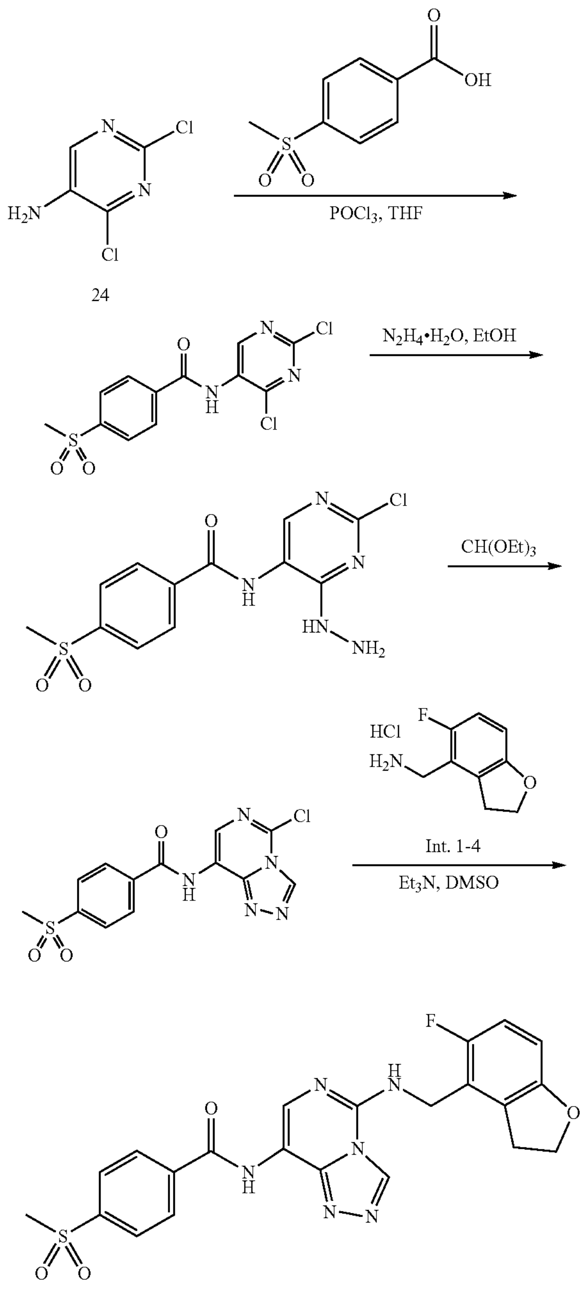

24

HJM-093

HJM-093 (40 mg) was prepared as a white solid using 4-methanesulfonylbenzoic acid as starting material according to the method similar to that for preparation example 71.

$^1$H NMR (400 MHz, DMSO-$d_6$) δ 10.51 (s, 1H), 9.47 (s, 1H), 8.65 (t, J=5.0 Hz, 1H), 8.23 (d, J=8.1 Hz, 2H), 8.11 (d, J=8.2 Hz, 2H), 7.91 (s, 1H), 6.96 (t, J=9.5 Hz, 1H), 6.72 (dd, J=8.6, 3.9 Hz, 1H), 4.70 (d, J=4.8 Hz, 2H), 4.56 (t, J=8.7 Hz, 2H), 3.32 (t, J=8.9 Hz, 2H), 3.31 (s, 3H). LCMS $[M+H]^+$=483.4.

Preparation Example 94: Synthesis of Compound HJM-094

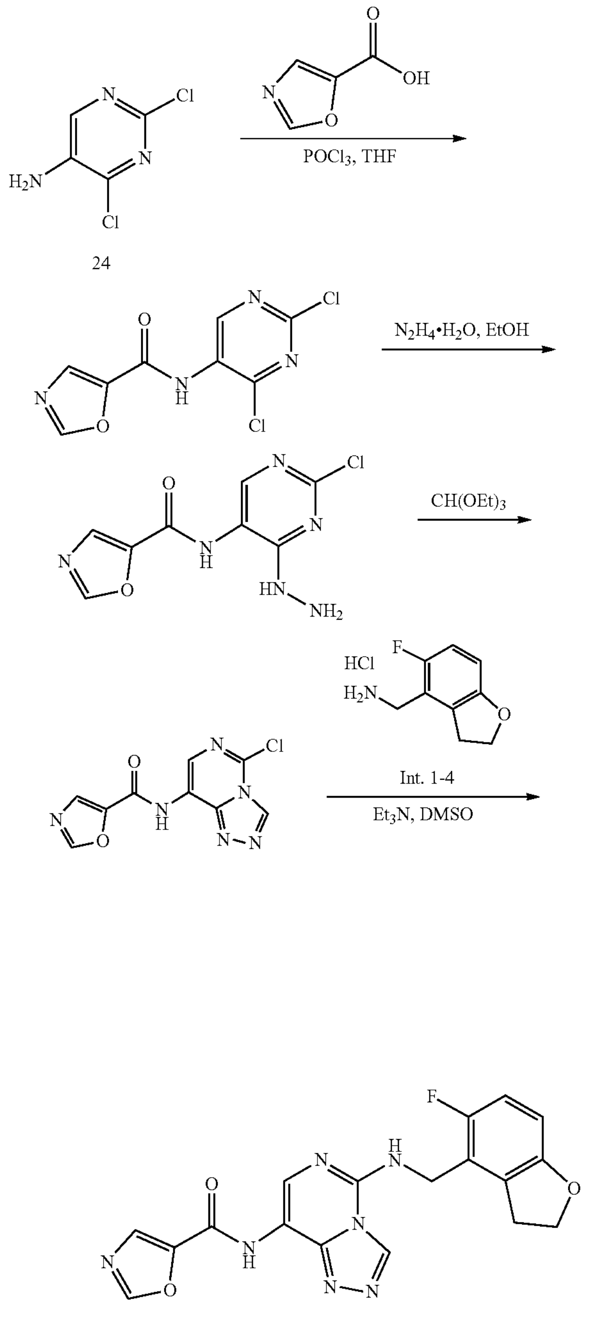

HJM-094

HJM-094 (10 mg) was prepared as a white solid using oxazole-5-carboxylic acid as starting material according to the method similar to that for preparation example 71.

$^1$H NMR (400 MHz, DMSO-$d_6$) δ 10.37 (s, 1H), 9.45 (s, 1H), 8.67 (s, 1H), 8.66-8.62 (m, 1H), 8.04 (s, 1H), 7.85 (s, 1H), 6.95 (t, J=9.5 Hz, 1H), 6.71 (dd, J=8.7, 3.9 Hz, 1H), 4.69 (d, J=4.1 Hz, 2H), 4.55 (t, J=8.7 Hz, 2H), 3.31 (t, J=8.7 Hz, 2H). LCMS $[M+H]^+$=396.3.

Preparation Example 95: Synthesis of Compound HJM-095

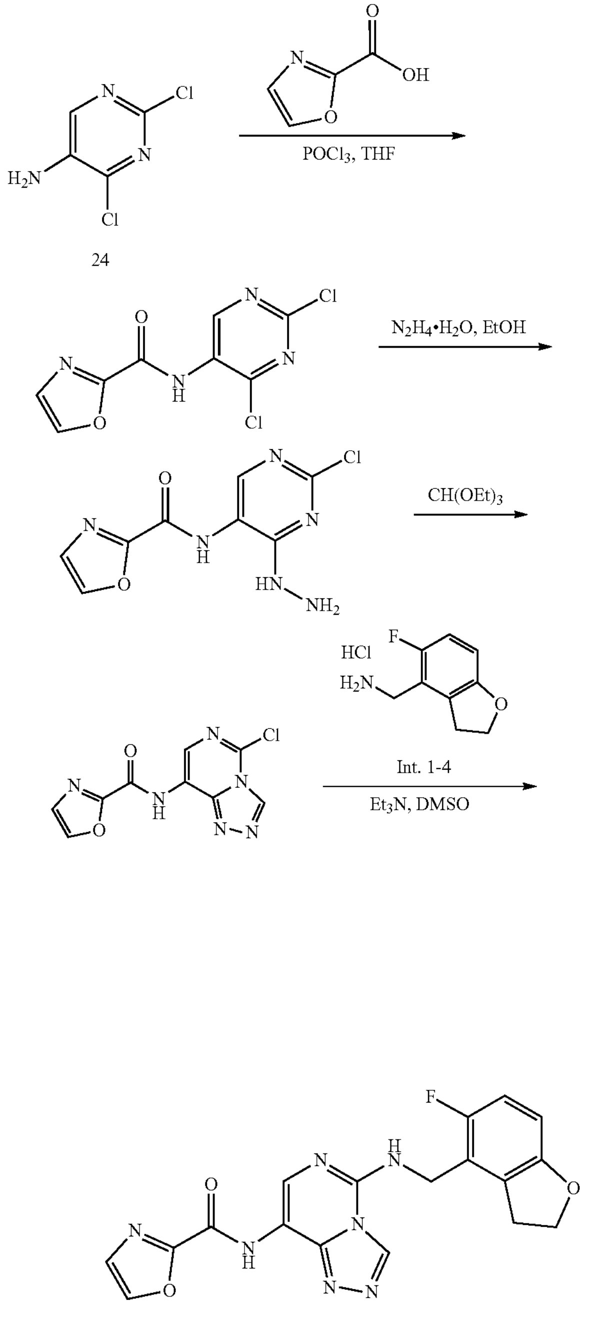

HJM-095

HJM-095 (2.5 mg) was prepared as a white solid using oxazole-2-carboxylic acid as starting material according to the method similar to that for preparation example 71.

$^1$H NMR (400 MHz, DMSO-$d_6$) δ 10.36 (s, 1H), 9.45 (s, 1H), 8.67 (t, J=5.1 Hz, 1H), 8.44 (s, 1H), 7.91 (s, 1H), 7.58 (s, 1H), 6.95 (dd, J=10.2, 8.7 Hz, 1H), 6.71 (dd, J=8.6, 3.9 Hz, 1H), 4.69 (d, J=4.9 Hz, 2H), 4.55 (t, J=8.7 Hz, 2H), 3.31 (t, J=8.8 Hz, 2H). LCMS $[M+H]^+$=396.0.

Preparation Example 96: Synthesis of Compound HJM-096
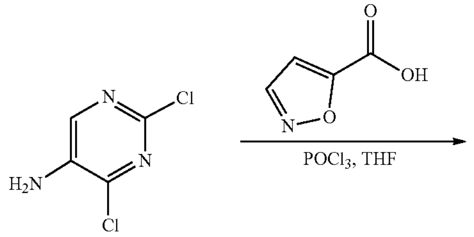
24
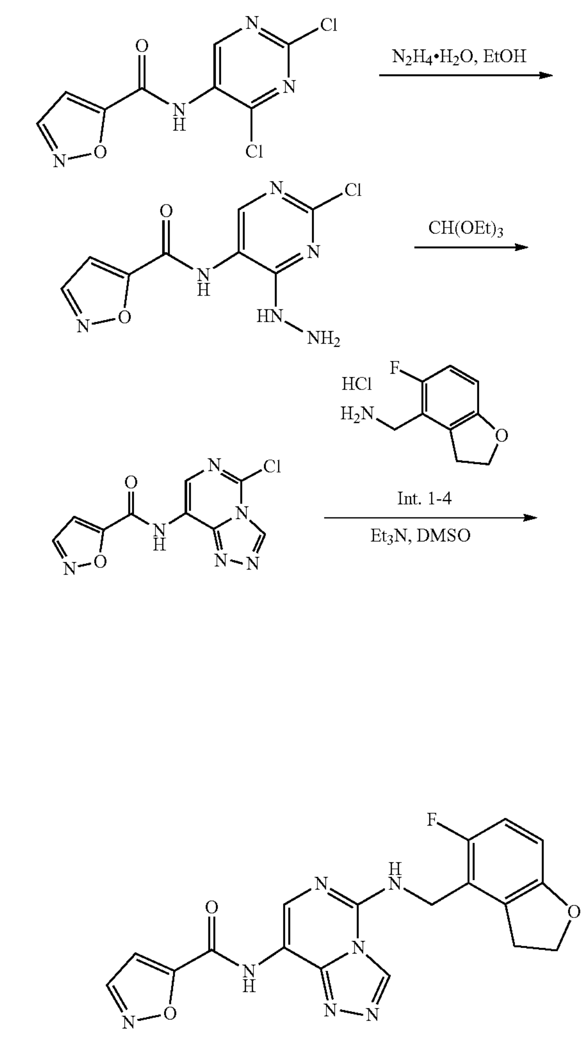
HJM-096
HJM-096 (4 mg) was prepared as a white solid using isoxazole-5-carboxylic acid as starting material according to the method similar to that for preparation example 71.
$^1$H NMR (400 MHz, DMSO-$d_6$) δ 10.61 (br s, 1H), 9.46 (s, 1H), 8.84 (s, 1H), 8.68 (br s, 1H), 7.85 (s, 1H), 7.32 (s, 1H), 6.95 (t, J=9.4 Hz, 1H), 6.71 (dd, J=8.7, 3.8 Hz, 1H), 4.69 (s, 2H), 4.55 (t, J=8.7 Hz, 2H), 3.31 (t, J=8.7 Hz, 2H). LCMS $[M+H]^+$=396.2.
Preparation Example 97: Synthesis of Compound HJM-097
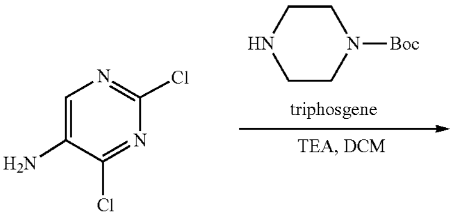
24
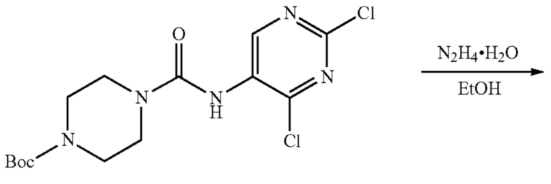
73
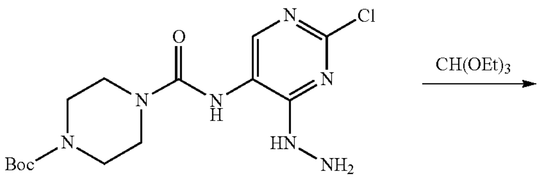
74
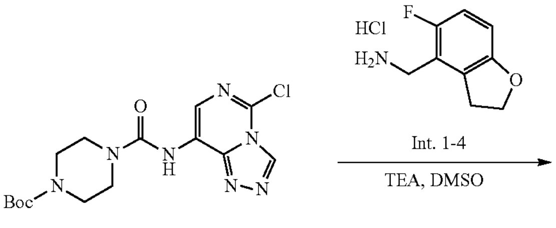
75
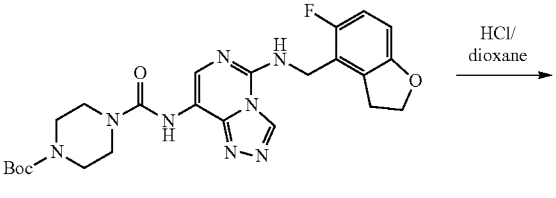
76
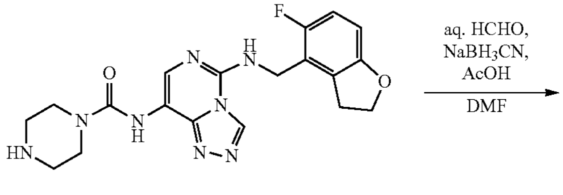
77

-continued

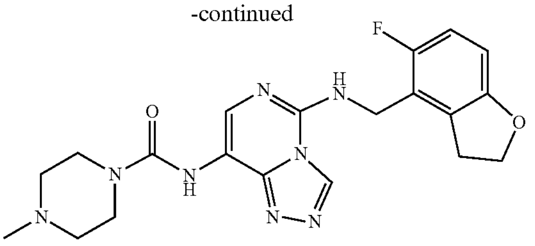

HJM-097

Step 1:

At 0° C., a solution of triphosgene (713 mg, 2.4 mmol) in dichloromethane (5 mL) was added dropwise to a solution of compound 5-amino-2,4-dichloropyrimidine 24 (656 mg, 4 mmol) and triethylamine (1.6 g, 16 mmol) in dichloromethane (10 mL). After the dropwise addition, the mixture was warmed to room temperature and stirred for 1 h. The mixture was then cooled to 0° C., and a solution of tert-butyl piperazine-1-carboxylate (818 mg, 4.4 mmol) in dichloromethane (5 mL) was added dropwise. After the dropwise addition, the mixture was warmed to room temperature and stirred for 30 min. The mixture was concentrated to afford a crude product. The crude product was purified by silica gel column chromatography (petroleum ether/ethyl acetate, ethyl acetate: 0-100%) to afford compound 73 (1 g, yield: 66.5%) as a white solid. LCMS $[M\text{-}tBu+H]^+$=320.0.

Step 2:

Compound 73 (560 mg, 1.49 mmol) was dissolved in ethanol (8 mL), 85% hydrazine hydrate (131 mg, 2.23 mmol) was added at room temperature, and the mixture was reacted at room temperature for 2 h. The mixture was filtered and concentrated to afford crude compound 74 (280 mg, yield: 50.8%) as a white solid. LCMS $[M+H]^+$=372.1.

Step 3:

Compound 74 (280 mg, 1 mmol) was added to triethyl orthoformate (10 mL), and the mixture was heated at 120° C. for 1.5 h. The mixture was cooled, and concentrated to afford crude compound 75 (300 mg), which was directly used in the next step. LCMS $[M+H]^+$=382.1.

Step 4:

The above compound 75 (282 mg, 1 mmol), Int.1-4 hydrochloride (203 mg, 1 mmol) and triethylamine (202 mg, 2 mmol) were dissolved in dimethyl sulfoxide (5 mL), and the mixture was stirred at room temperature for 2 h. The mixture was diluted with water, and extracted twice with ethyl acetate. The organic phases were combined, dried with anhydrous sodium sulfate, and filtered. The filtrate was concentrated to afford a crude product. The crude product was purified by preparative thin layer chromatography to afford compound 76 (300 mg, yield: 58.6%). LCMS $[M+H]^+$=513.2.

Step 5:

Compound 76 (300 mg, 0.59 mmol) was dissolved in 1,4-dioxane (5 mL), a solution of 4 M hydrochloric acid in 1,4-dioxane (1 mL) was added dropwise, and the mixture was stirred at room temperature for 30 min. The mixture was concentrated to afford crude compound 77 (220 mg, yield: 95.4%) as a yellow solid. LCMS $[M+H]^+$=413.2.

Step 6:

Compound 77 (90 mg, 0.22 mmol) was dissolved in N,N-dimethylformamide (4 mL), and 37% formaldehyde aqueous solution (0.5 mL) was added. A drop of acetic acid was added dropwise, and the mixture was stirred at 0° C. for 30 min. Sodium cyanobohydride (41 mg, 0.65 mmol) was added, and the mixture was stirred at room temperature for 4 h. The mixture was quenched with saturated sodium bicarbonate solution, and extracted twice with ethyl acetate. The organic phases were combined, dried with anhydrous sodium sulfate, and filtered. The filtrate was concentrated to afford a crude product. The crude product was purified by preparative HPLC to afford compound HJM-097 (7 mg, yield: 11.8%) as a white solid.

$^1$H NMR (400 MHz, DMSO-$d_6$) δ 9.91 (br s, 1H), 9.43 (s, 1H), 8.68 (s, 1H), 8.50 (t, J=5.2 Hz, 1H), 7.64 (s, 1H), 6.94 (t, J=9.5 Hz, 1H), 6.71 (dd, J=8.6, 3.8 Hz, 1H), 4.65 (d, J=4.6 Hz, 2H), 4.54 (t, J=8.7 Hz, 2H), 4.24 (d, J=14.1 Hz, 2H), 3.48 (d, J=12.1 Hz, 2H), 3.29 (t, J=8.7 Hz, 2H), 3.17 (t, J=12.8 Hz, 2H), 3.11-2.99 (m, 2H), 2.85 (s, 3H). LCMS $[M+H]^+$=427.2.

Preparation Example 98: Synthesis of Compound HJM-098

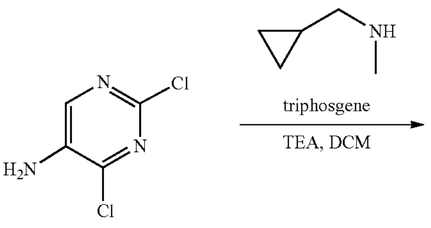

24

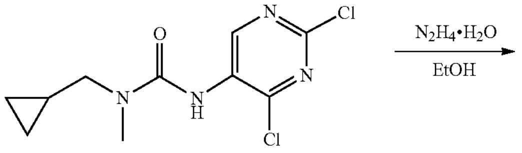

78

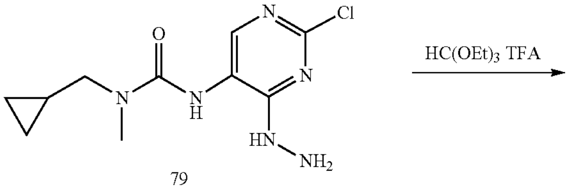

79

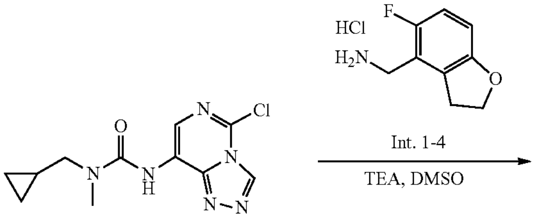

80

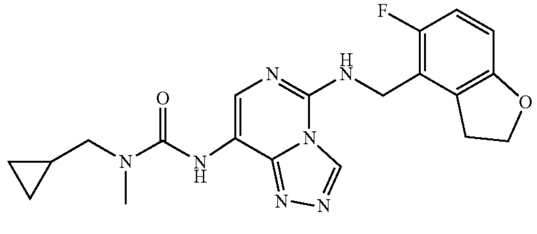

HJM-098

Step 1:

At 0° C., a solution of triphosgene (1.08 g, 3.65 mmol) in dichloromethane (5 mL) was added dropwise to a solution of compound 5-amino-2,4-dichloropyrimidine 24 (1 g, 6.09 mmol) and triethylamine (2.46 g, 24.36 mmol) in dichloromethane (30 mL). After the dropwise addition, the mixture was warmed to room temperature and stirred for 1 h. The mixture was then cooled to 0° C., and a solution of 1-cyclopropyl-N-methylmethylamine (570 mg, 6.69 mmol) in dichloromethane (5 mL) was added dropwise. After the dropwise addition, the mixture was warmed to room temperature and stirred for 30 min. The mixture was concentrated to afford a crude product. The crude product was purified by silica gel column chromatography (petroleum ether/ethyl acetate, ethyl acetate: 0-50%) to afford compound 78 (620 mg, yield: 37.3%) as a colorless oil. $^1$H NMR (400 MHz, $CDCl_3$) δ 9.49 (s, 1H), 6.84 (s, 1H), 3.30 (d, J=6.7 Hz, 2H), 3.13 (s, 3H), 1.10-0.98 (m, 1H), 0.65-0.58 (m, 2H), 0.34-0.27 (m, 2H). LCMS $[M+H]^+$=275.3.

Step 2:

Compound 78 (191 mg, 0.697 mmol) was dissolved in ethanol (3 mL), 85% hydrazine hydrate (50 mg, 0.836 mmol) was added at room temperature, and the mixture was reacted at room temperature for 30 min. The mixture was concentrated to afford a crude product. The crude product was purified by preparative thin layer chromatography to afford compound 79 (175 mg, yield: 93%) as a white solid.

$^1$H NMR (400 MHz, $CDCl_3$) δ 8.06 (s, 1H), 7.17 (br s, 1H), 6.71 (br s, 1H), 4.05 (br s, 2H), 3.26 (d, J=6.7 Hz, 2H), 3.09 (s, 3H), 1.07-0.95 (m, 1H), 0.62-0.55 (m, 2H), 0.31-0.24 (m, 2H). LCMS $[M+H]^+$=271.1.

Step 3:

Compound 79 (175 mg, 0.648 mmol) was added to triethyl orthoformate (5 mL), trifluoroacetic acid (0.5 mL) was added dropwise, and the mixture was heated at 100° C. for 1.5 h. The mixture was cooled, and concentrated to afford a crude product. The crude product was purified by preparative thin layer chromatography to afford compound 80 (44 mg, yield: 22.9%) as a white solid.

$^1$H NMR (400 MHz, $CD_3OD$) δ 9.40 (s, 1H), 8.41 (s, 1H), 3.37 (d, J=6.9 Hz, 2H), 3.20 (s, 3H), 1.18-1.04 (m, 1H), 0.63-0.53 (m, 2H), 0.38-0.30 (m, 2H). LCMS $[M+H]^+$=281.1.

Step 4:

The above compound 80 (44 mg, 0.157 mmol), Int.1-4 hydrochloride (38 mg, 0.188 mmol) and triethylamine (32 mg, 0.314 mmol) were dissolved in dimethyl sulfoxide (2 mL), and the mixture was stirred at 50° C. for 1 h. The mixture was cooled and purified by preparative HPLC to afford compound HJM-098 (35 mg, yield: 54.6%) as a white solid.

$^1$H NMR (400 MHz, $CD_3OD$) δ 9.25 (s, 1H), 7.74 (s, 1H), 6.84 (t, J=9.4 Hz, 1H), 6.63 (dd, J=8.7, 3.9 Hz, 1H), 4.75 (s, 2H), 4.57 (t, J=8.7 Hz, 2H), 3.36 (t, J=8.7 Hz, 2H), 3.14 (d, J=0.9 Hz, 3H), 1.17-1.04 (m, 1H), 0.59-0.50 (m, 2H), 0.34-0.24 (m, 2H). LCMS $[M+H]^+$=412.1.

Preparation Example 99: Synthesis of Compound HJM-099

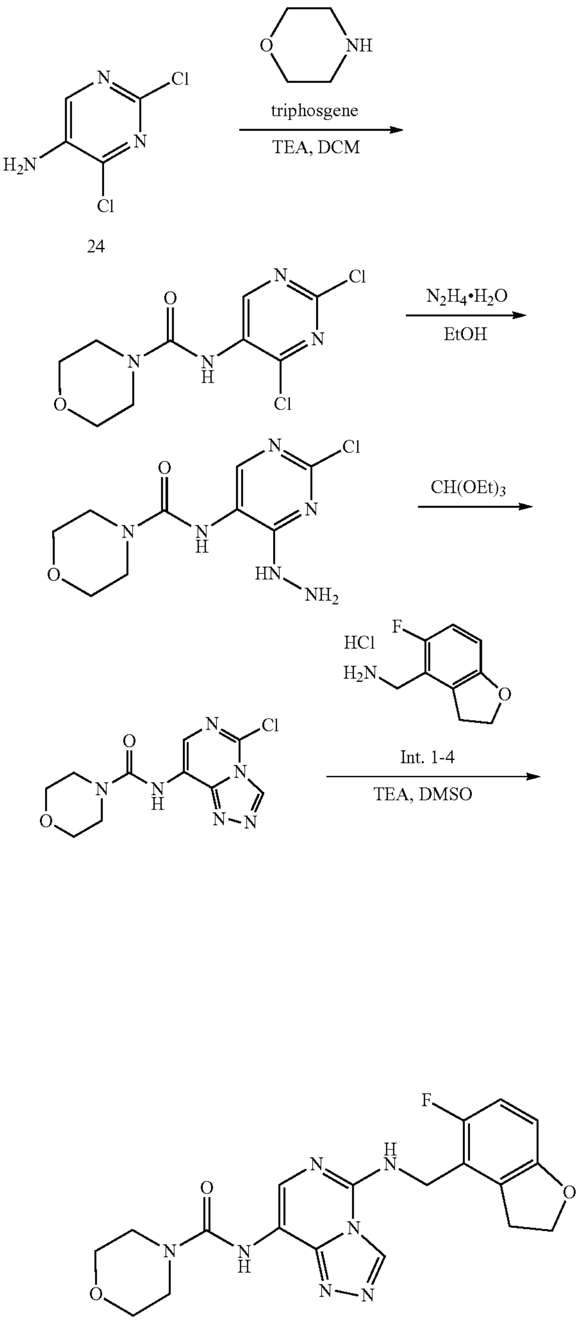

24

HJM-099

HJM-099 (9 mg) was prepared as a white solid using morpholine as starting material according to the method similar to that for preparation example 98.

$^1$H NMR (400 MHz, DMSO-$d_6$) δ 9.41 (s, 1H), 8.44 (t, J=4.9 Hz, 1H), 8.37 (s, 1H), 7.63 (s, 1H), 6.94 (t, J=9.4 Hz, 1H), 6.70 (dd, J=8.7, 3.9 Hz, 1H), 4.65 (d, J=4.9 Hz, 2H), 4.54 (t, J=8.7 Hz, 2H), 3.64-3.60 (m, 4H), 3.46-3.40 (m, 4H), 3.29 (t, J=8.7 Hz, 2H). LCMS $[M+H]^+$=414.1.

Preparation Example 100: Synthesis of Compound HJM-100

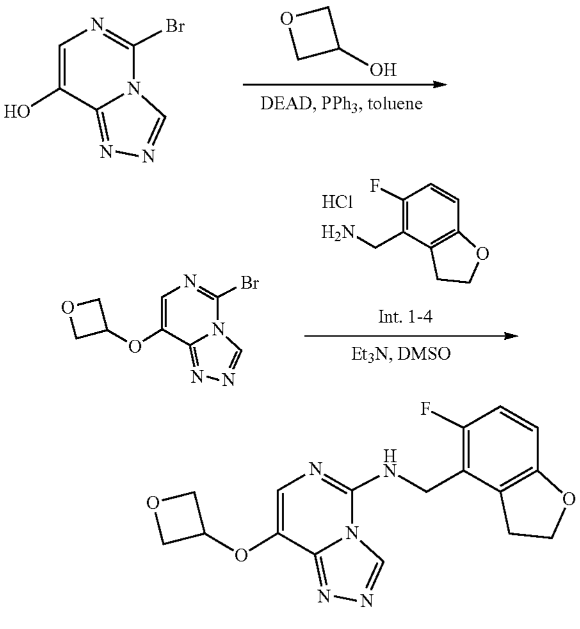

HJM-100

HJM-100 (32 mg) was prepared as a white solid using 5-bromo-[1,2,4]triazolo[4,3-c]pyrimidine-8-ol (an intermediate in preparation example 13) and 3-oxetanol as starting material according to the method similar to that for preparation example 16.

$^1$H NMR (400 MHz, $CD_3OD$) δ 9.25 (s, 1H), 7.13 (s, 1H), 6.83 (t, J=9.5 Hz, 1H), 6.63 (dd, J=8.6, 3.9 Hz, 1H), 5.42 (p, J=5.4 Hz, 1H), 5.01 (t, J=6.8 Hz, 2H), 4.69 (s, 2H), 4.64-4.52 (m, 4H), 3.35 (t, J=9.1 Hz, 2H). LCMS $[M+H]^+$=358.4.

Preparation Example 101: Synthesis of Compound HJM-101

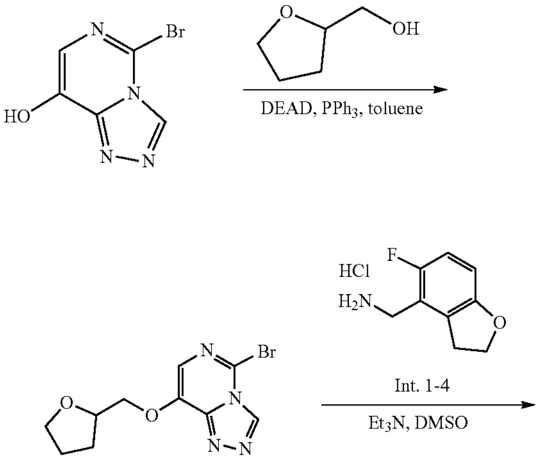

-continued

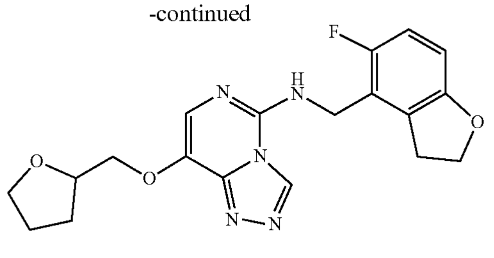

HJM-101

HJM-101 (32 mg) was prepared as a white solid using tetrahydrofuran-2-methanol as starting material according to the method similar to that for preparation example 100.

$^1$H NMR (400 MHz, DMSO-$d_6$) δ 9.39 (s, 1H), 8.13 (t, J=5.1 Hz, 1H), 7.30 (s, 1H), 6.93 (dd, J=10.3, 8.7 Hz, 1H), 6.69 (dd, J=8.7, 3.9 Hz, 1H), 4.59 (d, J=4.9 Hz, 2H), 4.53 (t, J=8.7 Hz, 2H), 4.23-4.02 (m, 3H), 3.85-3.74 (m, 1H), 3.73-3.63 (m, 1H), 3.27 (t, J=8.7 Hz, 2H), 2.06-1.94 (m, 1H), 1.94-1.77 (m, 2H), 1.75-1.63 (m, 1H). LCMS $[M+H]^+$=386.0.

Preparation Example 102: Synthesis of Compound HJM-102

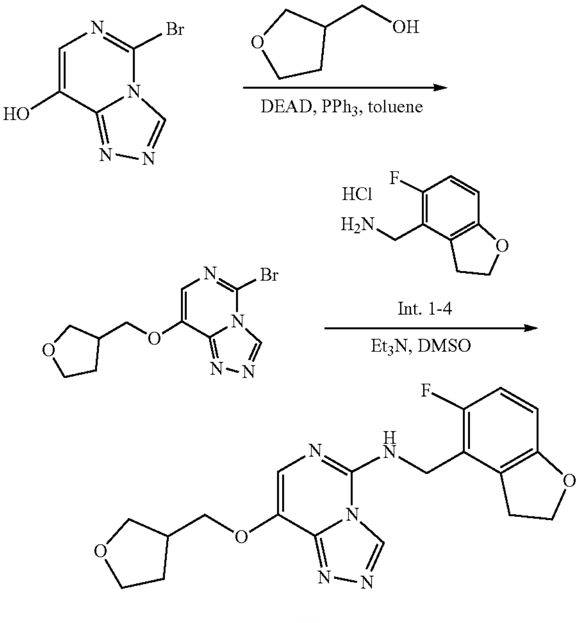

HJM-102

HJM-102 (100 mg) was prepared as a white solid using tetrahydrofuran-3-methanol as starting material according to the method similar to that for preparation example 100.

$^1$H NMR (400 MHz, DMSO-$d_6$) δ 9.41 (s, 1H), 8.19 (t, J=5.1 Hz, 1H), 7.35 (s, 1H), 6.93 (dd, J=10.3, 8.6 Hz, 1H), 6.69 (dd, J=8.6, 3.9 Hz, 1H), 4.60 (d, J=4.7 Hz, 2H), 4.53 (t, J=8.7 Hz, 2H), 4.11 (dd, J=9.5, 6.6 Hz, 1H), 4.03 (dd, J=9.6, 7.9 Hz, 1H), 3.83-3.72 (m, 2H), 3.65 (td, J=8.0, 6.8 Hz, 1H), 3.57 (dd, J=8.6, 5.4 Hz, 1H), 3.28 (t, J=8.7 Hz, 2H), 2.77-2.64 (m, 1H), 2.11-1.95 (m, 1H), 1.74-1.59 (m, 1H). LCMS $[M+H]^+$=386.1.

Preparation Example 103: Synthesis of Compound HJM-103

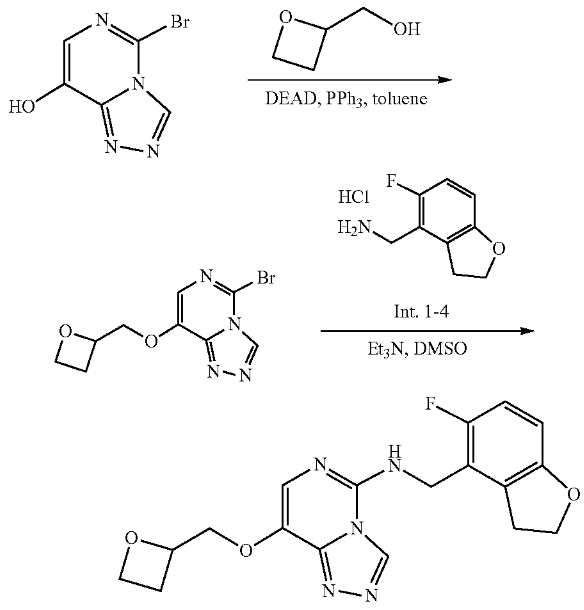

HJM-103

HJM-103 (17 mg) was prepared as a white solid using oxetane-2-methanol as starting material according to the method similar to that for preparation example 100.

$^1$H NMR (400 MHz, $CD_3OD$) δ 9.25 (s, 1H), 7.44 (s, 1H), 6.90-6.77 (m, 1H), 6.63 (dd, J=8.7, 3.9 Hz, 1H), 5.25-5.15 (m, 1H), 4.75-4.65 (m, 4H), 4.57 (t, J=8.7 Hz, 2H), 4.39-4.27 (m, 2H), 3.35 (t, J=9.2 Hz, 2H), 2.86-2.75 (m, 2H). LCMS $[M+H]^+$=372.1.

Preparation Example 104: Synthesis of Compound HJM-104

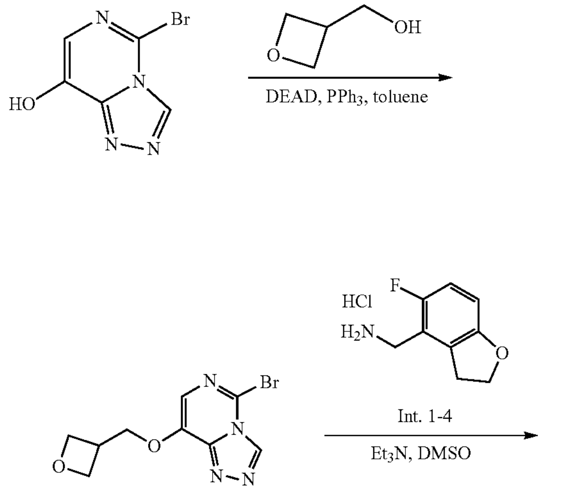

-continued

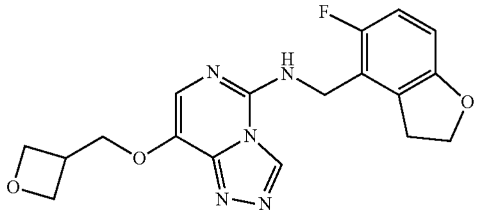

HJM-104

HJM-104 (36 mg) was prepared as a white solid using oxetane-3-methanol as starting material according to the method similar to that for preparation example 100.

$^1$H NMR (400 MHz, $CD_3OD$) δ 9.24 (s, 1H), 7.41 (s, 1H), 6.83 (dd, J=10.2, 8.7 Hz, 1H), 6.62 (dd, J=8.6, 3.9 Hz, 1H), 4.88 (dd, J=7.9, 6.2 Hz, 2H), 4.70 (s, 2H), 4.63 (t, J=6.1 Hz, 2H), 4.57 (t, J=8.7 Hz, 2H), 4.41 (d, J=6.8 Hz, 2H), 3.60-3.45 (m, 1H), 3.34 (t, J=8.7 Hz, 2H). LCMS $[M+H]^+$=372.0.

Preparation Example 105: Synthesis of Compound HJM-105

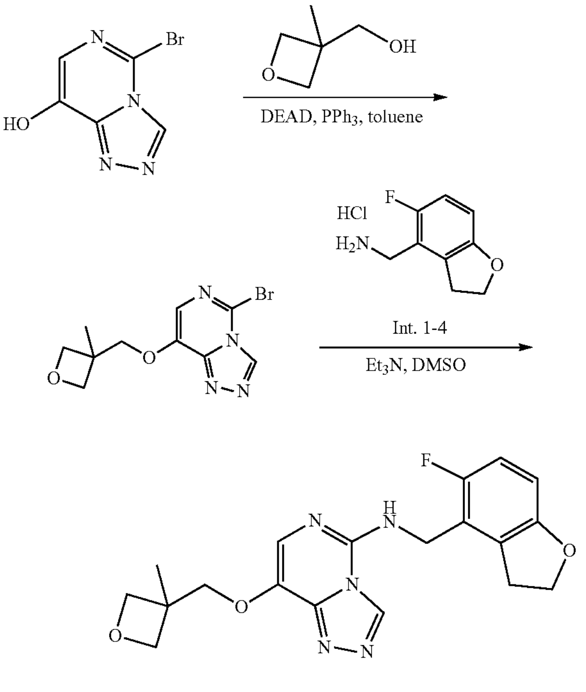

HJM-105

HJM-105 (35 mg) was prepared as a white solid using 3-methyloxetane-3-methanol as starting material according to the method similar to that for preparation example 100.

$^1$H NMR (400 MHz, $CD_3OD$) δ 9.26 (s, 1H), 7.42 (s, 1H), 6.82 (dd, J=10.2, 8.7 Hz, 1H), 6.61 (dd, J=8.7, 3.9 Hz, 1H), 4.73-4.68 (m, 4H), 4.56 (t, J=8.7 Hz, 2H), 4.46 (d, J=6.0 Hz, 2H), 4.26 (s, 2H), 3.34 (d, J=8.7 Hz, 2H), 1.49 (s, 3H). LCMS $[M+H]^+$=386.4.

Preparation Example 106: Synthesis of Compound HJM-106

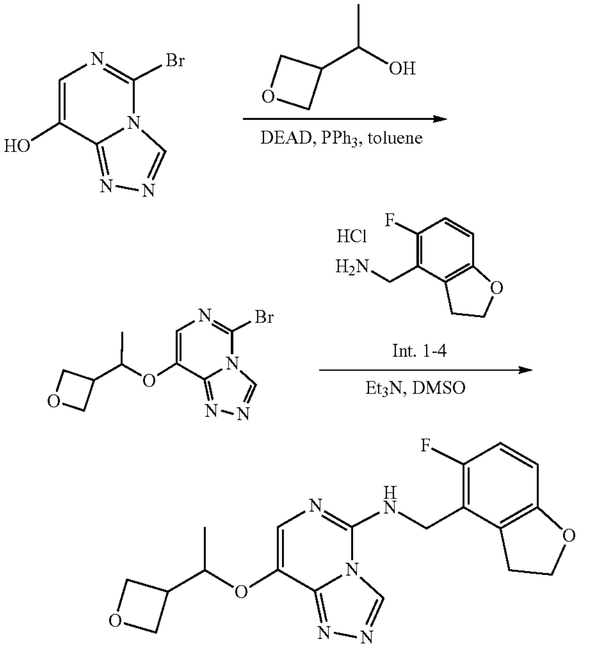

HJM-106

HJM-106 (20 mg) was prepared as a white solid using 1-(oxetan-3-yl)ethanol as starting material according to the method similar to that for preparation example 100.

$^{1}$H NMR (400 MHz, $CD_3OD$) δ 9.25 (s, 1H), 7.42 (s, 1H), 6.83 (t, J=9.4 Hz, 1H), 6.62 (dd, J=8.7, 3.9 Hz, 1H), 4.85-4.74 (m, 1H), 4.76-4.61 (m, 3H), 4.56 (t, J=8.7 Hz, 2H), 4.01-3.82 (m, 2H), 3.83-3.71 (m, 1H), 3.34 (t, J=8.7 Hz, 2H), 2.18 (h, J=5.5 Hz, 1H), 1.39 (d, J=6.4 Hz, 3H). LCMS $[M+H]^+$=386.1.

Preparation Example 107: Synthesis of Compound HJM-107

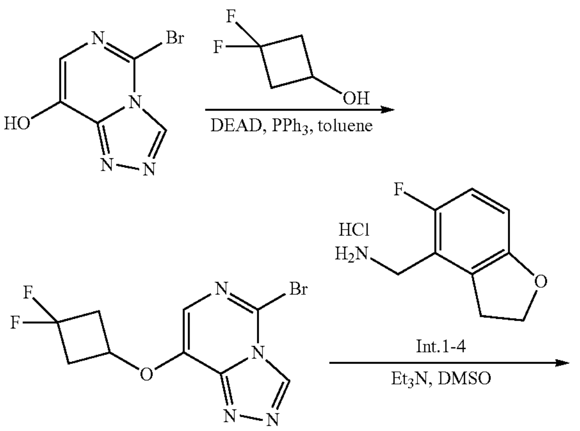

-continued

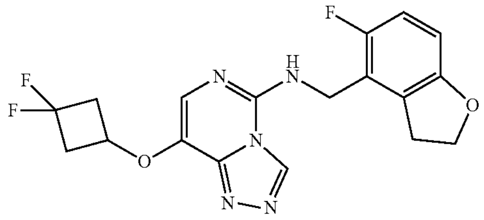

HJM-107

HJM-107 (7 mg) was prepared as a white solid using 3,3-difluorocyclobutanol as starting material according to the method similar to that for preparation example 100.

$^{1}$H NMR (400 MHz, $CD_3OD$) δ 9.25 (s, 1H), 7.28 (s, 1H), 6.83 (dd, J=10.5, 8.4 Hz, 1H), 6.63 (dd, J=8.7, 3.9 Hz, 1H), 4.96-4.88 (m, 1H), 4.70 (s, 2H), 4.57 (t, J=8.7 Hz, 2H), 3.34 (t, J=8.7 Hz, 2H), 3.19-3.07 (m, 2H), 2.92-2.78 (m, 2H). LCMS $[M+H]^+$=392.5.

Preparation Example 108: Synthesis of Compound HJM-108

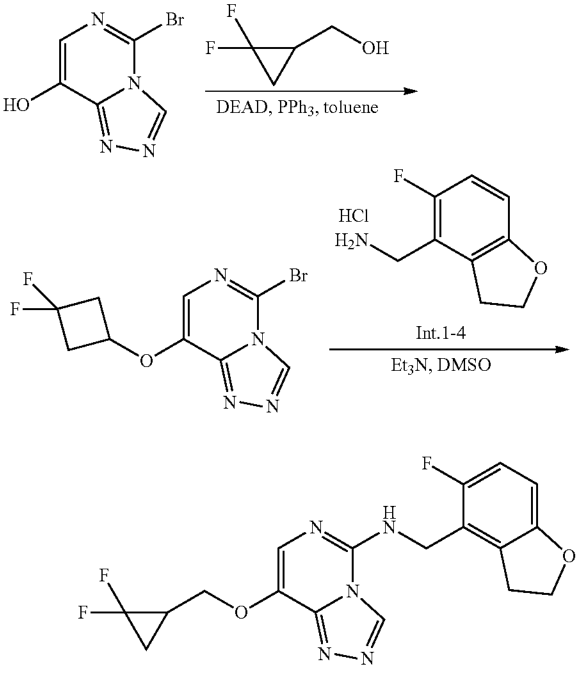

HJM-108

HJM-108 (6 mg) was prepared as a white solid using 2,2-difluorocyclopropylmethanol as starting material according to the method similar to that for preparation example 100.

$^{1}$H NMR (400 MHz, $CD_3OD$) δ 9.25 (s, 1H), 7.39 (s, 1H), 6.83 (dd, J=10.2, 8.7 Hz, 1H), 6.61 (dd, J=8.6, 3.9 Hz, 1H), 4.70 (s, 2H), 4.56 (t, J=8.7 Hz, 2H), 4.37-4.27 (m, 1H), 4.18 (ddd, J=10.6, 8.3, 1.9 Hz, 1H), 3.33 (t, J=8.6 Hz, 2H), 2.29-2.13 (m, 1H), 1.70-1.57 (m, 1H), 1.46-1.33 (m, 1H). LCMS $[M+H]^+$=392.5.

Preparation Example 109: Synthesis of Compound HJM-109

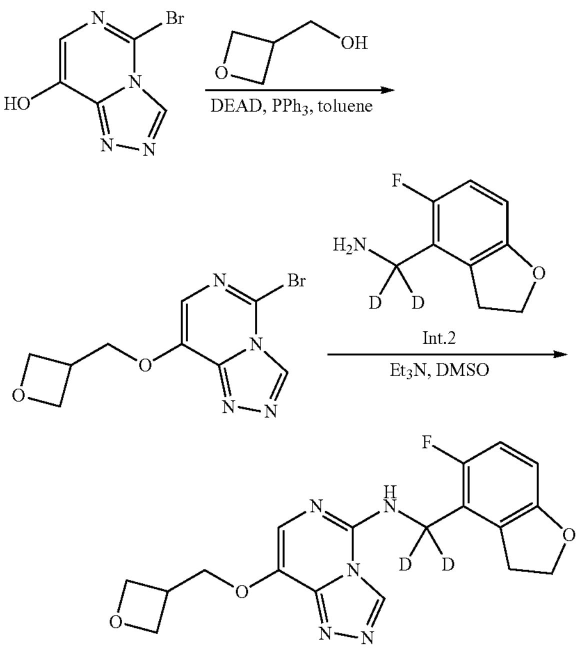

HJM-109

HJM-109 (14 mg) was prepared as a white solid using deuterated compound Int.2 as starting material according to the method similar to that for preparation example 104.

$^1$H NMR (400 MHz, $CD_3OD$) δ 9.24 (s, 1H), 7.42 (s, 1H), 6.84 (dd, J=10.2, 8.7 Hz, 1H), 6.63 (dd, J=8.7, 3.9 Hz, 1H), 4.89 (dd, J=7.9, 6.3 Hz, 2H), 4.63 (t, J=6.1 Hz, 2H), 4.57 (t, J=8.7 Hz, 2H), 4.41 (d, J=6.8 Hz, 2H), 3.60-3.47 (m, 1H), 3.35 (t, J=8.8 Hz, 2H). LCMS $[M+H]^+$=374.1.

Preparation Example 110: Synthesis of Compound HJM-110

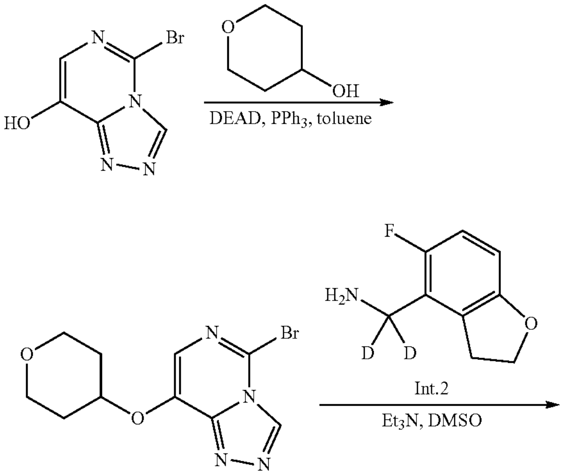

-continued

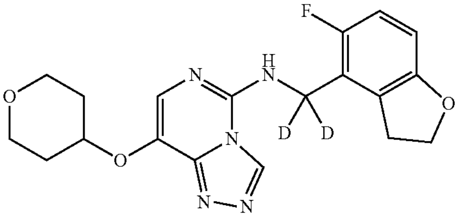

HJM-110

HJM-110 (43 mg) was prepared as a white solid using deuterated compound Int.2 as starting material according to the method similar to that for preparation example 16.

$^1$H NMR (400 MHz, $CD_3OD$) δ 9.25 (s, 1H), 7.43 (s, 1H), 6.83 (dd, J=10.2, 8.7 Hz, 1H), 6.62 (dd, J=8.6, 3.9 Hz, 1H), 4.69 (tt, J=8.2, 3.9 Hz, 1H), 4.56 (t, J=8.8 Hz, 2H), 4.00 (dt, J=11.7, 4.5 Hz, 2H), 3.55 (ddd, J=11.8, 8.7, 3.1 Hz, 2H), 3.34 (t, J=8.7 Hz, 2H), 2.09-2.01 (m, 2H), 1.86-1.75 (m, 2H). LCMS $[M+H]^+$=388.0.

Preparation Example 111: Synthesis of Compound HJM-111

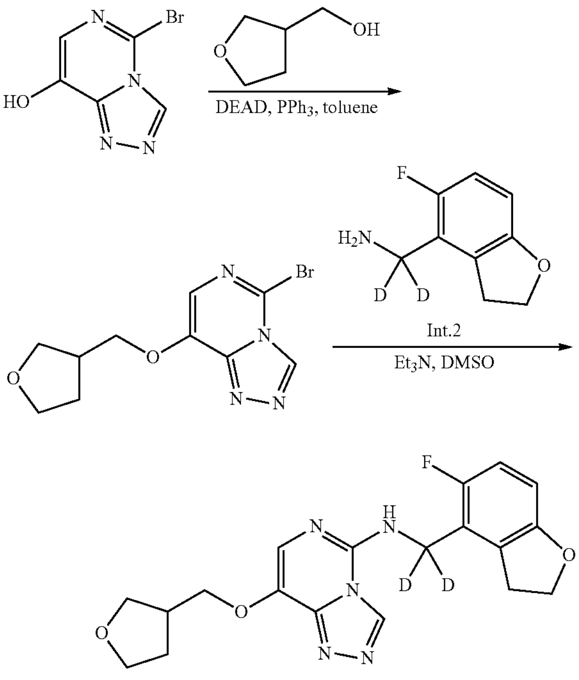

HJM-111

HJM-111 (45 mg) was prepared as a white solid using deuterated compound Int.2 as starting material according to the method similar to that for preparation example 102.

$^1$H NMR (400 MHz, $CD_3OD$) δ 9.24 (s, 1H), 7.36 (s, 1H), 6.83 (dd, J=10.2, 8.7 Hz, 1H), 6.62 (dd, J=8.7, 3.9 Hz, 1H), 4.56 (t, J=8.7 Hz, 2H), 4.15 (dd, J=9.3, 6.4 Hz, 1H), 4.07 (dd, J=9.3, 8.0 Hz, 1H), 3.97-3.87 (m, 2H), 3.82-3.72 (m, 2H), 3.34 (t, J=8.7 Hz, 2H), 2.89-2.75 (m, 1H), 2.21-2.10 (m, 1H), 1.87-1.76 (m, 1H). LCMS $[M+H]^+$=388.1.

Preparation Example 112: Synthesis of Compound HJM-112

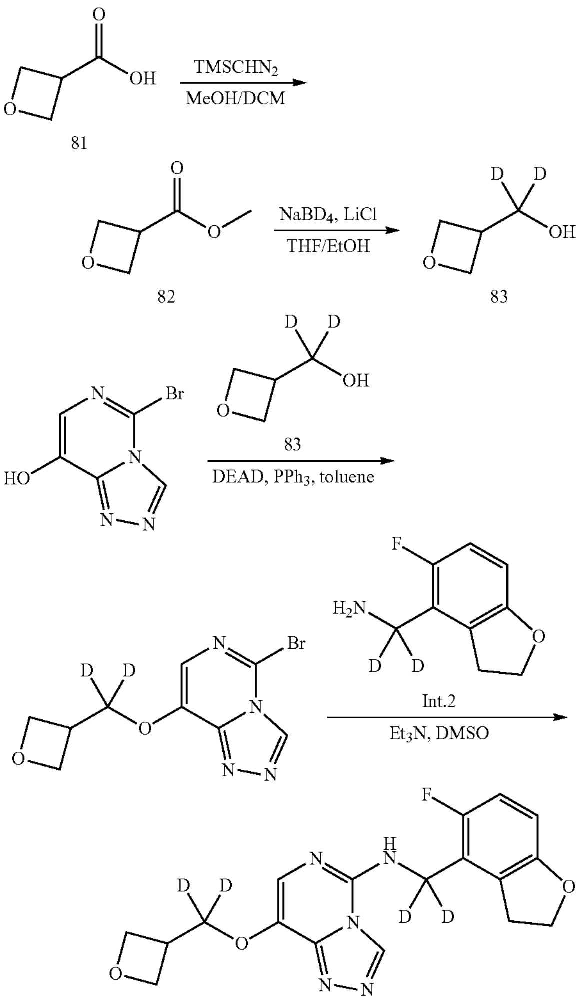

81

82

83

HJM-112

Step 1:

At 0° C., oxetane-3-carboxylic acid 81 (1.3 g, 12.73 mmol) was dissolved in a mixture of methanol (10 mL) and dichloromethane (10 mL), and trimethylsilyldiazomethane (2 M, 12.73 mL, 25.46 mmol) was slowly added. After the dropwise addition, the mixture was warmed to room temperature and stirred for 3 h. After the reaction was completed, acetic acid (0.05 mL) was added to the reaction mixture. The mixture was poured into water, and extracted with dichloromethane (2×30 mL). The organic phases were combined, and dried with anhydrous sodium sulfate. The mixture was filtered, and the filtrate was concentrated under reduced pressure to afford crude compound 82 (1.4 g, yield: 94.7%) as a colorless oil.

Step 2:

Compound 82 (1.4 g, 12.06 mmol) was dissolved in ethanol (10 mL) and tetrahydrofuran (5 mL), and lithium chloride (51.11 mg, 1.21 mmol) was added. Sodium deuterated borohydride (912.30 mg, 24.11 mmol) was added portionwise at 0° C., and the mixture was stirred at room temperature for 10 h. The mixture was cooled to 0° C., and then deuterium oxide (1 mL) was added. The mixture was stirred for 10 min, and then dried by adding anhydrous sodium sulfate. The mixture was filtered, and concentrated. The resulting crude product was purified by silica gel column chromatography (petroleum ether/ethyl acetate, ethyl acetate: 50%-100%) to afford deuterated compound 83 (0.4 g, yield: 36.8%) as a yellowish oil.

$^1$H NMR (400 MHz, DMSO-$d_6$) δ 4.58 (dd, J=7.8, 5.9 Hz, 1H), 4.29 (t, J=5.9 Hz, 1H), 3.03-2.93 (m, 1H).

In the following steps, HJM-112 (9 mg) was prepared as a white solid according to the method similar to that for preparation example 109.

$^1$H NMR (400 MHz, $CD_3OD$) δ 9.24 (s, 1H), 7.41 (s, 1H), 6.83 (dd, J=10.2, 8.7 Hz, 1H), 6.63 (dd, J=8.6, 3.9 Hz, 1H), 4.88 (dd, J=8.0, 6.3 Hz, 2H), 4.63 (t, J=6.1 Hz, 2H), 4.57 (t, J=8.7 Hz, 2H), 3.52 (p, J=6.9 Hz, 1H), 3.35 (t, J=8.8 Hz, 2H). LCMS $[M+H]^+$=376.3.

Preparation Example 113: Synthesis of Compound HJM-113

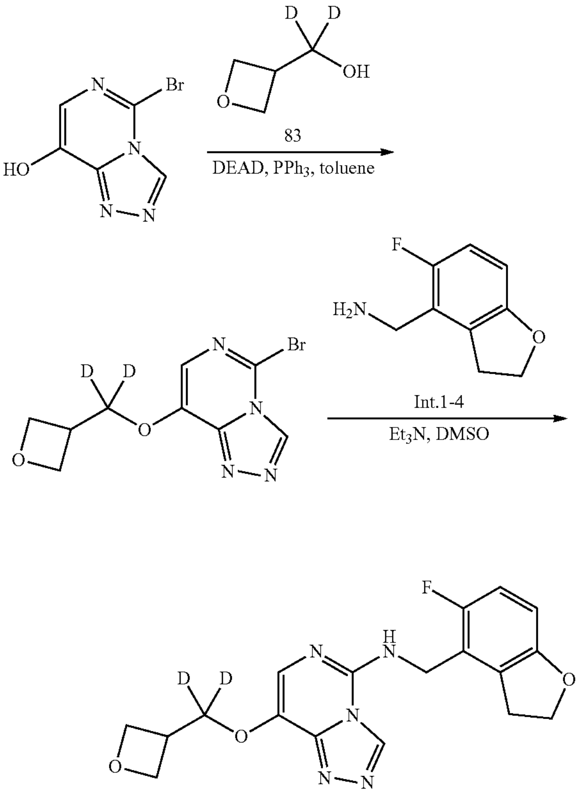

HJM-113

HJM-113 (10 mg) was prepared as a white solid using Int.1-4 as starting material according to the method similar to that for preparation example 112.

$^1$H NMR (400 MHz, $CD_3OD$) δ 9.24 (s, 1H), 7.42 (s, 1H), 6.87-6.80 (m, 1H), 6.63 (dd, J=8.7, 3.9 Hz, 1H), 4.89 (dd, J=8.0, 6.3 Hz, 2H), 4.71 (s, 2H), 4.63 (t, J=6.1 Hz, 2H), 4.57 (t, J=8.7 Hz, 2H), 3.52 (p, J=7.0 Hz, 1H), 3.35 (t, J=9.0 Hz, 2H). LCMS $[M+H]^+$=374.2.

Preparation Example 114: Synthesis of Compound HJM-114

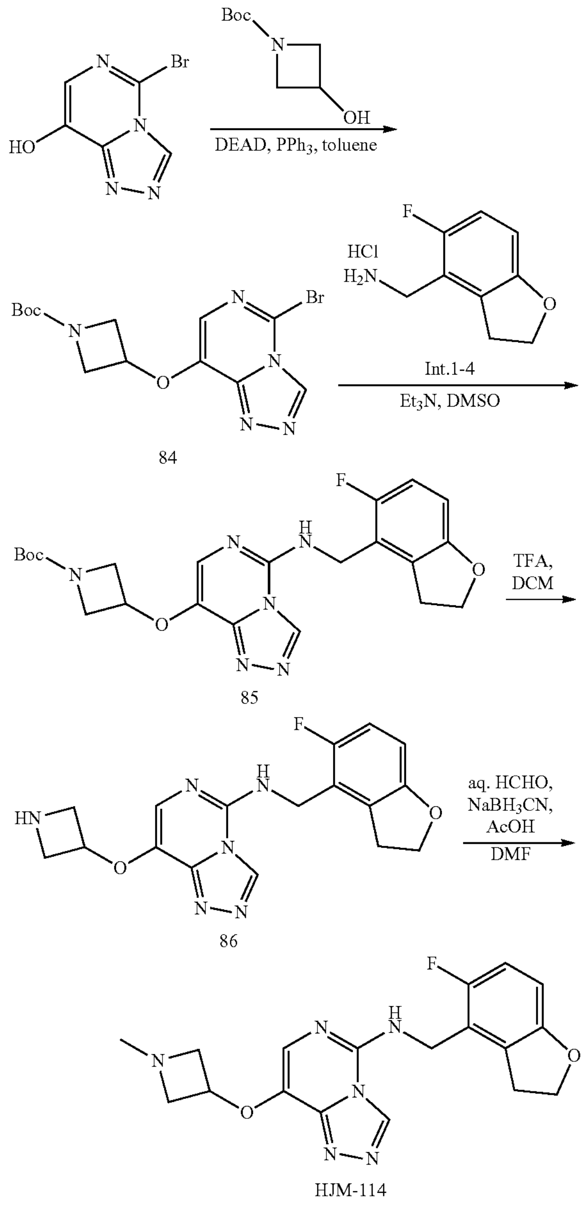

84

85

86

HJM-114

Step 1:

5-bromo-[1,2,4]triazolo[4,3-c]pyrimidine-8-ol (150 mg, 0.697 mmol), tert-butyl 3-hydroxyazetidine-1-carboxylate (181 mg, 1.05 mmol) and triphenyl phosphine (274 mg, 1.05 mmol) were added to toluene (10 mL), and the mixture was heated to 100° C. under nitrogen protection. Diethyl azodicarboxylate (180 mg, 1.05 mmol) was added dropwise. After the dropwise addition, the mixture was heated at 100° C. for 2 h. The mixture was cooled, and concentrated to afford a crude product. The crude compound 84 was directly used in the next step. LCMS $[M+H]^+$=370.3.

Step 2:

The above compound 84, Int.1-4 hydrochloride (164 mg, 0.81 mmol) and triethylamine (163 mg, 1.62 mmol) were dissolved in dimethyl sulfoxide (5 mL), and the mixture was stirred at room temperature for 2 h. The reaction mixture was poured into water and stirred for 10 min. The precipitated solid was filtered, and dried to afford crude compound 85 (200 mg, yield: 81.3%) as a yellow solid. LCMS $[M+H]^+$=457.1.

Step 3:

Compound 85 (200 mg, 0.438 mmol) was dissolved in dichloromethane (4 mL), and trifluoroacetic acid (1 mL) was added dropwise. After the dropwise addition, the mixture was stirred at room temperature for 2 h. The mixture was then concentrated to afford crude compound 86 (150 mg, yield: 72.8%).

Step 4:

Compound 86 (40 mg, 0.112 mmol) was dissolved in N,N-dimethylformamide (3 mL), and 37% formaldehyde aqueous solution (0.7 mL) was added. A drop of acetic acid was added dropwise, and the mixture was stirred at 0° C. for 10 min. Sodium cyanobohydride (15 mg, 0.224 mmol) was added, and the mixture was stirred at 0° C. for 2 h. The reaction was quenched with saturated aqueous sodium bicarbonate solution, and the mixture was extracted twice with ethyl acetate. The organic phases were combined, dried with anhydrous sodium sulfate, and filtered. The filtrate was concentrated to afford a crude product. The crude product was purified by preparative HPLC to afford compound HJM-114 hydrochloride (6 mg, yield: 14.4%) as a white solid.

$^1$H NMR (400 MHz, $CD_3OD$) δ 9.29 (s, 1H), 7.38 (s, 1H), 6.83 (t, J=9.4 Hz, 1H), 6.63 (dd, J=8.6, 3.9 Hz, 1H), 5.23 (br s, 1H), 4.70 (s, 2H), 4.57 (t, J=8.6 Hz, 2H), 4.55-4.20 (m, 4H), 3.35 (t, J=8.7 Hz, 2H), 3.04 (s, 3H). LCMS $[M+H]^+$=371.1.

Preparation Example 115: Synthesis of Compound HJM-115

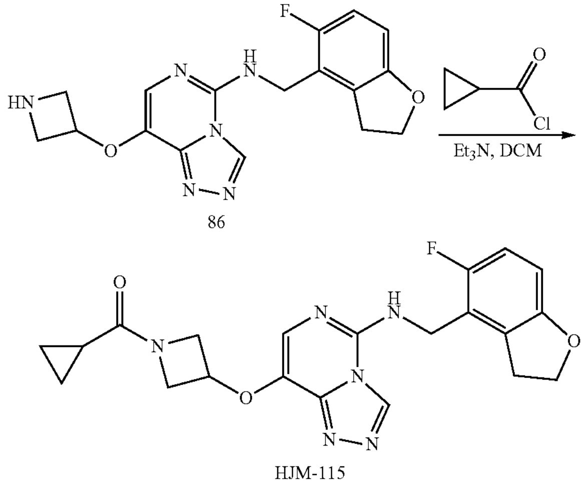

86

HJM-115

The crude compound 86 (75 mg, 0.21 mmol) and triethylamine (0.5 mL) were dissolved in dichloromethane (3 mL), cyclopropionyl chloride (44 mg, 0.42 mmol) was added dropwise, and the mixture was stirred at room temperature for 2 h. The mixture was concentrated to afford a crude product. The crude product was purified by preparative HPLC to afford compound HJM-115 (31 mg, yield: 34.7%) as a white solid.

$^1$H NMR (400 MHz, $CD_3OD$) δ 9.30 (s, 1H), 7.36 (s, 1H), 6.84 (t, J=9.4 Hz, 1H), 6.63 (dd, J=8.7, 3.8 Hz, 1H), 5.26 (tt, J=6.7, 3.7 Hz, 1H), 4.76 (dd, J=9.4, 6.5 Hz, 1H), 4.71 (s, 2H), 4.57 (t, J=8.7 Hz, 2H), 4.47 (dd, J=10.1, 3.6 Hz, 1H), 4.40 (dd, J=11.1, 6.4 Hz, 1H), 4.09 (dd, J=11.1, 3.7 Hz, 1H), 3.36 (t, J=8.7 Hz, 2H), 1.66-1.56 (m, 1H), 0.93-0.79 (m, 4H). LCMS $[M+H]^+$=425.4.

Preparation Example 116: Synthesis of Compound HJM-116

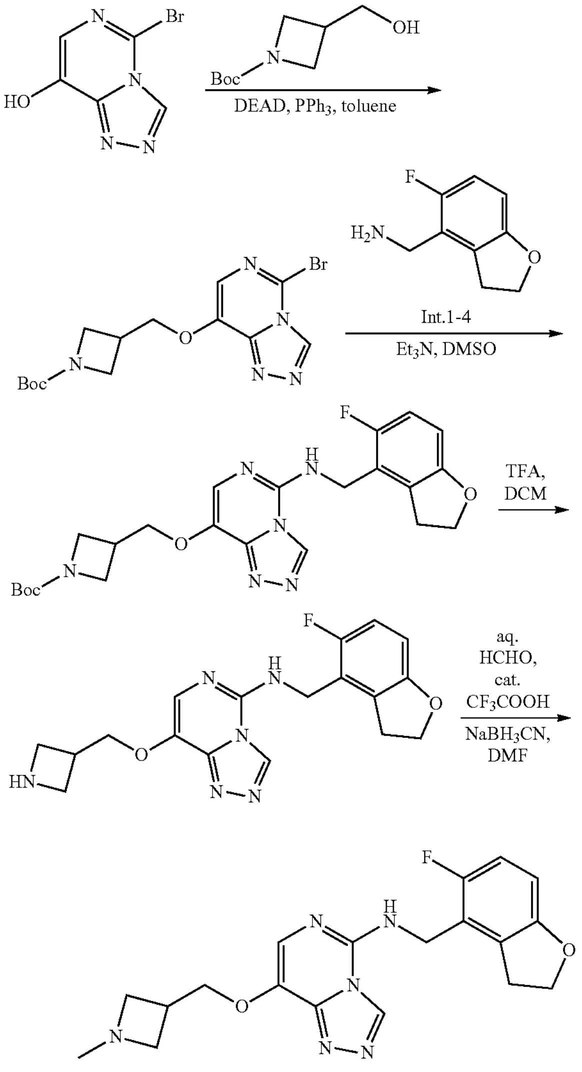

HJM-116

HJM-116 (10 mg) was prepared as a white solid using tert-butyl 3-hydroxymethylazetidine-1-carboxylate as starting material according to the method similar to that for preparation example 114.

$^1$H NMR (400 MHz, $CD_3OD$) δ 9.26 (s, 1H), 7.37 (s, 1H), 6.82 (dd, J=10.2, 8.7 Hz, 1H), 6.61 (dd, J=8.6, 3.8 Hz, 1H), 5.49 (s, 2H), 4.69 (s, 2H), 4.56 (t, J=8.7 Hz, 2H), 4.27 (d, J=6.3 Hz, 2H), 3.57 (t, J=8.0 Hz, 2H), 3.34 (t, J=8.1 Hz, 2H), 3.06-2.95 (m, 1H). LCMS $[M+H]^+$=385.5.

Preparation Example 117: Synthesis of Compound HJM-117

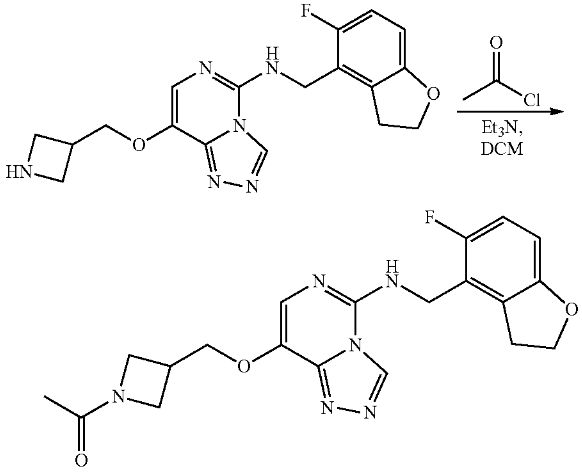

HJM-117

HJM-117 (15 mg) was prepared as a white solid using acetyl chloride as starting material according to the method similar to that for preparation example 115.

$^1$H NMR (400 MHz, DMSO-$d_6$) δ 9.40 (s, 1H), 7.93 (br s, 1H), 7.35 (s, 1H), 6.93 (t, J=9.0 Hz, 1H), 6.76-6.65 (m, 1H), 4.60 (s, 2H), 4.53 (t, J=8.2 Hz, 2H), 4.29 (d, J=5.9 Hz, 2H), 4.24 (t, J=8.2 Hz, 2H), 4.00-3.90 (m, 2H), 3.28 (t, J=8.4 Hz, 2H), 3.08-2.96 (m, 1H), 1.75 (s, 3H). LCMS $[M+H]^+$=413.4.

Preparation Example 118: Synthesis of Compound HJM-118

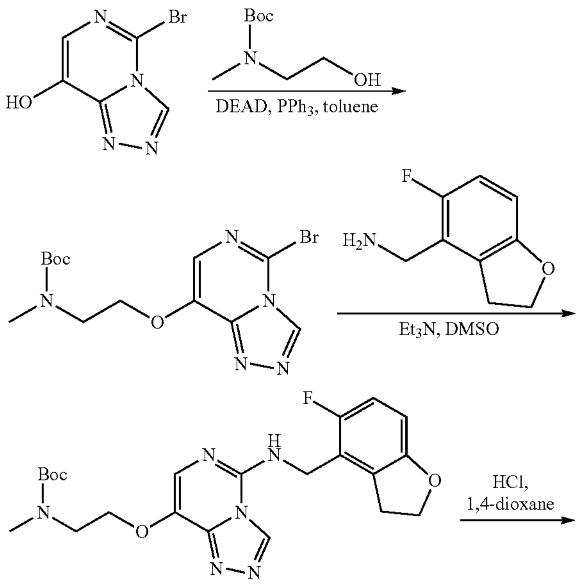

87

-continued

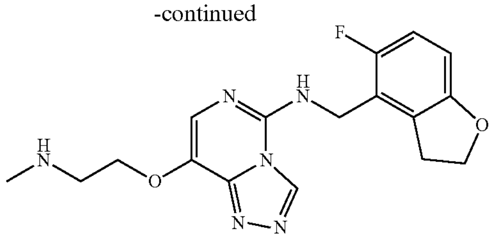

HJM-118

Steps 1-2:

Compound 87 (400 mg) was prepared using tert-butyl N-methyl-N-(2-hydroxyethyl)carbamate as starting material according to the method similar to that for preparation example 100. LCMS $[M+H]^+$=459.2.

Step 3:

Compound 87 (400 mg, 0.87 mmol) was dissolved in 1,4-dioxane (5 mL), a solution of 4 M hydrochloric acid in 1,4-dioxane (1 mL) was added dropwise, and the mixture was stirred at room temperature for 2 h. The mixture was concentrated to afford a crude product. The crude product was purified by preparative HPLC to afford compound HJM-118 (72 mg, yield: 24.0%) as a white solid.

$^1$H NMR (400 MHz, $CD_3OD$) δ 9.28 (s, 1H), 7.47 (s, 1H), 6.83 (dd, J=10.2, 8.7 Hz, 1H), 6.63 (dd, J=8.7, 3.9 Hz, 1H), 4.71 (s, 2H), 4.57 (t, J=8.7 Hz, 2H), 4.45-4.40 (m, 2H), 3.54-3.48 (m, 2H), 3.36 (t, J=8.7 Hz, 2H), 2.84 (s, 3H). LCMS $[M+H]^+$=359.1.

Preparation Example 119: Synthesis of Compound HJM-119

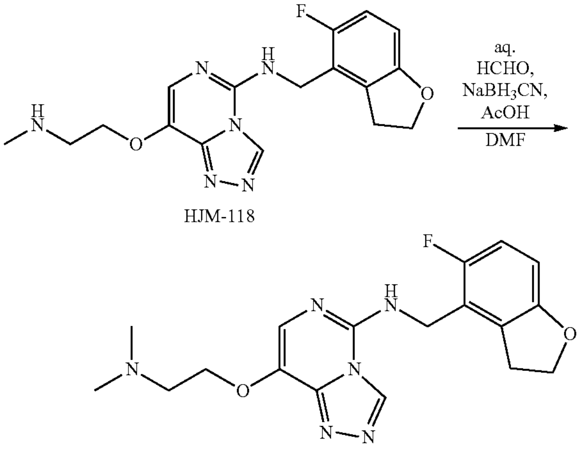

HJM-118

HJM-119

Compound HJM-118 (150 mg, 0.419 mmol) was dissolved in N,N-dimethylformamide (5 mL), and 37% formaldehyde aqueous solution (0.7 mL) was added. A drop of acetic acid was added dropwise, and the mixture was stirred at 0° C. for 30 min. Sodium cyanobohydride (80 mg, 1.26 mmol) was added, and the mixture was stirred at 0° C. for 4 h. The mixture was quenched with saturated aqueous sodium bicarbonate solution, and extracted twice with ethyl acetate. The organic phases were combined, dried with anhydrous sodium sulfate, and filtered. The filtrate was concentrated to afford a crude product. The crude product was purified by preparative HPLC to afford compound HJM-119 (7 mg, yield: 4.5%) as a white solid.

$^1$H NMR (400 MHz, $CD_3OD$) δ 9.28 (s, 1H), 7.48 (s, 1H), 6.87-6.80 (m, 1H), 6.63 (dd, J=8.7, 3.9 Hz, 1H), 4.71 (s, 2H), 4.57 (t, J=8.7 Hz, 2H), 4.54-4.47 (m, 2H), 3.68-3.63 (m, 2H), 3.36 (t, J=8.7 Hz, 2H), 3.04 (s, 6H). LCMS $[M+H]^+$=373.1.

Preparation Examples 120 and 121: Synthesis of Compounds HJM-120 and 121

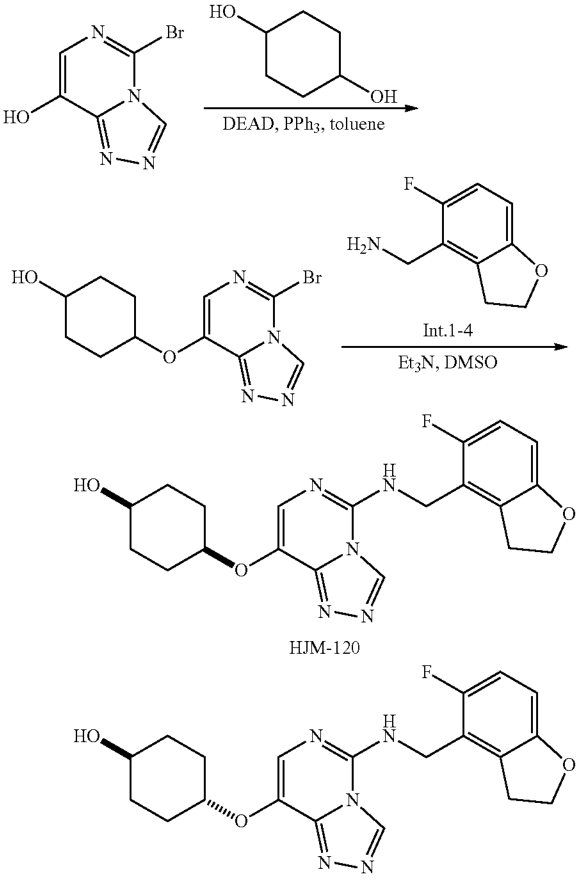

HJM-120

HJM-121

HJM-120 (19 mg) and HJM-121 (8 mg) were prepared as white solids using 1,4-cyclohexanediol as starting material according to the method similar to that for preparation example 100. Cis-trans configuration was not confirmed.

HJM-120: $^1$H NMR (400 MHz, DMSO-$d_6$) δ 9.39 (s, 1H), 8.18 (t, J=5.1 Hz, 1H), 7.34 (s, 1H), 6.93 (dd, J=10.0, 8.6 Hz, 2H), 6.69 (dd, J=8.6, 3.9 Hz, 1H), 4.60 (d, J=4.9 Hz, 2H), 4.53 (t, J=8.7 Hz, 2H), 4.52-4.45 (m, 1H), 3.58-3.48 (m, 1H), 3.28 (t, J=8.7 Hz, 2H), 2.05-1.95 (m, 2H), 1.88-1.79 (m, 2H), 1.51-1.39 (m, 2H), 1.31-1.20 (m, 2H). LCMS $[M+H]^+$=400.5. HPLC $t_R$=7.92 min. (SunFire C18 column 5 μm 4.6×150 mm, 25° C., mobile phase: acetonitrile and water containing 0.03% of TFA, flow rate: 1.0 mL/min, method duration: 16 min)

HJM-121: $^1$H NMR (400 MHz, DMSO-$d_6$) δ 9.39 (s, 1H), 8.17 (t, J=4.9 Hz, 1H), 7.35 (s, 1H), 6.94 (dd, J=9.9, 8.6 Hz, 2H), 6.70 (dd, J=8.5, 3.9 Hz, 1H), 4.60 (d, J=5.0 Hz, 3H), 4.54 (t, J=8.7 Hz, 2H), 3.62-3.55 (m, 1H), 3.28 (t, J=8.8 Hz,

2H), 1.90-1.79 (m, 2H), 1.69-1.48 (m, 6H). LCMS $[M+H]^+$=400.5. HPLC$_{tR}$=8.07 min. (SunFire C18 column 5 μm 4.6×150 mm, 25° C., mobile phase: acetonitrile and water containing 0.03% of TFA, flow rate: 1.0 mL/min, method duration: 16 min)

Preparation Example 122: Synthesis of Compound HJM-122

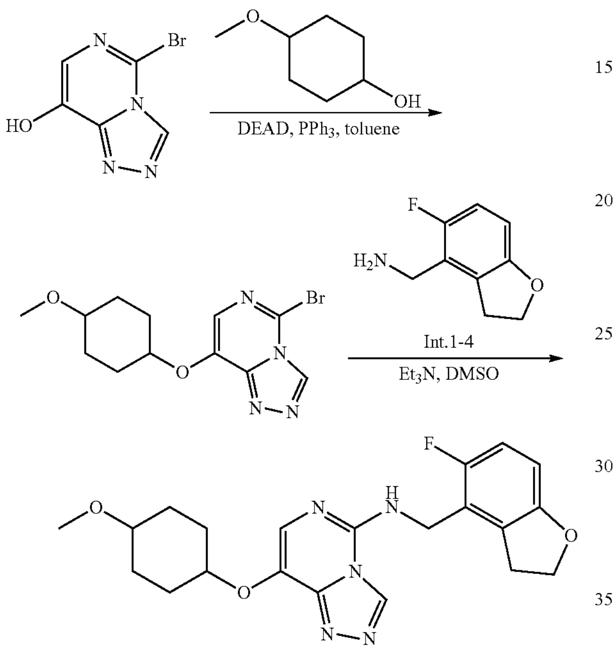

HJM-122

HJM-122 (52 mg) was prepared as a white solid, a mixture of cis- and trans-configurations, using 4-methoxy-cyclohexanol as starting material according to the method similar to that for preparation example 100.

$^1$H NMR (400 MHz, $CD_3OD$) δ 9.31 (s, 0.65H), 9.30 (s, 0.35H), 7.60 (s, 0.65H), 7.57 (s, 0.35H), 6.88-6.79 (m, 1H), 6.63 (dd, J=8.7, 3.9 Hz, 1H), 4.72 (s, 2H), 4.61-4.53 (m, 3H), 4.54-4.46 (m, 1H), 3.35 (t, J=8.6 Hz, 2H), 3.35 (s, 3H), 2.17-1.37 (m, 8H). LCMS $[M+H]^+$=414.3.

Preparation Example 123: Synthesis of Compound HJM-123

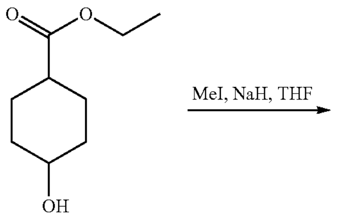

88

-continued

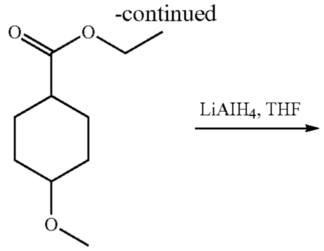

89

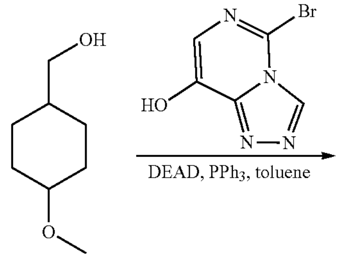

90

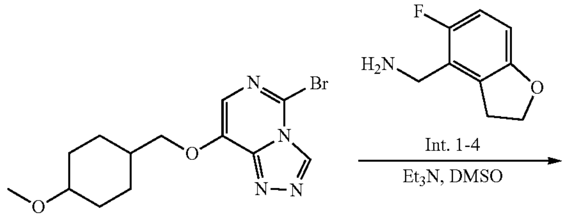

91

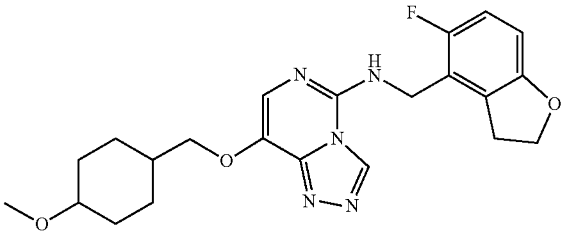

HJM-123

Step 1:

Compound ethyl 4-hydroxycyclohexyl formate 88 (1.0 g, 5.81 mmol) was dissolved in anhydrous tetrahydrofuran (10 mL). Sodium hydride (60%, 348 mg, 8.71 mmol) was added at 0° C. under nitrogen protection, and the mixture was stirred for 10 min. Iodomethane (1.64 g, 11.61 mmol) was added dropwise, and the mixture was stirred at room temperature for 2 h. Water was added to quench the reaction, and the mixture was extracted with ethyl acetate. The organic phase was dried with anhydrous sodium sulfate, and filtered. The filtrate was concentrated to afford crude compound 89.

Step 2:

The above compound 89 was dissolved in anhydrous tetrahydrofuran (10 mL). Lithium aluminum hydride (440 mg, 11.61 mmol) was added portionwise at 0° C., and the mixture was stirred at room temperature for 2 h. Ice was added to quench the reaction, and the mixture was further stirred for 30 min. The reaction mixture was filtered, and the filtrate was concentrated to afford crude compound 90 (240 mg, yield: 28.6%) as a colorless liquid.

Step 3:

5-Bromo-[1,2,4]triazolo[4,3-c]pyrimidine-8-ol (215 mg, 1.00 mmol), compound 90 (240 mg, 1.60 mmol) and triphenyl phosphine (393 mg, 1.50 mmol) were added to toluene (10 mL), and the mixture was heated to 100° C. under nitrogen protection. Diethyl azodicarboxylate (208 mg, 1.20 mmol) was added dropwise. After the dropwise addition, the mixture was heated at 100° C. for 2 h. The mixture was cooled, and concentrated to afford crude compound 91, which was directly used in the next step. LCMS $[M+H]^+$=341.0.

Step 4:

The above compound 91, Int.1-4 (134 mg, 0.80 mmol) and triethylamine (160 mg, 1.60 mmol) were dissolved in dimethyl sulfoxide (3 mL), and the mixture was stirred at room temperature for 2 h. The mixture was purified by preparative HPLC to afford compound HJM-123 (11 mg, yield: 3.2%) as a white solid.

$^1$H NMR (400 MHz, DMSO-$d_6$) δ 9.39 (s, 1H), 8.12 (t, J=5.1 Hz, 1H), 7.28 (s, 1H), 6.93 (dd, J=10.3, 8.7 Hz, 1H), 6.69 (dd, J=8.6, 3.8 Hz, 1H), 4.59 (d, J=4.9 Hz, 2H), 4.53 (t, J=8.7 Hz, 2H), 3.94 (d, J=6.4 Hz, 2H), 3.27 (t, J=8.8 Hz, 2H), 3.14-3.02 (m, 1H), 2.08-2.00 (m, 2H), 1.92-1.84 (m, 2H), 1.78-1.68 (m, 1H), 1.20-1.02 (m, 4H). LCMS $[M+H]^+$=428.2.

Preparation Examples 124 and 125: Synthesis of Compounds HJM-124 and 125

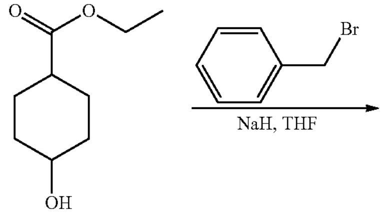

88

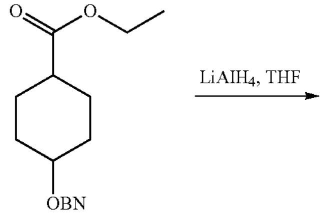

92

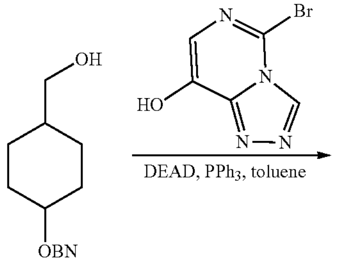

93

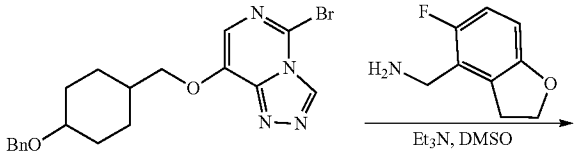

94

-continued

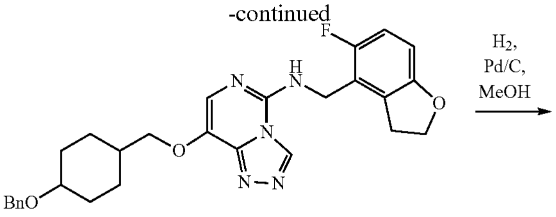

95

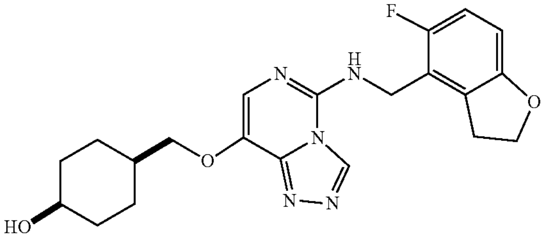

HJM-124

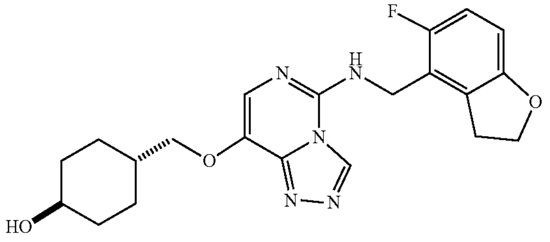

HJM-125

Steps 1-4:

Compound 95 (30 mg) was prepared using benzyl bromide instead of iodomethane as starting material according to the method similar to that for preparation example 123. LCMS $[M+H]^+$=504.3.

Step 5:

Compound 95 (30 mg, 0.06 mmol) was dissolved in methanol (3 mL), and 10% Pd/C (20 mg) was added under nitrogen protection. The atmosphere was replaced three times with hydrogen gas, and the mixture was stirred at 40° C. under a hydrogen balloon for 4 h. The mixture was filtered, and the filter cake was washed with methanol for three times. The filtrates were combined, and concentrated to afford a crude product. The crude product was purified by preparative HPLC to afford compound HJM-124 (1 mg) and HJM-125 (2.8 mg), total yield: 15.3%. Both were yellow oil. Cis-trans configuration was not confirmed.

HJM-124: $^1$H NMR (400 MHz, $CD_3OD$) δ 9.26 (s, 1H), 7.41 (s, 1H), 6.89-6.80 (m, 1H), 6.63 (dd, J=8.7, 3.9 Hz, 1H), 4.70 (s, 2H), 4.57 (t, J=8.7 Hz, 2H), 3.98 (d, J=6.3 Hz, 2H), 3.59-3.50 (m, 1H), 3.35 (t, J=8.8 Hz, 2H), 2.07-1.96 (m, 4H), 1.88-1.77 (m, 1H), 1.38-1.17 (m, 4H). LCMS $[M+H]^+$=414.3. $HPLC_{tR}$=7.967 min. (XBridge C18 column 5 μm 4.6×150 mm, 25° C., mobile phase: acetonitrile and water containing 0.03% $NH_3$—$H_2O$, flow rate: 1.0 mL/min, method duration: 16 min)

HJM-125: $^1$H NMR (400 MHz, $CD_3OD$) δ 9.29 (s, 1H), 7.51 (d, J=4.1 Hz, 1H), 6.84 (t, J=9.5 Hz, 1H), 6.64 (dd, J=8.6, 3.8 Hz, 1H), 4.71 (s, 2H), 4.57 (t, J=8.7 Hz, 2H), 4.04 (d, J=6.6 Hz, 2H), 3.98-3.93 (m, 1H), 3.36 (t, J=8.8 Hz, 2H), 2.06-1.90 (m, 1H), 1.83-1.57 (m, 8H). LCMS $[M+H]^+$=414.3. $HPLC_{tR}$=8.190 min. (XBridge C18 column 5 μm 4.6×150 mm, 25° C., mobile phase: acetonitrile and water containing 0.03% $NH_3$—$H_2O$, flow rate: 1.0 mL/min, method duration: 16 min)

Preparation Example 126: Synthesis of Compound HJM-126

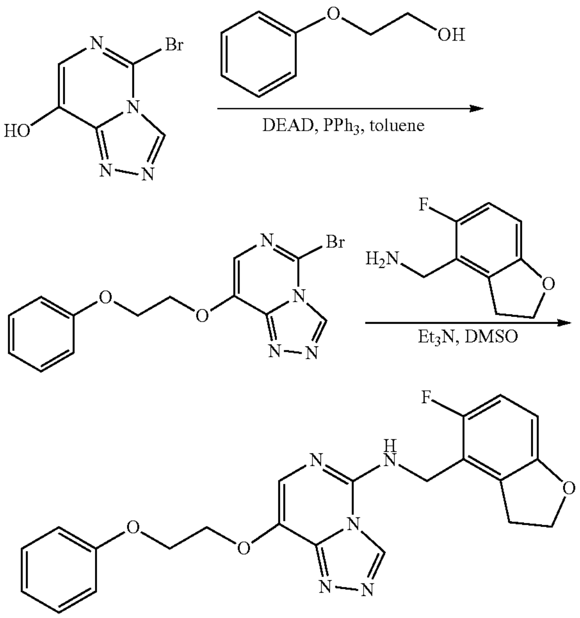

HJM-126

HJM-126 (38 mg) was prepared as a white solid using 2-phenoxyethanol as starting material according to the method similar to that for preparation example 100.

$^1$H NMR (400 MHz, DMSO-$d_6$) δ 9.40 (s, 1H), 8.17 (t, J=5.1 Hz, 1H), 7.36 (s, 1H), 7.33-7.27 (m, 2H), 7.01-6.90 (m, 4H), 6.69 (dd, J=8.7, 3.9 Hz, 1H), 4.61 (d, J=4.9 Hz, 2H), 4.53 (t, J=8.7 Hz, 2H), 4.50-4.46 (m, 2H), 4.35-4.31 (m, 2H), 3.27 (t, J=8.7 Hz, 2H). LCMS $[M+H]^+$=422.1.

Preparation Example 127: Synthesis of Compound HJM-127

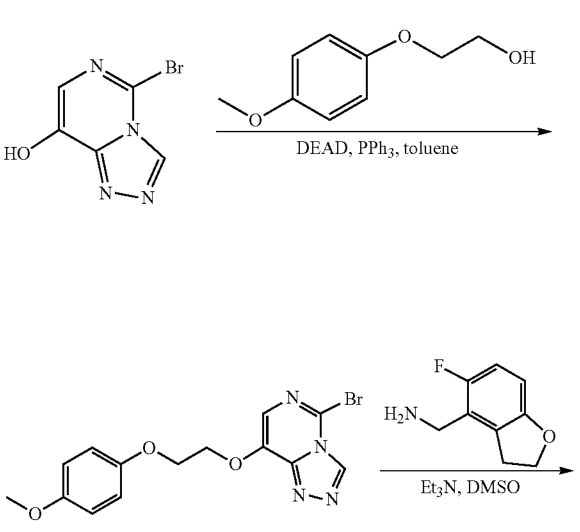

-continued

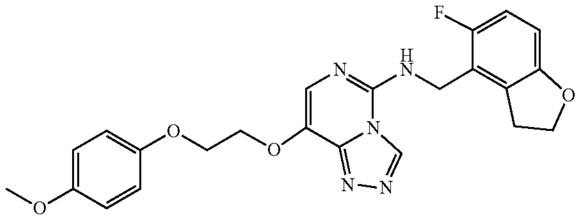

HJM-127

HJM-127 (26 mg) was prepared as a white solid using 2-(4-methoxyphenoxy)ethanol as starting material according to the method similar to that for preparation example 100.

$^1$H NMR (400 MHz, DMSO-$d_6$) δ 9.40 (s, 1H), 8.17 (t, J=5.1 Hz, 1H), 7.36 (s, 1H), 6.97-6.84 (m, 5H), 6.69 (dd, J=8.7, 3.9 Hz, 1H), 4.61 (d, J=5.0 Hz, 2H), 4.53 (t, J=8.7 Hz, 2H), 4.48-4.42 (m, 2H), 4.30-4.24 (m, 2H), 3.70 (s, 3H), 3.28 (t, J=8.7 Hz, 2H). LCMS $[M+H]^+$=452.3.

Preparation Example 128: Synthesis of Compound HJM-128

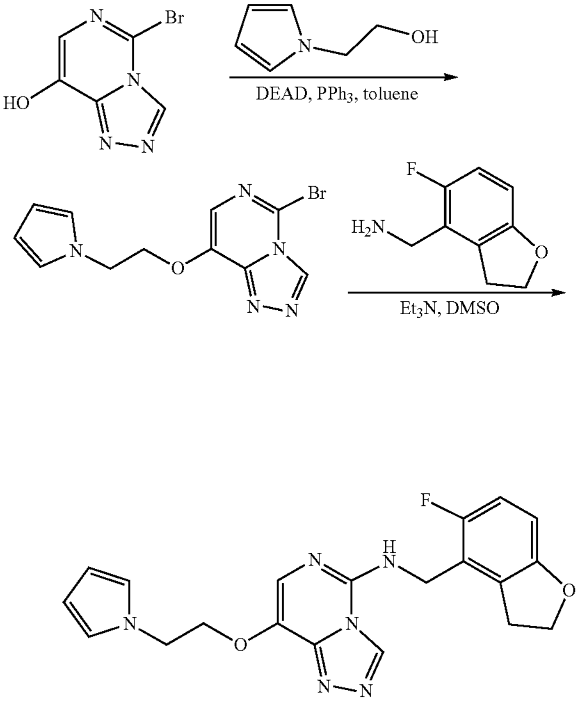

HJM-128

HJM-128 (13 mg) was prepared as a white solid using 2-(pyrrol-1-yl)ethanol as starting material according to the method similar to that for preparation example 100.

$^1$H NMR (400 MHz, $CD_3OD$) δ 9.23 (s, 1H), 7.21 (s, 1H), 6.86-6.80 (m, 3H), 6.62 (dd, J=8.7, 3.8 Hz, 1H), 6.01 (t, J=2.1 Hz, 2H), 4.67 (s, 2H), 4.56 (t, J=8.7 Hz, 2H), 4.42-4.37 (m, 2H), 4.37-4.30 (m, 2H), 3.32 (t, J=8.7 Hz, 2H). LCMS $[M+H]^+$=395.5.

Preparation Example 129: Synthesis of Compound HJM-129

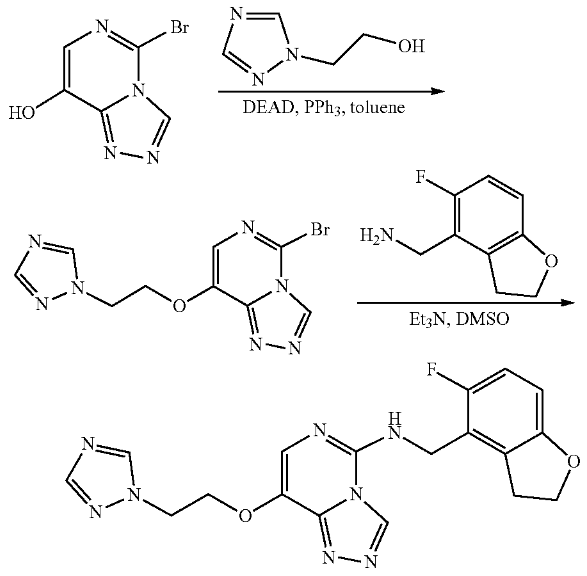

HJM-129

HJM-129 (18 mg) was prepared as a white solid using 2-(1,2,4-triazol-1-yl)ethanol as starting material according to the method similar to that for preparation example 100.

$^{1}$H NMR (400 MHz, DMSO-$d_6$) δ 9.39 (s, 1H), 8.62 (s, 1H), 8.21 (t, J=5.2 Hz, 1H), 8.00 (s, 1H), 7.31 (s, 1H), 6.98-6.88 (m, 1H), 6.69 (dd, J=8.7, 3.9 Hz, 1H), 4.63-4.58 (m, 4H), 4.56-4.50 (m, 4H), 3.27 (t, J=8.7 Hz, 2H). LCMS $[M+H]^+$=397.1.

Preparation Example 130: Synthesis of Compound HJM-130

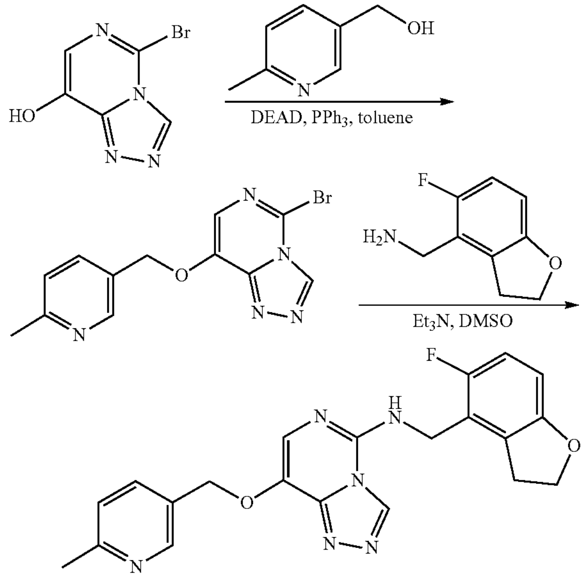

HJM-130

HJM-130 (55 mg) was prepared as a white solid using (6-methylpyridin-3-yl)methanol as starting material according to the method similar to that for preparation example 100.

$^{1}$H NMR (400 MHz, $CD_3OD$) δ 9.25 (s, 1H), 8.53 (d, J=2.2 Hz, 1H), 7.91 (dd, J=8.0, 2.3 Hz, 1H), 7.43 (s, 1H), 7.34 (d, J=8.0 Hz, 1H), 6.87-6.79 (m, 1H), 6.62 (dd, J=8.7, 3.8 Hz, 1H), 5.28 (s, 2H), 4.69 (s, 2H), 4.56 (t, J=8.7 Hz, 2H), 3.33 (t, J=8.5 Hz, 2H), 2.54 (s, 3H). LCMS $[M+H]^+$=407.5.

Preparation Example 131: Synthesis of Compound HJM-131

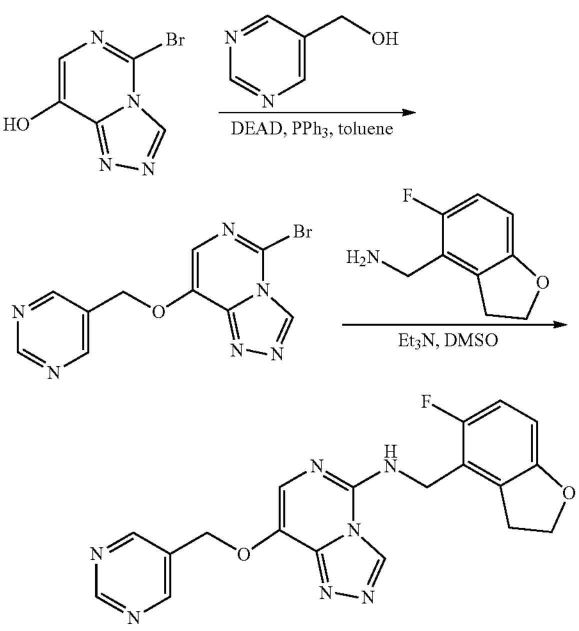

HJM-131

HJM-131 (80 mg) was prepared as a white solid using pyrimidin-5-ylmethanol as starting material according to the method similar to that for preparation example 100.

$^{1}$H NMR (400 MHz, DMSO-$d_6$) δ 9.43 (s, 1H), 9.19 (s, 1H), 8.93 (s, 2H), 8.26 (t, J=5.1 Hz, 1H), 7.45 (s, 1H), 6.93 (dd, J=10.3, 8.6 Hz, 1H), 6.69 (dd, J=8.6, 3.9 Hz, 1H), 5.35 (s, 2H), 4.61 (d, J=4.9 Hz, 2H), 4.53 (t, J=8.7 Hz, 2H), 3.27 (t, J=8.7 Hz, 2H). LCMS $[M+H]^+$=394.2.

Preparation Example 132: Synthesis of Compound HJM-132

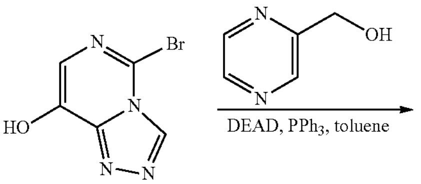

-continued

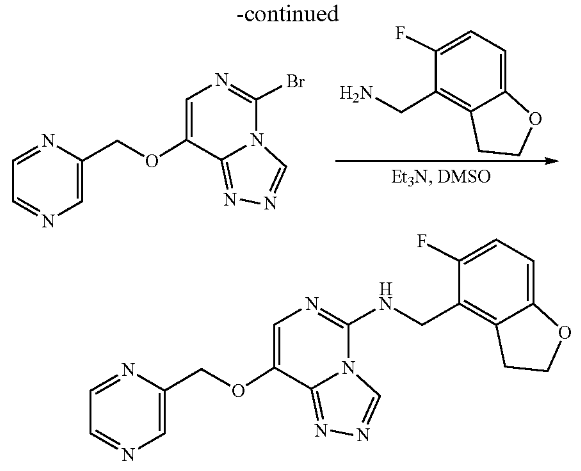

HJM-132

HJM-132 (117 mg) was prepared as a white solid using pyrazin-2-ylmethanol as starting material according to the method similar to that for preparation example 100.

$^1$H NMR (400 MHz, DMSO-d$_6$) δ 9.42 (s, 1H), 8.87 (d, J=1.5 Hz, 1H), 8.69-8.64 (m, 2H), 8.22 (t, J=5.0 Hz, 1H), 7.43 (s, 1H), 6.98-6.90 (m, 1H), 6.69 (dd, J=8.7, 3.9 Hz, 1H), 5.42 (s, 2H), 4.60 (d, J=5.0 Hz, 2H), 4.53 (t, J=8.7 Hz, 2H), 3.27 (t, J=8.8 Hz, 2H). LCMS [M+H]$^+$=394.1.

Preparation Example 133: Synthesis of Compound HJM-133

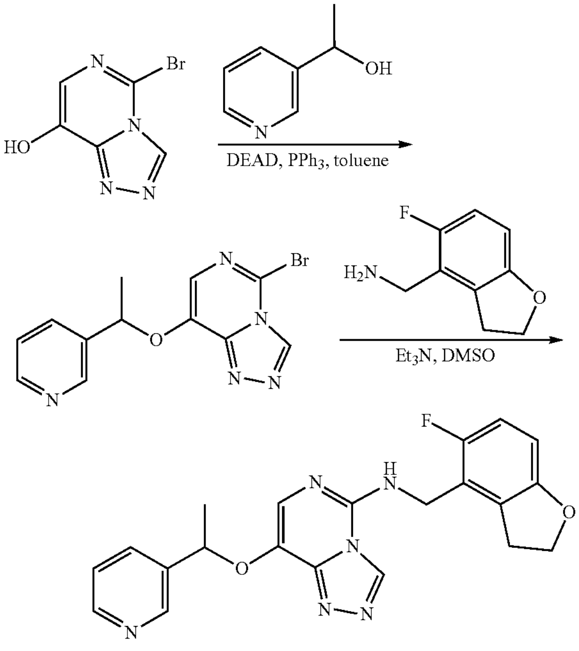

HJM-133

HJM-133 (108 mg) was prepared as a white solid using 3-(1-hydroxyethyl)pyridine as starting material according to the method similar to that for preparation example 100.

$^1$H NMR (400 MHz, DMSO-d$_6$) δ 9.38 (s, 1H), 8.63 (d, J=2.3 Hz, 1H), 8.48 (dd, J=4.8, 1.7 Hz, 1H), 8.18 (t, J=5.0 Hz, 1H), 7.87 (dt, J=7.9, 2.0 Hz, 1H), 7.38 (dd, J=7.9, 4.8 Hz, 1H), 7.24 (s, 1H), 6.91 (dd, J=10.2, 8.7 Hz, 1H), 6.68 (dd, J=8.6, 3.9 Hz, 1H), 5.82 (q, J=6.4 Hz, 1H), 4.55 (d, J=5.0 Hz, 2H), 4.51 (t, J=8.8 Hz, 2H), 3.22 (t, J=8.7 Hz, 2H), 1.63 (d, J=6.4 Hz, 3H). LCMS [M+H]$^+$=407.4.

Preparation Example 134: Synthesis of Compound HJM-134

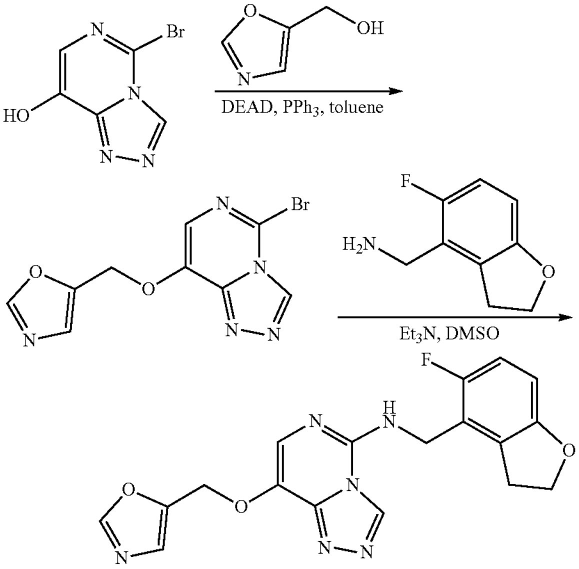

HJM-134

HJM-134 (20 mg) was prepared as a white solid using oxazol-5-methanol as starting material according to the method similar to that for preparation example 100.

$^1$H NMR (400 MHz, CD$_3$OD) δ 9.26 (s, 1H), 8.25 (s, 1H), 7.45 (s, 1H), 7.27 (s, 1H), 6.89-6.79 (m, 1H), 6.63 (dd, J=8.7, 3.9 Hz, 1H), 5.35 (s, 2H), 4.70 (s, 2H), 4.57 (t, J=8.7 Hz, 2H), 3.35 (t, J=8.7 Hz, 2H). LCMS [M+H]$^+$=383.2.

Preparation Example 135: Synthesis of Compound HJM-135

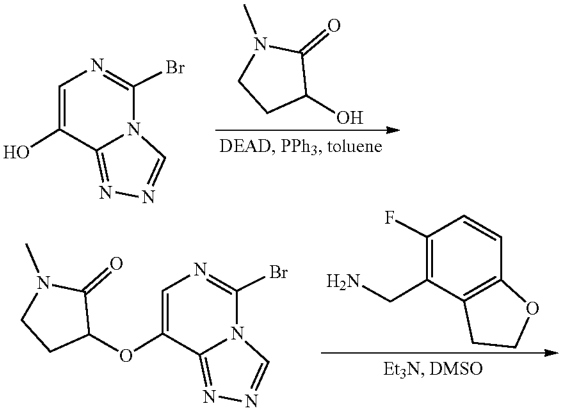

-continued

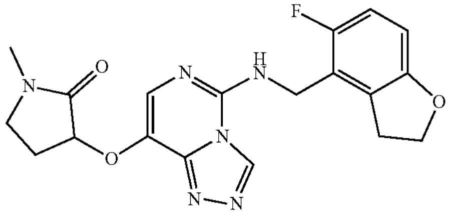

HJM-135

HJM-135 (22 mg) was prepared as a white solid using 3-hydroxy-1-methylpyrrolidone as starting material according to the method similar to that for preparation example 100.

$^{1}$H NMR (400 MHz, DMSO-$d_6$) δ 9.42 (s, 1H), 8.24 (br s, 1H), 7.43 (s, 1H), 6.93 (t, J=9.3 Hz, 1H), 6.69 (dd, J=8.4, 3.8 Hz, 1H), 5.18 (t, J=6.9 Hz, 1H), 4.61 (s, 2H), 4.54 (t, J=8.4 Hz, 2H), 3.47-3.38 (m, 1H), 3.32-3.23 (m, 3H), 2.79 (s, 3H), 2.58-2.50 (m, 1H), 2.11-1.94 (m, 1H). LCMS $[M+H]^+$=399.1.

Preparation Example 136: Synthesis of Compound HJM-136

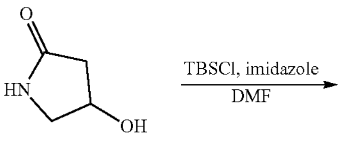

96

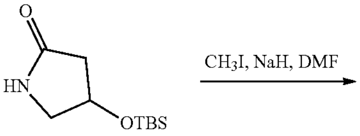

97

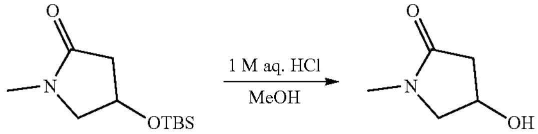

98 99

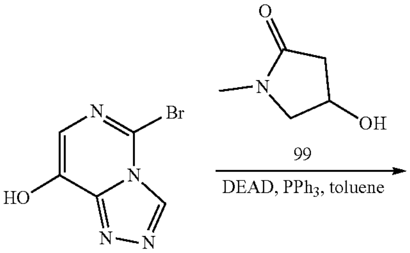

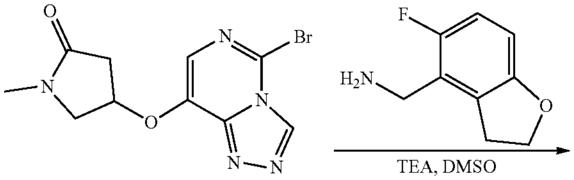

100

-continued

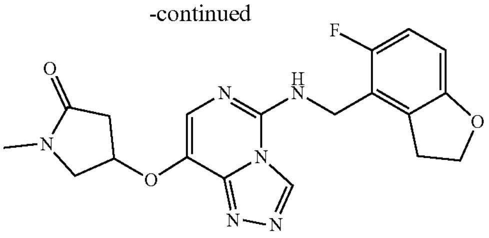

HJM-136

Step 1:

Compound 4-hydroxypyrrolidone 96 (1.01 g, 10 mmol) and imidazole (1.02 g, 15 mmol) were dissolved in N,N-dimethylformamide (10 mL). Tert-butyl dimethylchlorosilane (1.8 g, 12 mmol) was added, and the mixture was stirred at room temperature under nitrogen protection overnight. The mixture was diluted with water, and extracted twice with ethyl acetate. The organic phases were combined, dried with anhydrous sodium sulfate, and filtered. The filtrate was concentrated to afford compound 97 (1.55 g, yield: 72.1%).

$^{1}$H NMR (400 MHz, $CDCl_3$) δ 6.33 (br s, 1H), 4.54 (tt, J=6.7, 3.8 Hz, 1H), 3.58 (dd, J=10.1, 6.1 Hz, 1H), 3.23 (dd, J=10.0, 3.4 Hz, 1H), 2.53 (dd, J=16.9, 6.8 Hz, 1H), 2.25 (dd, J=16.9, 4.2 Hz, 1H), 0.87 (s, 9H), 0.06 (s, 6H).

Step 2:

Compound 97 (1.55 g, 7.21 mmol) was dissolved in anhydrous N,N-dimethylformamide (10 mL). 60% sodium hydride (346 mg, 8.65 mmol) was added at 0° C. under nitrogen protection, and the mixture was stirred under an ice-water bath for 30 min. Iodomethane (0.9 mL, 14.42 mmol) was added, and the mixture was stirred at 0° C. for 2 h. The mixture was diluted with water, and extracted twice with ethyl acetate. The organic phases were combined, dried with anhydrous sodium sulfate, and filtered. The filtrate was concentrated to afford a crude product. The crude product was purified by silica gel column chromatography (petroleum ether/ethyl acetate, ethyl acetate: 0-30%) to afford compound 98 (1.33 g, yield: 80.6%).

$^{1}$H NMR (400 MHz, $CDCl_3$) δ 4.45 (tt, J=7.0, 3.5 Hz, 1H), 3.57 (dd, J=10.2, 6.2 Hz, 1H), 3.22 (dd, J=10.2, 3.2 Hz, 1H), 2.84 (s, 1H), 2.60 (ddd, J=16.9, 7.0, 0.9 Hz, 1H), 2.32 (dd, J=17.0, 3.8 Hz, 1H), 0.87 (s, 9H), 0.06 (s, 6H).

Step 3:

Compound 98 (1.33 g, 5.81 mmol) was dissolved in methanol (10 mL). 1 M HCl aqueous solution (5 mL, 5 mmol) was added, and the mixture was stirred at room temperature for 1 h. The mixture was diluted with saturated aqueous sodium bicarbonate solution, and concentrated to dryness to afford a residue. The residue was purified by silica gel column chromatography (dichloromethane/methanol, methanol: 0-10%) to afford compound 99 (500 mg, yield: 75.0%) as a colorless liquid.

$^{1}$H NMR (400 MHz, $CDCl_3$) δ 4.49-4.40 (m, 1H), 4.15 (d, J=4.6 Hz, 1H), 3.61 (dd, J=10.8, 5.7 Hz, 1H), 3.29 (dd, J=10.9, 2.1 Hz, 1H), 2.82 (s, 3H), 2.65-2.58 (m, 1H), 2.32 (dd, J=17.4, 2.4 Hz, 1H).

Steps 4-5:

In the following steps, HJM-136 (10 mg) was prepared as a white solid according to the method similar to that for preparation example 100.

$^{1}$H NMR (400 MHz, $CD_3OD$) δ 9.27 (s, 1H), 7.43 (s, 1H), 6.88-6.79 (m, 1H), 6.63 (dd, J=8.7, 3.9 Hz, 1H), 5.29-5.21 (m, 1H), 4.71 (s, 2H), 4.57 (t, J=8.7 Hz, 2H), 3.89 (dd, J=11.8, 5.6 Hz, 1H), 3.70 (dd, J=11.7, 1.5 Hz, 1H), 3.36 (t,

J=8.7 Hz, 2H), 2.90 (s, 3H), 2.88 (dd, J=17.6, 6.7 Hz, 1H), 2.63 (d, J=17.9 Hz, 1H). LCMS $[M+H]^+$=399.1.

Preparation Example 137: Synthesis of Compound HJM-137

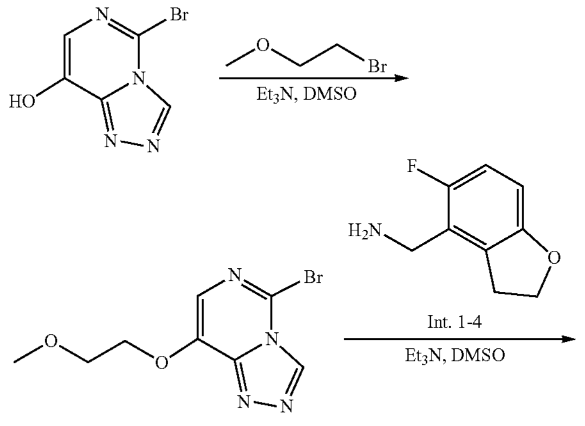

101

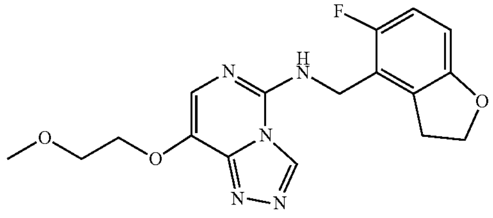

HJM-137

Step 1:

5-Bromo-[1,2,4]triazolo[4,3-c]pyrimidine-8-ol (300 mg, 1.40 mmol), 1-bromo-2-methoxyethane (290 mg, 2.09 mmol) and triethylamine (423 mg, 4.19 mmol) were dissolved in dimethyl sulfoxide (5 mL), and the mixture was heated at 80° C. under nitrogen protection for 2 h. The mixture was cooled and lyophilized to afford a residue. The residue was purified by preparative thin layer chromatography (petroleum ether/ethyl acetate=1:1) to afford compound 101 (80 mg, yield: 21.0%) as a yellow solid. LCMS $[M+H]^+$=272.9.

Step 2:

Compounds 101 (40 mg, 0.15 mmol), Int.1-4 (36 mg, 0.22 mmol) and triethylamine (44 mg, 0.44 mmol) were dissolved in dimethyl sulfoxide (2 mL), and the mixture was stirred at room temperature for 1 h. The mixture was filtered, and the filtrates were combined, and purified by preparative HPLC to afford compound HJM-137 (3 mg, yield: 5.7%) as a white solid.

$^1H$ NMR (400 MHz, $CD_3OD$) δ 9.24 (s, 1H), 7.38 (s, 1H), 6.83 (t, J=9.4 Hz, 1H), 6.62 (dd, J=9.2, 3.8 Hz, 1H), 4.70 (s, 2H), 4.56 (t, J=8.4 Hz, 2H), 4.30 (t, J=4.6 Hz, 2H), 3.79 (t, J=4.8 Hz, 2H), 3.42 (s, 3H), 3.34 (t, J=8.6 Hz, 2H). LCMS $[M+H]^+$=360.0.

Preparation Example 138: Synthesis of Compound HJM-138

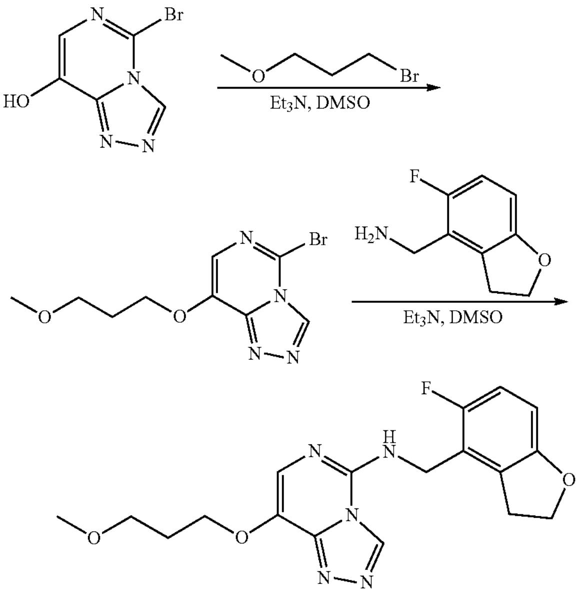

HJM-138

HJM-138 (10 mg) was prepared as a white solid using 1-bromo-3-methoxypropane as starting material according to the method similar to that for preparation example 137.

$^1H$ NMR (400 MHz, $CD_3OD$) δ 9.24 (s, 1H), 7.34 (s, 1H), 6.83 (dd, J=10.2, 8.6 Hz, 1H), 6.62 (dd, J=8.7, 3.9 Hz, 1H), 4.69 (s, 2H), 4.56 (t, J=8.7 Hz, 2H), 4.23 (t, J=6.3 Hz, 2H), 3.62 (t, J=6.2 Hz, 2H), 3.35 (s, 3H), 3.34 (t, J=8.3 Hz, 2H), 2.09 (p, J=6.2 Hz, 2H). LCMS $[M+H]^+$=374.5.

Preparation Example 139: Synthesis of Compound HJM-139

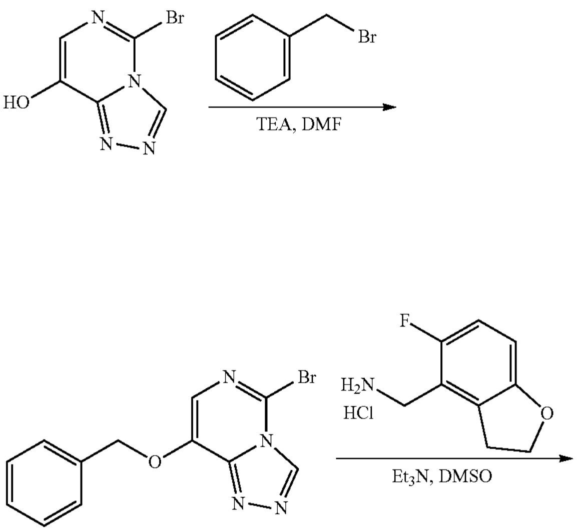

-continued

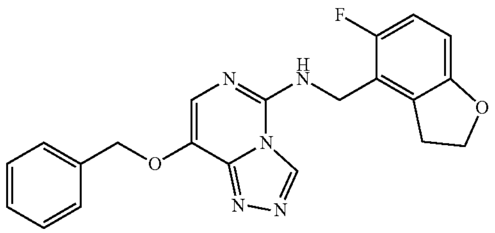

HJM-139

HJM-139 (95 mg) was prepared as a white solid using benzyl bromide as starting material according to the method similar to that for preparation example 137.

$^1$H NMR (400 MHz, DMSO-$d_6$) δ 9.41 (s, 1H), 7.47 (d, J=7.4 Hz, 2H), 7.40 (t, J=7.3 Hz, 2H), 7.37-7.32 (m, 2H), 6.93 (t, J=9.4 Hz, 1H), 6.69 (dd, J=8.6, 3.9 Hz, 1H), 6.04 (br s, 1H), 5.24 (s, 2H), 4.59 (s, 2H), 4.53 (t, J=8.7 Hz, 2H), 3.26 (t, J=8.7 Hz, 2H). LCMS $[M+H]^+$=392.1.

Preparation Example 140: Synthesis of Compound HJM-140

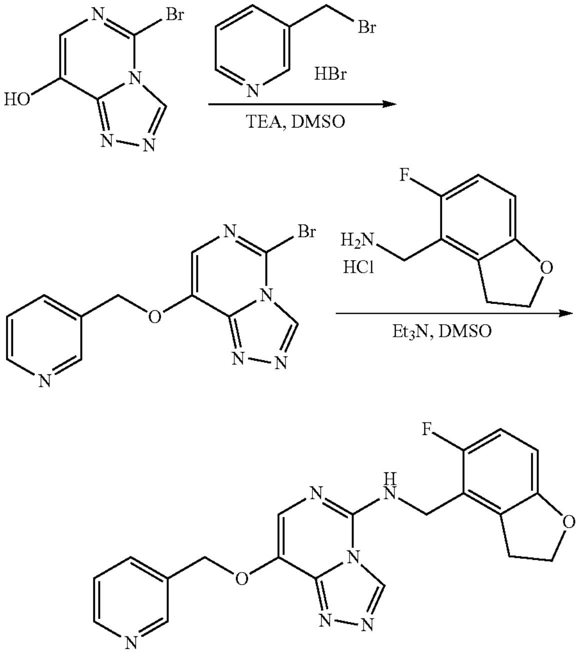

HJM-140

HJM-140 (3 mg) was prepared as a white solid using 3-bromomethylpyridine hydrobromide as starting material according to the method similar to that for preparation example 137.

$^1$H NMR (400 MHz, $CD_3OD$) δ 9.26 (s, 1H), 8.69 (s, 1H), 8.52 (d, J=4.9 Hz, 1H), 8.05 (d, J=8.0 Hz, 1H), 7.49 (dd, J=7.9, 4.9 Hz, 1H), 7.45 (s, 1H), 6.88-6.80 (m, 1H), 6.63 (dd, J=8.6, 3.8 Hz, 1H), 5.34 (s, 2H), 4.70 (s, 2H), 4.57 (t, J=8.7 Hz, 2H), 3.34 (t, J=8.7 Hz, 2H). LCMS $[M+H]^+$=393.1.

Preparation Example 141: Synthesis of Compound HJM-141

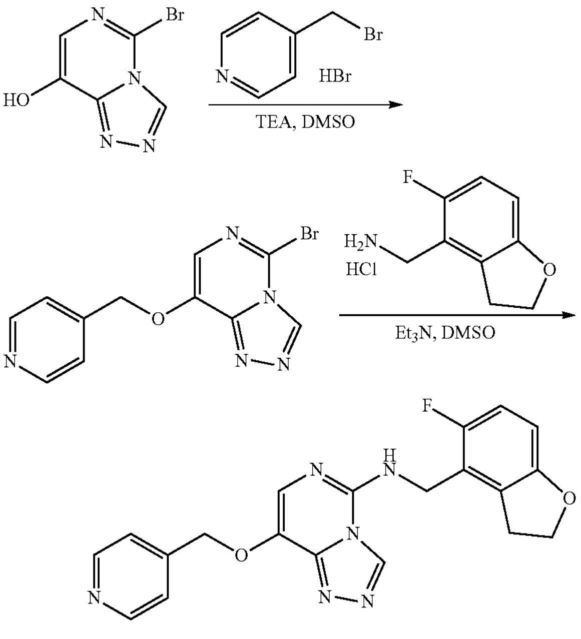

HJM-141

HJM-141 (15 mg) was prepared as a white solid using 4-bromomethylpyridine hydrobromide as starting material according to the method similar to that for preparation example 137.

$^1$H NMR (400 MHz, $CD_3OD$) δ 9.27 (s, 1H), 8.59-8.51 (m, 2H), 7.65-7.58 (m, 2H), 7.42 (s, 1H), 6.88-6.79 (m, 1H), 6.63 (dd, J=8.7, 3.9 Hz, 1H), 5.36 (s, 2H), 4.70 (s, 2H), 4.56 (t, J=8.7 Hz, 2H), 3.35 (t, J=8.7 Hz, 2H). LCMS $[M+H]^+$=393.1.

Preparation Example 142: Synthesis of Compound HJM-142

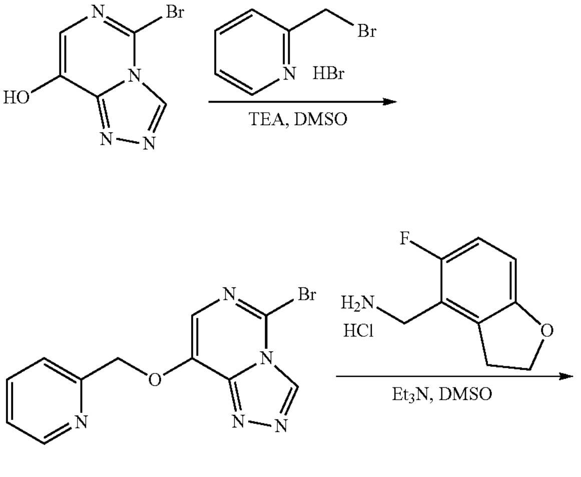

-continued

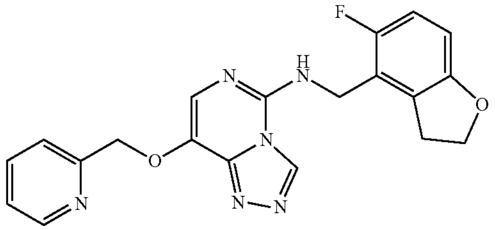

HJM-142

HJM-142 (10 mg) was prepared as a white solid using 2-bromomethylpyridine hydrobromide as starting material according to the method similar to that for preparation example 137.

$^1$H NMR (400 MHz, $CD_3OD$) δ 9.26 (s, 1H), 8.55 (d, J=4.5 Hz, 1H), 7.90 (td, J=7.7, 1.8 Hz, 1H), 7.77 (d, J=7.9 Hz, 1H), 7.43-7.36 (m, 2H), 6.88-6.78 (m, 1H), 6.63 (dd, J=8.6, 3.9 Hz, 1H), 5.35 (s, 2H), 4.69 (s, 2H), 4.56 (t, J=8.7 Hz, 2H), 3.34 (t, J=8.7 Hz, 2H). LCMS $[M+H]^+$=393.0.

Preparation Example 143: Synthesis of Compound HJM-143

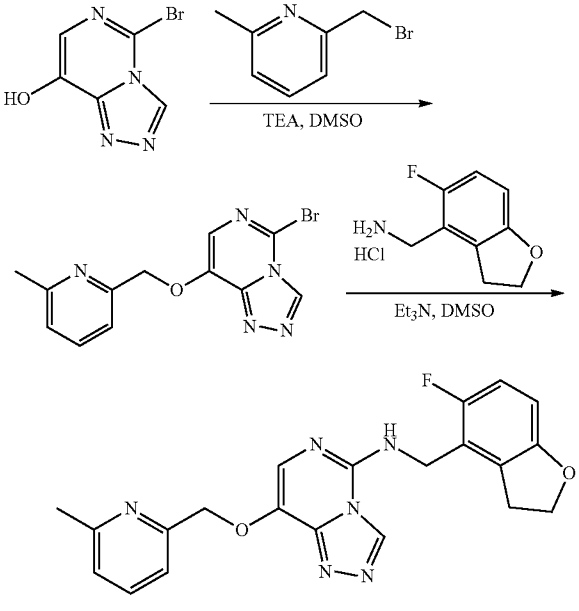

HJM-143

HJM-143 (11 mg) was prepared as a white solid using 2-bromomethyl-6-methylpyridine as starting material according to the method similar to that for preparation example 137.

$^1$H NMR (400 MHz, $CD_3OD$) δ 9.34 (s, 1H), 8.49 (t, J=7.9 Hz, 1H), 8.03 (d, J=7.9 Hz, 1H), 7.90 (d, J=8.0 Hz, 1H), 7.64 (s, 1H), 6.84 (dd, J=10.2, 8.7 Hz, 1H), 6.63 (dd, J=8.7, 3.9 Hz, 1H), 5.59 (s, 2H), 4.73 (s, 2H), 4.58 (t, J=8.7 Hz, 2H), 3.37 (t, J=8.7 Hz, 2H), 2.88 (s, 3H). LCMS $[M+H]^+$=407.5.

Preparation Example 144: Synthesis of Compound HJM-144

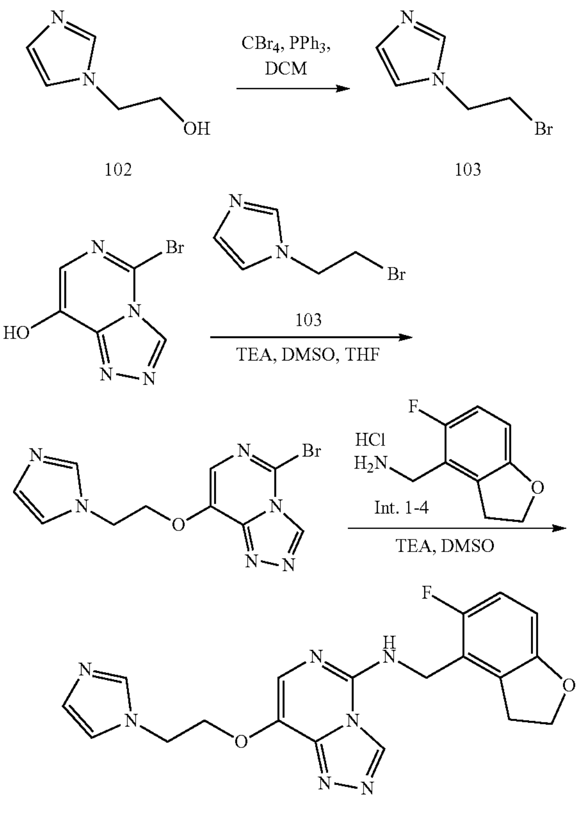

HJM-144

Step 1:

Compound 1-(2-hydroxyethyl) imidazole 102 (4.08 g, 36.42 mmol) and triphenyl phosphine (10.5 g, 40.06 mmol) were dissolved in dichloromethane (100 mL). Carbon tetrabromide (13.25 g, 40.06 mmol) was added at 0° C. under nitrogen protection in batches. After the addition, the mixture was stirred at room temperature for 3 h. The mixture was concentrated to afford a crude product. The crude product was purified by silica gel column chromatography (petroleum ether/ethyl acetate, ethyl acetate: 0-50%) to afford compound 103 (2.5 g, yield: 39.2%) as a colorless liquid.

$^1$H NMR (400 MHz, DMSO-$d_6$) δ 7.68 (s, 1H), 7.24 (s, 1H), 6.90 (s, 1H), 4.38 (t, J=6.1 Hz, 2H), 3.81 (t, J=6.1 Hz, 2H).

Steps 2-3:

In the following steps, HJM-144 (3 mg) was prepared as a white solid according to the method similar to that for preparation example 137.

$^1$H NMR (400 MHz, $CD_3OD$) δ 9.28 (s, 1H), 9.19 (s, 1H), 7.82 (s, 1H), 7.59 (s, 1H), 7.40 (s, 1H), 6.83 (t, J=9.4 Hz, 1H), 6.62 (dd, J=8.7, 3.8 Hz, 1H), 4.75 (t, J=4.7 Hz, 2H), 4.69 (s, 2H), 4.59-4.52 (m, 4H), 3.35 (t, J=8.7 Hz, 2H). LCMS $[M+H]^+$=396.0.

Preparation Example 145: Synthesis of Compound HJM-145

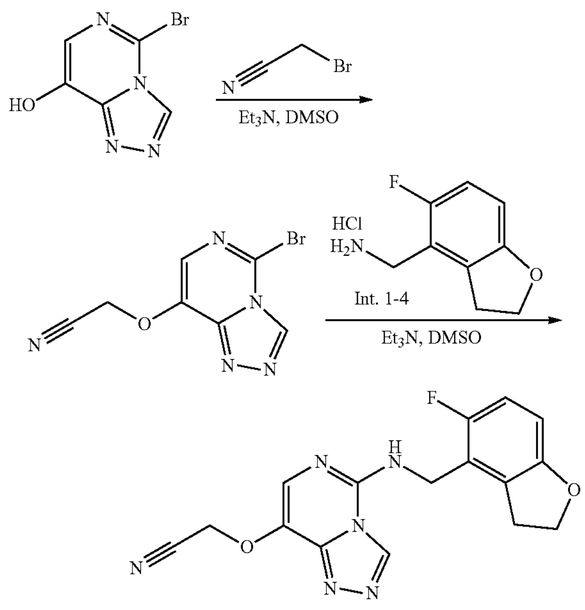

HJM-145

HJM-145 (9 mg) was prepared as a white solid using bromoacetonitrile as starting material according to the method similar to that for preparation example 137.

$^1$H NMR (400 MHz, DMSO-$d_6$) δ 9.44 (s, 1H), 8.39 (t, J=5.4 Hz, 1H), 7.51 (s, 1H), 6.94 (t, J=9.5 Hz, 1H), 6.70 (dd, J=8.7, 3.8 Hz, 1H), 5.32 (s, 2H), 4.63 (d, J=5.0 Hz, 2H), 4.54 (t, J=8.7 Hz, 2H), 3.29 (t, J=8.7 Hz, 2H). LCMS $[M+H]^+$=341.1.

Preparation Example 146: Synthesis of Compound HJM-146

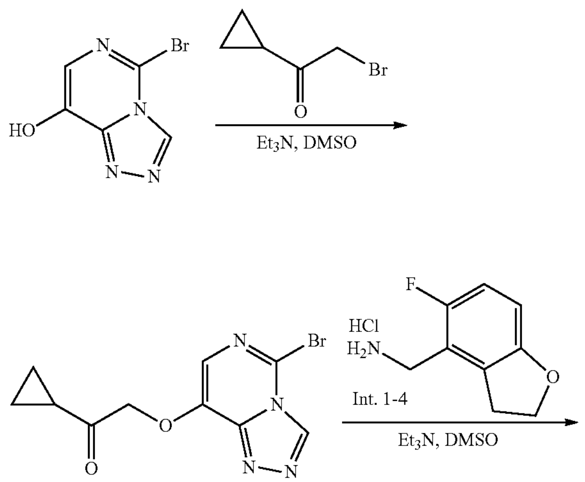

-continued

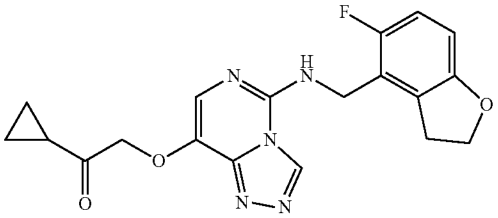

HJM-146

HJM-146 (37 mg) was prepared as a white solid using 2-bromo-1-cyclopropyl ethanone as starting material according to the method similar to that for preparation example 137.

$^1$H NMR (400 MHz, DMSO-$d_6$) δ 9.42 (s, 1H), 8.21 (t, J=5.0 Hz, 1H), 7.26 (s, 1H), 6.98-6.90 (m, 1H), 6.69 (dd, J=8.6, 3.9 Hz, 1H), 5.12 (s, 2H), 4.59 (d, J=4.8 Hz, 2H), 4.53 (t, J=8.7 Hz, 2H), 3.27 (t, J=8.8 Hz, 2H), 2.27-2.20 (m, 1H), 1.02-0.87 (m, 4H). LCMS $[M+H]^+$=384.2.

Preparation Example 147: Synthesis of Compound HJM-147

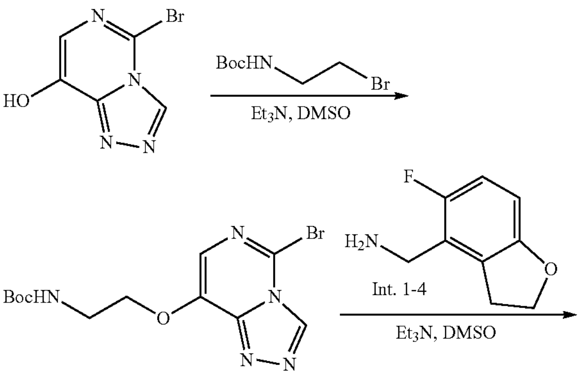

104

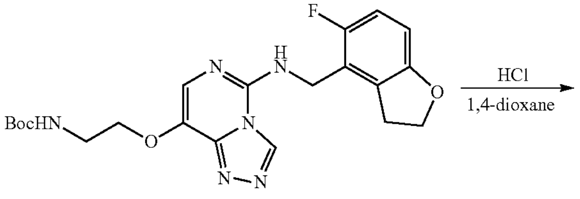

105

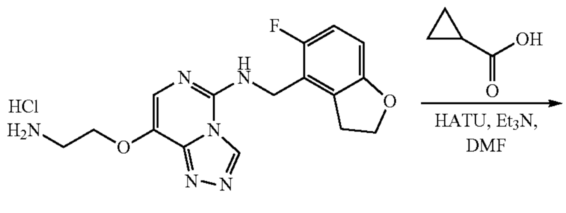

106

-continued

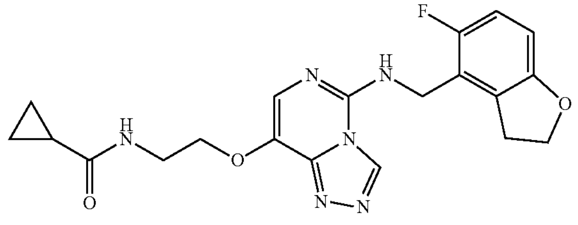

HJM-147

Step 1:

5-Bromo-[1,2,4]triazolo[4,3-c]pyrimidine-8-ol (400 mg, 1.86 mmol), tert-butyl 2-bromoethylcarbamate (500 mg, 2.23 mmol) and triethylamine (564 mg, 5.58 mmol) were dissolved in dimethyl sulfoxide (3 mL), and the mixture was heated at 80° C. under nitrogen protection for 3 h. The reaction mixture containing compound 104 was cooled, and directly used in the next step. LCMS $[M+H]^+$=358.0.

Step 2:

The above reaction mixture containing compound 104 was added to a solution of Int.1-4 (310 mg, 1.86 mmol) and triethylamine (44 mg, 0.44 mmol) in dimethyl sulfoxide (2 mL), and the mixture was heated at 80° C. for 2 h. The mixture was cooled, and purified by reversed-phase column chromatography to afford compound 105 (105 mg, yield: 12.7%) as a yellow oil. LCMS $[M+H]^+$=445.1.

Step 3:

Compound 105 (105 mg, 0.24 mmol) was added to a solution of 4 M HCl in 1,4-dioxane (3 mL), and the mixture was stirred at room temperature for 2 h. The mixture was concentrated to afford compound 106 (80 mg, yield: 98%) as a white solid.

Step 4:

Compound 106 (80 mg, 0.23 mmol), cyclopropylcarboxylic acid (20 mg, 0.23 mmol) and triethylamine (70 mg, 0.69 mmol) were dissolved in N,N-dimethylformamide (3 mL). O-(7-azabenzotriazol-1-yl)-N,N,N',N'-tetramethyl uronium hexafluorophosphate (HATU, 87 mg, 0.23 mmol) was added, and the mixture was stirred at room temperature for 2 h. The mixture was purified by preparative HPLC to afford compound HJM-147 (11 mg, yield: 11.6%) as a white solid.

$^1$H NMR (400 MHz, $CD_3OD$) δ 9.37 (s, 1H), 7.79 (s, 1H), 6.84 (t, J=9.4 Hz, 1H), 6.64 (dd, J=8.6, 3.8 Hz, 1H), 4.74 (s, 2H), 4.58 (t, J=8.7 Hz, 2H), 4.28 (t, J=5.3 Hz, 2H), 3.66 (t, J=5.3 Hz, 2H), 3.38 (t, J=8.7 Hz, 2H), 1.64-1.54 (m, 1H), 0.87-0.72 (m, 4H). LCMS $[M+H]^+$=413.3.

Preparation Example 148: Synthesis of Compound HJM-148

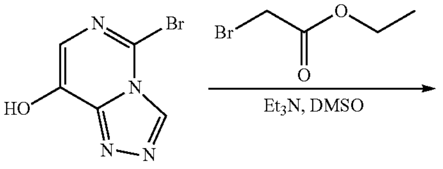

-continued

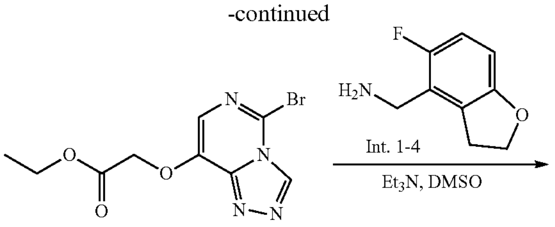

107

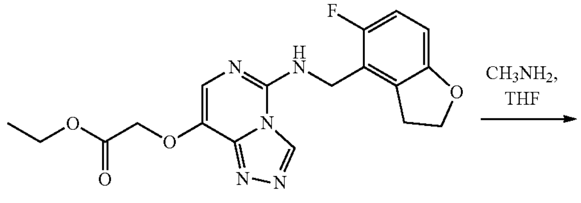

108

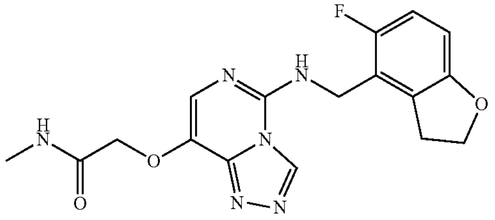

HJM-148

Step 1:

5-Bromo-[1,2,4]triazolo[4,3-c]pyrimidine-8-ol (150 mg, 0.697 mmol), ethyl bromoacetate (173 mg, 1.04 mmol) and triethylamine (140 mg, 1.39 mmol) were dissolved in dimethyl sulfoxide (5 mL), and the mixture was heated at 80° C. for 2 h. The mixture was cooled, and diluted by adding water. Solid was precipitated. The resulting solid was washed twice with water and dried to afford crude compound 107 (87 mg, yield: 41.8%) as a brown solid.

$^1$H NMR (400 MHz, DMSO-$d_6$) δ 9.47 (s, 1H), 7.57 (s, 1H), 5.14 (s, 2H), 4.20 (q, J=7.1 Hz, 2H), 1.23 (t, J=7.1 Hz, 3H). LCMS $[M+H]^+$=300.9.

Step 2:

Compound 107 (87 mg, 0.29 mmol), Int.1-4 (53 mg, 0.319 mmol) and triethylamine (59 mg, 0.58 mmol) were dissolved in dimethyl sulfoxide (3 mL), and the mixture was heated at 50° C. for 1 h. The mixture was cooled, diluted with water, and extracted twice with ethyl acetate. The organic phases were combined, dried with anhydrous sodium sulfate, and filtered. The filtrate was concentrated to afford a crude product. The crude product was purified by preparative thin layer chromatography to afford compound 108 (100 mg, yield: 90%) as a white solid.

$^1$H NMR (400 MHz, DMSO-$d_6$) δ 9.41 (s, 1H), 8.21 (t, J=5.1 Hz, 1H), 7.31 (s, 1H), 6.93 (t, J=9.5 Hz, 1H), 6.69 (dd, J=8.6, 3.9 Hz, 1H), 4.94 (s, 2H), 4.60 (d, J=5.0 Hz, 2H), 4.53 (t, J=8.7 Hz, 2H), 4.17 (q, J=7.1 Hz, 2H), 3.26 (t, J=8.7 Hz, 2H), 1.20 (t, J=7.1 Hz, 3H). LCMS $[M+H]^+$=388.1.

Step 3:

Compound 108 (40 mg, 0.103 mmol) was added to a solution of 2M methylamine in tetrahydrofuran (2 mL). The mixture was sealed, and heated at 80° C. for 2 h. The mixture was concentrated to afford a crude product. The crude product was purified by preparative HPLC to afford compound HJM-148 (13 mg, yield: 34.2%) as a white solid.

$^1$H NMR (400 MHz, DMSO-$d_6$) δ 9.42 (s, 1H), 8.25 (t, J=4.0 Hz, 1H), 8.01 (d, J=4.0 Hz, 1H), 7.33 (s, 1H), 6.93 (dd, J=10.3, 8.7 Hz, 1H), 6.69 (dd, J=8.6, 3.9 Hz, 1H), 4.65 (s, 2H), 4.60 (d, J=4.4 Hz, 2H), 4.53 (t, J=8.7 Hz, 2H), 3.28 (t, J=8.9 Hz, 2H), 2.66 (d, J=4.7 Hz, 3H). LCMS $[M+H]^+$=373.1.

Preparation Example 149: Synthesis of Compound HJM-149

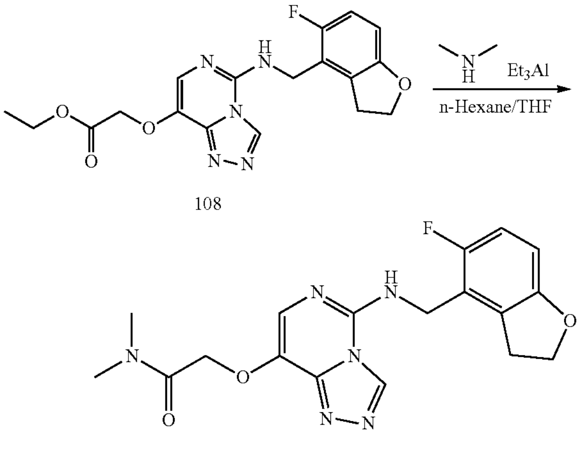

108

HJM-149

At 0° C., a solution of 2 M triethylaluminum in n-hexane (1 mL) was added dropwise to a solution of 2 M dimethylamine in tetrahydrofuran (1 mL) under nitrogen protection. After the dropwise addition, the mixture was warmed to room temperature and stirred for 30 min. A solution of compound 108 (40 mg, 0.1 mmol) in tetrahydrofuran (2 mL) was slowly added dropwise. After the dropwise addition, the mixture was heated to 80° C. and stirred for 5 h. The mixture was cooled to 0° C., and methanol (3 mL) was added dropwise to quench the reaction. The mixture was diluted with water and extracted twice with ethyl acetate. The organic phases were combined, dried with anhydrous sodium sulfate, and filtered. The filtrate was concentrated to afford a crude product. The crude product was purified by preparative HPLC to afford compound HJM-149 (1.2 mg, yield: 3%) as a white solid.

$^1$H NMR (400 MHz, $CD_3OD$) δ 9.25 (s, 1H), 7.38 (s, 1H), 6.83 (dd, J=10.2, 8.7 Hz, 1H), 6.62 (dd, J=8.6, 3.9 Hz, 1H), 5.02 (s, 2H), 4.69 (s, 2H), 4.56 (t, J=8.7 Hz, 2H), 3.35 (t, J=8.7 Hz, 2H), 3.10 (s, 3H), 2.97 (s, 3H). LCMS $[M+H]^+$ =387.5.

Preparation Example 150: Synthesis of Compound HJM-150

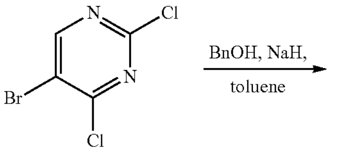

Int. 1-1

-continued

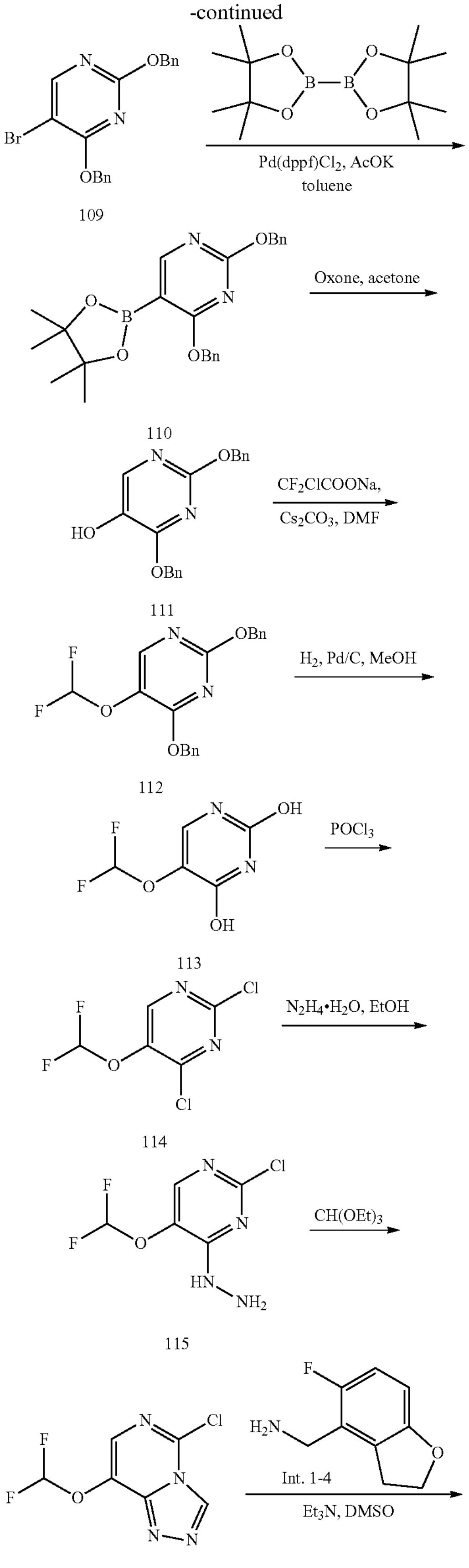

109

110

111

112

113

114

115

116

-continued

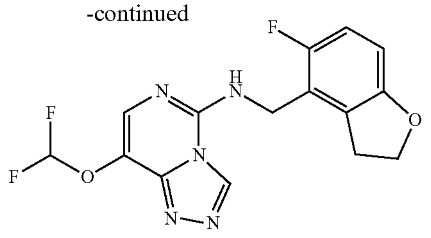

HJM-150

Step 1:

Under nitrogen protection, 60% sodium hydride (876 mg, 21.94 mmol) was added portionwise to a solution of benzyl alcohol (4.8 g, 43.88 mmol) in anhydrous toluene (50 mL), and the mixture was heated at 80° C. for 2 h. The mixture was cooled to room temperature. A solution of 5-bromo-2,4-dichloropyrimidine Int.1-1 (5 g, 21.94 mmol) in anhydrous toluene (10 mL) was added dropwise, and the mixture was stirred at room temperature overnight. The mixture was concentrated to afford a crude product. The crude product was purified by silica gel column chromatography (petroleum ether/ethyl acetate, ethyl acetate: 0-50%) to afford compound 109 (3 g, yield: 36.8%) as a white solid. LCMS $[M+H]^+$=371.3.

Step 2:

Compound 109 (1 g, 2.69 mmol) and bis(pinacolato) diboron (1 g, 4.04 mmol) were dissolved in toluene (10 mL). Potassium acetate (793 mg, 8.08 mmol) and Pd(dppf)$Cl_2$ (0.2 g, 0.27 mmol) were added, and the mixture was heated at 100° C. for 2 h. The mixture was cooled, and concentrated to afford a crude product. The crude product was purified by silica gel column chromatography (petroleum ether/ethyl acetate, ethyl acetate: 0-30%) to afford compound 110 (500 mg, yield: 44.4%) as a white solid. LCMS $[M+H]^+$=419.5.

Step 3:

Compound 110 (480 mg, 1.15 mmol) was dissolved in acetone (5 mL), and oxone (1.1 g, 1.72 mmol) was added portionwise at 0° C. After the addition, the mixture was warmed to room temperature and stirred for 2 h. The mixture was concentrated to afford a crude product. The crude product was purified by silica gel column chromatography (petroleum ether/ethyl acetate, ethyl acetate: 0-50%) to afford compound 111 (300 mg, yield: 84.8%) as a white solid. LCMS $[M+H]^+$=309.4.

Step 4:

Sodium difluorochloroacetate (207 mg, 1.36 mmol) and cesium carbonate (371 mg, 1.14 mmol) were added to a solution of compound 111 (280 mg, 0.91 mmol) in N,N-dimethylformamide (5 mL), and the mixture was heated at 100° C. for 2 h. The mixture was cooled, poured into water, and extracted twice with ethyl acetate. The organic phases were combined, dried with anhydrous sodium sulfate, and filtered. The filtrate was concentrated to afford a crude product. The crude product was purified by silica gel column chromatography (petroleum ether/ethyl acetate, ethyl acetate: 0-30%) to afford compound 112 (200 mg, yield: 61.2%) as a white solid. LCMS $[M+H]^+$=359.4.

Step 5:

Compound 112 (200 mg, 0.56 mmol) was dissolved in methanol (5 mL), and 10% Pd/C (20 mg) was added under nitrogen protection. The atmosphere was replaced three times with hydrogen gas, and the mixture was reacted under a hydrogen balloon for 2 h. The mixture was filtered, and the filter cake was washed with methanol for three times. The filtrates were combined, and concentrated to afford compound 113 (102 mg, yield: 99%) as a white solid. LCMS $[M+H]^+$=179.1.

Step 6:

Compound 113 (100 mg, 0.56 mmol) was added to phosphorus oxychloride (2 mL), and the mixture was heated at 105° C. for 12 h. The mixture was cooled, and concentrated to afford a crude product. The crude product was purified by silica gel column chromatography (petroleum ether/ethyl acetate, ethyl acetate: 0-20%) to afford compound 114 (60 mg, yield: 49.7%) as a yellow solid. LCMS $[M-H]^-$=213.5.

Step 7:

Compound 114 (60 mg, 0.28 mmol) was dissolved in ethanol (1 mL). A solution of 85% hydrazine hydrate (17.6 mg, 0.30 mmol) in ethanol (1 mL) was added, and the mixture was reacted at room temperature for 2 h. The mixture was concentrated to afford a crude product. The crude product was purified by silica gel column chromatography (dichloromethane/methanol, methanol: 0-5%) to afford compound 115 (40 mg, yield: 68.1%) as a yellow solid. LCMS $[M+H]^+$=211.0.

Step 8:

Compound 115 (40 mg, 0.19 mmol) was added to triethyl orthoformate (2 mL), and the mixture was heated at 120° C. and stirred for 2 h. The mixture was cooled, and concentrated to afford a crude product. The crude product was purified by silica gel column chromatography (petroleum ether/ethyl acetate, ethyl acetate: 0-50%) to afford compound 116 (25 mg, yield: 59.7%) as a brown solid. LCMS $[M+H]^+$=221.3.

Step 9:

Compound 116 (25 mg, 0.11 mmol), Int.1-4 (34 mg, 0.20 mmol) and triethylamine (34 mg, 0.34 mmol) were dissolved in dimethyl sulfoxide (1 mL), and the mixture was stirred at room temperature for 2 h. The mixture was purified by preparative HPLC to afford compound HJM-150 (10 mg, yield: 25.1%) as a white solid.

$^1$H NMR (400 MHz, $CD_3OD$) δ 9.29 (s, 1H), 7.67 (s, 1H), 6.95 (t, J=73.7 Hz, 1H), 6.85 (t, J=9.5 Hz, 1H), 6.64 (dd, J=8.7, 3.9 Hz, 1H), 4.75 (s, 2H), 4.57 (t, J=8.7 Hz, 2H), 3.35 (t, J=8.8 Hz, 2H). LCMS $[M+H]^+$=352.1.

Preparation Example 151: Synthesis of Compound HJM-151

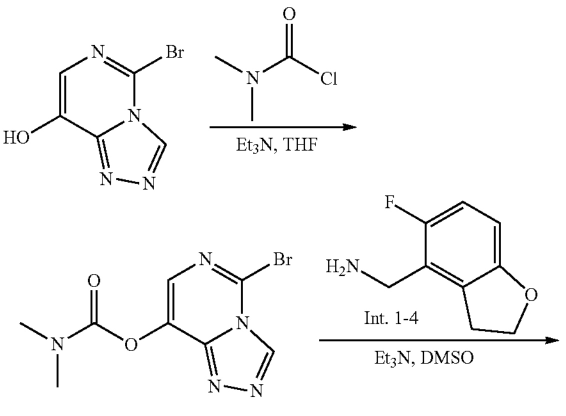

117

-continued

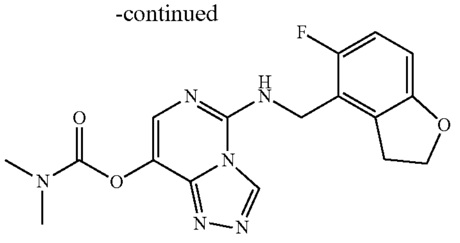

HJM-151

Step 1:

5-Bromo-[1,2,4]triazolo[4,3-c]pyrimidine-8-ol (100 mg, 0.47 mmol), dimethylcarbamic chloride (50 mg, 0.47 mmol) and triethylamine (141 mg, 1.40 mmol) were dissolved in tetrahydrofuran (3 mL), and the mixture was stirred at room temperature for 4 h. The mixture was concentrated to afford compound 117, which was directly used in the next step. LCMS $[M+H]^+$=285.9.

Step 2:

The above crude product compound 117, Int.1-4 (78 mg, 0.47 mmol) and triethylamine (141 mg, 1.40 mmol) were dissolved in dimethyl sulfoxide (2 mL), and the mixture was heated at 60° C. for 1 h. The mixture was cooled and purified by preparative HPLC to afford compound HJM-151 (2 mg, yield: 1.2%) as a white solid.

$^1$H NMR (400 MHz, $CD_3OD$) δ 9.28 (s, 1H), 7.63 (s, 1H), 6.85 (t, J=9.5 Hz, 1H), 6.64 (dd, J=8.7, 3.9 Hz, 1H), 4.76 (s, 2H), 4.57 (t, J=8.7 Hz, 2H), 3.36 (t, J=8.7 Hz, 3H), 3.19 (s, 3H), 3.03 (s, 3H). LCMS $[M+H]^+$=373.3.

Preparation Example 152: Synthesis of Compound HJM-152

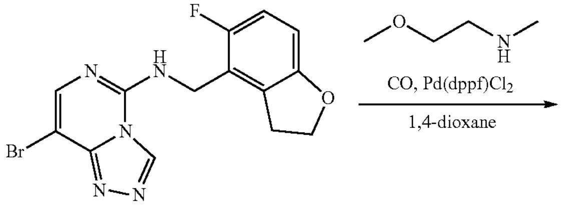

1

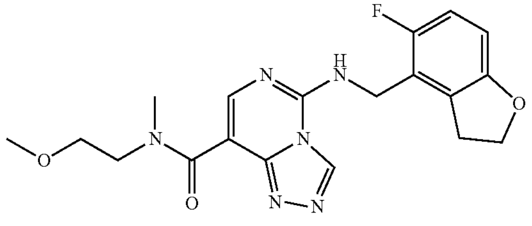

HJM-152

HJM-152 (22 mg) was prepared as a white solid using N-(2-methoxyethyl)methylamine as starting material according to the method similar to that for preparation example 25.

$^1$H NMR (400 MHz, $CD_3OD$) δ 9.30 (s, 1H), 7.87 (s, 1H), 6.86 (dd, J=10.2, 8.7 Hz, 1H), 6.65 (dd, J=8.7, 3.9 Hz, 1H), 4.81 (s, 2H), 4.58 (t, J=8.7 Hz, 2H), 3.85-3.63 (m, 2H), 3.59-3.43 (m, 2H), 3.43-3.22 (m, 5H), 3.21-2.99 (m, 3H). LCMS $[M+H]^+$=401.1.

Preparation Example 153: Synthesis of Compound HJM-153

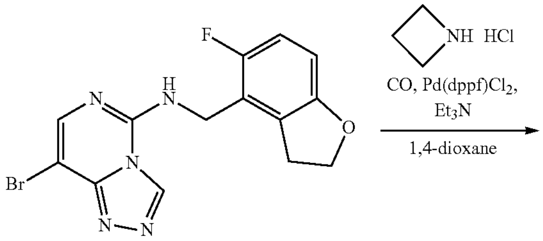

1

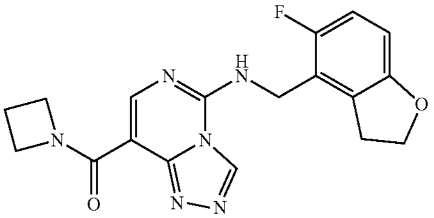

HJM-153

8-Bromo-N-((5-fluoro-2,3-dihydrobenzofuran-4-yl)methyl)-[1,2,4]triazolo[4,3-c]pyrimidine-5-amine 1 (40 mg, 0.11 mmol), cyclobutylamine hydrochloride (103 mg, 1.1 mmol) and triethylamine (167 mg, 1.65 mmol) were dissolved in 1,4-dioxane (2 mL). $Pd(dppf)Cl_2$ (15 mg, 0.02 mmol) was added. The atmosphere was replaced three times with CO, and the mixture was heated at 100° C. under a CO balloon for 2 h. The mixture was cooled, and concentrated to afford a crude product. The crude product was purified by preparative HPLC to afford compound HJM-153 (2 mg, yield: 5.0%) as a white solid.

$^1$H NMR (400 MHz, $CD_3OD$) δ 9.31 (s, 1H), 8.07 (s, 1H), 6.86 (t, J=9.5 Hz, 1H), 6.65 (dd, J=8.7, 3.9 Hz, 1H), 4.83 (s, 2H), 4.58 (t, J=8.8 Hz, 2H), 4.36-4.18 (m, 4H), 3.37 (t, J=9.0 Hz, 2H), 2.42-2.30 (m, 2H). LCMS $[M+H]^+$=369.0.

Pharmacological Activity and Application

As the core subunit of the PRC2 complex, EED is necessary for PRC2 to function although EED has no enzymatic activity. EED can specifically bind to H3K27me3, the catalytic product of PRC2, thereby helping PRC2 localize to genomic loci where H3K27me3 already exists on the one hand, and allosterically activating the catalytic activity of EZH2 or EZH1 on the other hand. This positive feedback mechanism enables H3K27me3 to extensively modify chromatin and to be efficiently transmitted between cell generations during the cell cycle, maintaining cell identity and epigenome stability. Small molecules targeting EED can directly bind to EED to allosterically inhibit the enzymatic activity of PRC2. This inhibition mechanism is different from that of PRC2 enzymatic activity inhibitors targeting EZH2, thereby providing a unique new perspective for the development of PRC2 inhibitors, and being able to effectively treat tumors that are resistant to PRC2 enzymatic activity inhibitors. The compounds of the present disclosure can be used to allosterically inhibit the enzymatic activity of PRC2, have a blocking effect on tumor cell proliferation, and can be used to treat EED- or PRC2-mediated diseases or symptoms, especially tumors.

The activity of the compounds of the present disclosure can be demonstrated using any of the following analytical methods. The ability of the compounds of the present disclosure to inhibit PRC2 activity in cells was assessed by analyzing the methylation of histone H3 lysine 27 in human tumor cells. The ability of the compounds of the disclosure to inhibit tumors was assessed by analyzing their effect on the proliferation of PRC2-specifically dependent tumor cells.

(1) Cellular H3K27 Methylation Assay

Human cervical cancer cells HeLa were cultured in petri dishes in a sterile incubator with 95% relative humidity and 5% $CO_2$ at 37° C. The culture medium was DMEM (Gibco, product No. 12100046) containing 10% fetal bovine serum (FBS, Gibco, product No. 10099141) and 0.1% penicillin/streptomycin solution (P/S). Cells in exponential growth phase were seeded into a 24-well plate (Greiner, product No. 662160) at a density of $2\times10^4$ cells/well with 1 mL of medium per well. Subsequently, different concentrations of compounds disclosed herein were added to the wells that had seeded with cells (6 concentrations were set for each compound at 3-fold serial dilution with the highest detection concentration of 10 μM or 1 μM), and the final concentration of DMSO was 0.1%. After 3 days, cells were lysed in SDS lysis solution (1.45 g SDS, 0.2 g Tris base, 6 mL glycerol, 20 mg bromophenol blue, 310 mg DTT, dd$H_2O$ to 40 mL). H3K27me3 levels were detected, quantified and analyzed by standard molecular biology technique Western Blot immunoblotting. The cell lysate was boiled at 95° C. for 12 minutes. After mixing and centrifugation, the total cell protein in the lysate was separated by SDS-PAGE. The blot was transferred to NC membrane (GE, product No.: 10600002), incubated and blocked in 5% nonfat dry milk-TBST (0.075% Tween-20) at room temperature for 60 minutes, and incubated with primary antibody at 4° C. overnight. Antibodies used were: anti-H3K27me3 (#9733S, 1:1000), anti-H3 (#9715S, 1:1000) and anti-EZH2 (#5246S, 1:1000) (all purchased from Cell Signaling Technology). Washing was carried out three times with TBST at room temperature for 10 minutes per time. After that, incubation was carried out in 5% nonfat dry milk-TBST containing secondary antibody (purchased from Pierce, product No.: 31460, 1:5000) at room temperature for 60 minutes. Washing was carried out three times with TBST at room temperature for 10 minutes per time. Finally, development was carried out using a chemiluminescent substrate, and quantification of imaging and exposure data was carried out on a GE imager 680. The data were fitted to dose-response curves using GraphPad prisim5 to obtain $IC_{50}$ values of the assay compounds. EED226 was used as a positive control in each assay to eliminate the interference of batch-to-batch error.

Table 1 shows the $IC_{50}$ values of some compounds of the present disclosure against cellular H3K27 methylation.

| Compound No. | PD $IC_{50}$ (uM) |
|---|---|
| HJM-001 | 0.4837 |
| HJM-002 | 0.0988 |
| HJM-003 | 0.0543 |
| HJM-004 | 0.1397 |
| HJM-005 | 0.454 |
| HJM-006 | 0.0487 |
| HJM-007 | 0.0499 |
| HJM-008 | 0.1119 |
| HJM-009 | 0.563 |
| HJM-010 | 0.0446 |
| HJM-011 | 0.0338 |
| HJM-012 | 0.1122 |
| HJM-013 | 0.2247 |
| HJM-014 | 0.0437 |

-continued

| Compound No. | PD $IC_{50}$ (uM) |
|---|---|
| HJM-015 | 0.0254 |
| HJM-016 | 0.0347 |
| HJM-017 | 0.0263 |
| HJM-018 | 0.0592 |
| HJM-019 | 0.0294 |
| HJM-020 | 0.0398 |
| HJM-021 | 0.2418 |
| HJM-022 | 0.2841 |
| HJM-023 | 1.159 |
| HJM-024 | 1.109 |
| HJM-025 | 0.0433 |
| HJM-026 | 0.0756 |
| HJM-027 | 0.0895 |
| HJM-028 | 0.0953 |
| HJM-029 | 0.0822 |
| HJM-030 | 0.0267 |
| HJM-031 | 0.0396 |
| HJM-032 | 0.3174 |
| HJM-033 | 0.0259 |
| HJM-034 | 0.0995 |
| HJM-035 | 0.0536 |
| HJM-036 | 0.1604 |
| HJM-037 | 0.0647 |
| HJM-038 | 0.1871 |
| HJM-039 | 0.0672 |
| HJM-040 | 0.1748 |
| HJM-041 | 0.3337 |
| HJM-042 | 0.0605 |
| HJM-043 | 0.1149 |
| HJM-044 | 0.2877 |
| HJM-045 | 0.013 |
| HJM-046 | 2.0 |
| HJM-047 | 7.0 |
| HJM-048 | 1.621 |
| HJM-049 | 0.2959 |
| HJM-050 | 0.0505 |
| HJM-051 | 0.1673 |
| HJM-052 | 0.01903 |
| HJM-053 | 0.02882 |
| HJM-054 | 0.03112 |
| HJM-055 | 0.00574 |
| HJM-056 | 0.01281 |
| HJM-057 | 0.0405 |
| HJM-058 | 0.131 |
| HJM-059 | 0.03854 |
| HJM-060 | 0.1414 |
| HJM-061 | 0.1097 |
| HJM-062 | 0.445 |
| HJM-063 | 0.6835 |
| HJM-064 | 0.1805 |
| HJM-065 | 0.3627 |
| HJM-066 | 0.2275 |
| HJM-067 | 0.0211 |
| HJM-068 | 0.1377 |
| HJM-069 | 0.3908 |
| HJM-070 | 0.08306 |
| HJM-071 | 0.07277 |
| HJM-072 | 0.03002 |
| HJM-073 | 0.03927 |
| HJM-074 | 0.5535 |
| HJM-075 | 0.6902 |
| HJM-076 | 0.00636 |
| HJM-077 | 0.01495 |
| HJM-078 | 0.01212 |
| HJM-079 | 0.0153 |
| HJM-080 | 0.03505 |
| HJM-081 | 0.0776 |
| HJM-082 | 0.0299 |
| HJM-083 | 0.0285 |
| HJM-084 | 0.084 |
| HJM-085 | 0.0625 |
| HJM-086 | 0.1878 |
| HJM-087 | 0.2346 |
| HJM-088 | 0.6008 |
| HJM-089 | 0.2558 |
| HJM-090 | 0.1984 |
| HJM-091 | 0.2906 |

-continued

| Compound No. | PD $IC_{50}$ (uM) |
|---|---|
| HJM-092 | 0.1394 |
| HJM-093 | 0.8139 |
| HJM-094 | 0.2233 |
| HJM-095 | 0.1776 |
| HJM-096 | 0.0899 |
| HJM-097 | 0.7923 |
| HJM-098 | 0.3092 |
| HJM-099 | 1.592 |
| HJM-100 | 0.0543 |
| HJM-101 | 0.0395 |
| HJM-102 | 0.0327 |
| HJM-103 | 0.0942 |
| HJM-104 | 0.0527 |
| HJM-105 | 0.02935 |
| HJM-106 | 0.05766 |
| HJM-107 | 0.04854 |
| HJM-108 | 0.1257 |
| HJM-109 | 0.02473 |
| HJM-110 | 0.03284 |
| HJM-111 | 0.03786 |
| HJM-112 | 0.0294 |
| HJM-113 | 0.0597 |
| HJM-114 | 0.068 |
| HJM-115 | 0.2009 |
| HJM-116 | 0.5505 |
| HJM-117 | 1.297 |
| HJM-118 | 0.7921 |
| HJM-119 | 0.2638 |
| HJM-120 | 0.1787 |
| HJM-121 | 0.494 |
| HJM-122 | 0.05489 |
| HJM-123 | 0.1317 |
| HJM-124 | 0.2498 |
| HJM-125 | 0.4627 |
| HJM-126 | 0.09205 |
| HJM-127 | 0.1075 |
| HJM-128 | 0.06204 |
| HJM-129 | 0.3886 |
| HJM-130 | 0.1044 |
| HJM-131 | 0.1298 |
| HJM-132 | 0.1232 |
| HJM-133 | 0.07436 |
| HJM-134 | 0.1588 |
| HJM-135 | 0.2859 |
| HJM-136 | 0.3935 |
| HJM-137 | 0.062 |
| HJM-138 | 0.04975 |
| HJM-139 | 0.1197 |
| HJM-140 | 0.0214 |
| HJM-141 | 0.0644 |
| HJM-142 | 0.0397 |
| HJM-143 | 0.2036 |
| HJM-144 | 0.0717 |
| HJM-145 | 0.0328 |
| HJM-146 | 0.1505 |
| HJM-147 | 0.0953 |
| HJM-148 | 1.09 |
| HJM-149 | 0.5462 |
| HJM-150 | 0.03847 |
| HJM-151 | 0.0911 |
| HJM-152 | 0.0732 |
| HJM-153 | 0.0932 |
| EED226 | 0.22 |

(2) Cell Proliferation Assay

Human B-cell non-Hodgkin's lymphoma cells WSU-DLCL2, Karpas422 and Pfeiffer were cultured in cell culture flasks in a sterile incubator with 95% relative humidity and 5% $CO_2$ at 37° C. The medium was RPMI-1640 (Gibco, product No. 31800022) containing 15% fetal bovine serum (FBS, Gibco, product No. 10099141) and 0.1% penicillin/streptomycin solution (P/S). In order to assay the effects of compounds on cell proliferation, cells in exponential growth phase were seeded into a 12-well plate (Nunc, product No. 150628) with 1 mL of medium per well, wherein WSU- DLCL2 and Karpas422 were seeded at a density of $1\times10^5$ cells/well, and Pfeiffer was seeded at a density of $2\times10^5$ cells/well. At the same time, different concentrations of compounds were added to the wells that had seeded with cells (6 concentrations were set for each compound at 3-fold serial dilution), and the final concentration of DMSO was 0.1%. After that, the number of viable cells was determined by Vi-CELL (Beckman Coulter) for WSU-DLCL2 and Pfeiffer every 3 days, and for Karpas422 on days 4, 7, and 11, respectively. The cells counted each time were seeded into a new 12-well plate at the same density, and supplemented with fresh medium to 1 mL. Different concentrations of compounds were added at the same time. WSU-DLCL2 and Pfeiffer were cultured to the 9th day, and Karpas422 was cultured to the 14th day. Cell data were collected uniformly, and analyzed with GraphPad prisim5. Dose curves were fitted, and $IC_{50}$ values of the assay compounds were obtained.

Table 2 shows the $IC_{50}$ values of the anti-WSU-DLCL2 cell proliferation assay of some compounds of the present disclosure.

| Compound No. | Anti-proliferation $IC_{50}$ (uM) |
|---|---|
| HJM-003 | 0.1314 |
| HJM-010 | 0.0778 |
| HJM-011 | 0.0863 |
| HJM-015 | 0.1152 |
| HJM-016 | 0.0864 |
| HJM-017 | 0.1131 |
| HJM-019 | 0.072 |
| HJM-020 | 0.0485 |
| HJM-025 | 0.0264 |
| HJM-027 | 0.058 |
| HJM-030 | 0.0396 |
| HJM-031 | 0.0806 |
| HJM-033 | 0.0947 |
| HJM-037 | 0.1153 |
| HJM-042 | 0.082 |
| HJM-045 | 0.0092 |
| HJM-067 | 0.0294 |
| HJM-072 | 0.1199 |
| HJM-073 | 0.0294 |
| HJM-079 | 0.0368 |
| HJM-082 | 0.1242 |
| HJM-083 | 0.028 |
| HJM-084 | 0.0869 |
| HJM-100 | 0.0548 |
| HJM-101 | 0.0526 |
| HJM-102 | 0.0251 |
| HJM-103 | 0.1484 |
| HJM-104 | 0.0296 |
| HJM-105 | 0.0354 |
| HJM-106 | 0.0398 |
| HJM-114 | 0.2108 |
| HJM-137 | 0.0514 |
| HJM-138 | 0.0432 |
| HJM-145 | 0.0473 |
| HJM-152 | 0.1062 |
| EED226 | 0.1311 |

Table 3 shows the $IC_{50}$ values of the anti-Karpas422 cell proliferation assay of some compounds of the present disclosure.

| Compound No. | Anti-proliferation $IC_{50}$ (uM) |
|---|---|
| HJM-016 | 0.0749 |
| HJM-030 | 0.0421 |
| HJM-045 | 0.0135 |

-continued

| Compound No. | Anti-proliferation $IC_{50}$ (uM) |
|---|---|
| HJM-067 | 0.0510 |
| HJM-102 | 0.0993 |
| HJM-104 | 0.1016 |
| EED226 | 0.1226 |

Multiple compounds of the present disclosure have good anti-proliferative activities on WSU-DLCL2 and Karpas422 cells, which are higher than that of the positive control EED226.

Table 4 shows the $IC_{50}$ values of the anti-Pfeiffer cell proliferation assay of some compounds of the present disclosure.

| Compound No. | Anti-proliferation $IC_{50}$ (uM) |
|---|---|
| HJM-016 | 0.0557 |
| HJM-045 | 0.0105 |
| HJM-102 | 0.0474 |
| HJM-104 | 0.0816 |

The data show that some compounds of the present disclosure also have good anti-proliferative activity on Pfeiffer cells.

(3) Pharmacokinetic Study in Rats

1. Assay Steps:

Six SPF SD rats, male, weighing 180-220 g, were randomly divided into 2 groups with 3 rats in each group. The compounds of the present disclosure were administered by oral gavage (PO) and intravenous injection (IV), respectively, and the assay compounds were formulated with a vehicle (5% DMSO+10% Solutol+85% pH 4.65 Acetate buffer).

Dosage: 1 mg/kg for intravenous injection and 2 mg/kg for oral administration.

Dosing volume: 5 mL/kg for intravenous injection and 10 mL/kg for oral administration.

The oral administration group was fasted overnight (10-14 h) before the assay, and drank water freely. After 4 hours of administration, they were fed uniformly. They were weighed before administration, and the dosage was calculated according to the body weight.

2. Blood Collection Time Point and Sample Processing:

Intravenous administration: 0.083, 0.25, 0.5, 1, 2, 4, 6, 8, 10 and 24 h after administration;

Oral gavage administration: 0.25, 0.5, 1, 2, 4, 6, 8, 10, 12 and 24 h after administration;

Blood was collected from the jugular vein of rats at the above set time points, about 0.2 mL each time. The blood was anticoagulated with heparin sodium, placed on ice after collection, and centrifuged within 1 hour to separate the plasma (centrifugation conditions: 6800 g, 6 minutes, 2-8° C.). Plasma samples were stored in a −80° C. freezer prior to analysis.

3. Sample Assaying and Data Analysis

The concentration of each compound in rat plasma was determined by LC/MS/MS method.

Through the plasma drug concentration data at different time points, pharmacokinetic parameters were calculated using Phoenix WinNonlin 7.0, thereby providing parameters such as $AUC_{0-t}$, $AUC_{0-\infty}$, $MRT_{0-\infty}$, $C_{max}$, $T_{max}$, and $T_{1/2}$ and mean and standard deviation thereof.

Table 5 shows the rat pharmacokinetic parameters of some compounds of the present disclosure.

| Compound No. | Way of administration | $T_{1/2}$ h | $T_{max}$ h | $C_{max}$ ng/mL | $AUC_{0-\infty}$ ng · h/mL | $MRT_{0-\infty}$ h | Cl mL/min/kg | F % |
|---|---|---|---|---|---|---|---|---|
| HJM-016 | IV | 2.33 | 0.08 | 931.5 | 2055.9 | 2.94 | 8.24 | |
| | PO | 2.80 | 4.00 | 481.6 | 3900.0 | 5.58 | | 98.86 |
| HJM-030 | IV | 1.70 | 0.08 | 1500.8 | 1233.1 | 1.02 | 13.55 | |
| | PO | 1.32 | 0.42 | 393.5 | 1445.1 | 2.93 | | 58.53 |
| HJM-045 | IV | 1.17 | 0.08 | 793.6 | 639.0 | 1.06 | 26.37 | |
| | PO | 1.46 | 2.83 | 119.2 | 628.2 | 3.51 | | 48.40 |
| HJM-067 | IV | 3.00 | 0.08 | 945.6 | 694.8 | 0.80 | 24.08 | |
| | PO | 3.03 | 0.83 | 305.9 | 845.6 | 2.70 | | 60.72 |
| HJM-079 | IV | 0.92 | 0.08 | 750.2 | 856.8 | 1.10 | 19.50 | |
| | PO | 1.72 | 0.42 | 222.3 | 705.5 | 2.94 | | 40.87 |
| HJM-102 | IV | 1.98 | 0.08 | 1181.4 | 1139.7 | 1.40 | 14.77 | |
| | PO | 1.68 | 1.50 | 368.9 | 1887.6 | 3.55 | | 82.62 |
| HJM-104 | IV | 2.70 | 0.08 | 1360.1 | 1976.8 | 2.37 | 8.47 | |
| | PO | 2.21 | 3.33 | 586.3 | 3473.8 | 4.43 | | 89.41 |
| HJM-105 | IV | 1.82 | 0.08 | 1595.3 | 1908.9 | 1.56 | 8.83 | |
| | PO | 1.41 | 2.83 | 342.0 | 1789.5 | 3.29 | | 47.22 |

The data show that some compounds of the present disclosure have better pharmacokinetic properties and bioavailability in rats.

(4) Pharmacokinetic Study in Canine

1. Assay Steps:

Six ordinary Beagle dogs, male, weighing 10-12 kg, were randomly divided into 2 groups with 3 dogs in each group. The compounds of the present disclosure were administered by oral gavage (PO) and intravenous injection (IV), respectively, and the assay compounds were formulated with the corresponding vehicles.

Dosage: 1 mg/kg for intravenous injection and 5 mg/kg for oral administration.

Dosing volume: 5 mL/kg for intravenous injection and 10 mL/kg for oral administration.

The oral administration group was fasted overnight (10-14 h) before the assay, and drank water freely. After 4 hours of administration, they were fed uniformly. They were weighed before administration, and the dosage was calculated according to the body weight. 2. Blood collection time point and sample processing:

Intravenous administration: 0.083, 0.25, 0.5, 1, 2, 4, 8, 12 and 24 h after administration;

Oral gavage administration: 0.25, 0.5, 1, 2, 4, 6, 8, 12 and 24 h after administration;

Blood was collected from the veins of extremities, about 0.5-1 mL each time. The blood was anticoagulated with heparin sodium, placed on ice after collection, and centrifuged within 1 hour to separate the plasma (centrifugation conditions: 6800 g, 6 minutes, 2-8° C.). Plasma samples were stored in a −80° C. freezer prior to analysis.

3. Sample Assaying and Data Analysis

The concentration of each compound in canine plasma was determined by LC/MS/MS method.

Through the plasma drug concentration data at different time points, pharmacokinetic parameters were calculated using Phoenix WinNonlin 7.0, thereby providing parameters such as $AUC_{0-t}$, $AUC_{0-\infty}$, $MRT_{0-\infty}$, $C_{max}$, $T_{max}$, and $T_{1/2}$ and mean and standard deviation thereof.

Table 6 shows canine pharmacokinetic parameters of some compounds of the present disclosure.

| Compound No. | Way of administration | $T_{1/2}$ h | $T_{max}$ h | $C_{max}$ ng/mL | $AUC_{0-\infty}$ ng · h/mL | $MRT_{0-\infty}$ h | Cl mL/min/kg | F % |
|---|---|---|---|---|---|---|---|---|
| HJM-016 | IV | 5.87 | 0.08 | 1223.4 | 8840.1 | 8.39 | 1.92 | |
| | PO | 5.18 | 2.00 | 2900.1 | 27166.9 | 7.97 | | 62.50 |
| HJM-045 | IV | 4.13 | 0.08 | 1145.1 | 4501.9 | 5.35 | 3.70 | |
| | PO | 4.29 | 0.50 | 3704.3 | 20674.5 | 5.75 | | 90.95 |
| HJM-104 | IV | 1.67 | 0.08 | 864.02 | 3232.7 | 2.86 | 5.90 | |
| | PO | 2.09 | 1.00 | 3379.7 | 16519.9 | 3.53 | | 102.43 |

Vehicles:

HJM-016: 2% DMSO + 5% Solutol + 93% Saline

HJM-045: 2% DMSO + 98% Saline

HJM-104: 5% DMSO + 20% PG + 20% PEG400 + 55% Saline

The data show that some compounds of the present disclosure have better pharmacokinetic properties and bioavailability in canines.

(5) Pharmacodynamic Study

Mouse Karpas422 CDX Model

Female balb/c nude mice aged 6-8 weeks were selected and housed under SPF conditions (i.e., 20-22° C.; 40-70% relative humidity) in individual ventilated cages at constant temperature and humidity. There were 5 or fewer animals in each cage. Animals had access to dry pelleted food sterilized by irradiation and sterile drinking water. Karpas 422 human B-cell lymphoma cells were cultured in RPMI-1640 (Gibco, product No. 31800022) containing 15% fetal bovine serum (FBS, Gibco, product No. 10099141) and 0.1% penicillin/streptomycin solution (P/S). The cells were cultured in a sterile incubator at a temperature of 37° C., a relative humidity of 95%, and 5% $CO_2$. Karpas 422 cells cultured in vitro were maintained at a concentration between $0.5\text{-}2\times10^6$ cells/mL cells in suspension culture and passaged at a 1:3 dilution every 2-4 days. To establish the xenograft model, cells were collected, resuspended in PBS, mixed 1:1 by volume with Matrigel (BD) at a concentration of $5\times10^7$ cells/mL, and then injected subcutaneously into the right side of balb/c nude mice (Vital River) with $5\times10^6$ cells per animal. When tumors grew to about 150 $mm^3$, mice were divided into groups with 6 mice in each group. The mice were administered intragastrically, and the tumor size and mouse body weight were measured twice a week. The two largest diameters of the transplanted tumor, width (W) and length (L), were manually measured with a vernier caliper, and the tumor volume was estimated using the formula: $0.5\times L\times W^2$. After the assay, the mice were euthanized.

The assay compounds were prepared as a suspension in pure water containing 0.5% HPMC+0.5% Tween 80 as a solvent. The dosing volume was 10 mL/kg.

Figure 2:
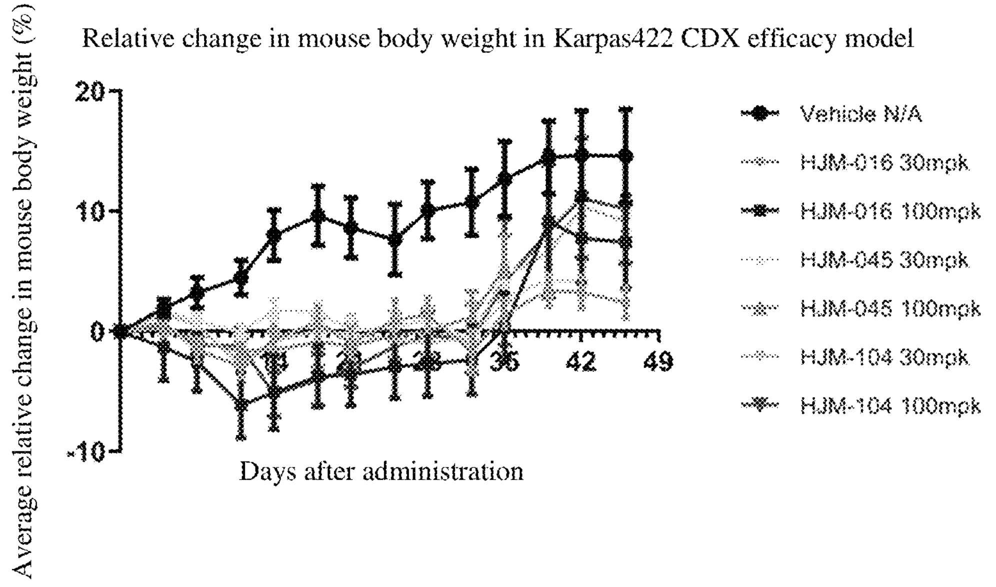
FIG. 2 shows the relative changes in the body weight of mice in the Karpas422 CDX efficacy study.

In this study, changes in mouse tumor volume and relative changes in mouse body weight were assayed, and the results were shown in FIGS. 1 and 2.

FIG. 1 and Table 7 show that the compounds HJM-016, HJM-045 and HJM-104 of the present disclosure have inhibitory effects on tumor growth at different dosages, all of which can achieve complete tumor disappearance and have good in vivo efficacy.

Table 7 shows tumor growth inhibition (TGI %) data of compounds of the present disclosure.

| Compound No. | Dosage | Day 11 after administration | Day 21 after administration |
|---|---|---|---|
| HJM-016 | 30 mg/kg | 8.5 | 56.1 |
| | 100 mg/kg | 52.3 | 105.39 |
| HJM-045 | 30 mg/kg | 0.25 | 60.06 |
| | 100 mg/kg | 10.7 | 81.43 |
| HJM-104 | 30 mg/kg | 39.4 | 93.29 |
| | 100 mg/kg | 88.9 | 111.9 |

FIG. 2 shows the relative changes in the body weight of mice with different dosages of the compounds HJM-016, HJM-045 and HJM-104 of the present disclosure. The body weight changes of the mice after administration were all less than 10%, indicating that the compounds of the present disclosure have better safety.

The above content is a further detailed description of the present disclosure in conjunction with specific alternative embodiments, and it cannot be assumed that the specific implementation of the present disclosure is limited to these descriptions. For those of ordinary skill in the technical field of the present disclosure, without departing from the concept of the present disclosure, some simple deductions or substitutions can also be made, all of which should be regarded as belonging to the protection scope of the present disclosure.

What is claimed is:

1. A compound of formula (X), or a tautomer, stereoisomer, prodrug, crystal form, pharmaceutically acceptable salt, hydrate or solvate thereof:

(X)

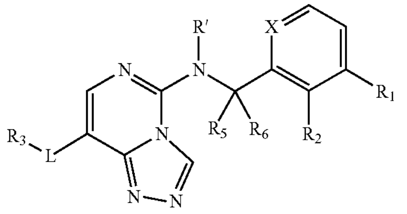

wherein

X is N or $C(R_x)$;

wherein $R_x$ is selected from H, halogen, $C_{1-6}$ alkyl, $C_{1-6}$ haloalkyl or $C_{1-6}$ alkoxy;

$R_1$ is selected from H, halogen, $C_{1-6}$ alkyl, $C_{1-6}$ haloalkyl or $C_{1-6}$ alkoxy;

$R_2$ is selected from H, halogen, $C_{1-6}$ alkyl, $C_{1-6}$ haloalkyl or $C_{1-6}$ alkoxy;

or $R_1$ and $R_2$ together form —$(CH_2)_p$Y—, —Y$(CH_2)_p$— or —Y$(CH_2)_p$Z— group;

wherein p is 1, 2, 3, 4 or 5;

Y is selected from O, S, NH or chemical bond;

Z is selected from O, S, NH or chemical bond;

R' is selected from H, $C_{1-6}$ alkyl or $C_{1-6}$ haloalkyl;

L is selected from —C(O)—N(R)—, —C(O)—O—, —N($R_3$')—C(O)—, —O—C(O)—, —$S(O)_q$—N(R)—, —$S(O)_q$—O—, —O—, —S—, —N(R")—, —$C_{1-4}$ alkylene- or —$C_{2-4}$ alkenylene-;

wherein R is selected from H, $C_{1-6}$ alkyl or $C_{1-6}$ haloalkyl;

$R_3$' is selected from H, $(CH_2)_m$—$C_{1-6}$ alkyl, $(CH_2)_m$—$C_{1-6}$ haloalkyl or $(CH_2)_n$—$C_{3-7}$ cycloalkyl;

R" is selected from H, $C_{1-6}$ alkyl or $C_{1-6}$ haloalkyl;

q is 0, 1 or 2;

$R_3$ is selected from $(CH_2)_m$—$C_{1-6}$ alkyl, $(CH_2)_m$—$C_{1-6}$ haloalkyl, $(CH_2)_n$—$C_{1-6}$ alkoxy, $(CH_2)_n$—$C_{1-6}$ haloalkoxy, $(CH_2)_n$—$NR_aR_b$, $(CH_2)_n$—$OR_a$, $(CH_2)_n$—$C_{3-7}$ cycloalkyl, $(CH_2)_n$-3- to 10-membered heterocyclyl, $(CH_2)_n$—$C_{6-10}$ aryl or $(CH_2)_n$-5- to 10-membered heteroaryl;

or, $R_3$, $R_3$' and the N atom to which they are attached together form a 4- to 7-membered heterocyclyl group;

wherein m is 0, 1, 2, 3, 4 or 5;

n is 0, 1, 2, 3, 4 or 5;

$R_a$ is selected from H, $C_{1-6}$ alkyl or $C_{1-6}$ haloalkyl;

$R_b$ is selected from H, $C_{1-6}$ alkyl or $C_{1-6}$ haloalkyl;

$R_5$ and $R_6$ are independently selected from H, D, $C_{1-6}$ alkyl or $C_{1-6}$ haloalkyl;

wherein $R_3$ is optionally substituted by one or more substituent groups selected from H, D, halogen, CN, OH, =O, $NR_cR_d$, $C_{1-6}$ alkyl, $C_{1-6}$ haloalkyl, $C_{1-6}$ alkoxy, $C_{3-7}$ cycloalkyl, 4- to 7-membered heterocyclyl, $C_{6-10}$ aryl, 5- to 10-membered heteroaryl, $(CH_2)_m$—$C_{1-6}$ alkyl, $(CH_2)_m$—$C_{1-6}$ haloalkyl, $(CH_2)_n$—$C_{1-6}$ alkoxy, $(CH_2)_n$—$C_{1-6}$ haloalkoxy, —O—$C_{3-7}$ cycloalkyl, —O-4- to 7-membered heterocyclyl, —O—$C_{6-10}$ aryl, —O-5- to 10-membered heteroaryl, —C(O)—$C_{1-6}$ alkyl, —C(O)—$C_{1-6}$ haloalkyl, —C(O)—$C_{3-7}$ cycloalkyl, —C(O)-4- to 7-membered heterocyclyl, —C(O)—$C_{6-10}$ aryl, —C(O)-5- to 10-membered heteroaryl, —$S(O)_q$—$C_{1-6}$ alkyl, —$S(O)_q$—$C_{1-6}$ haloalkyl, —$S(O)_q$—$C_{1-6}$ alkoxy, —$S(O)_q$—$C_{3-7}$ cycloalkyl, —$S(O)_q$-4- to 7-membered heterocyclyl, —$S(O)_q$—$C_{6-10}$ aryl or —$S(O)_q$-5- to 10-membered heteroaryl;

wherein $R_c$ is selected from H, $C_{1-6}$ alkyl, $C_{1-6}$ haloalkyl, —C(O)—$C_{3-7}$ cycloalkyl, —C(O)-4- to 7-membered heterocyclyl, —C(O)—$C_{6-10}$ aryl or —C(O)-5- to 10-membered heteroaryl;

$R_d$ is selected from H, $C_{1-6}$ alkyl, $C_{1-6}$ haloalkyl, —C(O)—$C_{3-7}$ cycloalkyl, —C(O)-4- to 7-membered heterocyclyl, —C(O)—$C_{6-10}$ aryl or —C(O)-5- to 10-membered heteroaryl;

wherein the alkyl, haloalkyl, alkoxy, haloalkoxy, cycloalkyl, heterocyclyl, aryl, heteroaryl, alkylene and alkenylene are optionally substituted with substituent groups selected from H, D, CN, OH, =O, halogen, $C_{1-6}$ alkyl, $C_{1-6}$ haloalkyl, $C_{1-6}$ alkoxy, $C_{3-7}$ cycloalkyl, 4- to 7-membered heterocyclyl, $C_{6-10}$ aryl, 5- to 10-membered heteroaryl, —O—$C_{3-7}$ cycloalkyl, —O-4- to 7-membered heterocyclyl, —O—$C_{6-10}$ aryl, —O-5- to 10-membered heteroaryl, —C(O)—$C_{1-6}$ alkyl, —C(O)—$C_{1-6}$ haloalkyl, —C(O)—$C_{3-7}$ cycloalkyl, —C(O)-4- to 7-membered heterocyclyl, —C(O)—$C_{6-10}$ aryl or —C(O)-5- to 10-membered heteroaryl, or substituted with one or more D, up to complete deuteration.

2. The compound, or the tautomer, stereoisomer, crystal form, pharmaceutically acceptable salt, hydrate or solvate thereof according to claim 1, which is a compound of formula (V):

(V)

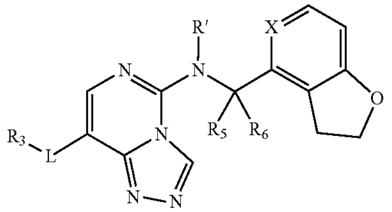

wherein

X is N or $C(R_x)$; alternatively, X is $C(R_x)$, wherein $R_x$ is selected from H, halogen, $C_{1-6}$ alkyl, $C_{1-6}$ haloalkyl or $C_{1-6}$ alkoxy; alternatively, $R_x$ is selected from H or halogen;

R' is selected from H, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration;

L is —C(O)—N(R)—, —C(O)—O—, —$S(O)_q$—N(R)— or —$S(O)_q$—O—;

wherein R is selected from H, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration;

q is 0, 1 or 2;

$R_3$ is selected from $(CR_7R_8)_m$—$C_{1-6}$ alkyl, $(CR_7R_8)_m$—$C_{1-6}$ haloalkyl, $(CR_7R_8)_n$—$C_{1-6}$ alkoxy, $(CR_7R_8)_n$—$C_{1-6}$ haloalkoxy, $(CR_7R_8)_n$—$NR_aR_b$, $(CR_7R_8)_n$—$C_{3-7}$ cycloalkyl, $(CR_7R_8)_n$-4- to 7-membered heterocyclyl, $(CR_7R_8)_n$—$C_{6-10}$ aryl or $(CR_7R_8)_n$-5- to 10-membered heteroaryl;

wherein m is 0, 1, 2, 3, 4 or 5;

n is 0, 1, 2, 3, 4 or 5;

$R_a$ is selected from H, $C_{1-6}$ alkyl or $C_{1-6}$ haloalkyl;
$R_b$ is selected from H, $C_{1-6}$ alkyl or $C_{1-6}$ haloalkyl;
$R_7$ and $R_8$ are independently selected from H, D, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration;
$R_5$ and $R_6$ are independently selected from H, D, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration; wherein $R_3$ is optionally substituted with a group selected from H, D, halogen, CN, OH, $C_{1-6}$ alkyl, $C_{1-6}$ haloalkyl, $C_{3-7}$ cycloalkyl, 4- to 7-membered heterocyclyl, $C_{6-10}$ aryl, 5- to 10-membered heteroaryl, $(CR_7R_8)_n$—$C_{1-6}$ alkoxy or —S(O)$_q$—$C_{1-6}$ alkyl;
wherein the alkyl, haloalkyl, alkoxy, haloalkoxy, cycloalkyl, heterocyclyl, aryl and heteroaryl are optionally substituted with one or more D, up to complete deuteration.

3. The compound of formula (V), or the tautomer, stereoisomer, crystal form, pharmaceutically acceptable salt, hydrate or solvate thereof according to claim 2,
wherein
X is C($R_x$),
wherein $R_x$ is selected from H or halogen;
R' is selected from H, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration;
L is —C(O)—N(R)—, —C(O)—O—, —S(O)$_q$—N(R)— or —S(O)$_q$—O—;
wherein R is selected from H, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration;
q is 0, 1 or 2;
$R_3$ is selected from $(CR_7R_8)_m$—$C_{1-6}$ alkyl, $(CR_7R_8)_m$—$C_{1-6}$ haloalkyl, $(CR_7R_8)_n$—$C_{1-6}$ alkoxy, $(CR_7R_8)_n$—$NR_aR_b$, $(CR_7R_8)_n$—$C_{3-7}$ cycloalkyl, $(CR_7R_8)_n$—$C_{6-10}$ aryl or $(CR_7R_8)_n$-5- to 10-membered heteroaryl;
wherein m is 0, 1, 2, 3, 4 or 5;
n is 0, 1, 2, 3, 4 or 5;
$R_a$ is selected from H, $C_{1-6}$ alkyl or $C_{1-6}$ haloalkyl;
$R_b$ is selected from H, $C_{1-6}$ alkyl or $C_{1-6}$ haloalkyl;
$R_7$ and $R_8$ are independently selected from H, D, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration;
$R_5$ and $R_6$ are independently selected from H, D, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration; wherein $R_3$ is optionally substituted with a group selected from H, D, halogen, $C_{1-6}$ alkyl, $C_{1-6}$ haloalkyl, $C_{1-6}$ alkoxy or $C_{3-7}$ cycloalkyl.

4. The compound of formula (V), or the tautomer, stereoisomer, crystal form, pharmaceutically acceptable salt, hydrate or solvate thereof according to claim 2, wherein
X is C($R_x$),
wherein $R_x$ is selected from H or halogen;
R' is selected from H, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration;
L is —C(O)—N(R)— or —C(O)—O—;
wherein R is selected from H, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration;
$R_3$ is selected from $(CR_7R_8)_m$—$C_{1-6}$ alkyl, $(CR_7R_8)_m$—$C_{1-6}$ haloalkyl, $(CR_7R_8)_n$—$C_{1-6}$ alkoxy, $(CR_7R_8)_n$—$NR^aR^b$ or $(CR_7R_8)_n$—$C_{3-4}$ cycloalkyl;
wherein m is 0, 1, 2, 3, 4 or 5;
n is 0, 1, 2, 3, 4 or 5;
$R_a$ is selected from H, $C_{1-6}$ alkyl or $C_{1-6}$ haloalkyl;
$R_b$ is selected from H, $C_{1-6}$ alkyl or $C_{1-6}$ haloalkyl;
$R_7$ and $R_8$ are independently selected from H or D;
$R_5$ and $R_6$ are independently selected from H or D;
wherein $R_3$ is optionally substituted with a group selected from H, D, $C_{1-6}$ alkyl, $C_{1-6}$ haloalkyl or $C_{1-6}$ alkoxy.

5. The compound of formula (V), or the tautomer, stereoisomer, crystal form, pharmaceutically acceptable salt, hydrate or solvate thereof according to claim 2, wherein
X is C($R_x$),
wherein $R_x$ is selected from H or halogen;
R' is selected from H, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration;
L is —C(O)—N(R)—;
wherein R is selected from H, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration;
$R_3$ is selected from $(CR_7R_8)_m$—$C_{1-6}$ haloalkyl or $(CR_7R_8)_n$—$C_{3-4}$ cycloalkyl;
wherein m is 0, 1, 2, 3, 4 or 5;
n is 0, 1, 2, 3, 4 or 5;
$R_7$ and $R_8$ are independently selected from H or D;
$R_5$ and $R_6$ are independently selected from H or D.

6. The compound, or the tautomer, stereoisomer, crystal form, pharmaceutically acceptable salt, hydrate or solvate thereof according to claim 1, which is a compound of formula (VI):

(VI)

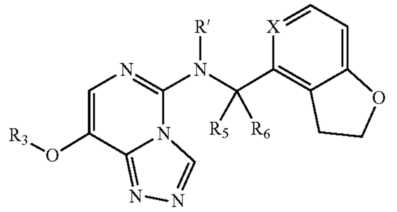

wherein
X is N or C($R_x$); alternatively, X is C($R_x$);
wherein $R_x$ is selected from H, halogen, $C_{1-6}$ alkyl, $C_{1-6}$ haloalkyl or $C_{1-6}$ alkoxy; alternatively, $R_x$ is selected from H or halogen;
R' is selected from H, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration;
$R_3$ is selected from $(CR_7R_8)_m$—$C_{1-6}$ alkyl, $(CR_7R_8)_m$—$C_{1-6}$ haloalkyl, $(CR_7R_8)_n$—$C_{3-7}$ cycloalkyl, $(CR_7R_8)_n$-4- to 7-membered heterocyclyl, $(CR_7R_8)_n$—$C_{6-10}$ aryl or $(CR_7R_8)_n$-5- to 10-membered heteroaryl;
wherein m is 0, 1, 2, 3, 4 or 5;
n is 0, 1, 2, 3, 4 or 5;
$R_7$ and $R_8$ are independently selected from H, D, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration; or $R_7$ and $R_8$ on the same carbon atom are combined to form =O;

$R_5$ and $R_6$ are independently selected from H, D, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration; wherein $R_3$ is optionally substituted by one or more substituent groups selected from H, D, halogen, CN, OH, =O, $NR_cR_d$, $C_{1-6}$ alkyl, $C_{1-6}$ haloalkyl, $C_{1-6}$ alkoxy, $C_{3-7}$ cycloalkyl, 4- to 7-membered heterocyclyl, $C_{6-10}$ aryl, 5- to 10-membered heteroaryl, —O—$C_{3-7}$ cycloalkyl, —O-4- to 7-membered heterocyclyl, —O—$C_{6-10}$ aryl, —O-5- to 10-membered heteroaryl, —C(O)—$C_{1-6}$ alkyl, —C(O)—$C_{1-6}$ haloalkyl, —C(O)—$C_{3-7}$ cycloalkyl, —C(O)-4- to 7-membered heterocyclyl, —C(O)—$C_{6-10}$ aryl, or —C(O)-5- to 10-membered heteroaryl;

wherein $R_c$ is selected from H, $C_{1-6}$ alkyl, $C_{1-6}$ haloalkyl, —C(O)—$C_{3-7}$ cycloalkyl, —C(O)-4- to 7-membered heterocyclyl, —C(O)—$C_{6-10}$ aryl or —C(O)-5- to 10-membered heteroaryl;

$R_d$ is selected from H, $C_{1-6}$ alkyl, $C_{1-6}$ haloalkyl, —C(O)—$C_{3-7}$ cycloalkyl, —C(O)-4- to 7-membered heterocyclyl, —C(O)—$C_{6-10}$ aryl or —C(O)-5- to 10-membered heteroaryl;

wherein the alkyl, haloalkyl, alkoxy, cycloalkyl, heterocyclyl, aryl and heteroaryl are optionally substituted with substituent groups selected from H, D, CN, OH, =O, halogen, $C_{1-6}$ alkyl, $C_{1-6}$ haloalkyl, $C_{1-6}$ alkoxy, $C_{3-7}$ cycloalkyl, 4- to 7-membered heterocyclyl, $C_{6-10}$ aryl, 5- to 10-membered heteroaryl, —O—$C_{3-7}$ cycloalkyl, —O-4- to 7-membered heterocyclyl, —O—$C_{6-10}$ aryl, —O-5- to 10-membered heteroaryl, —C(O)—$C_{1-6}$ alkyl, —C(O)—$C_{1-6}$ haloalkyl, —C(O)—$C_{3-7}$ cycloalkyl, —C(O)-4- to 7-membered heterocyclyl, —C(O)—$C_{6-10}$ aryl, or —C(O)-5- to 10-membered heteroaryl, or substituted with one or more D, up to complete deuteration;

alternatively, wherein $R_3$ is optionally substituted by one or more substituent groups selected from H, D, halogen, CN, OH, =O, $NR_cR_d$, $C_{1-6}$ alkyl, $C_{1-6}$ haloalkyl, $C_{1-6}$ alkoxy, $C_{3-7}$ cycloalkyl, —C(O)—$C_{1-6}$ alkyl, —C(O)—$C_{3-7}$ cycloalkyl or —O—$C_{6-10}$ aryl;

wherein $R_c$ is selected from H, $C_{1-6}$ alkyl, $C_{1-6}$ haloalkyl or —C(O)—$C_{3-7}$ cycloalkyl;

$R_d$ is selected from H, $C_{1-6}$ alkyl, $C_{1-6}$ haloalkyl or —C(O)—$C_{3-7}$ cycloalkyl;

wherein the alkyl, haloalkyl, alkoxy, cycloalkyl, heterocyclyl, aryl and heteroaryl are optionally substituted with substituent groups selected from H, D, CN, =O, halogen, $C_{1-6}$ alkyl, $C_{1-6}$ haloalkyl, $C_{1-6}$ alkoxy or —C(O)—$C_{1-6}$ alkyl, or substituted with one or more D, up to complete deuteration;

alternatively, wherein

X is C($R_x$);

wherein $R_x$ is selected from H or halogen;

R' is selected from H, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration;

$R_3$ is selected from $(CR_7R_8)_m$—$C_{1-6}$ alkyl, $(CR_7R_8)_m$—$C_{1-6}$ haloalkyl, $(CR_7R_8)_n$—$C_{3-7}$ cycloalkyl or $(CR_7R_8)_n$-4- to 7-membered heterocyclyl only containing O as heteroatom;

wherein m is 0, 1, 2, 3, 4 or 5;

n is 0, 1, 2, 3, 4 or 5;

$R_7$ and $R_8$ are independently selected from H, D, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration;

$R_5$ and $R_6$ are independently selected from H, D, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration; wherein $R_3$ is optionally substituted with a group selected from H, D, $C_{1-6}$ alkyl, $C_{1-6}$ haloalkyl or $C_{1-6}$ alkoxy;

alternatively, wherein

X is C($R_x$);

wherein $R_x$ is selected from H or halogen;

R' is selected from H, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration;

$R_3$ is selected from $(CR_7R_8)_m$—$C_{1-6}$ alkyl, $(CR_7R_8)_m$—$C_{1-6}$ haloalkyl or $(CR_7R_8)_n$-4- to 7-membered heterocyclyl only containing O as heteroatom;

wherein m is 0, 1, 2, 3, 4 or 5;

n is 0, 1, 2, 3, 4 or 5;

$R_7$ and $R_8$ are independently selected from H, D, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration;

$R_5$ and $R_6$ are independently selected from H, D, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration; wherein $R_3$ is optionally substituted with a group selected from H, D, $C_{1-6}$ alkyl, $C_{1-6}$ haloalkyl or $C_{1-6}$ alkoxy.

7. The compound, or the tautomer, stereoisomer, crystal form, pharmaceutically acceptable salt, hydrate or solvate thereof according to claim 1, which is a compound of formula (VII):

(VII)

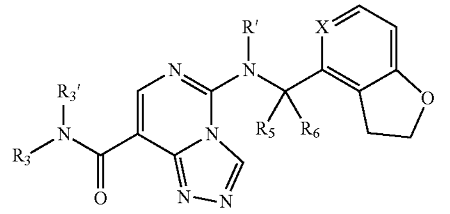

wherein

X is N or C($R_x$); alternatively, X is C($R_x$);

wherein $R_x$ is selected from H, halogen, $C_{1-6}$ alkyl, $C_{1-6}$ haloalkyl or $C_{1-6}$ alkoxy; alternatively, $R_x$ is selected from H or halogen;

R' is selected from H, $C_{1-6}$ alkyl or $C_{1-6}$ haloalkyl;

$R_3$ is selected from $(CR_7R_8)_m$—$C_{1-6}$ alkyl, $(CR_7R_8)_m$—$C_{1-6}$ haloalkyl, $(CR_7R_8)_n$—$C_{3-7}$ cycloalkyl, $(CR_7R_8)_n$-4- to 7-membered heterocyclyl, $(CR_7R_8)_n$—$C_{6-10}$ aryl or $(CR_7R_8)_n$-5- to 10-membered heteroaryl;

$R_3$' is selected from H, $(CR_7R_8)_m$—$C_{1-6}$ alkyl, $(CR_7R_8)_m$—$C_{1-6}$ haloalkyl or $(CR_7R_8)_n$—$C_{3-7}$ cycloalkyl; or, $R_3$, $R_3$' and the N atom to which they are attached together form a 4- to 7-membered heterocyclyl group;

wherein m is 0, 1, 2, 3, 4 or 5;

n is 0, 1, 2, 3, 4 or 5;

$R_7$ and $R_8$ are independently selected from H, D, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration; or $R_7$ and $R_8$ on the same carbon atom are combined to form ═O;

$R_5$ and $R_6$ are independently selected from H, D, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration; wherein $R_3$ is optionally substituted with one or more groups selected from H, D, halogen, $C_{1-6}$ alkyl, $C_{1-6}$ haloalkyl or $C_{1-6}$ alkoxy.

8. The compound of formula (VII), or the tautomer, stereoisomer, crystal form, pharmaceutically acceptable salt, hydrate or solvate thereof according to claim 7, wherein X is $C(R_x)$, wherein $R_x$ is selected from H or halogen;

R' is selected from H, $C_{1-6}$ alkyl or $C_{1-6}$ haloalkyl;

$R_3$ is selected from $(CR_7R_8)_m$—$C_{1-6}$ alkyl, $(CR_7R_8)_m$—$C_{1-6}$ haloalkyl or $(CR_7R_8)_n$—$C_{3-7}$ cycloalkyl;

$R_3$' is selected from H, $(CR_7R_8)_m$—$C_{1-6}$ alkyl, $(CR_7R_8)_m$—$C_{1-6}$ haloalkyl or $(CR_7R_8)_n$—$C_{3-7}$ cycloalkyl;

or, $R_3$, $R_3$' and the N atom to which they are attached together form a 4- to 7-membered heterocyclyl group;

m is 0, 1, 2, 3, 4 or 5;

n is 0, 1, 2, 3, 4 or 5;

$R_7$ and $R_8$ are independently selected from H, D, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration;

$R_5$ and $R_6$ are independently selected from H, D, $C_{1-6}$ alkyl or $C_{1-6}$ haloalkyl, wherein the $C_{1-6}$ alkyl or $C_{1-6}$ haloalkyl is optionally substituted with 1, 2, 3, 4, 5, 6, 7, 8 or 9 D, up to complete deuteration; wherein $R_3$ is optionally substituted with one or more groups selected from H, D, halogen, $C_{1-6}$ alkyl, $C_{1-6}$ haloalkyl or $C_{1-6}$ alkoxy.

9. The compound, or the tautomer, stereoisomer, crystal form, pharmaceutically acceptable salt, hydrate or solvate thereof according to claim 1, which is a compound of formula (I):

(I)

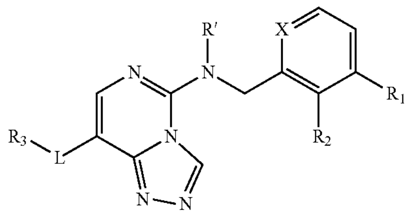

wherein

X is N or $C(R_x)$;

wherein $R_x$ is selected from H, halogen, $C_{1-6}$ alkyl, $C_{1-6}$ haloalkyl or $C_{1-6}$ alkoxy;

$R_1$ is selected from H, halogen, $C_{1-6}$ alkyl, $C_{1-6}$ haloalkyl or $C_{1-6}$ alkoxy;

$R_2$ is selected from H, halogen, $C_{1-6}$ alkyl, $C_{1-6}$ haloalkyl or $C_{1-6}$ alkoxy;

or $R_1$ and $R_2$ together form-$(CH_2)$ p Y—, —$Y(CH_2)_p$— or —$Y(CH_2)_pZ$— group;

wherein p is 1, 2, 3, 4 or 5;

Y is selected from O, S, NH or chemical bond;

Z is selected from O, S, NH or chemical bond;

R' is selected from H, $C_{1-6}$ alkyl or $C_{1-6}$ haloalkyl;

L is selected from —C(O)—N(R)—, —N($R_3$')—C(O)—, —O—, —S—, —N(R")—, —$C_{1-4}$ alkylene- or —$C_{2-4}$ alkenylene-;

wherein R is selected from H, $C_{1-6}$ alkyl or $C_{1-6}$ haloalkyl;

$R_3$' is selected from H, $(CH_2)_m$—$C_{1-6}$ alkyl, $(CH_2)_m$—$C_{1-6}$ haloalkyl or $(CH_2)_n$—$C_{3-7}$ cycloalkyl;

R" is selected from H, $C_{1-6}$ alkyl or $C_{1-6}$ haloalkyl;

$R_3$ is selected from $(CH_2)_m$—$C_{1-6}$ alkyl, $(CH_2)_m$—$C_{1-6}$ haloalkyl, $(CH_2)_n$—$C_{1-6}$ alkoxy, $(CH_2)_n$—$C_{1-6}$ haloalkoxy, $(CH_2)_n$—$C_{3-7}$ cycloalkyl, $(CH_2)_n$-3- to 10-membered heterocyclyl, $(CH_2)_n$—$C_{6-10}$ aryl or $(CH_2)_n$-5- to 10-membered heteroaryl;

or, $R_3$, $R_3$' and the N atom to which they are attached together form a 4- to 7-membered heterocyclyl group;

wherein m is 0, 1, 2, 3, 4 or 5;

n is 0, 1, 2, 3, 4 or 5.

10. The compound, or the tautomer, stereoisomer, crystal form, pharmaceutically acceptable salt, hydrate or solvate thereof according to claim 9, which is a compound of formula (II):

(II)

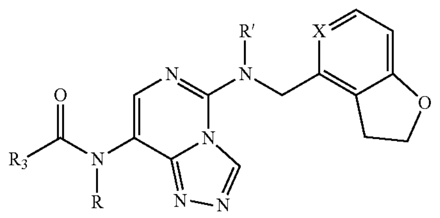

wherein

X is N or $C(R_x)$; alternatively, X is $C(R_x)$;

wherein $R_x$ is selected from H, halogen, $C_{1-6}$ alkyl, $C_{1-6}$ haloalkyl or $C_{1-6}$ alkoxy; alternatively, $R_x$ is selected from H or halogen;

R' is selected from H, $C_{1-6}$ alkyl or $C_{1-6}$ haloalkyl;

R is selected from H, $C_{1-6}$ alkyl or $C_{1-6}$ haloalkyl;

$R_3$ is selected from $(CH_2)_m$—$C_{1-6}$ alkyl, $(CH_2)_m$—$C_{1-6}$ haloalkyl, $(CH_2)_n$—$C_{1-6}$ alkoxy, $(CH_2)_n$—$C_{1-6}$ haloalkoxy, $(CH_2)_n$—$C_{3-7}$ cycloalkyl, $(CH_2)_n$-4- to 7-membered heterocyclyl, $(CH_2)_n$—$C_{6-10}$ aryl or $(CH_2)_n$-5- to 10-membered heteroaryl;

wherein m is 0, 1, 2, 3, 4 or 5;

n is 0, 1, 2, 3, 4 or 5;

alternatively, wherein

X is N or $C(R_x)$; alternatively, X is $C(R_x)$;

wherein $R_x$ is selected from H, halogen, $C_{1-6}$ alkyl or $C_{1-6}$ haloalkyl; alternatively, $R_x$ is selected from H or halogen;

R' is selected from H, $C_{1-6}$ alkyl or $C_{1-6}$ haloalkyl;

R is selected from H, $C_{1-6}$ alkyl or $C_{1-6}$ haloalkyl;

$R_3$ is selected from $(CH_2)_m$—$C_{1-6}$ alkyl, $(CH_2)_m$—$C_{1-6}$ haloalkyl, $(CH_2)_n$—$C_{1-6}$ alkoxy, $(CH_2)_n$—$C_{1-6}$ haloalkoxy, $(CH_2)_n$—$C_{3-4}$ cycloalkyl or $(CH_2)_n$—$C_{6-10}$ aryl;

wherein m is 0, 1, 2, 3, 4 or 5;

n is 0, 1, 2, 3, 4 or 5;

alternatively, wherein

X is N or $C(R_x)$; alternatively, X is $C(R_x)$;

wherein $R_x$ is selected from H, halogen, $C_{1-6}$ alkyl or $C_{1-6}$ haloalkyl; alternatively, $R_x$ is selected from H or halogen;

R' is selected from H, $C_{1-6}$ alkyl or $C_{1-6}$ haloalkyl;

R is selected from H, $C_{1-6}$ alkyl or $C_{1-6}$ haloalkyl;

$R_3$ is selected from $(CH_2)_m$—$C_{1-6}$ alkyl, $(CH_2)_m$—$C_{1-6}$ haloalkyl or $(CH_2)_n$—$C_{3-4}$ cycloalkyl; alternatively, $R_3$ is selected from $(CH_2)_m$—$C_{1-6}$ haloalkyl or $(CH_2)_n$—$C_{3-4}$ cycloalkyl;

wherein m is 0, 1, 2, 3, 4 or 5;

n is 0, 1, 2, 3, 4 or 5;

alternatively, wherein

X is $C(R_x)$;

wherein $R_x$ is selected from H or halogen;

R' is selected from H, $C_{1-6}$ alkyl or $C_{1-6}$ haloalkyl;

R is selected from H, $C_{1-6}$ alkyl or $C_{1-6}$ haloalkyl;

$R_3$ is selected from $(CH_2)_m$—$C_{1-6}$ haloalkyl or $(CH_2)_n$—$C_{3-4}$ cycloalkyl;

wherein m is 0, 1, 2 or 3;

n is 0, 1, 2 or 3.

11. The compound, or the tautomer, stereoisomer, crystal form, pharmaceutically acceptable salt, hydrate or solvate thereof according to claim 9, which is a compound of formula (III):

(III)

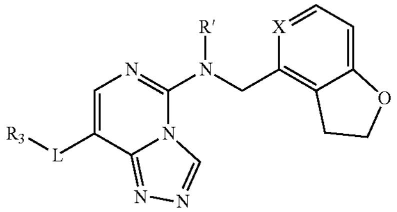

wherein

X is N or $C(R_x)$; alternatively, X is $C(R_x)$;

wherein $R_x$ is selected from H, halogen, $C_{1-6}$ alkyl, $C_{1-6}$ haloalkyl or $C_{1-6}$ alkoxy; alternatively, $R_x$ is selected from H or halogen;

R' is selected from H, $C_{1-6}$ alkyl or $C_{1-6}$ haloalkyl;

L is selected from —O—, —S—, —N(R")—, —$C_{1-4}$ alkylene- or —$C_{2-4}$ alkenylene-; alternatively, L is —O—;

wherein R" is selected from H, $C_{1-6}$ alkyl or $C_{1-6}$ haloalkyl;

$R_3$ is selected from $(CH_2)_m$—$C_{1-6}$ alkyl, $(CH_2)_m$—$C_{1-6}$ haloalkyl, $(CH_2)_n$—$C_{1-6}$ alkoxy, $(CH_2)_n$—$C_{1-6}$ haloalkoxy, $(CH_2)_n$—$C_{3-7}$ cycloalkyl, $(CH_2)_n$-4- to 7-membered heterocyclyl, $(CH_2)_n$—$C_{6-10}$ aryl or $(CH_2)_n$-5- to 10-membered heteroaryl; alternatively, $R_3$ is selected from $(CH_2)_m$—$C_{1-6}$ alkyl, $(CH_2)_m$—$C_{1-6}$ haloalkyl, $(CH_2)_n$—$C_{3-7}$ cycloalkyl, $(CH_2)_n$-4- to 7-membered heterocyclyl, $(CH_2)_n$—$C_{6-10}$ aryl or $(CH_2)_n$-5- to 10-membered heteroaryl;

wherein m is 0, 1, 2, 3, 4 or 5;

n is 0, 1, 2, 3, 4 or 5;

alternatively, wherein

X is $C(R_x)$;

wherein $R_x$ is selected from H or halogen;

R' is selected from H, $C_{1-6}$ alkyl or $C_{1-6}$ haloalkyl;

L is —O—;

$R_3$ is selected from $(CH_2)_n$—$C_{3-7}$ cycloalkyl or $(CH_2)_n$-4- to 7-membered heterocyclyl only containing O as heteroatom;

wherein m is 0, 1, 2, 3, 4 or 5;

n is 0, 1, 2, 3, 4 or 5;

alternatively, wherein

X is N or $C(R_x)$; alternatively, X is $C(R_x)$;

wherein $R_x$ is selected from H, halogen, $C_{1-6}$ alkyl or $C_{1-6}$ haloalkyl; alternatively, wherein $R_x$ is selected from H or halogen;

R' is selected from H, $C_{1-6}$ alkyl or $C_{1-6}$ haloalkyl;

L is O;

$R_3$ is selected from $(CH_2)_m$—$C_{1-6}$ alkyl, $(CH_2)_m$—$C_{1-6}$ haloalkyl, $(CH_2)_n$—$C_{3-7}$ cycloalkyl or $(CH_2)_n$-5- to 6-membered heteroaryl containing O as heteroatom;

wherein m is 0, 1, 2, 3, 4 or 5;

n is 0, 1, 2, 3, 4 or 5;

alternatively, wherein

X is N or $C(R_x)$; alternatively, X is $C(R_x)$;

wherein $R_x$ is selected from H, halogen, $C_{1-6}$ alkyl or $C_{1-6}$ haloalkyl; alternatively, wherein $R_x$ is selected from H or halogen;

R' is selected from H, $C_{1-6}$ alkyl or $C_{1-6}$ haloalkyl;

L is —O—;

$R_3$ is selected from $(CH_2)_m$—$C_{1-6}$ alkyl, $(CH_2)_m$—$C_{1-6}$ haloalkyl or $(CH_2)_n$—$C_{3-7}$ cycloalkyl;

wherein m is 0, 1, 2, 3, 4 or 5;

n is 0, 1, 2, 3, 4 or 5.

12. The compound, or the tautomer, stereoisomer, crystal form, pharmaceutically acceptable salt, hydrate or solvate thereof according to claim 9, which is a compound of formula (IV):

(IV)

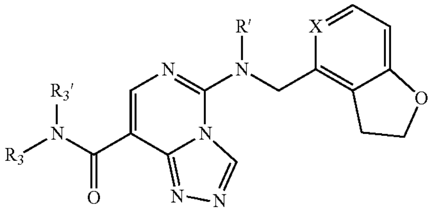

wherein

X is N or $C(R_x)$; alternatively, X is $C(R_x)$;

wherein $R_x$ is selected from H, halogen, $C_{1-6}$ alkyl, $C_{1-6}$ haloalkyl or $C_{1-6}$ alkoxy; alternatively, $R_x$ is selected from H or halogen;

R' is selected from H, $C_{1-6}$ alkyl or $C_{1-6}$ haloalkyl;

$R_3$ is selected from $(CH_2)_m$—$C_{1-6}$ alkyl, $(CH_2)_m$—$C_{1-6}$ haloalkyl, $(CH_2)_n$—$C_{3-7}$ cycloalkyl, $(CH_2)_n$-4- to 7-membered heterocyclyl, $(CH_2)_n$—$C_{6-10}$ aryl or $(CH_2)_n$-5- to 10-membered heteroaryl;

$R_3$' is selected from H, $(CH_2)_m$—$C_{1-6}$ alkyl, $(CH_2)_m$—$C_{1-6}$ haloalkyl or $(CH_2)_n$—$C_{3-7}$ cycloalkyl;

or, $R_3$, $R_3$' and the N atom to which they are attached together form a 4- to 7-membered heterocyclyl group;

wherein m is 0, 1, 2, 3, 4 or 5;

n is 0, 1, 2, 3, 4 or 5.

13. The compound of formula (IV), or the tautomer, stereoisomer, crystal form, pharmaceutically acceptable salt, hydrate or solvate thereof according to claim 12, wherein X is N or $C(R_x)$; alternatively, X is $C(R_x)$;

wherein $R_x$ is selected from H, halogen, $C_{1-6}$ alkyl, $C_{1-6}$ haloalkyl or $C_{1-6}$ alkoxy; alternatively, $R_x$ is selected from H or halogen;

R' is selected from H, $C_{1-6}$ alkyl or $C_{1-6}$ haloalkyl;

$R_3$ is selected from $(CH_2)_m$—$C_{1-6}$ alkyl, $(CH_2)_m$—$C_{1-6}$ haloalkyl or $(CH_2)_n$—$C_{3-7}$ cycloalkyl;

$R_3$' is selected from H, $(CH_2)_m$—$C_{1-6}$ alkyl, $(CH_2)_m$—$C_{1-6}$ haloalkyl or $(CH_2)_n$—$C_{3-7}$ cycloalkyl;

or, $R_3$, $R_3$' and the N atom to which they are attached together form a 4- to 7-membered heterocyclyl group;

wherein m is 0, 1, 2, 3, 4 or 5;

n is 0, 1, 2, 3, 4 or 5.

14. The compound, or the tautomer, stereoisomer, crystal form, pharmaceutically acceptable salt, hydrate or solvate thereof according to claim 1, wherein the compound is selected from:

HJM-005

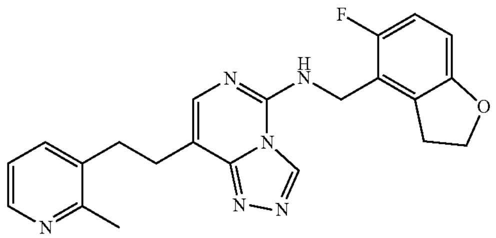

HJM-006

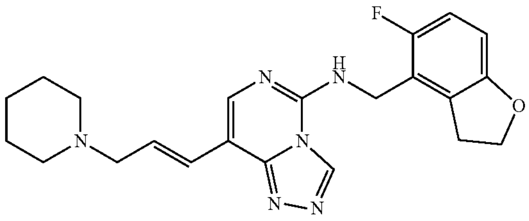

HJM-007

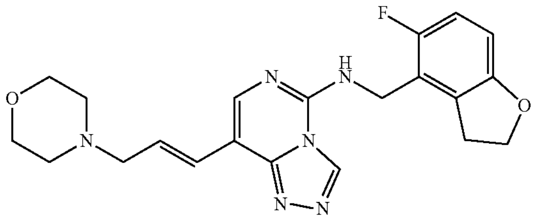

HJM-008

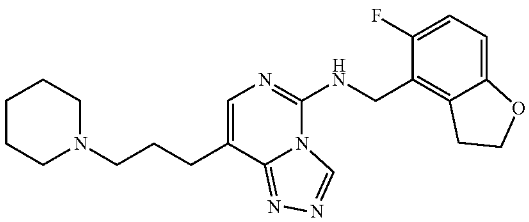

HJM-009

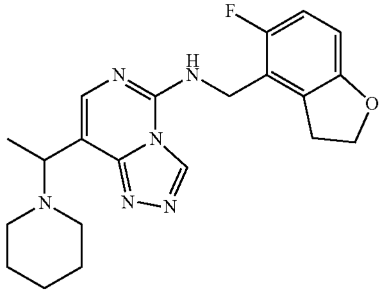

-continued

HJM-010

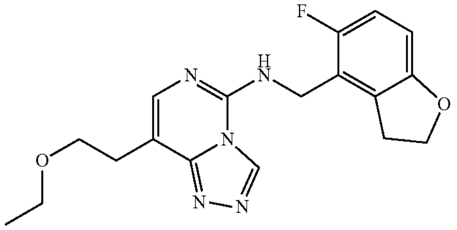

HJM-011

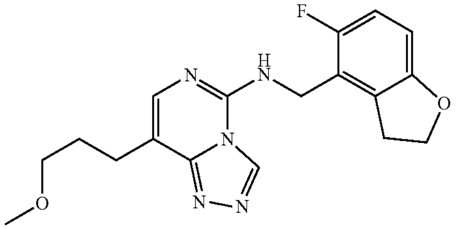

HJM-012

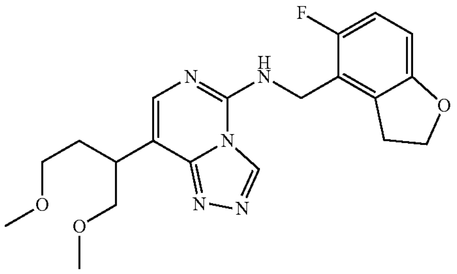

HJM-013

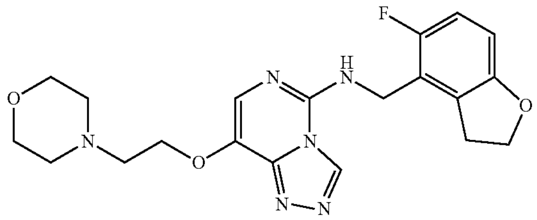

HJM-014

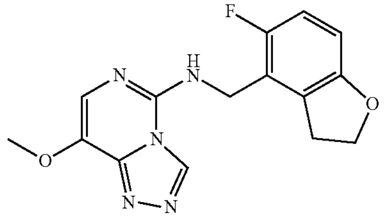

HJM-015

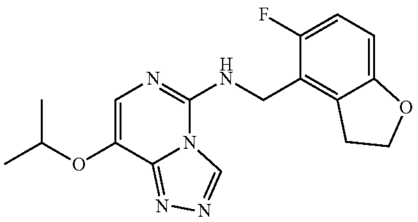

-continued
HJM-016
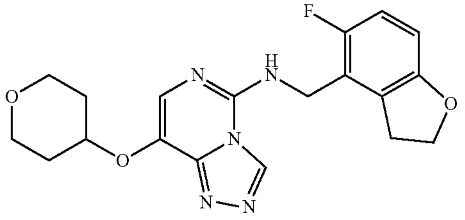
HJM-017
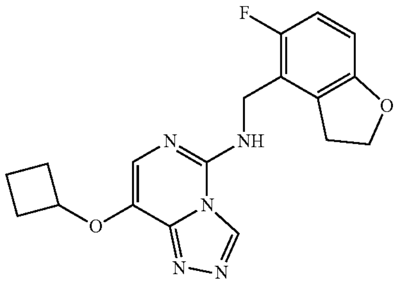
HJM-018
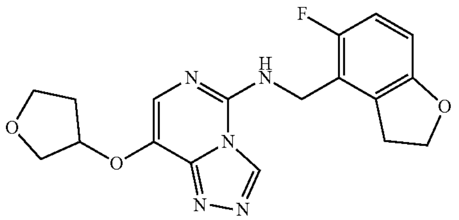
HJM-019
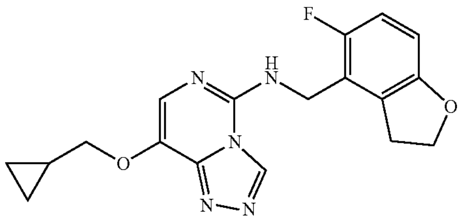
HJM-020
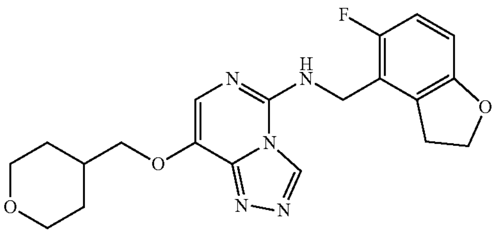
HJM-021
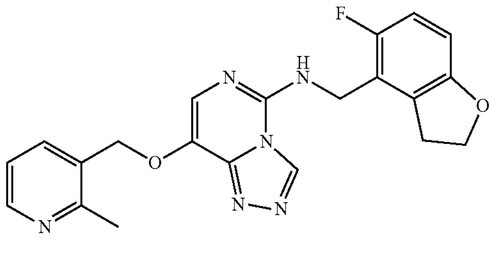
-continued
HJM-022
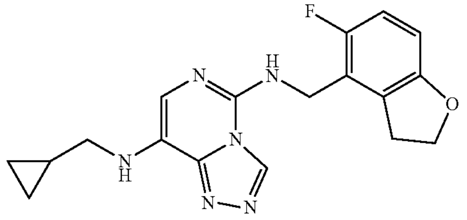
HJM-023
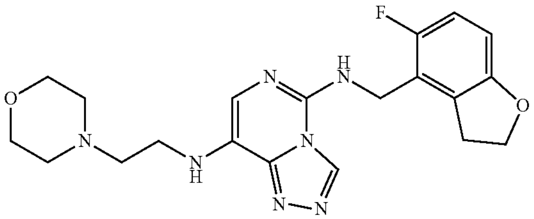
HJM-024
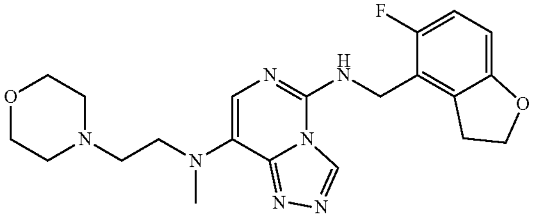
HJM-025
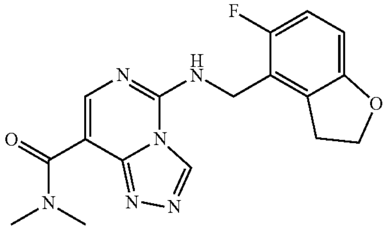
HJM-026
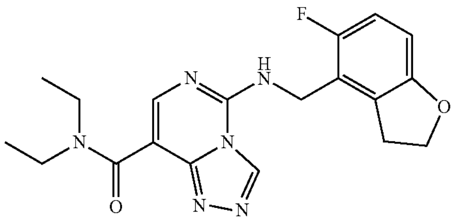
HJM-027
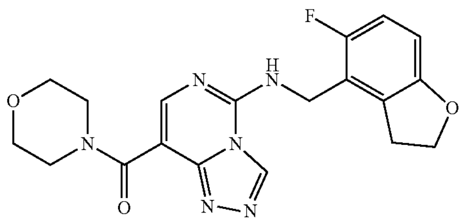

-continued
HJM-028
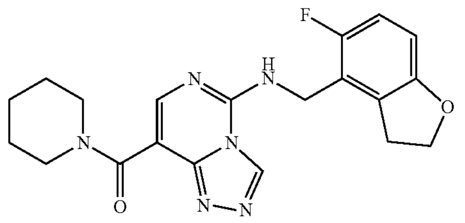
HJM-029
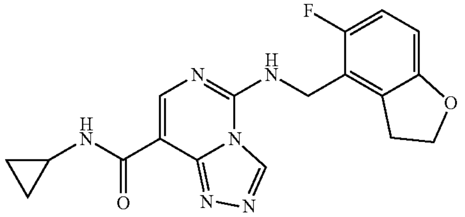
HJM-030
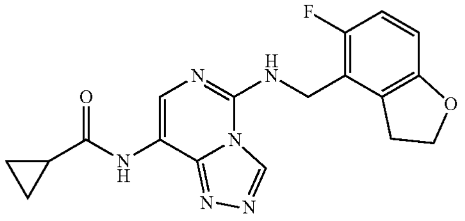
HJM-031
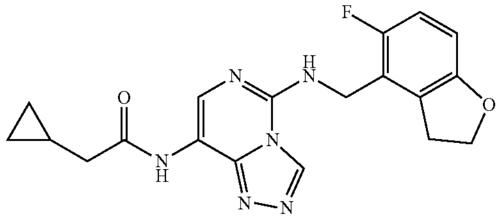
HJM-032
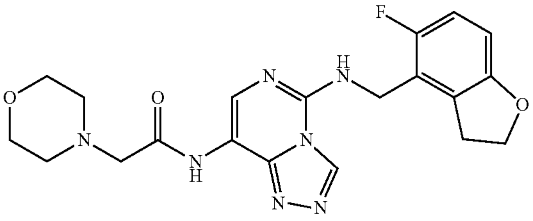
HJM-033
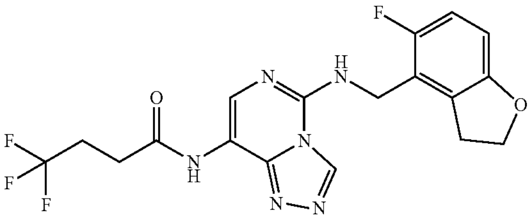
-continued
HJM-034
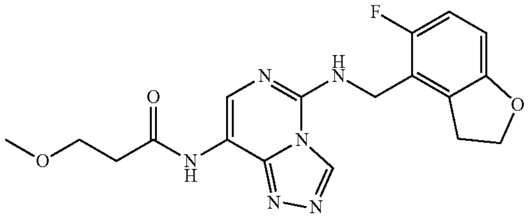
HJM-035
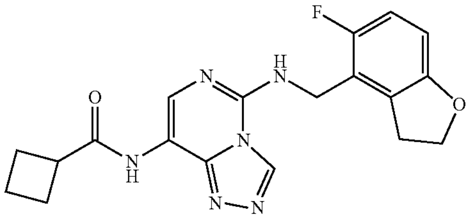
HJM-036
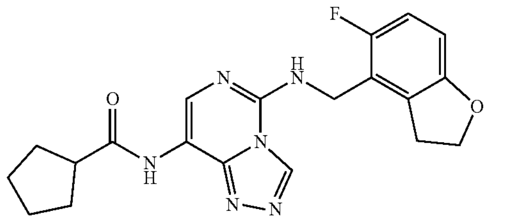
HJM-037
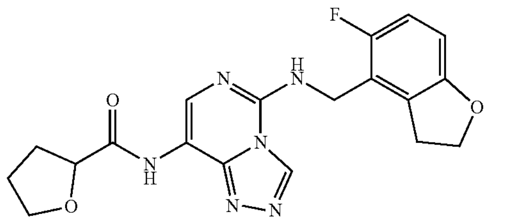
HJM-038
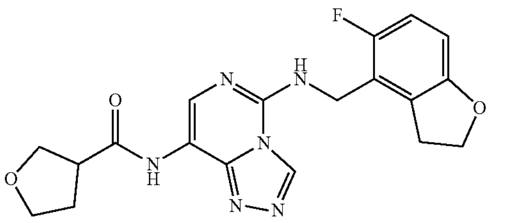
HJM-039
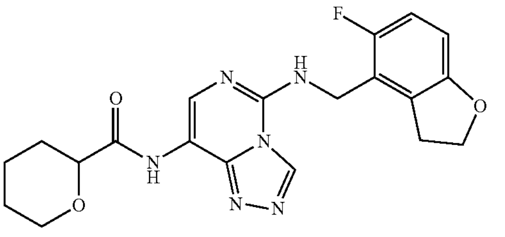

HJM-040
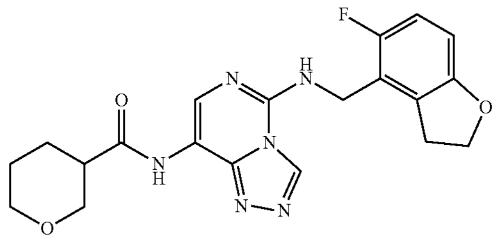
HJM-041
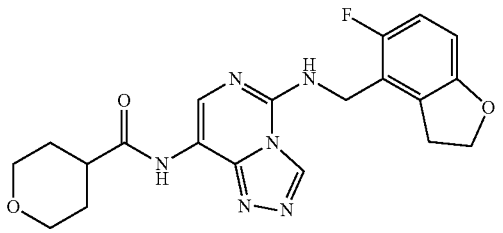
HJM-042
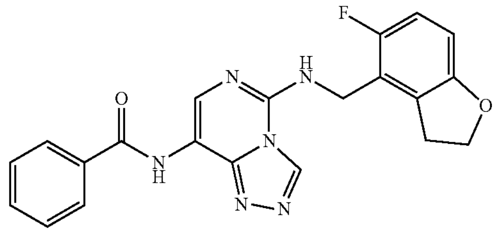
HJM-043
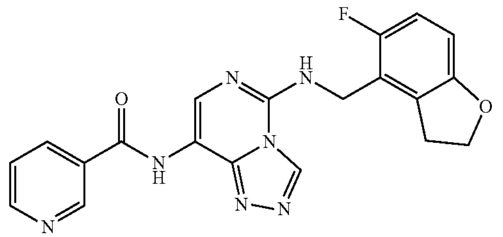
HJM-044
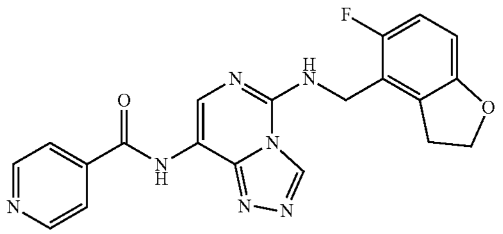
HJM-045
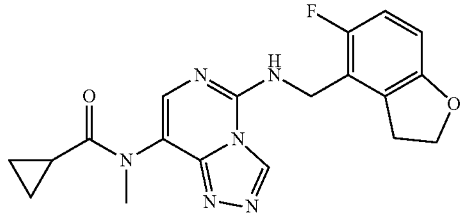
HJM-046
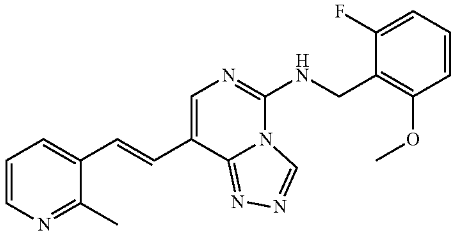
HJM-047
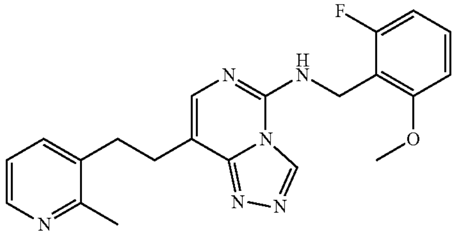
HJM-048
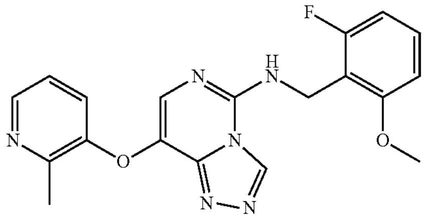
HJM-049
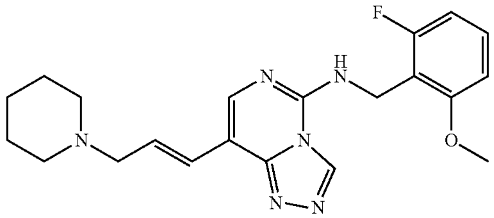
HJM-065
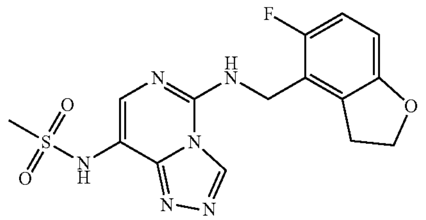
HJM-066
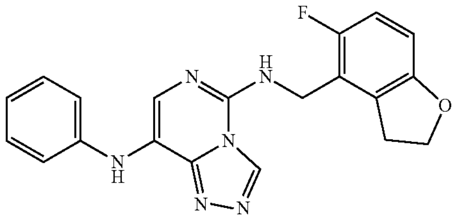
HJM-069
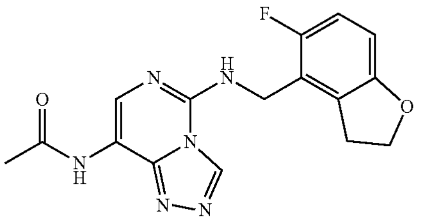

-continued
HJM-070
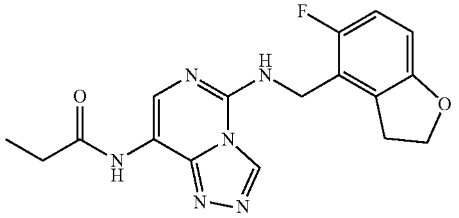
HJM-071
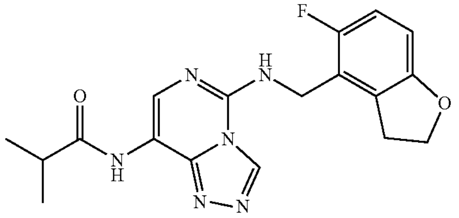
HJM-072
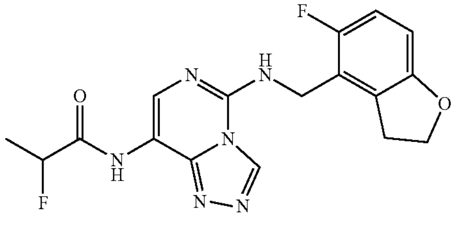
HJM-073
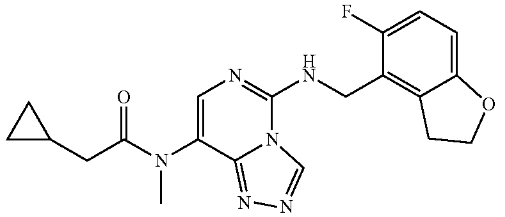
HJM-074
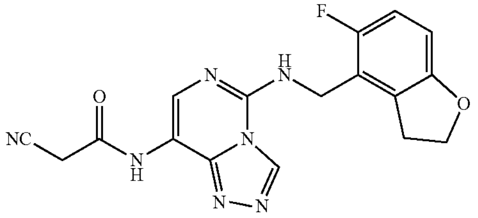
HJM-075
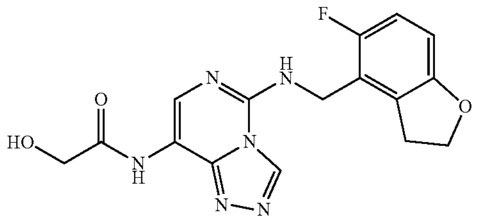
HJM-076
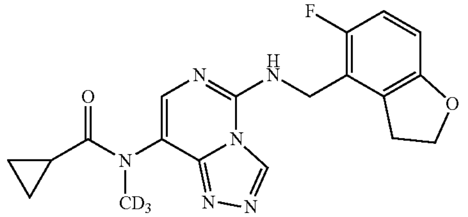
-continued
HJM-077
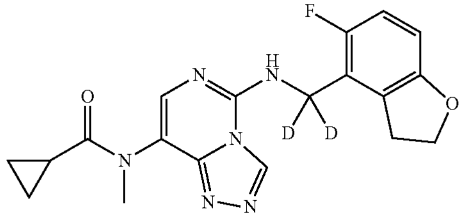
HJM-078
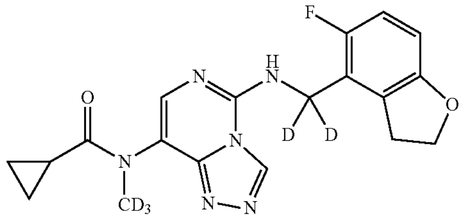
HJM-079
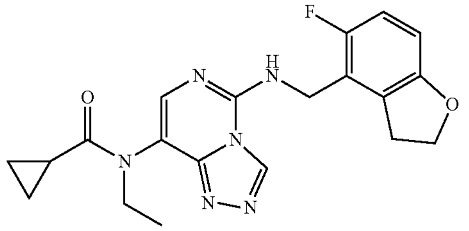
HJM-080
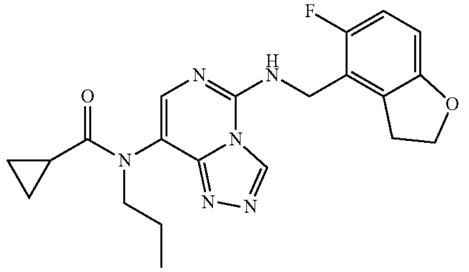
HJM-081
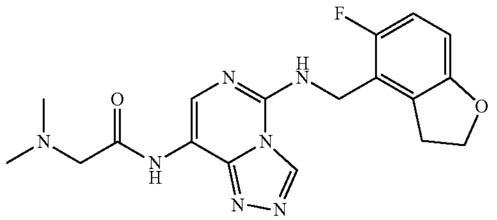
HJM-082
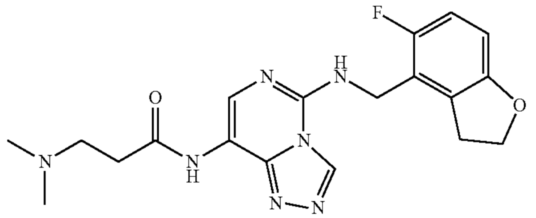

-continued
HJM-083
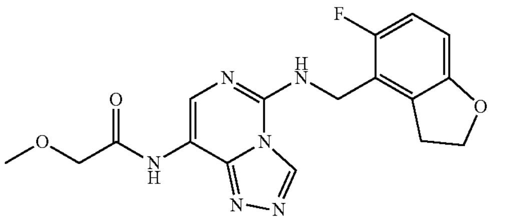
HJM-084
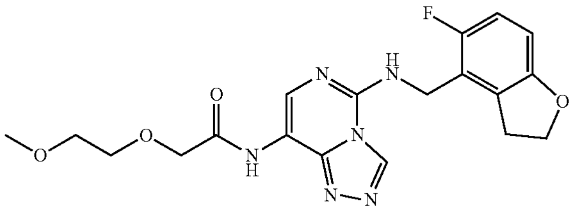
HJM-085
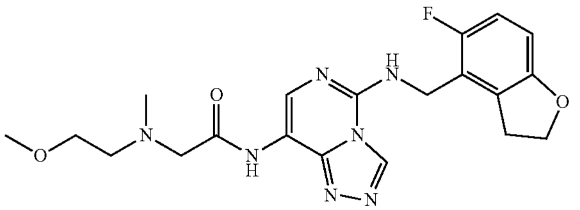
HJM-086
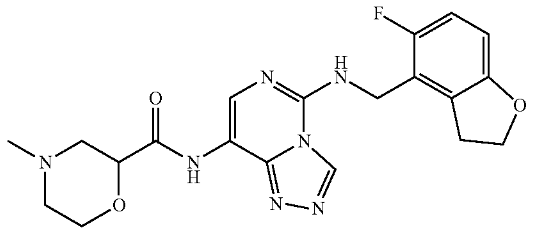
HJM-087
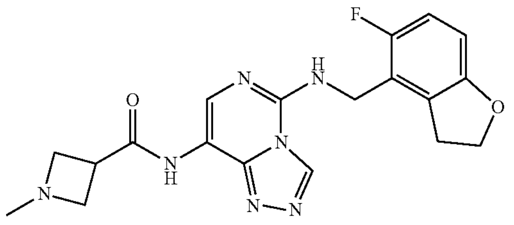
HJM-088
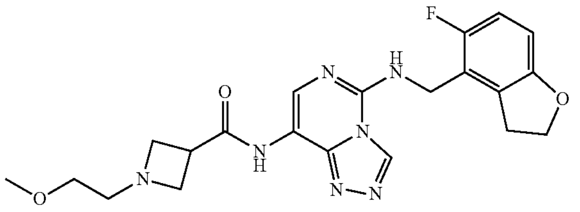
-continued
HJM-089
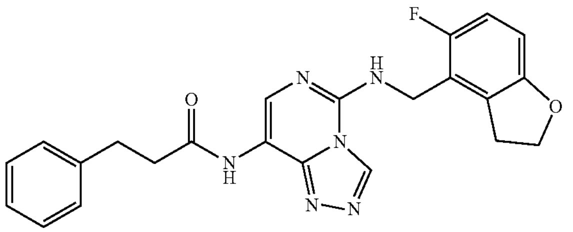
HJM-090
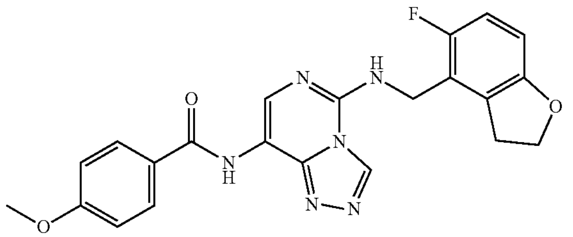
HJM-091
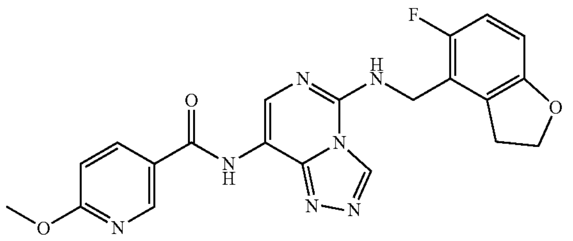
HJM-092
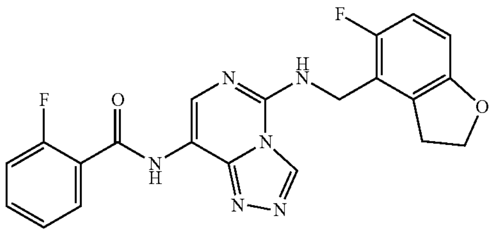
HJM-093
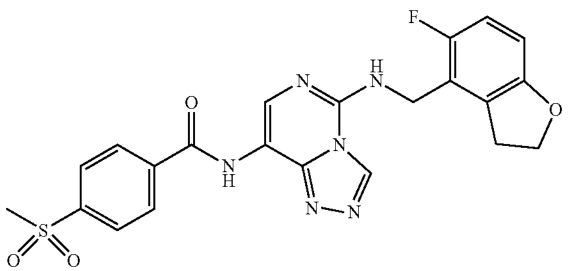
HJM-094
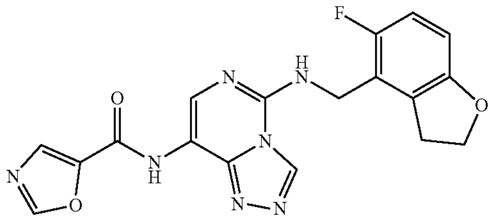

-continued
HJM-095
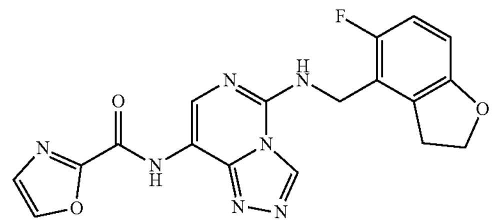
HJM-096
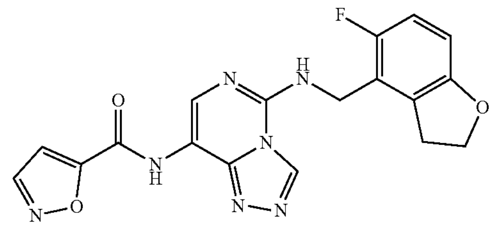
HJM-097
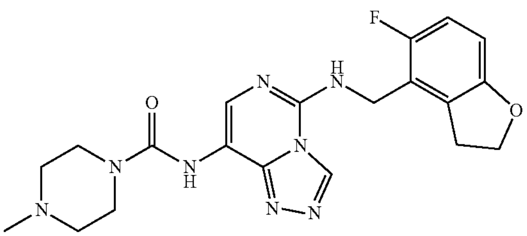
HJM-098
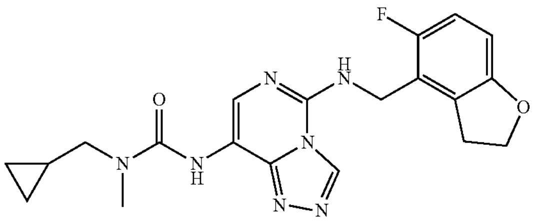
HJM-099
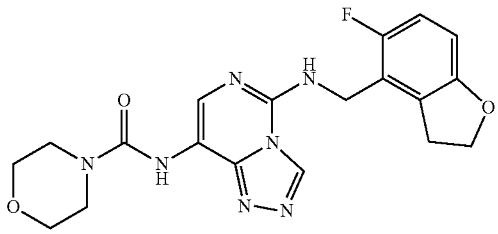
HJM-100
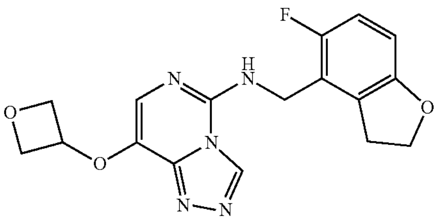
-continued
HJM-101
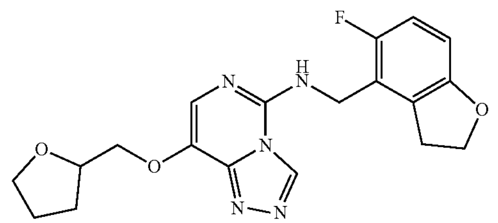
HJM-102
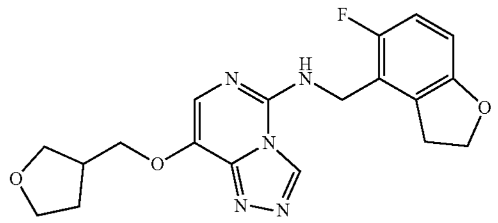
HJM-103
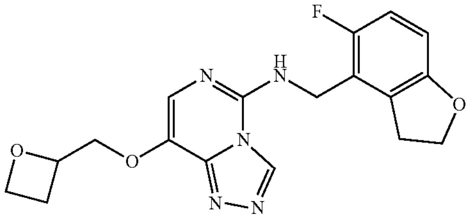
HJM-104
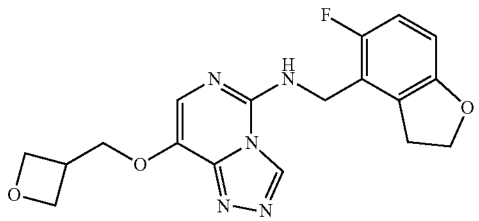
HJM-105
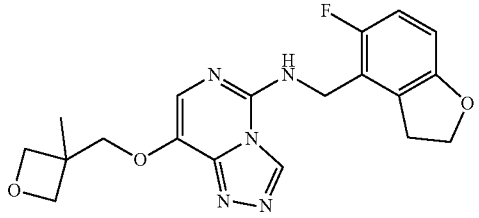
HJM-106
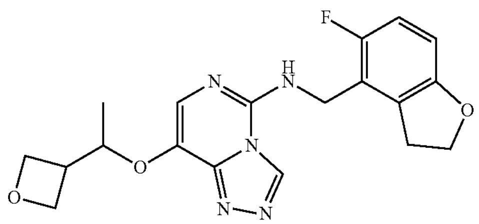

HJM-107
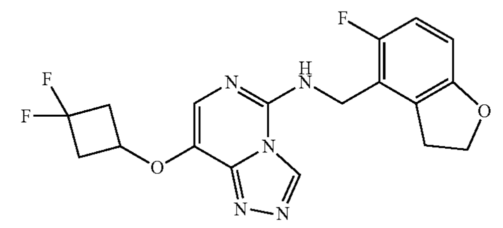
HJM-108
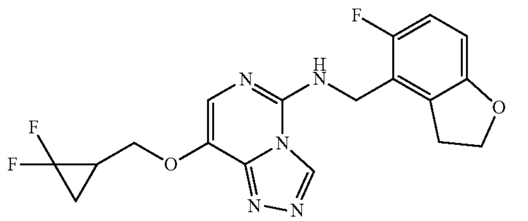
HJM-109
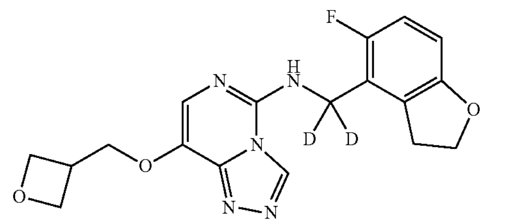
HJM-110
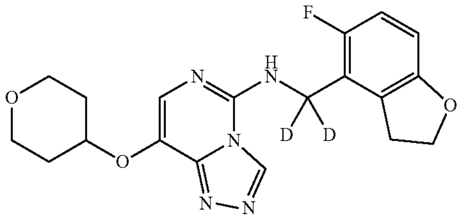
HJM-111
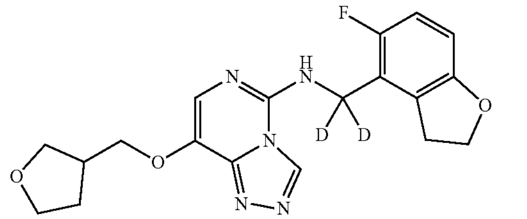
HJM-112
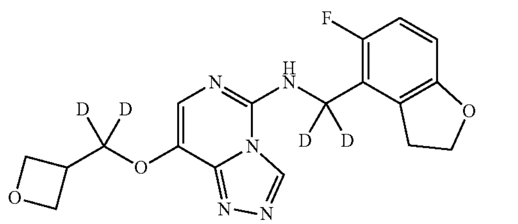
HJM-113
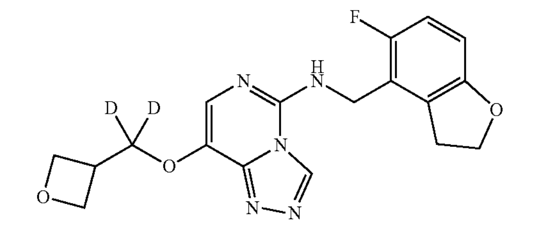
HJM-114
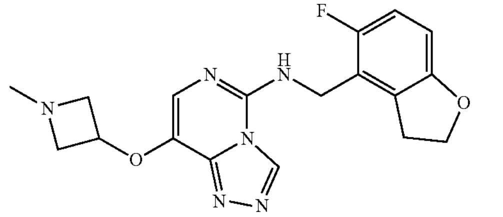
HJM-115
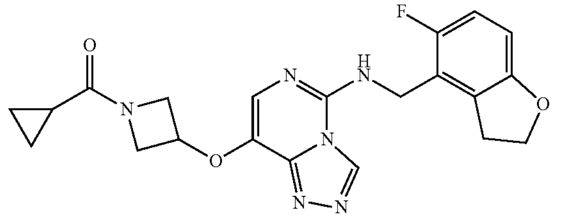
HJM-116
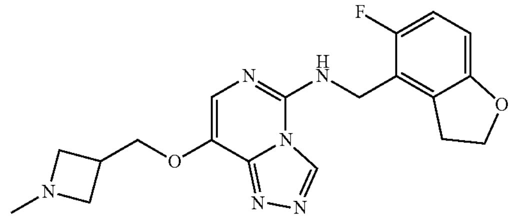
HJM-117
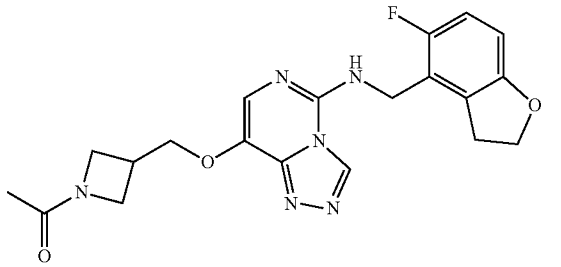
HJM-118
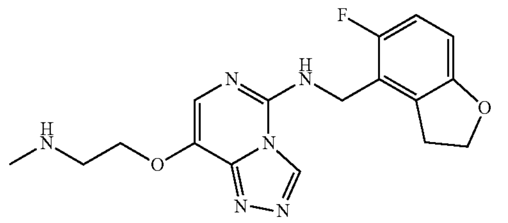

-continued
HJM-119
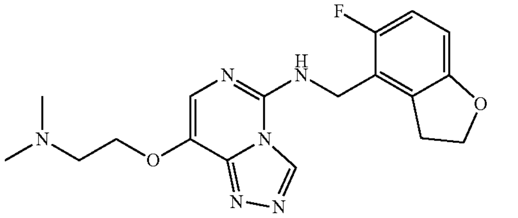
HJM-120
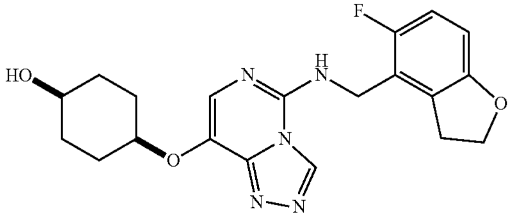
HJM-121
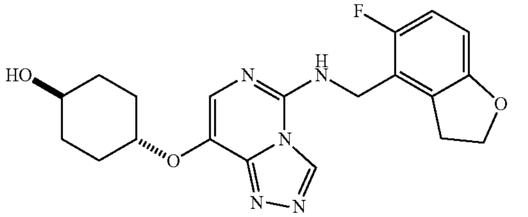
HJM-122
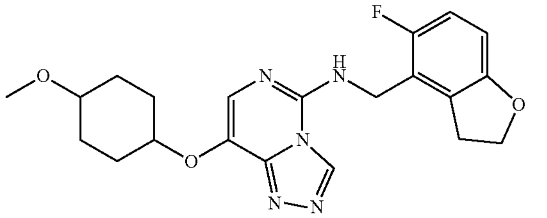
HJM-123
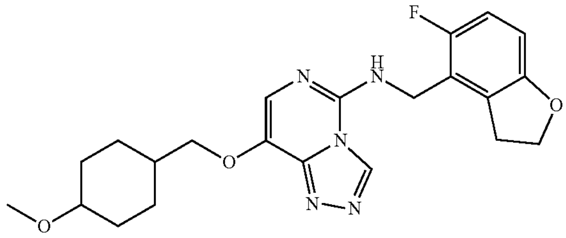
HJM-124
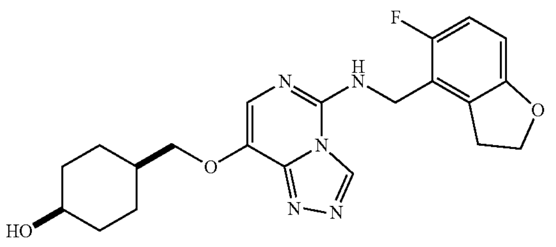
-continued
HJM-125
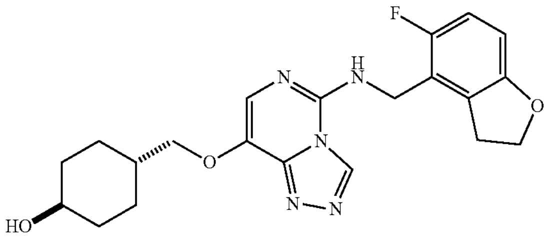
HJM-126
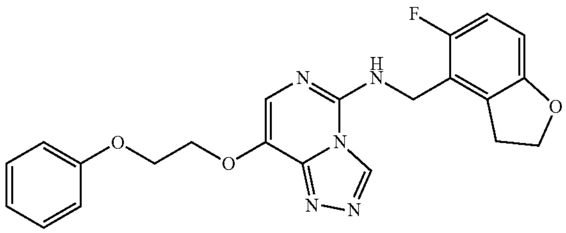
HJM-127
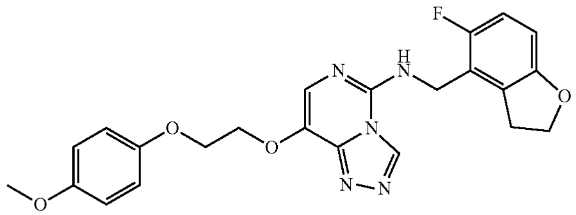
HJM-128
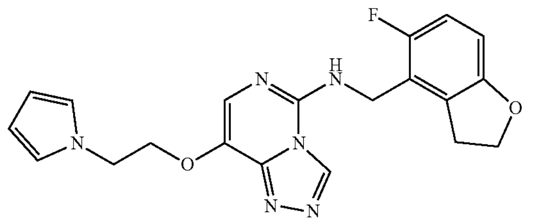
HJM-129
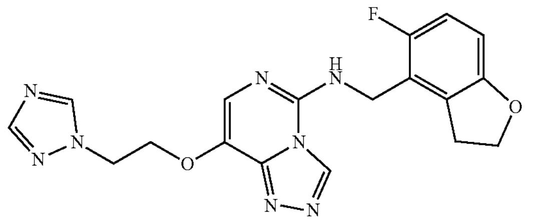
HJM-130
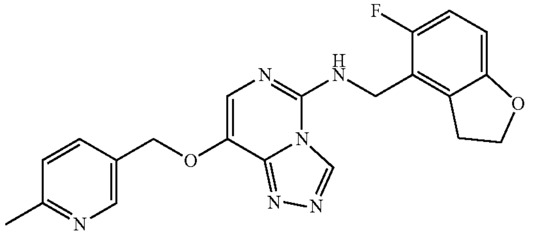

-continued
HJM-131
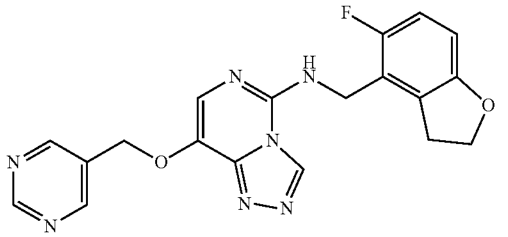
HJM-132
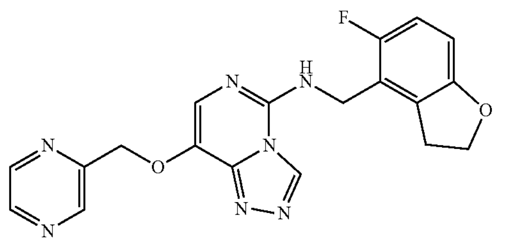
HJM-133
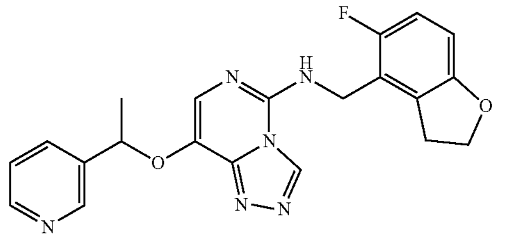
HJM-134
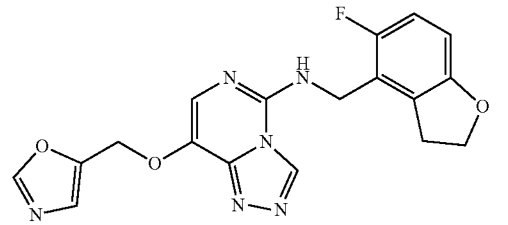
HJM-135
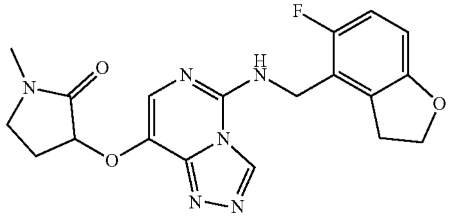
HJM-136
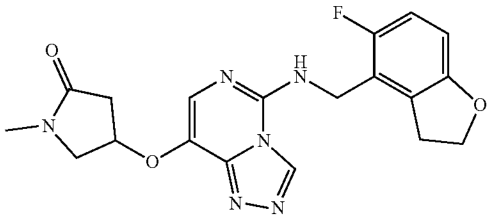
-continued
HJM-137
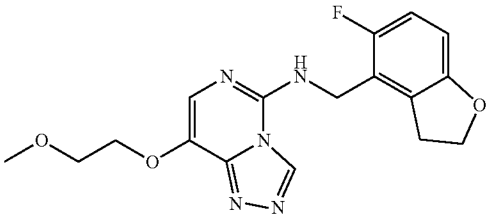
HJM-138
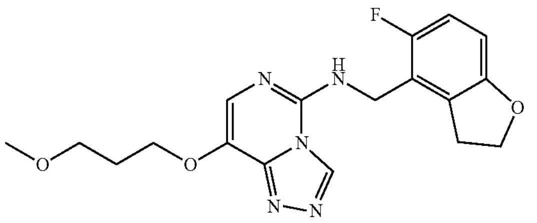
HJM-139
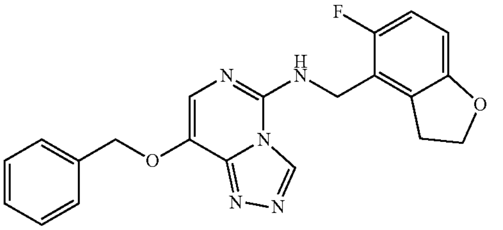
HJM-140
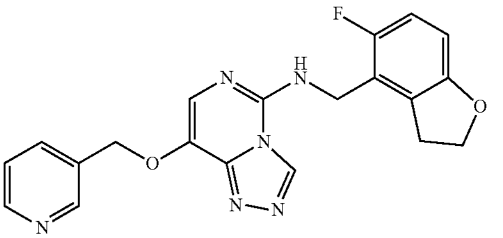
HJM-141
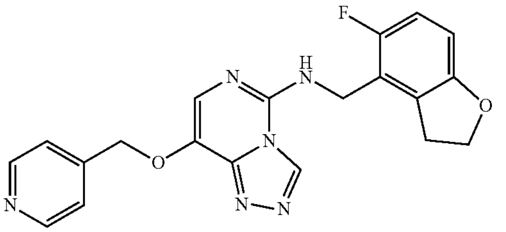
HJM-142
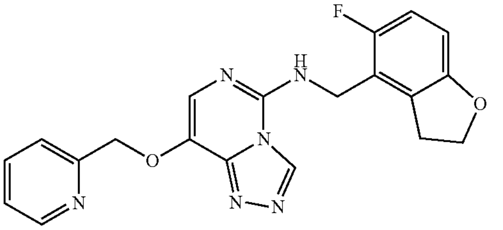

-continued

HJM-143

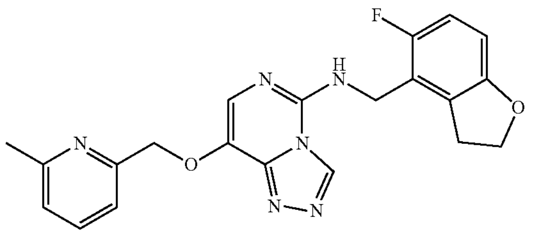

HJM-144

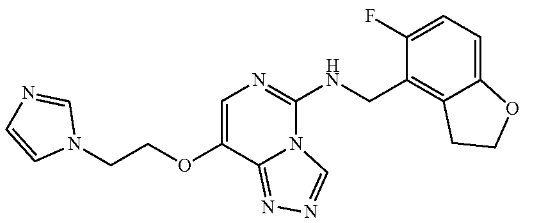

HJM-145

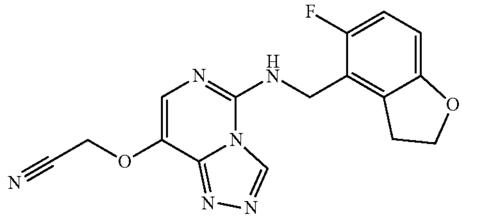

HJM-146

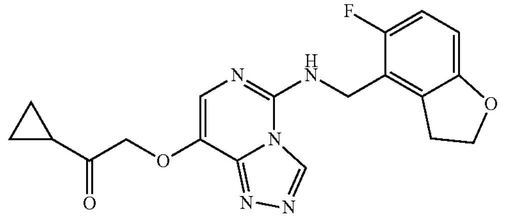

HJM-147

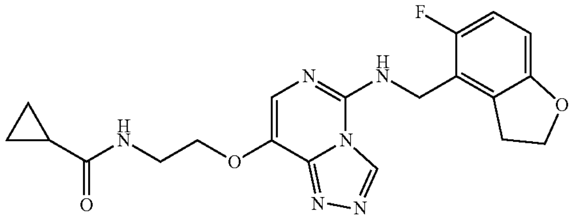

HJM-148

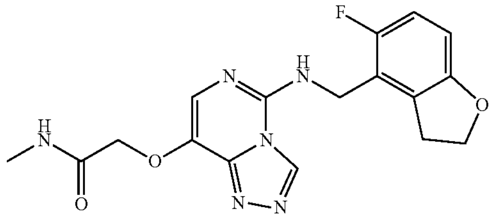

-continued

HJM-149

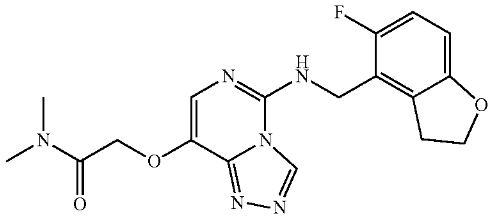

HJM-150

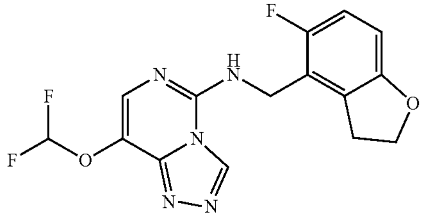

HJM-151

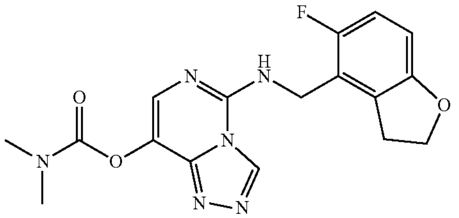

HJM-152

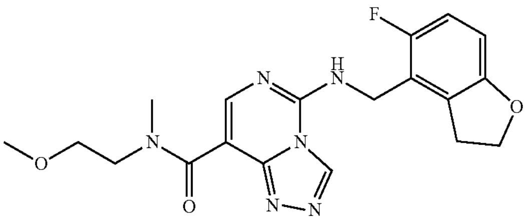

HJM-153

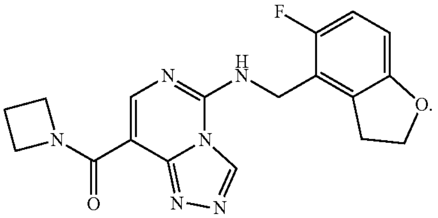

15. A pharmaceutical composition, containing the compound or the tautomer, stereoisomer, crystal form, pharmaceutically acceptable salt, hydrate or solvate thereof according to claim 1, and pharmaceutically acceptable excipient(s).

16. The pharmaceutical composition according to claim 15, which is used in combination with immune checkpoint inhibitors, wherein the immune checkpoint inhibitor is selected from PD-1, PD-L1, and CTLA-4 antibodies.

17. A drug combination, comprising the compound or the tautomer, stereoisomer, crystal form, pharmaceutically acceptable salt, hydrate or solvate thereof according to claim 1, and immune checkpoint inhibitor(s).

18. A method of treating an EED- and/or PRC2-mediated disease in a subject, comprising administering to the subject the compound or the tautomer, stereoisomer, prodrug, crystal form, pharmaceutically acceptable salt, hydrate or solvate thereof according to claim 1.

19. The method according to claim 18, wherein the EED- and/or PRC2-mediated disease is a tumor-related disease, an immunodeficiency disease or an autoimmune disease.

20. The method according to claim 19, wherein the tumor-related disease is selected from diffuse large B-cell lymphoma, follicular lymphoma, non-Hodgins's lymphoma, leukemia, multiple myeloma, mesothelioma, gastric cancer, malignant rhabdomyoma, liver cancer, prostate cancer, breast cancer, bile duct and gallbladder cancer, bladder cancer, brain tumors, cervical cancer, colon cancer, melanoma, endometrial cancer, esophageal cancer, head and neck cancer, lung cancer, nasopharyngeal cancer, ovarian cancer, pancreatic cancer, renal cell cancer, rectal cancer, thyroid cancer, parathyroid tumor, uterine tumor and soft tissue sarcoma; wherein the immunodeficiency disease or autoimmune disease is selected from systemic lupus erythematosus, Crohn's disease, ulcerative colitis, multiple sclerosis, aplastic anemia due to autoimmunity, and rejection reaction due to organ transplantation.

21. The method according to claim 20, wherein the tumor-related disease is selected from neuroblastoma, schwannoma, glioma, glioblastoma and astrocytoma.

* * * * *